(12) United States Patent
Boddupalli et al.

(10) Patent No.: US 12,203,086 B2
(45) Date of Patent: Jan. 21, 2025

(54) LETTUCE WITH INCREASED SHELF LIFE

(71) Applicant: GREENVENUS, LLC, Davis, CA (US)

(72) Inventors: Sekhar Boddupalli, Germantown, MD (US); Arianne Tremblay, Germantown, MD (US); Eric Aasen, Germantown, MD (US); Jyoti R. Rout, Woodland, CA (US); Zhongsen Li, Germantown, MD (US)

(73) Assignee: GREENVENUS, LLC, Davis, CA (US)

( * ) Notice: Subject to any disclaimer, the term of this patent is extended or adjusted under 35 U.S.C. 154(b) by 96 days.

(21) Appl. No.: 17/771,687

(22) PCT Filed: Oct. 2, 2020

(86) PCT No.: PCT/US2020/054082
§ 371 (c)(1),
(2) Date: Apr. 25, 2022

(87) PCT Pub. No.: WO2021/080761
PCT Pub. Date: Apr. 29, 2021

(65) Prior Publication Data
US 2023/0220408 A1    Jul. 13, 2023

Related U.S. Application Data

(60) Provisional application No. 62/925,853, filed on Oct. 25, 2019.

(51) Int. Cl.
*C12N 15/82* (2006.01)
*C12N 9/02* (2006.01)
*C12N 9/22* (2006.01)
*C12N 15/11* (2006.01)

(52) U.S. Cl.
CPC ....... *C12N 15/8243* (2013.01); *C12N 9/0061* (2013.01); *C12N 9/22* (2013.01); *C12N 15/11* (2013.01); *C12N 15/8213* (2013.01); *C12Y 110/03002* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2005/0191739 A1* | 9/2005 | Robinson | C12Y 110/03001 435/6.12 |
| 2011/0296556 A1 | 12/2011 | Sammons et al. | |
| 2015/0247153 A1* | 9/2015 | Fillatti | C12N 9/0059 435/6.12 |
| 2017/0114418 A1* | 4/2017 | Feikert | C12Q 1/6895 |

FOREIGN PATENT DOCUMENTS

WO    2014/047623 A1    3/2014

OTHER PUBLICATIONS

Hystad et al. (Theor Appl Genet, Aug. 2015, vol. 128, No. 8, pp. 1605-1615).*
Hystad et al. (Theor. Appl. Genet., 128:1605-1615,2015).*
Thipyapong et al. (Planta, 220: 105-117, 2004).*
Bonawitz et al.,(Annu. Rev. Genet. 44: 337-363, 2010).*
Paul et al., (Plant Cell Reports; 35:1417-1427; 2016).*
Yee et al. (The FEBS Journal, 283:3329-3248, 2016).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13: 1768-1774, 2003).*
Arziman et al. (Nucleic Acids Research, 33:582-588, 2005).*
Woo et al. (Nature Biotechnology, 23: 1162-1165, 2015).*
International Search Report and Written Opinion for corresponding PCT Application No. PCT/US20/54082 mailed Mar. 3, 2021 (28 pgs.).
Hystad et al., "Genetic Characterization and Expression Analysis of Wheat (*Triticum aestivum*) Line 07OR1074 Exhibiting Very Low Polyphenol Oxidase (PPO) Activity," Theor Appl Genet 128(8):1605-1615 (May 16, 2015).
International Preliminary Report on Patentability for corresponding PCT Application No. PCT/US20/54082 mailed Apr. 26, 2022.
Thipyapong et al., "Antisense Downregulation of Polyphenol Oxidase Susceptibility," Planta 220:105-117 (2004).
Examination Report for Great Britain Application No. 2207619.4 dated May 16, 2024.

* cited by examiner

*Primary Examiner* — Vinod Kumar
(74) *Attorney, Agent, or Firm* — Troutman Pepper Hamilton Sanders LLP (Rochester)

(57) ABSTRACT

The present application is directed to lettuce plants comprising a mutation in each of at least two different PPO genes, where said mutations reduce the activity of PPO protein compared to a wild type lettuce plant. The present application is also directed to methods for making such lettuce plants.

15 Claims, 47 Drawing Sheets

Specification includes a Sequence Listing.

PPO-B PCR amplicon deep sequencing

| | |
|---|---|
| C217p221 (WT) | AGTTCCAAGACTTCTACTCTTTTTCATGGGTAGTCCTTATCG-T-GCAGGCGATGATGC (SEQ ID NO:156) |
| C217p10 | AGTTCCAAGACTTCTACTCTTTTTCATGGGTAGTCCTTATCGTGCAGGCGATGATGCTA (SEQ ID NO:157) |
| C217p55 | AGTTCCAAGACTTCTACTCTTTTTCATGGGTAGTCCTTATCG-GCAGGGGATGATGCTA (SEQ ID NO:158) |
| C214p189 | AGTTCCAAGACTTCTACTCTTTTTCATGGGTAGTCCTTATCGTGCAGGCGATGATGCTA (SEQ ID NO:159) |
| C219p1 | AGTTCCAAGACTTCTACTCTTTTTCATGGGTAGTCCTTA----GCAGGGGATGATGCTA (SEQ ID NO:160) |

FIG. 2A

PPO-G PCR amplicon deep sequencing

C321p110(WT)  GTGACAAACGCCACCGACCCCACAGCTTTCTTCGGTGGTGA-------GTATCGTGCCGAATCGAACCCATTAGCGGTGG
              (SEQ ID NO:161)

C231p110      GTGTCTTAATGCCAAGACTGCTAGTCTTTCATGGTAGTCC-------TTATCGTGCCAGTGATCACCCTAGCCCTGGTGC
              (SEQ ID NO:162)

C246p115      GTGACAAACGCCACCGACCCCACAGCTTTCTTCGGTGGTGA-------GTATCGTGCCGAATCGAACCCATTAGCGGTGG
              (SEQ ID NO:163)

C246p4        GTGACAAACGCCACCGACCCCACAGCTTTCTTCGGTGGTGA-------GTATCGTGCCGAATCGAACCCATTAGCGGTGG
              (SEQ ID NO:164)

C246p90       GTGACAAACGCCACCGACCCCACAGCTTTCTTCGGTGGTGGTGACAAACGCCACCGACCCCACAGCTTTCTTCGGTAAGTATCGTGCCGAATCGAACCCATTAGCGGTGG
              (SEQ ID NO:165)

C284p114      GTGACAAACGCCACCGACCCCACAGCTTTCTTCGGTGGTGGTGACAAACGCCACCGACCCCACAGCTTTCTTCGGTGTTGTGAGTATCGTGCCGAATCGAACCCATTAGCGGTGG
              (SEQ ID NO:166)

C284p64       GTGACAAACGCCACCGACCCCACAGCTTTCTTCGGTGGTGGTGACAAACGCCACCGACCCCACAGCTTTCTTCGGTGGTTAGTATCGTGCCCCGAATCGAACCCATTAGCGGTGG
              (SEQ ID NO:167)

C284p58       GTGACAAACGCCACCGACCCCACAGCTTTCTTCGGTGGTGA-------GTATCGTGCCGAATCGAACCCATTAGCGGTGG
              (SEQ ID NO:168)

C246p87       GTGACAAACGCCACCGACCCCACAGCTTTCTTCGGTGGTGA-------GTATCGTGCCGAATCGAACCCATTAGCGGTGG
              (SEQ ID NO:169)

FIG. 2B

| Construct | Line ID | PPO-expression | G | E | O | S | B | A | R | C | P | D | N |
|---|---|---|---|---|---|---|---|---|---|---|---|---|---|
| ID 123 | 8-14-13 | | Het | Het | Homo | Het | Het | WT | Het | WT | Het | Het | WT |
| ID 123 | 8-8-4 | | Het | Het | WT | Homo | Het | Het | WT | WT | WT | Het | Het |
| ID 123 | 8-10-3 | | Het | Het | Het | WT | Het | WT | Het | WT | WT | WT | WT |
| ID 124 | 13-01-17 | | Het | WT | WT | Het | Het | Het | Het | WT | WT | WT | WT |
| ID 124 | 9-01-10 | | Het | WT | Het | Het | Het | Het | WT | WT | WT | WT | WT |
| ID 124 | 9-01-2 | | Het | WT | Het | WT | Het | WT | WT | WT | WT | WT | WT |
| ID 123 | 8-3-1 | | WT | WT | WT | Het | Het | Het | Het | WT | WT | WT | WT |

T0 lines

FIG. 6

| Genotype | PPO Activity (units/mg of protein) | %PPO Activity of WT |
|---|---|---|
| 8-8-4-24 | -2.4 | 0% |
| 8-8-4-73 | 205.163 | 6.7% |
| 8-8-4-94 | 626.63 | 20.6% |
| 8-14-13-4 | 836.6139 | 27.4% |
| 8-14-13-25 | -260.894 | 0% |
| 8-14-13-40 | 62.5714 | 2% |
| WT-1 | 1054.3 | 100% |
| WT-2 | 5029.781 | |

| | T0 | | | T1 | | | | T2 | | |
|---|---|---|---|---|---|---|---|---|---|---|
| | Homo | Het | WT | | Homo | Het | WT | | Homo | Het | WT |
| 8-8-4 | S | A,B,D,E,G,N | C,O,P,R | 8-8-4-24 | B,D,E,G,S | | A,C,N,O,P,R | 8-8-4-24-All | B,D,E,G,S | | A,C,G,N,O,P,R |
| | | | | 8-8-4-23 | B,D,E,S | | A,C,G,N,O,P,R | 8-8-4-23-All | B,D,E,S | | A,C,G,N,O,P,R |
| | | | | 8-8-4-17 | D,E,S | A,B | C,G,N,O,P,R | 8-8-4-17-1 | B,D,E,S | | A,C,G,N,O,P,R |
| | | | | | | | | 8-8-4-17-5 | B,D,E,S | | A,C,G,N,O,P,R |
| | | | | | | | | 8-8-4-17-6 | B,D,E,S | | A,C,G,N,O,P,R |
| | | | | | | | | 8-8-4-17-14 | B,D,E,S | | A,C,G,N,O,P,R |
| | | | | | | | | 8-8-4-17-15 | B,D,E,S | | A,C,G,N,O,P,R |
| | | | | | | | | 8-8-4-17-16 | B,D,E,S | | A,C,G,N,O,P,R |
| | | | | | | | | 8-8-4-17-22 | B,D,E,S | | A,C,G,N,O,P,R |
| | | | | | | | | 8-8-4-17-27 | B,D,E,S | | A,C,G,N,O,P,R |
| | | | | | | | | 8-8-4-17-29 | B,D,E,S | | A,C,G,N,O,P,R |
| | | | | 8-8-4-30 | D,E,S | A,B | C,G,N,O,P,R | 8-8-4-30-6 | B,D,E,S | | A,C,G,N,O,P,R |
| | | | | | | | | 8-8-4-30-24 | B,D,E,S | | A,C,G,N,O,P,R |
| | | | | | | | | 8-8-4-30-29 | B,D,E,S | | A,C,G,N,O,P,R |
| | | | | 8-8-4-73 | B,E,S | A,G | C,N,O,P,R | 8-8-4-73-2 | A,B,D,E,S | | C,G,N,O,P,R |
| | | | | | | | | 8-8-4-73-4 | A,B,D,E,S | | C,G,N,O,P,R |
| | | | | | | | | 8-8-4-73-10 | A,B,D,E,S | | C,G,N,O,P,R |

FIG. 8

| | | | |
|---|---|---|---|
| 8-8-4-73-14 | A,B,D,E,S | | C,G,N,O,P,R |
| 8-8-4-73-19 | B,D,E,G,S | | A,C,N,O,P,R |
| 8-8-4-73-29 | B,D,E,S | | A,C,G,N,O,P,R |
| 8-8-4-96-2 | B,D,E,G,S | | A,C,N,O,P,R |
| 8-8-4-96-3 | B,D,E,G,S | | A,C,N,O,P,R |
| 8-8-4-96-6 | B,D,E,G,S | | A,C,N,O,P,R |
| 8-8-4-96-7 | B,D,E,G,S | | A,C,N,O,P,R |
| 8-8-4-96-9 | A,B,D,E,G,S | | C,N,O,P,R |
| 8-8-4-96-13 | A,B,D,E,G,S | | C,N,O,P,R |
| 8-8-4-96-14 | A,B,D,E,G,S | | C,N,O,P,R |
| 8-8-4-96-15 | B,D,E,G,S | | A,C,N,O,P,R |
| 8-8-4-96-16 | B,D,E,G,S | | A,C,N,O,P,R |
| 8-8-4-96-18 | A,B,D,E,G,S | | C,N,O,P,R |
| 8-8-4-96-22 | B,D,E,G,S | | A,C,N,O,P,R |
| 8-8-4-96-23 | B,D,E,G,S | | A,C,N,O,P,R |
| 8-8-4-96-25 | B,D,E,G,S | | A,C,N,O,P,R |
| 8-8-4-96-26 | A,B,D,E,G,S | | C,N,O,P,R |
| 8-8-4-96-28 | B,D,E,G,S | | A,C,N,O,P,R |
| 8-8-4-97-4 | A,B,D,E,S | | C,G,N,O,P,R |

| | | | | |
|---|---|---|---|---|
| 8-8-4-96 | B,D,E,G,S | A | C,N,O,P,R | |
| 8-8-4-97 | A,B,E,S | D,G,N | C,O,R | |

*FIG. 8 (cont.)*

| | | | | |
|---|---|---|---|---|
| 8-14-13 | 0 | B,D,E,G,P,R,S | A,C,N | |
| | | | 8-14-13-23 | |
| | | | | 8-8-4-97-6 | A,B,D,E,G,S | | C,N,O,P,R |
| | | | | 8-8-4-97-9 | A,B,D,E,S | | C,G,N,O,P,R |
| | | | | 8-8-4-97-11 | A,B,D,E,S | | C,G,N,O,P,R |
| | | | | 8-8-4-97-12 | A,B,D,E,S | | C,G,N,O,P,R |
| | | | | 8-8-4-97-13 | A,B,D,E,S | | C,G,N,O,P,R |
| | | | | 8-8-4-97-17 | A,B,D,E,S | | C,G,N,O,P,R |
| | | | | 8-8-4-97-22 | A,B,D,E,S | | C,G,N,O,P,R |
| | | | | 8-8-4-97-23 | A,B,D,E,S | | C,G,N,O,P,R |
| | | | | 8-8-4-97-25 | A,B,D,E,S | | C,G,N,O,P,R |
| | | | | 8-8-4-97-26 | A,B,D,E,S | | C,G,N,O,P,R |
| | | | | 8-8-4-97-29 | A,B,D,E,G,S | | C,N,O,P,R |
| | | | | 8-14-13-23-1 | D,E,O,R,S | B? | A,C,N |
| | | | | 8-14-13-23-4 | E,O,P,R,S | B | A,C,D,N |
| | | | | 8-14-13-23-6 | E,O,P,R,S | B | A,C,D,N |
| | | | | 8-14-13-23-7 | D,E,O,R,S | B | A,C,N,P |
| | | | | 8-14-13-23-16 | E,O,P,R,S | B | A,C,D,N |
| | | | | 8-14-13-23-23 | D,E,O,R,S | B | A,C,N,P |
| | | | | 8-14-13-23-30 | E,O,P,R,S | B | A,C,D,N |

FIG. 8 (cont.)

| ID | Genotype | PPO-A | PPO-B | PPO-C | PPO-D | PPO-E | PPO-G | PPO-N | PPO-O | PPO-P | PPO-R | PPO-S | Gen |
|---|---|---|---|---|---|---|---|---|---|---|---|---|---|
| 15-1-17-8 | B,S | WT | T insertion bp 1008-1009 | WT | WT | WT | WT | WT | WT | WT | WT | T insertion bp 1044-1045 | T2/T3 |
| 15-1-7-22 | B,R,S | WT | T insertion bp 1008-1009 | WT | WT | WT | WT | WT | WT | WT | C insertion bp 1023-1024 | T insertion bp 1044-1045 | T3 |
| 15-1-9-1 | B,G,R,S | WT | T insertion bp 1008-1009 | WT | WT | WT | CG deletion bp 985-988 | WT | WT | WT | C insertion bp 1023-1024 | T insertion bp 1044-1045 | T2/T3 |
| 15-1-9-11 | B,G,R | WT | T insertion bp 1008-1009 | WT | WT | WT | CG deletion bp 985-988 | WT | WT | WT | C insertion bp 1023-1024 | WT | T2/T3 |
| 14-2-24-21 | B,D,E,G,S | WT | T insertion bp 1008-1009 | WT | T insertion bp 1131-1132 | T insertion bp 1112-1113 | T insertion bp 988-989 | WT | WT | WT | WT | T insertion bp 1044-1045 | T2/T3 |

FIG. 10

| | | | | | | | | | |
|---|---|---|---|---|---|---|---|---|---|
| 14-2-24-5 | B,D,E,G,S | WT | T insertion bp 1008-1009 | WT | T insertion bp 1131-1132 | T insertion bp 1112-1113 | T insertion bp 988-989 | WT | WT | WT | T insertion bp 1044-1045 | T2/T3 |
| 14-2-73-14 | A,B,D,E,S | T insertion bp 976-977 | HET | WT | T insertion bp 1131-1132 | T insertion bp 1112-1113 | T insertion bp 988-989 | WT | WT | WT | T insertion bp 1044-1045 | T2/T3 |
| 14-2-96-13 | A,B,D,E,G,S | T insertion bp 977-978 | HET | WT | T insertion bp 1131-1132 | T insertion bp 1112-1113 | T insertion bp 988-989 | WT | WT | WT | T insertion bp 1044-1045 | T2/T3 |
| 14-2-96-9 | A,B,D,E,G,S | T insertion bp 977-978 | HET | WT | T insertion bp 1131-1132 | T insertion bp 1112-1113 | T insertion bp 988-989 | WT | WT | WT | T insertion bp 1044-1045 | T2/T3 |
| 14-2-97-17 | A,B,D,E,S | T insertion bp 977-978 | HET | WT | T insertion bp 1131-1132 | T insertion bp 1112-1113 | WT | WT | WT | WT | T insertion bp 1044-1045 | T2/T3 |

*FIG. 10 (cont.)*

| | PPO Edited GreenVenus Lettuce Varieties | | | | Control Romaine Types | |
|---|---|---|---|---|---|---|
| | 24-21 | 24-5 | 73-14 | 96-13 | Green Romaine | Red Romaine |
| Vitamin C Harvest | 3.78 mg/g | 4.31 mg/g | 3.42 mg/g | 4.45 mg/g | 3.98 mg/g | 4.7 mg/g |
| Vitamin C 21 day post harvest | 3.81 mg/g* | 3.95 mg/g* | >0.1 mg/g | 3.6 mg/g* | >0.1 mg/g | >0.1 mg/g |
| Vitamin E Harvest | 1.11 mg/g | 1.15 mg/g | 1.12 mg/g | 1.09 mg/g | 1 mg/g | 1.41 mg/g |
| Vitamin E 21 day post harvest | 1.02 mg/g | 1.13 mg/g | 1.12 mg/g | .55 mg/g | 1.04 mg/g | 1.57 mg/g |
| Vitamin A Harvest | 189 ug/g | 178 ug/g | 185 ug/g | 225 ug/g | 198 ug/g | 131 ug/g |
| Beta Carotene 21 day post harvest | 27 ppm* | 28.6 ppm* | 35.6 ppm* | 24.6 ppm | 10.4 ppm | 26 ppm |

| Variety | Fat % | Protein % | Moisture % | Ash % | Calories/100 g | Carbs % |
|---|---|---|---|---|---|---|
| 73.14 | 0.2 | 1 | 94.2 | 0.5 | 22 | 4.1 |
| 24.5 | 0.3 | 0.8 | 94.8 | 0.6 | 20 | 3.5 |
| 96.13 | 0.3 | 1 | 94.5 | 0.6 | 21 | 3.6 |
| WT | 0.2 | 0.9 | 96.2 | 0.5 | 14 | 2.2 |

*FIG. 29*

| name | Failure % (of replicates), day 0-27 | | | | (day) |
|---|---|---|---|---|---|
| | 7 | 13 | 21 | 27 | |
| 24.21 | 0% | 0% | 17% | 100% | |
| 24.5 | 0% | 0% | 17% | 100% | |
| 73.14 | 0% | 0% | 29% | 100% | |
| 96.13 | 0% | 0% | 0% | 100% | |
| GR | 0% | 17% | 67% | 100% | |
| RR | 0% | 0% | 33% | 100% | |

LETTUCE WITH INCREASED SHELF LIFE

This application is a national stage application under 35 U.S.C. § 371 of International Application No. PCT/US2020/054082, filed Oct. 2, 2020, which claims the priority benefit of U.S. Provisional Patent Application Ser. No. 62/925,853, filed Oct. 25, 2019, which are hereby incorporated by reference in their entirety.

SEQUENCE LISTING

The present application contains a Sequence Listing which has been submitted electronically in ASCII format and is hereby incorporated by reference in its entirety. Said ASCII copy, created on Oct. 10, 2022, is named 257432_001002_ST25.txt, and is 152,736 bytes in size.

FIELD

The present application is directed to lettuce plants with increased shelf life. The lettuce plants have combinations of polyphenol oxidase ("PPO") gene mutations to reduce browning, reduce tip burn, create longer shelf life, and improve nutrition as compared to non-mutated varieties.

BACKGROUND

Lettuce is one of the most commonly consumed "ready to eat" leafy vegetables in the United States and world. The United States alone produces over 8 billion pounds of lettuce worth $1.9B (USDA-ERS: Vegetable and Pulses Data-2017). At least 90% of that total is consumed domestically. Cut salads, however, are a highly perishable commodity and significant loss occurs due to cut-surface browning during storage and distribution. Several practices such as optimized growing conditions (reduced irrigation/nitrogen and early-harvesting) and post-harvest practices (application of anti-oxidant chemicals, low oxygen-packing, and storage at low temperature) are utilized to reduce browning; however, they are not completely effective in addition to adding significantly to the cost of production and storage. Key enzymes in plants responsible for the browning are polyphenol oxidase ("PPO"), phenylalanine ammonia lyase ("PAL"), and peroxidases. PPO is among the major contributors in wound-induced browning in most fruits and vegetables. Breeding strategies targeting PAL and PPO pathways have been attempted with limited success.

The lettuce genome contains at least 19 putative PPO genes, and the expression level of PPO genes in lettuce varies significantly. It is unknown which genes or combination of genes, when mutated or when gene function is suppressed are necessary and sufficient to achieve non-browning lettuce.

There is a need in the art to determine the PPO gene(s), when mutated or suppressed, that is/are necessary and sufficient to achieve a variety of non-browning lettuce that will have longer shelf life to help reduce waste of cultivated lettuce for consumption.

SUMMARY

One aspect of the present application is directed to a lettuce plant comprising a mutation in each of at least two different PPO genes, where said mutations reduce the activity of PPO protein compared to a wild type lettuce plant.

Another aspect of the present application is directed to a method of making a lettuce plant with reduced PPO activity. This method involves introducing a mutation into each of at least two different PPO genes of a lettuce plant, where said mutations reduce the activity of PPO protein compared to a wild type lettuce plant.

A further aspect of the present application is directed to a method of editing PPO genes of lettuce plant. This method involves introducing into a lettuce plant a polynucleotide construct comprising a first nucleic acid sequence encoding a gene editing nuclease, a promoter that is functional in plants operably linked to said first nucleic acid sequence, a second nucleic acid sequence encoding a plurality of gRNAs in a polycistronic arrangement targeting at least two PPO genes of choice to edit, and a second promoter that is functional in plants, operably linked to said second nucleic acid sequence.

Another aspect of the present application is directed to a polynucleotide construct for editing polyphenol oxidase genes of a plant comprising a nucleic acid sequence encoding a plurality of gRNAs targeting at least two PPO genes operably linked to a promoter.

BRIEF DESCRIPTION OF THE DRAWINGS

FIGS. 2A-B show examples of detected edits made by the SynNuc1 nuclease in the PPO-B gene (FIG. 2A) (SEQ ID NOs:156-160) and the PPO-G gene (FIG. 2B) (SEQ ID NOs:161-169) by deep sequencing.

FIG. 6 is a table showing individual events corresponding to ID and ID constructs listed as a line ID. "Het" and "Homo" represent one or both copies of PPO genes mutated, respectively. "WT" represents wild type PPO. Arrows represent events that were advanced to T1.

FIG. 8 shows the progression of events to fixed genotypes from $T_0$ to $T_2$.

FIG. 9C shows images of agarose gels showing the result of PCR screening of T1 plants with the indicated primers sets. Plant 8-14-13-44 is a control. A178/A181 amplifies the endogenous PDF gene and is a PCR positive control.

FIG. 10 is a table showing the results of sequencing of edited PPO genes in 10 PPO KO varieties at the $T_2$ and $T_3$ generation.

FIG. 20A shows the average shelf life score (with standard deviation) for 6 lines and 1 control lettuce; * indicates statistical significance from control at Day 20; ‡ indicates statistical significance from control at Day 28; FIG. 20B shows the number of projected days for which each line and control would have an acceptable shelf life score (i.e., <13 days) and the number of days added to shelf life as compared to control.

FIG. 24A shows the average discoloration of cut lettuce at 1, 7, 10, 14, 20, and 27 days after processing with a score of 5 being severe discoloration and a score of 1 being no discoloration. GVR-110 had significantly less discoloration at days 14, 20, and 27 after processing (P<0.024). FIG. 24B shows the average overall visual quality score at 1, 7, 10, 14, 20, and 27 days after processing with a score of 9 being excellent quality and a score of 1 being unusable. GVR-110 maintained a high average visual quality score throughout the study and had significantly higher quality scores compared to isogenic controls at day 20 (P<0.016) and day 27 (P<0.0003) after processing.

FIG. 29 is a table and graph showing the nutritional composition of PPO mutant lines GVR-102 ("Seed Type A"), GVR-108 ("Seed Type C"), GVR-110 ("Seed Type D"), and an isogenic control ("Control") at 30 days after processing.

FIGS. 32A-F show that the lettuce varieties are identical in their PPO-A, B, D, E, G, and S tyrosinase gene sequences, respectively.

DETAILED DESCRIPTION

Figure 1:
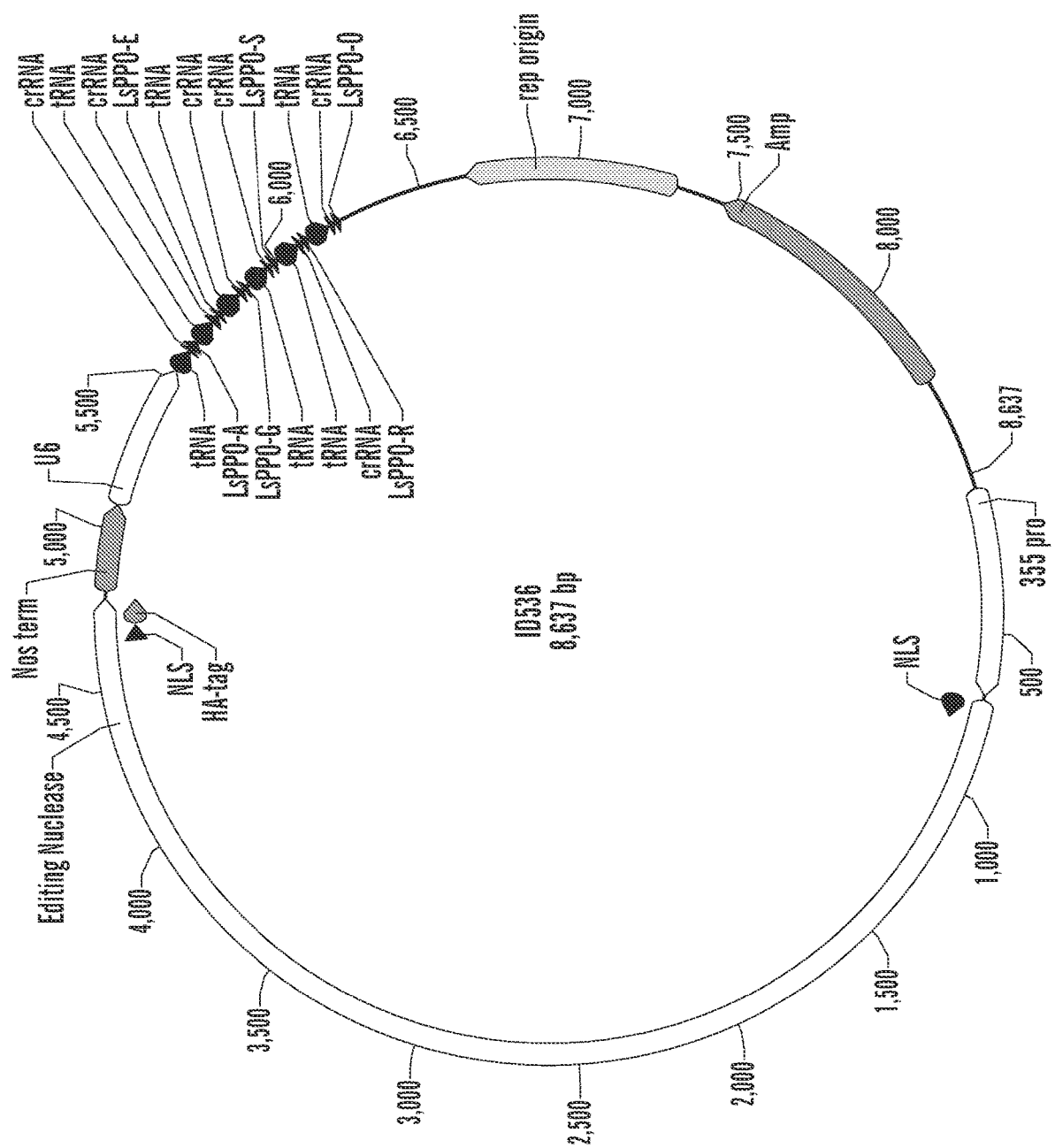
FIG. 1 is a schematic illustration showing the ID536 expression vector for polycistronic expression of gRNAs for editing PPO genes in lettuce.
Figure 3A:
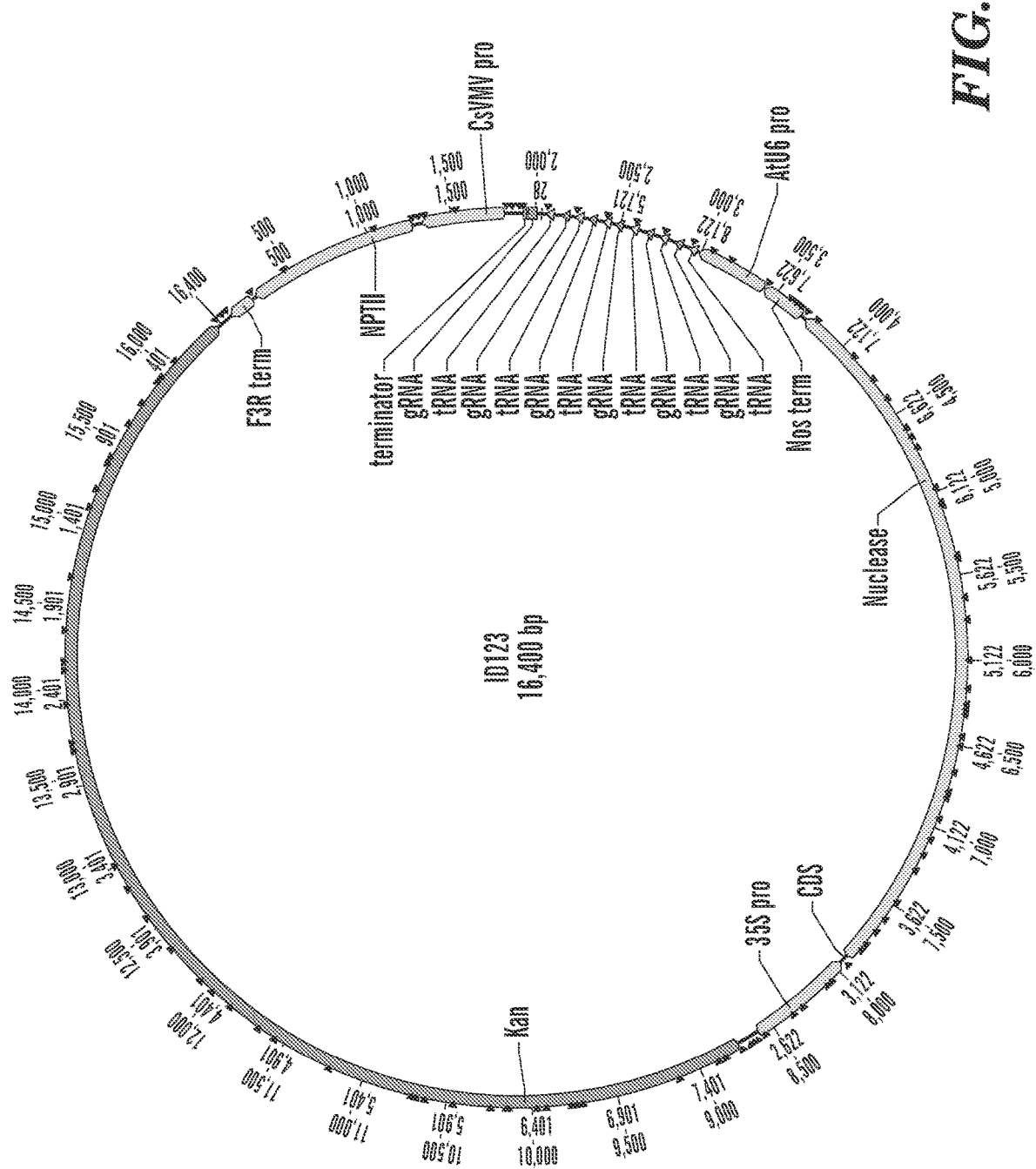
FIGS. 3A-B are a schematic illustration showing the ID123 expression vector for polycistronic expression of gRNAs for editing PPO genes in lettuce in FIG. 3A and the ID124 expression vector for polycistronic expression of gRNAs for editing PPO genes in lettuce in FIG. 3B.
Figure 3B:
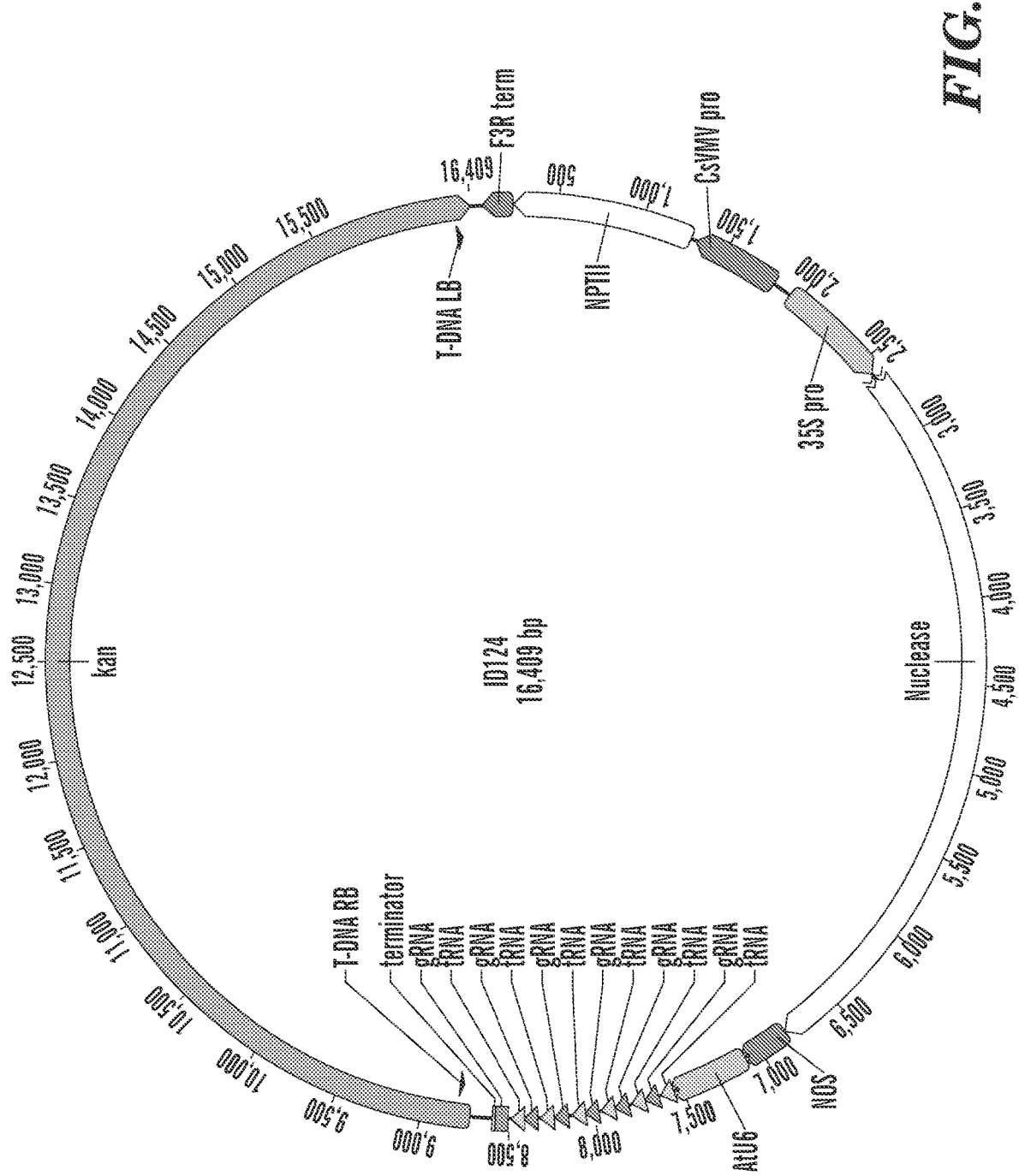

In this disclosure, a number of terms and abbreviations are used. The following definitions are provided and should be helpful in understanding the scope and practice of the present invention.

The term "mutation" means a human-induced change in the genetic sequence compared to a wild type sequence. The mutation may be, without limitation, from one or more nucleotide insertions, one or more nucleotide substitutions, one or more nucleotide deletions, or any combination thereof. In one embodiment, mutations are those that cause the gene to not be expressed or not be properly expressed, or those that inactivate the protein, such as from the introduction of a frameshift to the coding region leading to a premature stop codon. A mutation that leads to a change in the expression of the gene such that the function of the encoded protein is eliminated or substantially decreased, such as a premature stop codon, is referred to herein as a "knockout" mutation.

The term "isolated" for the purposes of the present application designates a biological material (e.g., nucleic acid or protein) that has been removed from its original environment (the environment in which it is naturally present). For example, a polynucleotide present in the natural state in a plant or an animal is not isolated. The same polynucleotide is "isolated" if it is separated from the adjacent nucleic acids in which it is naturally present. The term "purified" does not require the material to be present in a form exhibiting absolute purity, exclusive of the presence of other compounds. Rather, it is a relative definition. A polynucleotide is in the "purified" state after purification of the starting material or of the natural material by at least one order of magnitude, preferably 2 or 3 and preferably 4 or 5 orders of magnitude.

A "nucleic acid", "nucleotide", or "polynucleotide" is a polymeric compound comprised of covalently linked subunits called nucleotides. Nucleic acids include polyribonucleic acid ("RNA") and polydeoxyribonucleic acid ("DNA"), both of which may be single-stranded or double-stranded. DNA includes but is not limited to, cDNA, genomic DNA, plasmid DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single-stranded form, or a double-stranded helix. Double stranded DNA-DNA, DNA-RNA, and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" when referring to a polynucleotide will be understood to mean a nucleotide sequence of reduced length relative to the reference nucleic acid and comprising, over the common portion, a nucleotide sequence identical to the reference nucleic acid. Such a nucleic acid fragment according to the present application may be, where appropriate, included in a larger polynucleotide of which it is a constituent. Such fragments comprise, or alternatively consist of, oligonucleotides ranging in length from at least 8, 10, 12, 15, 18, 20 to 25, 30, 40, 50, 70, 80, 100, 200, 500, 1000, 1500, or any number or range therein, consecutive nucleotides of a nucleic acid according to the present application.

As used herein, an "isolated nucleic acid fragment" is a polymer of RNA or DNA that is single- or double-stranded, optionally containing synthetic, non-natural, or altered nucleotide bases. An isolated nucleic acid fragment in the form of a polymer of DNA may be comprised of one or more segments of cDNA, genomic DNA, or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, optionally including regulatory sequences preceding (5' noncoding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene or polynucleotides foreign to the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters"

or "regulatable promoters." It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the disclosure herein, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase or transcription factors.

A coding sequence is "under the control" of transcriptional and translational control sequences in a cell when RNA polymerase transcribes the coding sequence into mRNA, which is then RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

As used herein a "protein" is a polypeptide that performs a structural or functional role in a living cell.

An "isolated polypeptide" or "isolated protein" or "isolated peptide" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

As used herein "reference sequence" means a nucleic acid or amino acid used as a comparator for another nucleic acid or amino acid, respectively, when determining sequence identity.

As used herein "percent identity" or "% identical" refers to the exactness of a match between a reference sequence and a sequence being compared to it when optimally aligned. For example, sequence alignments and percent identity calculations may be determined using a variety of comparison methods designed to detect homologous sequences including, but not limited to, the Multalin program (Corpet, "Multiple Sequence Alignment with Hierarchical Clustering," *Nucleic Acids Res.* 16:10881-90 (1988), which is hereby incorporated by reference in its entirety) or the Megalign® program of the LASERGENE® bioinformatics computing suite (DNASTAR® Inc., Madison, Wis.). Sequences may also be aligned using algorithms known in the art including, but not limited to, CLUSTAL V algorithm or the BLASTN or BLAST 2 sequence programs.

As used herein, "operatively linked" DNA segments, means one polynucleotide sequence is joined to another so that the polynucleotides are in association for transcriptional and/or translation control and can be expressed in a suitable host cell.

The term "about" typically encompasses a range up to 10% of a stated value.

The term "control" plant or "wild type" plant refer to a plant that does not contain any of the mutations described in the present application.

Lettuce Plants with PPO Gene Mutations

One aspect of the present application is directed to a lettuce plant comprising a mutation in each of at least two different PPO genes, where said mutations reduce the activity of PPO protein compared to a wild type lettuce plant.

Mutations occurring in the PPO genes of the lettuce plant of the present application may be present in any of a lettuce plant's PPO genes. In one embodiment, the lettuce plant comprises a mutation in each of at least two different PPO genes. In certain embodiments, the at least two different PPO genes are selected from the group consisting of PPO-A, PPO-B, PPO-C, PPO-D, PPO-E, PPO-G, PPO-J, PPO-M, PPO-N, PPO-O, PPO-P, PPO-Q, PPO-R, and PPO-S. In some embodiments, the at least two different PPO genes are selected from the group consisting of PPO-A, PPO-B, PPO-C, PPO-D, PPO-E, PPO-G, PPO-O, PPO-P, PPO-R, and PPO-S. Non-limiting examples of gene and protein sequences of PPO genes in lettuce are provided as follows.

```
PPO-A gene sequence (SEQ ID NO: 1):
ACAATATCTG CACGCTCAAA ATAAGACAAT GGCATCTCTT GCACAATCAC CAACCACCAC

CACCACCACC GGTGGACGGT GCTTCTCCTC CTCCTCCACG TACTCTTCTT CCTTCTCTTT

CAAATCATCT CAAGTTCCCA TAGCACGAAT CACGAACCAT CGCCATGCAG TTTCATGCAA

AGGCGCCCTA GATGATGATG ACCATCACCA TGAAAACTCA GGCAAATTTG ATAGGAGAAA

CGTCTTATTA GGTCTCGGAG GTCTTTACGG CGCCGCCGCC ACTTTTGGGT CAAACTCATT

GGCGTATGCA GCTCCGATTA TGGCACCGGA CCTCACAAAA TGTGGTCCGG CTGACTTACC

CCAAGGGGCT GTACCTACAA ACTGTTGCCC TCCATACACC ACAAAGATTC ACGATTTCAA

ACTTCCACCA CCGTCAACCA CCTTCCGAGT CCGTCCGGCA GCTCATTTGG CTAATAAAGA

TTACATAGCC AAGTTCAATA AAGCCATCGA GCTCATGAAA GGTCTCGGAG ATGACGATCC

TCGTAGTTTC AAGCAACAAG CTGCTGTTCA TTGTGCGTAT TGCGATGGGG CATACGATCA

AGTCGGTTTC CCTGATCTCG AGCTTCAAGT CCATGGCTCA TGGTTGTTCT TACCTTTCCA

CCGCTATTAC TTATACTTCT TCGAGAAAAT TTGTGGCAAA TTAATCGATG ATCCAAATTT
```

-continued

```
CGCAATCCCT TTTTGGAACT GGGATGCACC TGATGGCATG AAGATCCCTG ATATTTACAC

GAATAAGAAA TCTCCGTTGT ACGATGCTCT TCGTGATGCG AAGCATCAAC CACCGTCTCT

GATTGATCTT GACTACAATG GTGACGATGA AAATCTTAGC CGATCGAAAC AAACCTCCAC

AAATCTCACA ATTATGTACA GACAAATGGT GTCTAGTTCC AAGACTGCTA GTCTTTTCAT

GGGTAGTCCT TATCGTGCAG GTGATGAGGC TAGCCCTGGC TCTGGCTCGC TCGAGAGCAT

ACCACATGGC CCGGTTCATA TCTGGACCGG AGATAGGAAC CAGCAAAATG GTGAAGACAT

GGGTAACTTT TATTCTGCAG CCAGAGACCC TATTTTCTAT GCACATCATG CGAATATCGA

CAGAATGTGG TCAGTTTGGA AAACTCTAGG AGGAAGAAGG AATGATTTTA CAGATAAAGA

CTGGCTTGAT TCTTCGTTCT TGTTCTACGA TGAGAACGCT GAAATGGTTC GAGTCAAGGT

GAGGGATTGT CTCGACTCCA AGAAGCTTGG GTACGTTTAT CAGGATGTAG AGATACCATG

GCTAAAAGC AAACCCGAAC CACGTCTGAA AAGGGCTTTG AGCAAGATCA AGAAGCTCGC

TGTAGCTCGA GCCGATGAAC ACATACCCTT TGCAAAAGAT GTTTTTCCGG CGAGTCTTGA

TAAGGTGATA AAAGTGCTGG TTCCAAGGCC GAAGAAATCA AGGAGCAAGA AACAGAAAGA

GGATGAAGAA GAAATTTTGG TGATAGAAGG AATTGAACTG AAGAGAGATG AGTTTGCGAA

GTTTGATGTG TTTGTGAACG ATGAAGATGA CGGGATGAGG GCCACGGCTG ATAAGACGGA

GTTCGCCGGA AGTTTTGTTA ATGTCCCTCA TAAGCATAAG CATGGGAAGA ATGTGAAGAC

AAGATTGAGG TTAGGAATAA GTGAGCTTTT GGAGGATTTG GGAGCTGAAG ATGATGACAA

CGTGTTGGTG ACATTGGTGC CGAAAAACAA AGGTGGTGAA GTTTCCATTA AAGGGATTAA

AATCGAGCAT GAGGATTGAT AAAAATAACT TTTCATTTTC TTGAAAAATA AAAAACTATG

ATTTTGAGTT GTTTCGGTAA ATATGTTGTC GCTTGGTTAA TGTATCATCA ATAAAAATAA

ATTTCGAAAT CAAAGTTGGA TTTGAACCCC ACAA
```

PPO-A protein sequence (SEQ ID NO: 2):
```
MASLAQSPTT TTTTGGRCFS SSSTYSSSFS FKSSQVPIAR ITNHRHAVSC KGALDDDDHH

HENSGKFDRR NVLLGLGGLY GAAATFGSNS LAYAAPIMAP DLTKCGPADL PQGAVPTNCC

PPYTTKIHDF KLPPPSTTFR VRPAAHLANK DYIAKFNKAI ELMKALPDDD PRSFKQQAAV

HCAYCDGAYD QVGFPDLELQ VHGSWLFLPF HRYYLYFFEK ICGKLIDDPN FAIPFWNWDA

PDGMKIPDIY TNKKSPLYDA LRDAKHQPPS LIDLDYNGDD ENLSRSKQTS TNLTIMYRQM

VSSSKTASLF MGSPYRAGDE ASPGSGSLES IPHGPVHIWT GDRNQQNGED MGNFYSAARD

PIFYAHHANI DRMWSVWKTL GGRRNDFTDK DWLDSSFLFY DENAEMVRVK VRDCLDSKKL

GYVYQDVEIP WLKSKPEPRL KRALSKIKKL AVARADEHIP FAKDVFPASL DKVIKVLVPR

PKKSRSKKQK EDEEEILVIE GIELKRDEFA KFDVFVNDED DGMRATADKT EFAGSFVNVP

HKHKHGKNVK TRLRLGISEL LEDLGAEDDD NVLVTLVPKN KGGEVSIKGI KEIHED
```

PPO-B gene sequence (SEQ ID NO: 3):
```
TTATATAAAT ATAGATCACT TCACATAATC TCATGCATCG TGCTCAAAAT TATGACATCC

TTTGCATCAT CACCGACCAA AACCCTAACA GGCACGGCCT CCAGGAGTGA AAGGAGGATC

TCTTCCTCAT CCAACTACTC TTCTTCCTTC TCTTTTAAGT CATCTCAAGT TCCCATAGCC

AGAATCTCCA AACATCGCCA TGCAGTTTCA TGCAAAACCC TAGATGACGA TCACCACCAC

CATGCAAACT CCGGCAAACT TGATAGGAGA ACATCCTGT TAGGCCTCGG TGGTCTTTAT

GGTACTGCCG CCACTTTTGG GTCTAATTCA CCAGCCATTG CAGCTCCGAT CATGGCACCC

GACCTCTCAA AATGTGGTCC GGCCGACTTG CCCGAAGGTG CTGTATCCAC AGACTGTTGC

CCTCCATACA CCACAAAGAT TCTCGATTTC AAACTTCCAC CACCGTCAAA CACCTTCCGA

GTCCGTCCGG CAGCTCATTT GGCTAATGAA GATTACATAG GCAAGTTCAA TAAAGCCATC
```

-continued

```
GAGCTCATGA AAGCTCTCCC AGATGACGAT CCTCGTAGCT TTAAGCAGCA AGCAAATGTT
CATTGTGCCT ATTGCGATGG CGCGTATGAC CAAGTCGGTT TTCCAGATCT GGAGCTTCAA
GTACATAACT CATGGCTGTT CTTCCCTTTC CATCGCTATT ACATGTACTT CTTCGAGAAA
ATTTGTGGCA AGTTAATTGA TGACCCAAAT TTCGCAATTC CATTTTGGAA CTGGGATGCA
CCAGATGGGA TGAAAATCCC TGATATTTAC ACAAATAAGA AATCTTCGTT GTATGATCCT
CTTCGCGATG TGGACCATCA ACCACCGTCT TTGATTGATC TTGACTTCAA TGGTGTCGAC
GAAAATCTTA GCCCCTCTGA ACAAACGTCC AAAAATCTCA CAGTTATGTA TAGACAAATG
GTGTCTAGTT CCAAGACTTC TACTCTTTTC ATGGGTAGTC CTTATCGTGC AGGCGATGAT
GCTAGCCCTG GTAGTGGTTC GATCGAGAAC ACACCACATA ACCCAGTTCA TATCTGGGCC
GGTGAGTGGA AGCATAATAA TGGCAAAAAC ATGGGCAAAC TTTATTCTGC AGCCAGGGAC
CCTCTTTTCT ATGCACATCA TGGGAATATT GATAGAATGT GGTCAGTTTG GAAAACACTA
GGTGGAAGAA GGAAGGACTT TACTGATAAA GATTGGCTTG ATTCTTCGTT CTTGTTTTAC
GATGAGAACG CTGAGTTGAA TCGAGTCAAG GTGAGGGATT GTCTCGACAC CAAGAATCTT
GGCTACGTTT ATCAAGATGT AGAGATACCA TGGCTAAAAA GCAAACCTGT TCCACGTCGG
ACAAAGCCCA AGGAGAAGCC CAAAAACAAA ACAACAAGC AAGCTGTGGC TCGAGCCGAC
GAATACATAC CATTTGCAAA AGATGTTTTT CCGGCGAGTC TTAATGAGGT CATCAAAGTG
CTGGTTCCAC GGCCCAAGAT ATCAAGGAGT AAGAAACAGA AGAAGAAGA AGAAGAGATT
TTGGTGATCG AAGGAATTGA AGTGAAGATA GATGAGTTTG TGAAGTTTGA TGTGTTTGTC
AATGATGAAG ATGACGGGAT GAGGGCCACC GCAGATAAGA CGGAGTTTGC CGGAAGTTTT
GTGAATGTCC CTCATACTCA TAAGCATGGG AAGAATTTGA AGACGAGATT GAGGCTAGGG
ATAAGTGAGC TTTTGGAGGA TTTGAATGCT GAAGATGATG AAAATGTGTT GGTGACATTG
GTGCCCAAAA CTAGGGGTAG TGGAATTTCC ATTGCAGAGA TCAAAATCGA GCATGAAGAA
TGATCAAAAT ACGTTCACTT TCTCTAAAAT AAAAATAAAG GAACGTTTAT GATGGAGGAA
TATATTATGT TTTTCGATAT GTATTACCAT ATAAAAATAA TTTTCGCAAT CAAATAAAGG
AACGTTTATG ATGGAGGAAT A
```

PPO-B protein sequence (SEQ ID NO: 4):

```
MTSFASSPTK TLTGTASRSE RRISSSSNYS SSFSFKSSQV PIARISKHRH AVSCKTLDDD
HHHHANSGKL DRRNILLGLG GLYGTAATFG SNSPAIAAPI MAPDLSKCGP ADLPEGAVST
DCCPPYTTKI LDFKLPPPSN TFRVRPAAHL ANEDYIGKFN KAIELMKALP DDDPRSFKQQ
ANVHCAYCDG AYDQVGFPDL ELQVHNSWLF FPFHRYYMYF FEKICGKLID DPNFAIPFWN
WDAPDGMKIP DIYTNKKSSL YDPLRDVDHQ PPSLIDLDFN GVDENLSPSE QTSKNLTVMY
RQMVSSSKTS TLFMGSPYRA GDDASPGSGS IENTPHNPVH IWAGEWKHNN GKNMGKLYSA
ARDPLFYAHH GNIDRMWSVW KTLGGRRKDF TDKDWLDSSF LFYDENAELN RVKVRDCLDT
KNLGYVYQDV EIPWLKSKPV PRRTKPKQKP KNKNNKQAVA RADEYIPFAK DVFPASLNEV
IKVLVPRPKI SRSKKQKEEE EEILVIEGIE VKIDEFVKFD VFVNDEDDGM RATADKTEFA
GSFVNVPHTH KHGKNLKTRL RLGISELLED LNAEDDENVL VTLVPKTRGS GISIAEIKIE
HEE
```

PPO-C gene sequence (SEQ ID NO: 5):

```
CTCTTCACAT ATTTCATGCA CGCTCAAACT ACAAGACTAT GGCATCCTTT TCACCATCAC
AAGCCACCTC TTACACGAGT GGAAGGAGGT TCTCTTCCTC ATCGACCTAC TCTTCTTCCT
TCTCTTTTAA GTCATCTCAA GTTCCCATAG CCAGAATCTC CAAACATCGC CATGCAGTTT
```

-continued

```
CATGCAAAAC CCTAGATGAT GATCACCACC ACCATGCAAA TTCCGGCAAA CTTGATAGGA

GAAACGTCCT TTTAGGCCTT GGAGGTCTTT ATGGTACTGC CGCCAACTTT GGGTCTAATT

CACTGGCCTT TGCAGATCCG ATCATGGGAC CCGACCTCAG TAAATGTGGT CCGGCTGAGT

TACCCCAAGG GGCTATACCT ACAAATTGTT GTCCTCCATT CACCACAAAG ATTATCGATT

TCAAACTTCC ACCACAGTCA AACCCCCTCC GTGTTCGACC AGCTGCACAT TTGGTTGATA

AAGACTACAT AGACAAATTC AGTAAAGCTA TCGAACTCAT GAAAGCTCTC CCAGATGACG

ATCCTCGTAG TTTCAAGCAA CAAGCTAATG TTCACTGTGC CTATTGTGAT GCCGCATATG

TCCAACTCGG TTATCCAGAT GTGGAGCTTC AAGTACATAA CTCATGGCTG TTCTTCCCTT

TCCATCGTTG TTACCTATAC TTCTTTGAGA AAATTTGTGG CAAATTAATT GATGACCCAA

CTTTTGCAAT TCCATTTTGG AACTGGGATG CGCCAGTTGG GATGAAAATC CCTGATATTT

ACACAGATAA GAATTCTTCG TTATACGATA CTCTTCGTGA TGCGAAACAT CAACCACCGA

CTGTGGTTGA TCTTGACTAC AATGGTTTCG ACAACAATCT TAGCCCCTCT GAACAAACGT

CCACAAATCT CACGATTATG TATAGACAAA TGGTGTCTAA TGCCAAGACT GCTAGTCTTT

TCATGGGTAG TCCTTATCGT GCAGGTGATG ACCCTAGCCC TGGTGCTGGC TCGCTCGAGA

GCGTGCCACA TAACCCGGTT CATATCTGGA CCGGGGATGA GAACCAGCCA ATGGTGAAG

ACATGGGTAA CTTTTATTCT GCAGGCAAAG ACCCTATTTT CTTTGCACAT CATGGGAATC

TCGATAGATT GTGGTCAGTT TGGAAAACAC TAGGTGGAAG AAGGAAGGAT TTACTGATA

ATGATTGGCT TGATTCTTCG TTCTTGTTGT ACGATGAGAA CGCTGAGTTG AATCGAGTCA

AGGTGAGGGA TTGTGTCGAC TCCAAGAATA TGAATTATGT TTATCAAGAT GTTGAGTTAC

CATGGCTAGA AAGCAAACCT GTTCCACGAC TGCAAAAGGC TTCCAGAAAC ATCAAGAAGC

ATGCCCATGA ACACATACCC TTTGCAAAAG ATGTTTTTCC GGCGAGTCTT GATAAGGTGA

TCAAAGTGCG GGTTCCAAGG CTTAAGAAAT CAAGGACCAA GAAACAGAAA GAGGAGGAAG

AAGAGATTTT GGTTATTGAA GGGATTGAAG TGAAGAGAGA TGAGTTTGTG AAGTTTGATG

TGTTGGTGAA CGATGATGAT GATGGGACCC AGGCCACAGC AGCTAAAACG GAGTTCGCCG

GAAGTTTTGC GAGTGTCCCT CATATGCATA AGCATGGGAA GAATTGGAAG ACGAAATTGA

GGATAGGGAT AACTGACCTT TTGGAGGATT TGAAGGATGA AGAAGATCAC AATGTGTTGG

TGACATTGGT GCCCAAAACT AGTGGTGGTG ATATTTCCAT TGGAGGGATC AAAATCGAGC

ATGAAGAATG TTAAACAGAC GTTCTCACTT TCTATAAATA AAATAAAAGA AAGTCTATGA

TCTATTAAGA TATTATGTTT CTCTATATGT ATTACCTATT AAAAGTAATT ATCACAATAA

AGTTATATAT GATTCGAACT TGTGAATGTT AATTGCAAGT CATTGAA
```

PPO-C protein sequence (SEQ ID NO: 6):

```
MASFSPSQAT SYTSGRRFSS SSTYSSSFSF KSSQVPIARI SKHRHAVSCK TLDDDHHHHA

NSGKLDRRNV LLGLGGLYGT AANFGSNSLA FADPIMGPDL SKCGPAELPQ GAIPTNCCPP

FTTKIIDFKL PPQSNPLRVR PAAHLVDKDY IDKFSKAIEL MKALPDDDPR SFKQQANVHC

AYCDAAYVQL GYPDVELQVH NSWLFFPFHR CYLYFFEKIC GKLIDDPTFA IPFWNWDAPV

GMKIPDIYTD KNSSLYDTLR DAKHQPPTVV DLDYNGFDNN LSPSEQTSTN LTIMYRQMVS

NAKTASLFMG SPYRAGDDPS PGAGSLESVP HNPVHIWTGD RNQPNGEDMG NFYSAGKDPI

FFAHHGNLDR LWSVWKTLGG RRKDFTDNDW LDSSFLLYDE NAELNRVKVR DCVDSKNMNY

VYQDVELPWL ESKPVPRLQK ASRNIKKHAH EHIPFAKDVF PASLDKVIKV RVPRLKKSRT

KKQKEEEEEI LVIEGIEVKR DEFVKFDVLV NDDDDGTQAT AAKTEFAGSF ASVPHMHKHG

KNWKTKLRIG ITDLLEDLKD EEDHNVLVTL VPKTSGGDIS IGGIKIEHEE C
```

PPO-D gene sequence (SEQ ID NO: 7):
ACCACACCAC CTATAGATGA TGGCTTCCCT CAGCTTGTCC ACTCTTCCCA CCTCCACCCC

CACAAAAAAG CCTTTATTTT CCAAAACCTC CTCCCACGTG AAGCAATCCC ATCGCTTCAA

AGTCTCATGC AACTCCGCCG CTAACAACAA TGAGAAAACA GTCAAAAACT CTGAAACCCC

GAAGCTCATA CTACCCAAAA CACCACTTGA AATGCAGAAT GTTGACCGGA GAAACCTGCT

CCTGGGGCTT GGAGGTCTCT ACGGCGCTGC CAACTTGACA TCCATCCCAT CAGCCTTTGG

CACTCCCATC GCTGCTCCGG ACAATATTTC AGATTGTGTT ACTGCGTCGT CAAACCTCCA

GAACGCCAAT GACGCTGTAA GGGGTTTAGC TTGTTGCCCT CCAGTACTCT CAACAGATAA

ACCAAAAGAT TACGTCTTGC CTACCAACCC AGTCCTTCGT GTTCGACCAG CTGCACAGAG

AGCTACTGAC GAGTACATCG TAAAGTACAA AGCAGCGATT CAAGCCATGA AGAATCTCCC

CGACGAGCAT CCACACAGTT GGAAGCAACA AGCTAAGATC CACTGCGCTT ATTGCAACGG

TGGTTACAAT CAAGAACAGA GTGGTTTCCC GGACATACAA CTCCAGATTC ACAACACATG

GCTCTTCTTT CCTTTCCACC GATGGTACCT CTACTTCTAC GAGAGGATTT TGGGGAAGTT

GATTAATGAT CCAACTTTCG CTTTACCATA CTGGAACTGG GATAACCCTA CCGGAATGGT

GCTCCCTGCC ATGTTCGAAA CCGACGGCAA AAGGAACCCT ATCTTTGACC CTTACAGGAA

TGCCACACAC CTCCCACCAG CTATCTTTGA AGTGGGATAT AATGGGACAG ACAGTGGCGC

CACTTGTATA GACCAGATAA GCGCTAATCT GTCTTTGATG TACAAGCAAA TGATCACCAA

CGCTCCTGAT ACAACAACGT TCTTCGGTGG AGAATTTGTT GCTGGGGATG ACCCTCTTAA

CAAAGAGTTT AACGTTGCTG GTCCATAGA GGCTGGGGTT CACACTGCGG CGCATAGATG

GGTGGGTGAT CCTAGGATGG CCAACAGCGA GGACATGGGG AACTTCTACT CCGCAGGGTA

TGATCCTCTC TTTTACGTCC ACCATGCCAA CGTCGACCGG ATGTGGAAAA TCTGGAAAGA

TTTGGGAATC AAGGGACACA CTGAACCGAC GTCCACCGAC TGGCTAGATG CTTCATACGT

GTTTTATGAT GAGAACGAAG AGCTTGTACG TGTCTATAAC CGAGACAGTG TAAACATGAC

TGCAATGGGA TACGACTATG AAAGGTCCGA ATCCCGTGG CTCCATAGTC GATCGGTTCC

ACATACCAAG GGGGCCAATG TTGCAGCTAA ACTGGTCGGA ATCGTGAAGA AGGTGGAAGA

CGTTACATTC CCGTTGAAGT TAAATGAGAC AGTGAAGGTT CTTGTGAAAA GGCCTACTAA

GAAGAGGAAC AAGAAGAACA AGCAGGAAGC GAATGAGATG TTGTTCTTGA ATAAAATCAA

GTTCGATGGC GAGGAGTTTG TCAAGTTTGA CGTGTTTGTC AATGACGTTG ACGATGGAGT

GGAGACTACC GCAGCTGAGA GTGAGTTTGC TGGTAGTTTC TCACAATTGC CCCATGGCCA

TAAACATGGC ACCAAGATGT CAATGACGAG TGGGGCGGCG TTTGGGCTTA CGGAGCTGTT

GGAGGACATT GAAGCTGAAG ATGATGACTC TATTTTGGTG ACTTTGGTGC CAAGATAGG

GTGTGATGAT GTGACTGTCG GTGAGATTAA GATTAAGTTG GTTCCCATTG TCTGAAGTTC

ATTGATGTAA CATCGTTTTC ATTTGCGTTT GTATGCATGG GTAAAACAGT TTTCTGTGTT

TGGTCATACG AGGATGTTTG TGGTTCTCGT AATCTAATAA TGACCATTTT GTCAAGTTTG

TTGTCATGCT TGATTGTAAC TCCTATGTTT GGATATCAAT AAACATTATC GAGTACTATT

TTAGT

PPO-D protein sequence (SEQ ID NO: 8):
MMASLSLSTL PTSTPTKKPL FSKTSSHVKQ SHRFKVSCNS AANNNEKTVK NSETPKLILP

KTPLEMQNVD RRNLLLGLGG LYGAANLTSI PSAFGTPIAA PDNISDCVTA SSNLQNANDA

VRGLACCPPV LSTDKPKDYV LPTNPVLRVR PAAQRATDEY IVKYKAAIQA MKNLPDEHPH

SWKQQAKIHC AYCNGGYNQE QSGFPDIQLQ IHNTWLFFPF HRWYLYFYER ILGKLINDPT

FALPYWNWDN PTGMVLPAME ETDGKRNPIF DPYRNATHLP PAIFEVGYNG TDSGATCTDQ

-continued

```
ISANLSLMYK QMITNAPDTT TFFGGEFVAG DDPLNKEFNV AGSIEAGVHT AAHRWVGDPR
MANSEDMGNF YSAGYDPLFY VHHANVDRMW KIWKDLGIKG HTEPTSTDWL DASYVFYDEN
EELVRVYNRD SVNMTAMGYD YERSEIPWLH SRSVPHTKGA NVAAKLVGIV KKVEDVTFPL
KLNETVKVLV KRPTKKRNKK NKQEANEMLF LNKIKFDGEE FVKFDVFVND VDDGVETTAA
ESEFAGSFSQ LPHGHKHGTK MSMTSGAAFG LTELLEDIEA EDDDSILVTL VPKIGCDDVT
VGEIKIKLVP TV
```

PPO-E gene sequence (SEQ ID NO: 9):
```
CTTATAGCAC CACCCATAGA TGATGGCTTC TCTCGCCTTG TCTAGTCTTC CCACCTCCAC
CACAACCAAA AAACCCTTAT TTTCCAAAAC ATCCTCGCAT GTTAAGCCAT TCCATCGCTT
CAAAGTTTCA TGCAATGCAC CCGCTGATAA CAATGACAAA ACCGTCAATA ATTCTGATAC
CCCAAAGCTC ATACTACCCA AAACACCACT TGAAACGCAG AACGTAGACA GGAGAAACTT
GCTTCTGGGA CTCGGAGGTC TCTACGGCGC TGCCAACTTG ACGACCATTC CGTCAGCCTT
TGGCATTCCC ATCGCTGCTC CAGACAATAT TTCAGACTGT GTTGCTGCGA CTTCAAACCT
AAGGAACAGC AAAGACGCTA TAAGGGGACT AGCGTGTTGT CCTCCGGTGC TTTCAACAAA
CAAACCAATG GATTACGTCC TTCCTTCAAA CCCTGTGATT CGTGTTCGAC CAGCTGCACA
GAAAGCCACT GCCGATTACA TTGCTAAGTA TCAACAAGCA ATTCAAGCCA TGAAGGATCT
CCCCGAGGAC CACCCACATA GCTGGAAGCA ACAAGGCAAG ATTCACTGTG CTTATTGCAA
CGGTGGTTAC AATCAAGAAC AAAGTGGTTA CCCGAATTTA CAACTTCAGA TTCACAACTC
ATGGCTCTTC TTTCCTTTCC ACCGGTGGTA CCTCTATTTC TACGAGAAGA TATTGGGGAA
GTTGATTAAT GATCCAACTT TCGCTCTACC TTACTGGAAC TGGGATAACC CTACTGGAAT
GGTTATTCCT GCCATGTTCG AACAGAACAG CAAAACTAAC TCTCTGTTTG ACCCTTTAAG
GGATGCGAAA CACCTCCCAC CTTCTATCTT TGATGTTGAA TATGCTGGTG CAGACACTGG
TGCCACTTGT ATAGACCAGA TAGCCATTAA TCTGTCTTCA ATGTACAGAC AGATGGTCAC
CAACTCCACT GATACAAAAC GATTCTTCGG TGGCGAATTT GTAGCTGGAA ATGACCCTCT
TGCGAGCGAG TTCAACGTAG CTGGGACCGT AGAAGCTGGG GTTCACACTG CGGCTCACCG
CTGGGTGGGT AATTCTAGGA TGGCCAACAG CGAAGACATG GGGAACTTCT ACTCTCGCAG
GATATGATCC TCTCTTTTAC GTCCACCATG CGAATGTCGA CAGGATGTGG CAAATCTGGA
AAGATATTGA CAAGAAGACA CACAAGGATC CGACCTCTGG CGACTGGCTA AATGCATCAT
ACGTGTTTTA CGATGAGAAT GAAAATCTTG TACGTGTCTA CAACCGAGAC TGTGTAGACA
TTAATCGGAT GGGATATGAC TACGAAAGGT CAGCAATCCC ATGGATCCGT AGTCGGCCGA
CTGCACATGC GAAGGGGCG AACGTTGCTG CTAAGTCTGC TGGAATCGTG CAGAAGGTGG
AGGATATCGT ATTCCCGCTG AAGTTAAACA AGATAGTGAA GGTTCTAGTG AAGAGGCCAG
CTACAAACAG GACCAAGGAG GAAAAGGAGA AAGCAAATGA GCTGTTGTTC GTGAATGGAA
TCACGTTTGA TGCTGAGCGG TTTCTAAAGA TTGACGTGTT TGTCAACGAC GTCGACGATG
GAATTCAGAC CACCGCTGCT GATAGTGAGT TTGCTGGTAG TTTCGCACAG TTGCCACATA
ACCATGGCGA CAAGATGTTT ATGAGGAGTG GGGCAGCGTT CGGGATCACG GAGCTCTTGG
AAGACATTGA AGCTGAAGGT GATGACTCTG TTGTTGTGAC ATTGGTGCCG AGAACAGGGT
GTGATGAAGT AACTATTGGC GAGATCAAGA TTCAGCTGGT TCCCATTGTT TAAAGTCTAT
TGAAGTAATG CATTTTCAAT TGTCATTAGT ATGCATGGGT ACGTAAATCT GTTCGCTGTC
TGGTTATCGA GGATTTTTGA TGTTCTCGTA ACCAAATAAT AAGGATTGTC ATTCCATGTT
TGGAATCGTG TAACCGCAGG CATGCATATG TTTGATTGTT ATTTTTAGTT GAAGCACTTC
```

-continued

```
TGTTTTAGTA ATCTCTGTTT TCCTGTTTTA CAAAAGGTAA AGAATTCGCT GTATGTGCTT

TGCATAA
```

PPO-E protein sequence (SEQ ID NO: 10):
```
MMASLALSSL PTSTTTKKPL FSKTSSHVKP FHRFKVSCNA PADNNDKTVN NDSTPKLILP

KTPLETQNVD RRNLLLGLGG LYGAANLTTI PSAFGIPIAA PDNISDCVAA TSNLRNSKDA

IRGLACCPPV LSTNKPMDYV LPSNPVIRVR PAAQKATADY IAKYQQAIQA MKDLPEDHPH

SWKQQGKIHC AYCNGGYNQE QSGYPNLQLQ IHNSWLFFPF HRWYLYFYEK ILGKLINDPT

FALPYWNWDN PTGMVIPAMF EQNSKTNSLF DPLRDAKHLP PSIFDVEYAG ADTGATCIDQ

IAINLSSMYR QMVTNSTDTK RFFGGEFVAG NDPLASEFNV AGTVEAGVHT AAHRWVGNSR

MANSEDMGNF YSRRI
```

PPO-G gene sequence (SEQ ID NO: 11):
```
CGATCAACGT TAGCATGCAC ACCACCAAAA GCTCATGGCT TCTCTTCCCA CACCAACAGT

TACAGCTGCC GGAGCCACCA CTAAAACCTA CTCTTCTTCT TTCACCACCA CTTCCCCTGT

CATCTCTTCT TGGCCGTTGT TCTCGAAGAA ATGTGCCCTT AATAAGCCAC TAAAACACAA

AATCTCTTGC AATGCTGGTT CTTCTGAGAA CTCCTTGAAC AACCTTGATC GCCGGAATGT

TCTTCTCGGT CTCGGTGGTC TTGCCGGAGC TGTGAACTTG ACGTCTGTTC CGTCTGTCGG

AGCTGCGCCA ATATCCGCCC CGGATATTTC CAAATGTGGG ACTAACCCTC TTTCAGGGTT

TAGACCTGGG GAGAGCACTC CCACCGGCGG CGACTGTTGC CCGCCTGACT CCCCCCAGAT

CATGGACTTC AAGTTCCCTA AGAATGAGGC GTTCAGGGTG AGACCCGCAG CCCATTTGCT

CAGCCCTAAG TACATTGCTA AATTCAACGA AGCGATCAAA CGCATGAAGG AACTTCCCGA

AACCGATCCT CGAAACTTTC TGCAACAAGC ACACATTCAC TGTGCTTACT GCAATGGCGC

TTACACTCAA TCTTCAAGTG GATTTCCCGA TATTGAAATC CAGATTCATA ACTCATGGCT

GTTCTTCCCC TTCCACCGTT GGTATCTCTA CTTTTACGAG AGAATCCTGG GGAGCTTGAT

CGATGATCCC ACTTTCGCTT TGCCATTCTG GAACTGGGAC ACCCCTGCCG GAATGACAAT

TCCGAAATAC TTTAACGATC CCAAAAACGC AGTTTTTGAT CCCAAAAGAA ACCAAGGTCA

CTTGCAAGGA GTCGTCGATC TGGGTTACAA TGGGAAAGAT TGAGACACTA CTGATATCGA

AAAGGTGAAG AACAATCTCG CGATAATGTA TCGTCAAATG GTGACAAACG CCACCGACCC

CACAGCTTTC TTCGGTGGTG AGTATCGTGC CGGAATCGAA CCCATTAGCG GTGGTGGATC

AGTCGAACAA AGCCCACACA CACCTGTTCA CCGGTGGGTC GGTGACCCAA GAGAACTTAA

CGGTGAAAAC CTCGGTAACT TCTACTCCGC CGGTCGTGAC ACGCTCTTTT ACTGTCACCA

TTCCAACGTC GATCGAATGT GGTCGTTGTG GAAGATGCAG GGAGGCAAAC ACAAGGACAT

CACCGATCCC GATTGGCTCA ACACCTCTTT CGTGTTTTAC GACGAAAACA GAAATCTTGT

TCGAGTGTAT GTTAAGGATT GTTTGTACAC AAACCAGCTA GGGTACGACT ACCAGAGAGT

CGACGTACCA TGGCTAAAAA GCAAGCCAGT CCCACGTGCA CCCAGGTCTG GAGTTGCGAG

GAAATCCATC GGAAAAGTAA AACAGGGGAA GGAAGTTTCC TTCCCGGTGA AACTCGACAA

GACCGTGAAG GTTTTGGTGG CAAGACCGAA GAAATCAAGA AGCAAGAAGG AGAAGGAGGA

CCAAGAGGAG CTTTTGATTG TTCAGGGTAT CACTTATGAT AGCGAGAAGT ACGTGAAGTT

TGATGTGTAT GTGAACGACG AGGACGACGA TGCTAGTGCA CCAGATCAGA CTGAGTTCGC

CGGAAGTTTC GCACAGTTGC CACACAAACA CAAGGGTAAG ACGATGAGCA AGACCAACTT

CCGCGCCGGA CTGACGGAGC TGCTGGAGGA TCTGGAGGCC GACGACGACG ACAATGTTTT

GGTGACGATT GTCCCAAGGT CTGGATCCGA AGACATCACC ATTGATAACA TCAAGATCAT
```

-continued

```
CTACGCTTGA TTTCAAGATT TGACGACTCT CAGTTGGGAT CATTAGTTAA ATATGTTTGA

TTAATGATCT TGCTATTCCC TTAATTATTA TTATTATTAT CAGGGTAGTT CGACCCTTGA

TTAGTGGTGA GGGTTGATGG TTGTCACCGG AATGTTTGGG TTTGAGTCCG AGTTCATGTG

ATTATGGGTC GGATTTAAAA TAAAATCTGA GTCGAGTCTG TGGTCATGTC GTAATTTGGG

GTTTCACTTT TGACCAAATC AATGTTAATT ATAATTTAAA TAAATTATTA TTAGTTCTCC

A
```

PPO-G protein sequence (SEQ ID NO: 12):
```
MASLPTPTVT AAGATTKTYS SSFTTTSPVI SSWPLFSKKC ALNKPLKHKI ACNAGSSENS

LNNLDRRNVL LGLGGLAGAV NLTSVPSVGA APISAPDISK CGTNPLSGFR PGESTPTGGD

CCPPDSPQIM DFKFPKNEAF RVRPAAHLLS PKYIAKFNEA IKRMKELPET DPRNFLQQAH

IHCAYCNGAY TQSSSGFPDI EIQIHNSWLF FPFHRWYLYF YERILGSLID DPTFALPFWN

WDTPAGMTIP KYFNDPKNAV FDPKRNQGHL QGVVDLGYNG KDSDTTDIEK VKNNLAIMYR

QMVTNATDPT AFFGGEYRAG IEPISGGGSV EQSPHTPVHR WVGDPRELNG ENLGNFYSAG

RDTLFYCHHS NVDRMWSLWK MQGGKHKDIT DPDWLNTSFV FYDENKNLVR VYVKDCLYTN

QLGYDYQRVD VPWLKSKPVP RAPRSGVARK SIGKVKQAKE VSFPVKLDKT VKVLVARPKK

SRSKKEKEDQ EELLIVQGIT YDSEKYVKFD VYVNDEDDDA SAPDQTEFAG SFAQLPHKHK

GKTMSKTNFR AGLTELLEDL EADDDDNVLV TIVPRSGSED ITIDNIKIIY A
```

PPO-J gene sequence (SEQ ID NO: 13):
```
GTTTTTGTAT GTTTTCTTTC CAATCTTTTG CAACCTTCAC TTCCATCACC ACCAGAACAC

TACCAAATTC CACCTCGGAT CGCCGCTACA ACAGTTACCC CAAACAAATC CACCACCTTC

AAATCTCATG CAACGTCGCA CCAGATGACA AAGAGAAGTT AGTCGTAGTC CCAGAAACCC

AAAAACTTAT TCTGCCAAAA TCATCTCTCG ACACACTTAA TGTAGATCGG AGGAACATGC

TCCTCGGGCT TGGGGGCCTT ACACCACCG TCAACTTCAC CTCCCCTGCA GCATTTGCTG

CACCTATCAC GACGCCAAAC TTCTCCACAT GCGTGACCTC AAATTTAGGT TTCCAGGACC

CAAATAAGGC CGTCAGAAGC AGAGCATGTT GTCCACCGGC GCCAGCGACG TCAACAGCCC

CCAAAGACTT TGTGTTCCCT AAAGACCAAG TGATCCGGAT TAGACCAGGG GCACATAGAA

CCACCACCGA GTACGTTGCT AAGTACAAAG CAGCAATCCA AGCGATGAGA GATCTCCCAG

ATGAACACCC ACACAGTTTC GTTGCACAAG CAAAAATTCA TTGCGCTTAC TGCAACGGTG

GTTACACTCA AATCGCGAGT GGTTTTCCAG ATAAAGAACT CCAGATTCAC AACTCATGGC

TCTTCTTTCC TTTCCATCGT TGGTACTTGT ATTTCTACGA GAATCCTC GGGAAGTTAA

TCGATGATCC AACTTTCGCT TTACCTTACT GGAACTGGGA CCATCCCAAC GGAATGACGT

TTCCCGCATT TTTGGAGGAC GATTCTGCCT TCGACGCTTA CCGTAATCGA AAGCACTTAC

CACCAGCACT TGTTGACCTC AACTACAGTG GCTCAGATAG ACACGCTACT TGTATTCGAC

AGATAACTAG CAATATGACA TTAATGTATA AGCAAATGAT CAGCAACGCC GGTGACACGA

CAAGCTTCTT TGGTAGCGAA TATCGGGCTG GCAACGACGC GTATAGAAAT GGTGACCCAT

CTGTCGGGTC GATAGAGGCT GGTTGTCACA CTGCGGTGCA TAGATGGATG GGTGACCCAG

GAATGCCGAA CAACGAGGAC ATGGGGAACT TCTACTCTGC GGGGTATGAC CCTGCGTTCT

ACATCCACCA TGCCAATGTC GACCGGATGT GGAAACTATG GAAGGATATG GGCATCAAAG

GACACTCTGA ACCTACACAT CTGGATTGGC GTAACGCATC GTACGTGTTT TATGATGAAA

ACGAACAGCT TGTTCGTGTC TACAACAAAG ATTGCGTCAG TTTGGAAAAG CTAAAATACG

ATTATGAATA CTCCCCACCC CTCTGGAAAA TAAGCCGATC CAGTATACGT CGTACCCTTC

CCGAACCCAT TCCATATAAC ATGAAATCTG CTGAAACGGT TAAACAACTG CCAGACGTGA
```

```
                                        -continued
AGTTCCCCTT GAAGCTAGAC AAGATAACGA AGGTAGTAGT GAAGAGGCCA GCCAAAAGCA

GAAGTCAAGA AGACAAGGAA AAAGCAAATG AGCTGTTGTT GATTAAAGGA ATCAAGTTTA

ATAGCGACAA GTTCATCAAG TTTGATGTGT TTGTGAATGG ACAAGATGAT GTCAGCGAAA

GTTTTGAAGA AGAGAGTGAG TTTGCAGGTA GTTTCGCGCA GTTGCCACAT AACCATGGTG

ACGACATGTT AATGAAGAGT GGCATAAGGT TTGGGTTAAC GGAGCTTTTG GAGGAAATGG

AGGCGGAGGA TGATGAGTTT ATTTTGGTGA CTTTGGTGCC AAAGGTGTGG TTTGAGGAAG

TGACCATTGA CGAAATCAAG GTGGAGTTGG TTCCTATTAT CTGATTCATA ATCTAAAATT

GATGAGCATC GGGTACGTAA TTAACGTAGC GTATACGTAC CAACGCTGTA AATACAAAAA

AGTATTATTA TTCAACTAAA GTACCAAAGA GATACTCAAT TTAGTTGTAG TAACGGAGAA

GG
PPO-J protein sequence (SEQ ID NO: 14):
MFSFQSFATF TSITTRTLPN STSDRRYNSY PKQIHHLQIS CVNAPDDKEK LVVVPETQKL

ILPKSSLDTL NVDRRNMLLG LGGLYTTVNF TSPAAGAAPI TTPNFSTCVT SNLGFQDPNK

AVRSRACCPP APATSTAPKD FVFPKDQVIR IRPAAHRTTT EYVAKYKAAI QAMRDLPDEH

PHSFVAQAKI HCAYCNGGYT QIASGFPDKE LQIHNSWLFF PFHRWYLYFY ERILGKLIDD

PTFALPYWNW DHPNGMTFPA FLEDDSAFDA YRNRKHLPPA LVDLNYSGSD RHATCIRQIT

SNMTLMYKQM ISNAGDTTSF FGSEYRAGND AYRNGDPSVG SIEAGCHTAV HRWMGDPGMP

NNEDMGNFYS AGYDPAFYTH HANVDRMWKL WKDMGIKGHS EPTHLDWRNA SYVFYDENEQ

LVRVYNKDCV SLEKLKYDYE YSPPLWKISR SSIRRTLPEP IPYNMKSAET VKQLPDVKFP

LKLDKITKVV VKRPAKSRSQ EDKEKANELL LIKGIKFNSD KFIKFDVFVN GQDDVSESFE

EESEFAGSFA QLPHNHGDDM LMKSGIRFGL TELLEEMEAE DDEFILVTLV PKVWFEEVTI

DEIKVELVPI I
PPO-M gene sequence (SEQ ID NO: 15):
ATGGCTTCAC TGAGCTTCAC TTTAGCTATG GCCACCACCC CCTCTTCTTC CCCATTCTTT

TCCAAACCAG CGAACCAACG TCAGTTGATA AAGACACATG CTAAGCAAAC CCACCGCTTC

CAAATGTCAT GCAATGTTCC ATCAGACGAC CATGAAAAAC CAATCATCAA TACCCCTCAA

CATCAAAAGC TCATACTACC AAAAACATCA CTCGACATGC AGAACGTAGA CAGAAGGAAT

TGCTCCTGG GGCTTGGTGG GCTCTACAGC GCCGTCAACT TGACGGGTCT CCCATCCGCT

TTTGCCGATC CTATCAGGAC TCCTTCTTTT AATCCAAATT GCAGGGACGC CGGAACGGGC

TTCGATGTCA AAAAAGGCCT TCTTAGAACT ACTGCATGTT GCCCTCCGGA GTCCAAGAAG

GGTCCCGAGA ACAATTCGA ATTCCCTAAA CATGACGAAA TACGCATCAG ATATCCCATA

CACTGTGCCC CGGAAGGATA CATGAATAAA TTTAAGGAGG CGATGAGGCT AATGAGGGCT

CTCCCAGATG ACGACCCTCG CAGTTTCAAG AACCAAGCCA AAATTCATTG CGCCTACTGC

AATGGCAGCT ACACTCAAAT GGCTACAGGT TCCCAACAAG AACTCCTGAT TCACTTCAAC

TGGCTGTTTT TTCCCTTCCA TCGATGGTAC CTTTATTTCT TCGAGAGGAT ACTCGGAGAA

CTGATTGGTG ATCCAACATT CGGGTTACCA TACTGGAGCT GGGACGAGCG TGAGGGAATG

AAAATTCCAC CTACGTTCCG AGAAGGGGGA GAGTCTAACC CTTTATATGA TATCTACCGG

AATAACATTC GCAACTATGA AGCTATTGTC GATCTTGACT TCAATGGTAA AGATCGCGAA

GATACGACTG AGGACTATCA GATAAAAATC AATCAGCATG CTATGTATCG CCAGATGATG

AGAAATGCCT TCGATACAAA AAGCTTCTTT GGTGGTAAGT ATGTCGCTGG TAATACACCC

ATTGATGCCA AAGACTCTTC AGTTGCATCC ATAGAGGCCG GTTGTCATAC CGCGATTCAC
```

-continued

```
AGATGGGTGC GTGACCCTGG AAGTCCGAAT GGTGAAGACA TGGGTAATTT CTACTCTGCC

GGGTATGATC CTTTGTTCTA TGTCCACCAT TCCAATGTCG ACAGGATGTG GGCACTTTGG

AAAGAAATGG GGGAAAGCAA CCGCGACCCC ATACACCCAG ACTGGTTAAA CGCATCATAT

GTGTTTTACG ACGAGAAACA AAATCCTGTT CGTGTCTACA ATAAACAATG CGTGGATATG

GAAAAGCTCA ATACAAATA CCATGGTCCA GAAATCCCCA GCTGGGTCAA TTCTCGGCCG

AAACCAAAGT GCAGCGCTTC GGAAAGATCC CAAATCGATA TCACGTCAGC CACAAAAGAT

GTGAAGAACC GAACCCTCAC CAACGTAGAT ACGTTTGTGT TAGTGAGGCC TGAAACTGCT

AGAACAAGGA CCGTGGATGA ATCAGAAATA GAGGTCTTGA CGTTAACAA CATTAGTTTC

AACGGTAACA AAGCCGTCAA GTTTGACGTG CTTGTTAACG CTTGTAACAT TGACACAAAC

AAGTTCACCC CGGCTGATAG CGAGTATGCG GGTTCTTTTG CAACAGTTCC ACATAACCAT

GACATGAAAA TTAGTACTAC GTTCAGGTTT CCCTTAAGAG AGCTGTTGAA AGATATTGGA

GCTGAGGGAA ATACAGCAAT TCAAGTCACC ATTGTGACGC AAGAGAAAGA AACCGAGAAT

ATCAGCATTG GCGAGATCAA GATCGAGGAT TACTCTTTAG CCGAGATCTC GAAGGCGTCA

CTTCCCACTG GCTCAGGGTG TGCCGGAGCT AATGTCGGCG TCGACGATCT AACAGAATAG
```

PPO-M protein sequence (SEQ ID NO: 16):
```
MASLSFTLAM ATTPSSSPFF SKPANQRQLI KTHAKQTHRF QMSCNVPSDD HEKPIINTPQ

HQKLILPKTS LDMQNVDRRN LLLGLGGLYS AVNLTGLPSA FADPITTPSF NPNCRDAGTG

FDVKKGLLRT TACCPPESKK GPEKQFEFPK HDEIRIRYPI HCAPEGYMNK FKEAMRLMRA

LPDDDPRSFK NQAKIHCAYC NGSYTQMATG SQQELLIHFN WLFFPFHRWY LYFFERILGE

LIGDPTFGLP YWSWDEREGM KIPPTFREGG ESNPLYDIYR NNIRNYEAIV DLDFNGKDRE

DTTDDYQIKI NQHAMYRQMM RNAFDTKSFF GGKYVAGNTP IDAKDSSVAS IEAGCHTAIH

RWVRDPGSPN GEDMGNFYSA GYDPLFYVHH SNVDRMWALW KEMGESNRDP IHPDWLNASY

VFYDEKQNPV RVYNKQCVDM EKLKYKYHGP EIPSWVNSRP KPKCSASERS QIDITSATKD

VKNRTLTNVD TFVLVRPETA RTRTVDESEI EVLTLNNISF NGNKAVKFDV LVNACNIDTN

KFTPADSEYA GSFATVPHNH DMKISTTFRF PLRELLKDIG AEGNTAIQVT IVTQEKETEN

ISIGEIKIED YSLAEISKAS LPTGLQGAGA NVGVDDLTE
```

PPO-N gene sequence (SEQ ID NO: 17):
```
ATGGCTTCTT TTAGCTTTTA CACTCTTCCT ACTTCCACCT CCACCATCAA GAATCCCTTA

TTTTCTAAAA GCTCCTCCCA TGTGAAGCAC TCACATCGCT TCAGGTCTTC ATGCAAAGCC

GCTGCTGATA GCAATGACAA ATATGTCGAA AATCCTGATA CCCCAAAACT CATACTACCA

AAATCACCCT CGCTTGATAC GCAGAACGTT GACAGGAGAA ACTTGCTCCT GGGACTCGGA

GGTCTCTACA GCGCTGCCAA CTTCACCAGC ATTCCGTCAG CCTTTGGCGT TCCCATCGAA

GCACGAGACA TTAATATTTC AAAGTGTGTT ACTGCCACCG TAAGGGGAGT CTCAGCAGAG

GCTATAAGGG GATTAACTTG TTGCCCTCCG GTGTTTGACT CATCGGCCAA ACCAGCGCCG

TACGAATTTC CGGATAACCA GGTAATTCGT ATGCGACCAG CGGCACAGAG AGTCAGTGCA

GACTACAAAA AAGACTTTCG AAAGGCAGTT GAGATAATGA AGGGATATAA CGACAATGAC

CCACACAGTT GGACGCAACA AGCTAAAGTT CATTGTGCGT ACTGCAACGG CGCTTACACT

CAAGTAAAAA GTGGTTTGGA GTTCGAGAAG TATATAATCC AAGTTCACAA CTCATGGCTC

TTCTTTCCAT TCCACCGTTG GTACCTCTAT TTCCTCGAGA AGATAATGGG AAAGGCGCTC

GGGGATGACA CTTTCGCTCT ACCATACTGG AACTGGGACC ACCCTACCGG AATGACGATT

CCTGCCATGT ACGAAGACAA ATTAAAAAAT CCGGATGGCA ACGTTGATAC CCCTGAAAAC

ACTAGATTCA ACTCTCTCTT TGATCCTTTA AGGAATACAT CACACATCGC ACCAGCTCTA
```

```
                                  -continued
ATTGATTTTC AGTATTATCC TCAGAAACAA GAAGTTTATA ATTGTGCAGA CCAGATAGAG

ATTAATCTGT CTATAATGTA CAATCAGATG ATCGCCAACG CGCTTGATAC AAAATCGTTC

TTTGGTGGCG AACTTGTGGC TGGTGAAAAC CCCAATGAAA ACAAAAAGGC TGGGTCCATA

GAGGATGGGG TTCACACGAT TGCCCACCAA TGGGTGGGTA ACAATAGATT GAAGAACGGA

GAAGACATGG GAAACTTCTA CTCCGCAGGC TATGACCCTC TGTTTTACGG CCACCATGCG

AACGTTGACC GGATGTGGAA AATCTGGAAA GGTATGAACA GGAGACACCA TGCACCATCC

TCGACCGACT GGCTAGATGC ATCCTACGTA TTTTATGATG AGAATAGAAA ACTTGTACGT

GTCTACAACC GTGACTGTGT AGACACTAGA ACGATGGGGT ATGATTATGA GAGGTCCGAG

ATCCCATGGA TCCGAAATCG ACCTAATCCA CATCCCAAGG GAGGCAAAGA TAAGGAAAT

GCTCGCAAAC CCGACAAAGC GACGGTGAAG GATCTCAGTT TCCCAGTGAG GTTAAACCAG

ACATTGGAGG TTCGAGTGAT GAGACCTGCG AAAAGGACTA CGGAGGACAA GGAGCGCACC

GAGATCGCGA TTGAGAAGTT GGTCCTTCAA GGCGTACGAT ATGATTGTGA GCGCTTTGTC

AAGTTCGATG TGATAATGAA CGACCCTGAT AATGGAGTCG ATGTCACCCC AGTTGACACT

GAGTTTCTTG GTTATTTCTC ACGGTTGCCC CATGGCATGG TCGCTGAAAA CAGAATGAAA

GAGATTAGTG GGATATCATT TGCCATCAAA GACCGCTTGA AAATCCTAAA AGTTGAAAAT

GATGATTCTA TTGTTGTGAA AATTGTGCCC AGAGCAGGGT GCGAGGATGT AACTATTCAG

AACATCGAGG TTGTGATGGA TCCCGTAGAC AATATTGTAC CTTTAGCGGA GAGCCTGGTT

GTGCAAGATC GGAACAGCGA TGAACTTACT TTGGAGGGCC CGACTGCGCT GGATTCGAAT

TCGGACGACT CTGGCTCGGA GTGATAAATT AAATCGTGTC GTTGTGTATC TTGTATATGT

GTGATCACTT TATAAGTTTA AGTTTGTATT CGAATCGCCA ATGTGGTGAT ATTTGCATTT

TGCCATTATT AATAATAATC CAATGCTCTT GTAGAAGAAA TTGCTCTGAG TGTCTAGAGT

TTTGTCTGAA TGGGTACGTA CGGTTACTTT TTTGTACGTC AATAATGCAC TTATTTGACT

TA
PPO-N protein sequence (SEQ ID NO: 18):
MASFSFYTLP TSTSTIKNPL FSKSSSHVKH SHRFRSSCKA AADSNDKYVE NPDTPKLILP

KSPSLDTQNV DRRNLLLGLG GLYSAANFTS IPSAFGVPIE APDINISKCV TATVRGVSAE

AIRGLTCCPP VFDSSAKPAP YEFPDNQVIR MRPAAQRVSA DYKKDFRKAV EIMKGYNDND

PHSWTQQAKV HCAYCNGAYT QVKSGLEFEK YIIQVHNSWL FFPFHRWYLY FLEKIMGKAL

GDDTFALPYW NWDHPTGMTI PAMYEDKLKN PDGNVDTPEN TRFNSLFDPL RNTSHIAPAL

IDFQYYPQKQ EVYNCADQIE INLSIMYNQM IANALDTKSF FGGELVAGEN PNENKKAGSI

EDGVHTIAHQ WVGNNRLKNG EDMGNFYSAG YDPLFYGHHA NVDRMWKIWK GMNRRHHAPS

STDWLDASYV FYDENRKLVR VYNRDCVDTR TMGYDYERSE IPWIRNRPNP HPKGGKDKGN

ARKPDKATVK DLSFPVRLNQ TLEVRVMRPA KRTTEDKERT EIAIEKLVLQ GVRYDCERFV

KFDVIMNDPD NGVDVTPVDT EFLGYFSRLP HGMVAENRMK EISGISFAIK DRLKILKVEN

DDSIVVKIVP RAGCEDVTIQ NIEVVMDPVD NIVPLAESLV VQDRNSDELT LEGPTALDSN

SDDSGSE
PPO-O gene sequence (SEQ ID NO: 19):
TTGAATTGTT TATTATAAAG ATTTAGCAGA ATGAAAAGC TCTTTGCATT GATCACAAGG

TTCTTTAACT TCTTTTTAGC AAACCCAACA TGGCCGGAAT ACCAACTACA CCTGCCACTT

TTCCGATGAG TCTAGACAAA CCAACGACGG TGATGGTGGC GAGGCCAGCA AAGAAGGAAA

GAGAGAAGGA GGAAGAAGAA GTATTGGTGA TAGAAGGGAT AGAAATCAAT AGAAATGAGT
```

-continued

```
                TTGTGAAGTT TGATGTGTTC ATTAACGATG AGGATGAGGA GACAGCGGCT GGTGGTGGGG

CTGAGAAAGC TGAGTGTGCC GGTAGCTTTG TGAACGTGCC ACATAAGCAC AGGAACGGAC

ATAGTGGTGA TGGTGGGAAG GTGAAAAAGA CACAGTTGAG AATTGGAATA AGTGAGTTAT

TGGAGGATTT GGGTGTCGAA GAAGATGACG AAGATGTGGT GGTGAAATTG GTGCCAAGGT

GTGAAAATGT TCATGTCACA ATTGGTGGTA TTAAGATTGA GAATGAGTGA TTAATTAATT

AATTAATGAG TTCTTATCTT AGTTATTTTC TTTTGTTATC GAGTGGTTTA TGATCCCTTA

TAATAAATGT TATACTTAAT GTTGTCAAGA TC
PPO-O protein sequence (SEQ ID NO: 20):
MAGIPTTPAT FPMSLDKPTT VMVARPAKKE REKEEEEVLV IEGIEINRNE FVKFDVFIND

EDEETAAGGG AEKAECAGSF VNVPHKHRNG HSGDGGKVKK TQLRIGISEL LEDLGVEEDD

EDVVVKLVPR CENVHVTIGG IKIENE
PPO-P gene sequence (SEQ ID NO: 21):
TTTCCCACAA TCCGCGTCTA TATAATGGAG CTCAGCAGAA CGGATTTAAC ACCTACGACA

ATGATGGCTT CATATATCTT TTCCACCGTT CCCTCAGCCA CCGAAGTCAC CACCAACAAC

TTCTCCCATT CCTCGATATT TTCCAAAACT TCCACTCACC GATTCAAATA TACTCATGAA

AACCAAACCC ATCGTTTCAA AGTCTCATGC AACAAAACCT CAGACGACAA ATATGATACA

CTGGAAACAT CACTTGACAA GAAGAATGTA GACCGAAGAA ACTTGCTTCT GGGGCTCGGT

GGAACTCTCT ACGGTGCCGC CAACTTGACC TTCCTCCCGT CCGCCTTCTC GGTGCCCATT

GCTGCTCCCA ATGTTTCAGA CTGTGCTATT GCCAGTAAAG GTATACACAA CATCAAAGAT

GCTGTAAGGG GGGTAGCTTG TTGCCCACCA GTACTGACAC TAAATTCCCC AAAAAATTAC

GTCTTCCCGA AGGAGACCGC AGTTCGTATC CGTCCGGCAG CACAAAGAGC CTCTGACGAT

TACATTGACA AGTATAAAGC AGCAATTAAG GCCATGAGGG ATCTCCCAGA TGACCACCCA

CACAGTTTCA AGCAACAAGC CAAGATCCAT TGCGCTTATT GCAATGGCTC TTACACTCAA

AAAGAGAGTG GCAAGGAATA TGAACACCTC ACACTCCAGA TTCATAACTC GTGGCTCTTC

TTTCCTTTCC ACCGGTGGTA CCTCTATTTC TACGAAAGGA TATTGGGAAA GTTGATTGAC

GACCCAACTT TCGCGATACC ATACTGGAAT TGGGACAACC CCACCGGAAT GATAATCCCT

GACTTGTTTG AAAAACCCAT CCAAGTAAGG GAACGCAAAG AAAACCCCGT CTTTGACGCT

TACAGGGATG CCAGACACCT CCCACCAGCT CTTGTTGATA TCGATTATAA CGGTGAAGAC

CGTGGCGTTT CATGTATAGA CCAAATAACT ATTAATTTGT CTGCAATGTA TAAGCAGATG

ATCAGTAATG CTAGTGACCC AACAAGCTTC TTCGGTGGCA GATACGTCGC TGGGATGGAC

CACGATGACA AAAATAGTCA TGGAAATCCA TCGGTTGGGT CCATAGAAGC TGGTTGTCAC

ACAGCGGTGC ACCGATGGGT GGCTGATCCT CGGATGCCGA ACAATGAAGA CATGGGAAAC

TTCTACTCCG CAGGGTATGA CCCTATCTTT TATGCCCACC ACGCCAATGT TGACCGGATG

TGGAAAATCT GGAAAGAGTT GGGTATCAGG GGACACCGTG AACCAACCGA CAAGGACTGG

CTAGATGCAT CATACGTGTT TTACGATGAG AATGAAGAAC TTGTACGTGT CTATAACCGA

GACTGTGTGG ACTTGAATAA GCTTAACTAC GACTATGAAA CATCCCGTAT CCCGTGGGCC

AGGAATCGGC CGATCCCACG TGCTAAGAAT CCTCAAATGG CAGCGAGGTC AGCCCGAATG

GGGAGGAGTT TTCATGACGT GCAATTTCCG GTGAAGTTAG ACGGGATAGT AAAGGTGCTA

GTGAAGAGAC CTTATGTAAA CAGGACTAAG GAGGAGAAGG AGAAAGCAAA TGAGATATTG

ATGTTGAATG GGATTTGTTT TGATAGCGAG AAGTTTGTAA AGTTTGATGT GTATGTGGAT

GACAAGGACG ATGAACCAGA AACCACTGCG GCTGATAGCG AGTTTGCAGG TAGCTTTGCG

CAGTTGCCTC ACCATCAATC AGGCGAGAAG ATGTTCATGA CAAGTGCCGC GAGATTCGGG
```

-continued

```
TTAACAGAGT TGTTGGAGGA CATTGAAGCT GAAGATGATG AATCTATTAT GGTGACTTTG

GTTCCTAGGA CAGGGTCCGA TGATATCACA ATTTCAGACG TCAAGATTGA GCTGGTCCCC

ATCGTTTGAA CTTCAATAAT GTAATCGCAT TTTCATGTCC ATGTAATATG TTCGTTTTCT

GTGTTGTGTT TAATTAGGAG AATTTGCTGA GTTCTCTTAA CCTCAAAAAA GGGCAATAAG

TTGGTAGCGT TAATGTGTTA TCACTCGTGC ATCTCTATTT CAATTAAAGT TGATCAACTA

ATAAAAAATT TTTTGTTG
```

PPO-P protein sequence (SEQ ID NO: 22):
```
MELSRTDLTP TTMMASYIFS TVPSATEVTT NNFSHSSIFS KTSTHRFKYT HENQTHRFKV

SCNKTSDDKY DTLETSLDKK NVDRRNLLLG LGGTLYGAAN LTFLPSAFSV PIAAPNVSDC

AIASKGIHNI KDAVRGVACC PPVLTLNSPK NYVFPKETAV RIRPAAQRAS DDYIDKYKAA

IKAMRDLPDD HPHSFKQQAK IHCAYCNCSY TQKESGKEYE HLTLQIHNSW LFFPFHRWYL

YFYERILGKL IDDPTFAIPY WNWDNPTGMI IPDLFEKPIQ VRERKENPVF DAYRDARHLP

PALVDIDYNG EDRGVSCIDQ ITINLSAMYK QMISNASDPT SFFGGRYVAG MDHDDKNSHG

NPSVGSIEAG CHTAVHRWVA DPRMPNNEDM GNFYSAGYDP IFYAHHANVD RMWKIWKELG

IRGHREPTDK DWLDASYVFY DENEELVRVY NRDCVDLNKL NYDYETSRIP WARNRPIPRA

KNPQMAARSA RMGRSFHDVQ FPVKLDGIVK VLVKRPYVNR TREEKEKANE ILMLNGICFD

SEKFVKFDVY VDDKDDEPET TAADSEFAGS FAQLPHHQSG EKMFMTSAAR FGLTELLEDI

EAEDDESIMV TLVPRTGSDD ITISEIKIEL VPIV
```

PPO-Q gene sequence (SEQ ID NO: 23):
```
TTTTTTGGGA ATATAAATAG TGAACGCTAG TTCTCGTAAT TCGGGTAGGT GTATGATGGC

TTCTTTTAAC TTGTACACCG TTCCCGCCGC CACTACGGCC ACCACCAACA TAATCAAAAC

TAACTACTAC CAACTTAAGA CTCAAGCAAA GCAAACCCAT CGCTTGAAAG CGTCATGCAA

CGCAATCCCG GATAAAAACA ATGATAAAGC ACTTGAAACT TCACTTCAAA TGATAAACAT

TGACCGGAGA AACATAATAC TCCGCCTCGG TGGTCTCTTT GTGGCCAGCA ACATGACCTC

GGTTCCTTTG GCCTACGCTA ATGCAATTGC AGCTCGGTCT AATCACTCGG TTTGTGCTGC

TTCGCCTTTA GGCATACAGA ATCTTGGAAC CCCCGTAAAG GAACCCATGG AGAATAGGGA

AGATGTAGAC ACGAATAAGC TCGGATACGA ATACAAATGG TCCGAAATCC CATGGGGAAG

GAGTCAACCG ACTGAATATG GCAAGGATTC AAAATTTGTA GATAAGTCTA TAGGAATAGA

GAAGAAGGTG GGGGAGGTGG AATTTCCAGT GAAGTTAAAC AAGACAGTTA AGGTACTCGT

GAAGAGGCCG GCTGTTAATA GGACCAAGGA GGACAAACAG AAAGCGAATG AGATTTTGTT

GGTAAATGGA GTGAGATTCG ATGGTGAGAA GTACGTCAAG TTCGATGTCT TTGTCAACGA

CATAGACAAT GGAACCGAGA CCACCCCGGC TGACAGTGAG TTTGCTGGTA GTTTCGCACA

GCTTCCGCAT GGCAAAACCG ACAGGATGAT GATGATGAGC GGAGTTAGGT TTGGGTTAAC

GGAGCTTTTG GAGGACATAA AAGCTGAAGA TGATGAATAT GTTTTGGTGA AATTGGTGCC

TAGGACTGGG TGTGATGACG TTACAGTTTC CGAGATCAAG ATTGAACTGG AGGGAATAAT

GTCAATGGAC AAGAAGTCAA AGTTTGTTGA ATCTGAATAT GAGAATGTGA TTGATTACTT

GTACATATGT TTATAG
```

PPO-Q protein sequence (SEQ ID NO: 24):
```
MMASFNLYTV PAATTATTNI IKTNYYQLKT QAKQTHRLKA SCNAIPDKNN DKALETSLQM

INIDRRNIIL RLGGLFVASN MTSVPLAYAN AIAARSNHSV CAASPLGIQN LGTPVKEPME

NREDVDTNKL GYEYKWSEIP WGRSQPTEYG KDSKFVDKSI GIEKKVGEVE FPVKLNKTVK

VLVKRPAVNR TKEDKQKANE ILLVNGVRFD GEKYVKFDVF VNDIDNGTET TPADSEFAGS
```

FAQLPHGKTD RMMMMSGVRF GLTELLEDIK AEDDEYVLVK LVPRTGCDDV TVSEIKIELE

GIMSMDKKSK FVESEYENVI DYLYICL

PPO-R gene sequence (SEQ ID NO: 25):
GTTCGAAGAA GTGAGTGGAG TAACCCAAAA CAAATAACA ATGGCTTCTT TCCAACTTGT

TAACCCCTTC GCCAGCACCA CAAGAAAACT GCCAGATTCC ACCTCCAGCC GTCGTCTCAA

GACTCACCCT CAAAAAAACC ACCGCTTCAA AGTCTCATGC AACGTCGCAC AAGATGGCAA

TGAGAAGCTA CTCTTAGTCC CAGATAGCAA AAACCTTATA CTACCTAAAC CATCACTCGA

CACGCTTAAT GTAGATCGGA GGAACTTGCT ACTGGGACTC GGTGGCCTTT ACAGCACCGT

CAACTTCACC TCTCTTCCGG CGGCCATTGC CGCCCCTATC ACCACGCCTG ACATCTCCAC

ATGCATCCCG TCAGAGCAAG GCTTCAACGT GCAGGACTCC GTAAGAAGCA ACCAATGTTG

TCCGCCGATG ATGACCACAA CCCCGAAAGA CTTTGTGTTC CCAAAAGACA AAACAATTCG

GGTTAGACCA GCGGCACATA GAGCCACCCC CGAGTACATA GCAAAGTACA AAGCAGCAAT

CCAAGCGATG AAAGATCTCC CAGATGACCA CCCACATAGT TTCGTTCAAC AAGCTAAAAT

TCATTGCGCT TACTCAACG GTGGTTATAC TCAAGTCGCA AGTGGTTATG CTGATAAGCA

ACTCCAGATT CACAACTCAT GGCTCTTCTT TCCTTTCCAT CGCTGGTACT TGTATTTCTA

CGAGAGAATC CTCGGGAAGT TAATTGATGA TCCCACTTTC GCTTTACCTT ACTGGAACTG

GGACAATCCC GCCGGAATGT CATTTCCAGC TTTTTTTGAA ACCGACGGCA GAGAAAACCC

TGTCTTTGAC GCGTTCCGCA ACGTCAACCA TGTATCACCA GAAACAGTTG TCGATCTCGA

CTACAATGGC TCAGATAGTG GCGCTCCTTG TCTTCAACAG ATAAGCACCA ATCTTGCTGC

AATGTATAAG CAGATGATCA GCAACGCTAC TGACCCGTTA AGTTTCTTTG GTGGCGAGTT

TCGGGCTGGA GATGACCCTT TGGAAATAG TGACCCATCT GTCGGATCAA TAGAGGCTGG

TTGTCACACT GCGATGCACA GATGGACGGG AAATCCGAGA ATGCCAAACA ACGAGGACAT

GGGGAATTTC TACTCTGCGG GGTACGACCC TGCGTTCTAC GTCCACCATG CGAATGTTGA

CCGTATGTGG AAAGTATGGA AGGATTTAGG TATCAAAGGA CACACTGAAC CTACGGACCC

TGATTGGCTT AATGCATCAT ATGTGTTTTA TGATGAAAAC GAAGAGCTTG TACGTGTTTA

CAACAAAGAT TGTGTCCAAA CTGAAAACTT AAAATATGAT TTCGAATTAT CCCCACTCCC

TTGGCTCAAG AACCGACCGG TTGCACATAC CAAACCAGAG ACCACCACGA AACCTGTTGA

AAAGGTTAAA GTGCCGGACG TGAAGTTCCC CATTAAGCTA GACAAGATAC AGAAGGTCCT

TGTGAAGCGG CCAGCGAAAA ACCGAAGCCA ATCAGAAAAA GAAAAAGCGA CTGAGCAGTT

GTTGATCAAA GGAATCAAGT TTAATGTCTC CAAGTTCGTC AAGTTTGATG TGTTTGTTAA

TGACCAAGAT GATGTTCCCA CAAGCTCTGC ATCCGAGAGC GAGTTTGCAG GTAGTTTCGC

ACAGTTGCCT CATCACCATG GTGGCCACAA AAAGTTAATG ACAAGTGCAG CAAGGTTCGG

TTTAACAGAG CTTTTGGAGG ACATCGGAGC CGAGGATGAT GAGTATATTT TGGTGACATT

GGTGCCAAAG GTAGGGGCCG AAGATCTCAC CGTTGATGAA ATCAAAGTGG AGTTGGTTCC

TATTGTTTAA CAACCATGT AATCTTATCT ACACAATAAG GTATATATTT AAATAATTCG

TAGGCCTTGC ATTCCATTGC ATGGTTGCGA CTTTTATGTA CGAATATTAA TAACTTCATT

GTGTCCTTTT TCTACGAGTA AATGGAGTGA ACTCAACATC TTTTGCTTGT TC

PPO-R protein sequence (SEQ ID NO: 26):
MASFQLVNPF ASTTRKLPDS TSSRRLKTHP QKNHRFKVSC NVAQDGNEKL LLVPDSKNLI

LPKPSLDTLN VDRRNLLLGL GGLYSTVNFT SLPAAIAAPI TTPDISTCIP SEQGFNVQDS

VRSNQCCPPM MTTTPKDFVF PKDKTIRVRP AAHRATPEYI AKYKAAIQAM KDLPDDHPHS

```
FVQQAKIHCA YCNGGYTQVA SGYADKQLQI HNSWLFFPFH RWYLYFYERI LGKLIDDPTF

ALPYWNWDNP AGMSFPAFFE TDGKRNPVFD AFRNVNHVSP ETVVDLDYNG SDSGAPCLQQ

ISTNLAAMYK QMISNATDPL SFFGGEFRAG DDPFGNSDPS VGSIEAGCHT AMHRWTGNPR

MPNNEDMGNF YSAGYDPAFY VHHANVDRMW KVWKDLGIKG HTEPTDPDWL NASYVFYDEN

EELVRVYNKD CVQTENLKYD FELSPLPWLK NRPVAHTKPE TTTKPVEKVK VPDVKFPIKL

DKIQKVLVKR PAKNRSQSEK EKATEQLLIK GIKFNVSKFV KFDVFVNDQF DVPTSSASES

EFAGSFAQLP HHHGGHKKLM TSAARFGLTE LLEDIGAEDD EYILVTLVPK VGAEDLTVDE

IKVELVPIV

PPO-S gene sequence (SEQ ID NO: 27):
AAAGGAGTAT GAAGCACACC AAACCAACAT GGCTTCTTTG AGCTTTACTT TAGCCACTCC

CACCACCTCT TCCTCGCCGT TCTTTTCACA ACAACCACC AAACAACGAC GGTTGATGAA

GACACATGGG AAGCAAACCC ATCGCTTCCA AGTCTCATGC AACGTCTCAT CAAATAACCA

TGAAAAACCA CTCCCCAAAA ACCCTCAACC ACAAAAACTT ATACTACCAC AAACATCACT

CGACTTGCAG AACGTCGACA GAAGGAATTT GCTCCTGGGT CTCGGCGGAG TCTACAGCAC

CGCCACCTTG TCCGGTCTGC CACCGGCCTT TGCAGAAGCT ATCAAGGCTC CGTTCAATCA

GCCTGATCGA CCATGCAAAG ATGCCGTATC CGGCTTCGAC ATTAATAAAA AGCTACTTAG

ACCTATTGAC TGTTGCCCTC TGTCCAAAAA TGGCCCGGAG AGTCATTTCA AGTTCCCTGA

TAAATCAAGC AAAACTCGCA TCAGATATCC ACTACACAAA CTTCCAGTCG GTATCTCGA

TAAATATATG GATGCGATTC AGAAAATGAA GGATCTCCCA GATAGCGACC CACGCAGTTT

CAATAACCAA GCTAAAGTTC ATTGCGCTTA CTGCAATGGC AGTTACACTC AAAACGGTCA

AGAACTCCAG ATTCACAACT CCTGGCTCTT CTTTCCCTTC CATCGGTGGT ACCTTTATTT

CTACGAGAGG ATACTGGGAG ATCTCATTGG TGATTCGACA TTCGGGTTAC CCTACTGGAA

CTGGGACAAC CCCGAAGGAA TGACAATTCC ACACTTCTTC GTAGAGAAAC AATGTAACAA

CTATAAGTTC GAAAACGGAG AAAACCCTCT ATATGATAAG TATCGGGACG AAAGTCACCT

TCGGTATGAA TTGGTCGATC TTGACTACTC AGGGAGAAAC CGCGACCTGT GTTACGATCA

GAAAGAAATC AATCTGGCTA CTATGAATAG GCAGATGATG CGCAACGCCT TTGATGCAAC

AAGCTTCTTC GGTGGCAAAT ATGTAGCCGG TGATGAACCG ATTCCCCGAG GAGATAATGT

AGTTGGATCC GTGGAGGCTG GTTGTCATAC GGCTGTTCAC AGATGGGTTG GGAACCCTGA

TCCAAAAGGG AATAAAGAGG ACATGGGCAA CTTCTACTCT GCGGGATATG ATCCTTTGTT

CTACGTCCAC CATTCTAATG TGGACCGAAT GTGGACTCTT TGGAAGCAAA TGGGAGGCAA

AGAACCGACA GATACTGACT GGGAAAACGC GTCATACGTG TTTTACGATG AGAAACAAAA

TCCCGTACGT GTCTACAACA ACAATCGGT GGATTTGAGC AACCTTAAAT ACGAATACCA

CAGCTCAGCC ACTCCATGGA CGGATAGACC ACCAAGATCA CGCTGCAACA GACCCGGTTA

CCCGAAGAGG AACAACACAA AGGACTTCCC AAATCAGAAG ACCCGCCAG AAGCTTTGAC

ATTAACCGAT AGTACTGTGA GGCTTCGAGT AAAGAGGCCT CCTGCTTCTA AAAACAGGAA

CGCTGAGCAA AAGAAAAGTG AAAAAGAGAT CTTGTGCTTG ATTGGAATCA GTTTCGATTG

TACCGAAGCT GCAAAATTTG ACGTGTTTGT GAATGATTGT GACGAAGAAC AGATCACCCC

GTGTGATAGT GAGAATGTGG GTTCTTTCGC GGCTGTTCCA CATGCTAAAG GCATGGCAAT

GGGTTGCAAG TCTGGGATGA GGTTTTCGTT AACAGAGTTG TTGGAGGAAA CAAAAGCTGA

GGGGGATGAG TCTATTCGGG TGACAATTGT GCCGAGGACG ACACCCGGCA AGAAAGTCAA

AGTCACCATT GATGCTATCG AGATCCGGTT GATTCCGGTT CTTGAAAAAT AATCAAACTG
```

-continued

```
ATCAAATGCG TTGATGATGG ATTCCACAAT CACGAAATGA ATAAGTTGGA GTCTGTGTAG

TTCGATAAAC GTACGTTGTG ATTTCTAATG CATGTTTTAT TTGAATAGAA ATTTGTTTTA

AACAAAAGTC TCTTCATTTC

PPO-S protein sequence (SEQ ID NO: 28):
MASLSFTLAT PTTSSSPFFS QTTTKQRRLM KTHGKQTHRF QVSCNVSSNN HEKPLPKNPQ

PQKLILPQTS LDLQNVDRRN LLLGLGGVYS TATLSGLPPA FAEAIKAPFN QPDRPCKDAV

SGFDINKKLL RPIDCCPLSK NGPESHFKFP DKSSKTRIRY PLHKLPVGYL DKYMDAIQKM

KDLPDSDPRS FNNQAKVHCA YCNGSYTQNG QELQIHNSWL FFPFHRWYLY FYERILDGLI

GDSTFGLPYW NWDNPEGMTI PHFFVEKQCN NYKFENGENP LYDKYRDESH LRYELVDLDY

SGRNRDLCYD QKEINLATMN RQMMRNAFDA TSFFGGKYVA DGEPIPRGDN VVGSVEAGCH

TAVHRWVGNP DPKGNKEDMG NFYSAGYDPL FYVHHSNVDR MWTLWKQMGG KEPTDTDWEN

ASYVFYDEKQ NPVRVYNKQS VDLSNLKYEY HSSATPWTDR PPRSRCNRPG YPKRNNTKDF

PNQKDPPEAL TLTDSTVRLR VKRPPASKNR NAEQKKSEKE ILCLIGISFD CTEAAKFDVF

VNDCDEEQIT PCDSENVGSF AAVPHAKGMA MGCKSGMRFS LTELLEETKA EGDESIRVTI

VPRTTPGKKV KVTIDAIEIR LIPVLEK
```

PPO genes may have different sequences among different varieties of lettuce. In some embodiments, a PPO gene has at least 99%, 98%, 97%, 96%, 95%, 90%, 85%, 80%, 75%, or 70% identify to SEQ ID NOs:1, 3, 5, 7, 9, 11, 13, 15, 17, 19, 21, 23, 25, or 27. In some embodiments, the PPO protein sequences have at least 99%, 98%, 97%, 96%, 95%, 90%, 85%, 80%, 75%, or 70% identity to SEQ ID NOs:2, 4, 6, 8, 10, 12, 14, 16, 18, 20, 22, 24, 26, or 28.

In one embodiment of the lettuce plant of the present application, the mutation in a PPO gene occurs in both alleles of the PPO gene. In other words, the mutation is a homozygous mutation.

In another embodiment of the lettuce plant of the present application, the mutation in a PPO gene occurs in only one allele of the PPO gene. In other words, the mutation is a heterozygous mutation.

Lettuce plants may contain only homozygous PPO gene mutations, only heterozygous PPO gene mutations, or a combination of homozygous and heterozygous PPO gene mutations.

In another embodiment of the lettuce plant of the present application, different mutations in a PPO gene occur in each allele of the PPO gene such that both alleles comprise mutations in the PPO gene.

Mutations of PPO genes may be made throughout the gene sequence. Mutations may also be made by targeting nucleotides in the tyrosinase domain of the PPO genes. The mutation may be an insertion, a deletion, a missense mutation, a splice junction mutation, or any combination of mutation thereof. In some embodiments, mutations substantially reduce or inactivate the function of the PPO protein. For example, a mutation may mutate an amino acid required for enzymatic function of the PPO enzyme. The mutation may create a frameshift resulting in a premature stop codon, such that a functional PPO protein is not made. Non-limiting examples of such mutations with respect to the sequences provided herein to exemplify PPO genes include those shown in Table 1.

TABLE 1

Exemplary Mutations in PPO Genes of Lettuce

| PPO gene | Allele | Mutation type | Location | Reference Sequence |
|---|---|---|---|---|
| PPO-A | PPO-A1 | Deletion of 26 or 27 bp | between bp 971-996 or 997 | SEQ ID NO: 1 |
| PPO-A | PPO-A2 | Insertion of T or A | between bp 976-977 | SEQ ID NO: 1 |
| PPO-B | PPO-B1 | Insertion of T or A | between bp 1007-1008 | SEQ ID NO: 3 |
| PPO-B | PPO-B2 | Insertion of TA | between bp 1007-1008 | SEQ ID NO: 3 |
| PPO-B | PPO-B3 | Deletion of T | bp 1008 | SEQ ID NO: 3 |
| PPO-D | PPO-D1 | Insertion of T | between bp 1131-1132 | SEQ ID NO: 7 |
| PPO-E | PPO-E1 | Insertion of T or A | between bp 1112-1113 | SEQ ID NO: 9 |
| PPO-G | PPO-G1 | Deletion of G | bp 987 | SEQ ID NO: 11 |
| PPO-G | PPO-G2 | Insertion of T | between bp 988-989 | SEQ ID NO: 11 |
| PPO-G | PPO-G3 | Deletion of CG | bp 986-987 | SEQ ID NO: 11 |
| PPO-R | PPO-R1 | Insertion of CC | between bp 1024-1025 | SEQ ID NO: 25 |
| PPO-R | PPO-R2 | Insertion of A | between bp 1024-1025 | SEQ ID NO: 25 |
| PPO-S | PPO-S1 | Insertion of T | between bp 1044-1045 | SEQ ID NO: 27 |
| PPO-S | PPO-S2 | Deletion of 3 bp | bp 1045-1047 | SEQ ID NO: 27 |
| PPO-S | PPO-S3 | Deletion of 7 bp | bp 1045-1051 | SEQ ID NO: 27 |

In the lettuce plants of the present application, mutations in the PPO genes reduce the amount and/or activity of PPO protein(s) to confer improved plant traits in the lettuce plant. In one embodiment, mutations in the PPO genes reduce the amount of PPO protein(s) in the mutated lettuce plant compared to a wild type lettuce plant (i.e., a lettuce plant without any mutations in its PPO genes). In another embodiment, mutations in the PPO genes reduce the activity of PPO protein(s) in the mutated lettuce plant compared to a wild type lettuce plant. In yet another embodiment, mutations in the PPO genes reduce the amount and activity of PPO protein in the mutated lettuce plant compared to a wild type lettuce plant.

In the lettuce plants of the present application, mutation in the PPO genes reduce the expression of PPO gene(s) to confer improved plant traits in the lettuce plant. In one embodiment, mutations in the PPO genes reduce the amount of PPO gene expression in the mutated lettuce plant compared to a wild type lettuce plant.

Alteration of PPO genes, PPO gene expression, PPO protein amounts, or PPO enzymatic activity may be determined using standard procedures in the art, for example, as described by Sambrook et al., *Molecular Cloning: A Laboratory Manual*, Second Edition, Cold Spring Harbor, NY, Cold Spring Harbor Press (1989), and Ausubel et al., *Current Protocols in Molecular Biology*, New York, NY, John Wiley & Sons (1989), which are hereby incorporated by reference in their entirety.

Mutation of PPO genes may be determined using any method that identifies nucleotide differences between wild type and mutant sequences. These methods may include, for example and without limitation, PCR, sequencing, denaturing high pressure liquid chromatography (dHPLC), constant denaturant capillary electrophoresis (CDCE), temperature gradient capillary electrophoresis (TGCE), or by fragmentation using enzymatic cleavage, such as used in the high throughput method described by Colbert et al., "High-Throughput Screening for Induced Mutations," *Plant Physiology* 126:480-484 (2001), which is hereby incorporated by reference in its entirety. Multiple plants and multiple PPO gene mutations may be assessed simultaneously by Next Generation Sequencing ("NGS") approaches.

The "expression" of a PPO gene refers to the transcription of a PPO gene. PPO gene expression levels may be measured by any means known in the art such as, without limitation, qRTPCR (quantitative real time PCR), semi-quantitative PCR, RNA-seq, and Northern blot analysis.

In some embodiments, the expression of a PPO gene is 90% or less, 80% or less, 70% or less, 60% or less, 50% or less, 40% or less, 30% or less, 20% or less, 10% or less, or 5% or less of the expression of a PPO gene in wild type lettuce plant. In some embodiments, the expression of a PPO gene is undetectable.

The "amount" of a protein refers to the level of a particular protein, for example PPO-D, which may be measured by any means known in the art such as, without limitation, Western blot analysis, ELISA, other forms of immunological detection, or mass spectrometry.

In some embodiments, the amount of a PPO protein is 90% or less, 80% or less, 70% or less, 60% or less, 50% or less, 40% or less, 30% or less, 20% or less, 10% or less, or 5% or less of the amount of a PPO protein in wild type lettuce plant. In some embodiments, the amount of a PPO protein is undetectable.

PPO protein "activity" or "PPO activity" refers to the enzymatic activity of the PPO protein(s). PPO protein activity may be measured biochemically by methods known in the art including, but not limited to, the detection of products formed by the enzyme in the presence of any number of heterologous substrates, for example, catechol. PPO protein activity may also be measured functionally, for example, by assessing its effects on phenotypic traits of a lettuce plant, such as leaf browning or other traits described herein.

In one embodiment, the lettuce plant of the present application has a reduced activity of PPO that is 99% or less of the activity of PPO in wild type lettuce. In some embodiments, the lettuce plant has a reduced activity of PPO that is 90% or less of the activity of PPO in wild type lettuce. In some embodiments, the lettuce plant has a reduced activity of PPO that is 80% or less of the activity of PPO in wild type lettuce. In some embodiments, the lettuce plant has a reduced activity of PPO that is 70% or less of the activity of PPO in wild type lettuce. In some embodiments, the lettuce plant has a reduced activity of PPO that is 60% or less of the activity of PPO in wild type lettuce. In some embodiments, the lettuce plant has a reduced activity of PPO that is 50% or less of the activity of PPO in wild type lettuce. In some embodiments, the lettuce plant has a reduced activity of PPO that is 40% or less of the activity of PPO in wild type lettuce. In some embodiments, the lettuce plant has a reduced activity of PPO that is 30% or less of the activity of PPO in wild type lettuce. In some embodiments, the lettuce plant has a reduced activity of PPO that is 20% or less of the activity of PPO in wild type lettuce. In some embodiments, the lettuce plant has a reduced activity of PPO that is 10% or less of the activity of PPO in wild type lettuce. In some embodiments, the lettuce plant has a reduced activity of PPO that is 5% or less, 4% or less, 3% or less, 2% or less or 1% or less or 0% of the activity of PPO in wild type lettuce. In some embodiments, the lettuce plant has undetectable PPO activity. The reduction in PPO activity may vary depending on a number of factors including, but not limited to, the source of the PPO, the developmental stage of a plant or plant material, the method of cultivation, the harvesting conditions, the experimental conditions, and combinations and variations thereof.

As discussed supra, lettuce plants of the present application comprise a mutation in each of at least two different PPO genes. For example, a lettuce plant may comprise a mutation in any two of the following PPO genes: PPO-A, PPO-B, PPO-C, PPO-D, PPO-E, PPO-G, PPO-J, PPO-M, PPO-N, PPO-O, PPO-P, PPO-Q, PPO-R, or PPO-S.

In one embodiment, the lettuce plant comprises a mutation in at least its PPO-B gene and one or both of its PPO-S or PPO-G genes. In some embodiments, the lettuce plant comprising a mutation in at least its PPO-B gene and one or both of its PPO-S or PPO-G genes further comprises a mutation in one or both of its PPO-D and PPO-E genes. In further embodiments, the lettuce plant comprising a mutation in at least its PPO-B gene and one or both of its PPO-S or PPO-G genes further comprises a mutation in one or more of PPO-A, PPO-C, PPO-O, and PPO-R. In some embodiments, the lettuce plant comprising a mutation in at least its PPO-B gene and one or both of its PPO-S or PPO-G genes further comprises a mutation in PPO-S. In some embodiments, the lettuce plant comprising a mutation in at least its PPO-B gene and one or both of its PPO-S or PPO-G genes further comprises a mutation in PPO-G.

The present application also encompasses lettuce plants with any of the preceding embodiments and lettuce plants that further comprise a mutation in one or more of PPO-A, PPO-C, PPO-O, PPO-P, or PPO-R.

In some embodiments of the lettuce plant of the present application, the mutation is a frameshift mutation. In some embodiments of the lettuce plant of the present application, the frameshift mutation is a knockout mutation causing a premature stop codon.

In some embodiments, the lettuce plant of the present application comprises a PPO-D knockout, which is caused by a nucleotide insertion in the PPO-D gene sequence between nucleotides 1131 and 1132 of SEQ ID NO:7, or an equivalent thereof. As used herein, the term "or an equivalent thereof" means an equivalent PPO gene in a different lettuce plant, which may or may not be identical in sequence, but is sufficiently similar to identify the sequence as the same PPO gene.

In some embodiments, the lettuce plant of the present application comprises a PPO-E knockout, which is caused by a nucleotide insertion between nucleotides 1112 and 1113 of SEQ ID NO:9, or an equivalent thereof.

In some embodiments, the lettuce plant of the present application comprises a PPO-G knockout, which is caused by a nucleotide insertion between nucleotides 988 and 989 of SEQ ID NO:11, or an equivalent thereof, or a deletion (e.g., of two nucleotides) between nucleotides 986-987 of SEQ ID NO:11, or an equivalent thereof, or a deletion (e.g., of one nucleotide) at nucleotide 987 of SEQ ID NO:11, or an equivalent thereof.

In some embodiments, the lettuce plant of the present application comprises a PPO-S knockout, which is caused by a nucleotide insertion between nucleotides 1044-1045 of SEQ ID NO:27, or an equivalent thereof, or by a deletion (e.g., of three nucleotides) between nucleotides 1045-1047 of SEQ ID NO:27, or an equivalent thereof, or by a deletion (e.g., of 7 nucleotides) between nucleotides 1045-1051 of SEQ ID NO:27, or an equivalent thereof.

In some embodiments, the lettuce plant of the present application comprises a PPO-A knockout, which is caused by an insertion between nucleotides 976 and 977 of SEQ ID NO:1, or an equivalent thereof, or by a deletion of 26 or 27 nucleotides between nucleotides 971-996 or 971-997 of SEQ ID NO:1, or an equivalent thereof.

In some embodiments, the lettuce plant of the present application comprises a PPO-B knockout, which is caused by an insertion of one nucleotide between nucleotides 1007 and 1008 or an insertion of two nucleotides between nucleotides 1007 and 1008 of SEQ ID NO:3, or an equivalent thereof, or by a deletion (e.g., of one nucleotide) of nucleotide 1008 of SEQ ID NO:3, or an equivalent thereof.

In some embodiments, the lettuce plant of the present application comprises a PPO-R knockout, which is caused by an insertion of one or two nucleotides between nucleotides 1024 and 1025 of SEQ ID NO:25, or an equivalent thereof.

Lettuce Plants with Combinations of Mutant PPO Genes

PPO mutant plants of the present application may have combinations of knockouts among their PPO genes. Such combinations may create plants with the best shelf-life (or other trait) performance.

For example, best performing plants in terms of some or all phenotypes such as reduced browning, reduced tip-burn, reduced yellowing of the midvein, increased levels of polyphenolics, increased shelf life, increased vitamins, increased vitamin retention, reduced fermentation, and increased carbohydrate retention may be those plants with knockouts of at least their PPO-B and PPO-S genes. Therefore, the present application is directed to plants comprising knockout mutations of at least the PPO-B and PPO-S genes. Examples of plants with improved non-browning and reduced tip burn traits, with mutations in PPO-B and PPO-S genes are 15.1.17.8, 15.1.7.22, 15.1.9.1, 14.2.24.21, 14.2.24.5, and 14.2.97.6, described below.

In some embodiments, the plants further comprise a knockout mutation of the PPO-D and PPO-E genes (i.e., PPO-B, PPO-D, PPO-E, and PPO-S knockouts). Examples of plants with improved traits with mutations in PPO-B, PPO-D, PPO-E, and PPO-S are 14.2.24.21, 14.2.24.5, 14.2.73.14, 14.2.96.13, 14.2.96.9, 14.2.97.17, and 14.2.97.6, described below. In further embodiments, the plants also comprise a knockout mutation of a PPO-A gene (i.e., PPO-A, PPO-B, PPO-D, PPO-E, and PPO-S knockouts). Examples of such plants are 14-2-73-14, 14-2-96-17, 14.2.96.13, and 14.2.96.9, described below. In further embodiments, the plants also include a knockout mutation of a PPO-G gene (i.e., PPO-A, PPO-B, PPO-D, PPO-E, PPO-G, and PPO-S knockouts). Examples of such plants are 14.2.96.13 and 14.2.96.9, described below. In some embodiments, the plants comprise a knockout mutation of the PPO-G gene, but not the PPO-A gene (i.e., PPO-B, PPO-D, PPO-E, PPO-G, and PPO-S knockouts). Example plants include 14.2.24.21 and 14.2.24.5, described below.

In some embodiments, the plants comprise PPO-B and PPO-S gene knockouts and further comprise a knockout mutation of the PPO-R gene (i.e., PPO-B, PPO-R, and PPO-S knockout). Examples include 15-1-7-22 and 15-1-9-1, described below. In some embodiments, the PPO-B, PPO-R, and PPO-S gene knockouts further comprise a homozygous knockout of the PPO-G gene (i.e., PPO-B, PPO-G, PPO-R, and PPO-S knockouts). An example plant is 15-1-9-1, described below.

In some embodiments, a lettuce plant of the present application comprises knockouts of the PPO-B, PPO-G, and PPO-R genes (i.e., PPO-B, PPO-G, and PPO-R knockouts). An example plant is 15.1.9.11, described below.

In some embodiments, a lettuce plant of the present application comprises both homozygous and heterozygous knockouts of PPO genes. In some embodiments, the plant comprises a modification of at least a heterozygous mutation of its PPO-E gene and at least a heterozygous mutation of its PPO-D or PPO-G genes; where when the mutation of both PPO-E and PPO-D or PPO-G are heterozygous mutations, there is a homozygous mutation of both PPO-O and PPO-R. In some embodiments, the PPO-E mutation is a homozygous mutation. In some embodiments, the PPO-D mutation is a homozygous mutation. In some embodiments, both the PPO-D and PPO-E mutations are homozygous mutation and the plant further comprises a heterozygous or homozygous mutation of the PPO-S gene. In some embodiments, each of the mutations of PPO-D, PPO-E, and PPO-S gene are homozygous mutations. In some of these, the plants further comprise at least a heterozygous mutation of the PPO-G gene.

The mutations may also be homozygous mutations of PPO-D and PPO-E genes where the plant further comprises at least a heterozygous or homozygous mutation of its PPO-G gene. The mutations may also be homozygous mutations of PPO-E and PPO-S genes and the plant further comprises at least a heterozygous mutation of the PPO-G gene.

In the foregoing described plants, the plants may further comprise at least a heterozygous mutation of at least one PPO gene of PPO-A, PPO-B, PPO-O, PPO-R, or PPO-P. As such, in some embodiments the plant comprises:
 (a) homozygous mutations of PPO-A, PPO-D, PPO-E, and PPO-S; and a heterozygous mutation of PPO-B;

(b) homozygous mutations of PPO-B, PPO-D, PPO-E, PPO-G, and PPO-S;
(c) homozygous mutations of PPO-B, PPO-D, PPO-E, PPO-G, and PPO-S; and a heterozygous mutation of PPO-A;
(d) homozygous mutations of PPO-A, PPO-B, and PPO-S; and heterozygous mutations of PPO-G and PPO-E;
(e) homozygous mutations of PPO-O and PPO-R; and heterozygous mutations of PPO-B, PPO-G, PPO-E, PPO-S, PPO-P, and PPO-D;
(f) homozygous mutations of PPO-D, PPO-E, PPO-O, and PPO-S; and heterozygous mutations of PPO-B and PPO-R;
(g) homozygous mutations of PPO-G, PPO-O, and PPO-R; and heterozygous mutations of PPO-E, PPO-S, PPO-P, and PPO-D; or
(h) homozygous mutations of PPO-B, PPO-D, PPO-E, PPO-O, PPO-R, and PPO-S; and a heterozygous mutation of PPO-G.

In some embodiments, the mutation is a knockout of the gene.

Phenotypic, Organoleptic, and Nutritional Aspects of PPO Mutant Lines

The PPO mutations described herein confer multiple beneficial phenotypes on the lettuce plant at harvest and during multiple days after harvest. These phenotypes include, without limitation, reduced browning, reduced tipburn, reduced yellowing of the midvein, increased levels of polyphenolics, increased shelf life, increased vitamins, increased vitamin retention, reduced fermentation, and increased carbohydrate retention.

For example, the present application is directed to a lettuce plant that exhibits reduced-browning. As used herein, "reduced-browning" (or similar terminology) means that when lettuce leaves are harvested, cut, sliced, or processed in a manner where cell wall destruction takes place, browning will be detectably less than in a control (wild type) lettuce variety. Any reduction in browning (such as a reduction in browning visible to the naked eye relative to a control) may be advantageous.

In one embodiment, the rate of browning of lettuce leaves produced from a PPO mutant plant is reduced relative to leaves a control plant. In another embodiment, the total quantity or degree of browning of lettuce leaves produced from a PPO mutant plant is reduced relative to leaves from a control plant.

Any detectable level of reduced browning that is detectable to the naked eye may constitute a reduction in browning. Beyond this, reduced browning may be detected by a device, such as a chromameter, even if not visible to the human eye. Browning may be determined by known methods including, but not limited to, spectroscopy (e.g., light absorption, laser-induced fluorescence spectroscopy, time-delayed integration spectroscopy, large aperture spectrometer); colorimetry (e.g., tri stimulus, "spekol" spectrocolorimeter); and visual inspection/scoring.

The PPO mutant plant may be considered reduced-browning if the PPO mutant sample visual score is at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, at least 50%, at least 60%, at least 70%, at least 80% or at least 90% less than the control.

The skilled person would appreciate that browning may vary depending on a number of factors including, but not limited to, the manner and ambient conditions in which plant material is bruised. For example, lettuce leaves stored at 4° C. may show different browning characteristics from lettuce leaves stored at 24° C., as detected by the eye or by an instrument, such as a chromameter, or like devices.

The present application is also directed to a lettuce plant that exhibits reduced tip burn. As used herein, "tip burn" means a browning of the edges or tips of lettuce leaves that is a physiological response to a lack of calcium in growing tissues.

In some embodiments, the lettuce plant of the present application exhibits less tip burn as compared to a wild type variety under the same conditions. In some embodiments, the lettuce of the present application exhibits no tip burn at harvest. In some embodiments, the lettuce plant exhibits at least 10% less, at least 20% less, at least 30% less, at least 40% less, at least 50% less, at least 60% less, at least 70% less, at least 80% less, or at least 90% less tip burn at harvest compared to a control plant.

In some embodiments, the lettuce plant of the present application exhibits less yellowing of the midvein compared to a wild type variety under the same conditions as assessed by midvein scoring. In other embodiments, the lettuce plant exhibits less than 5% yellowing through day 7 post-harvest as assessed by midvein scoring. In other embodiments, the lettuce plant exhibits less than 5% yellowing through day 14 post-harvest as assessed by midvein scoring. In still other embodiments, the lettuce plant exhibits less than 20% yellowing through day 22 post-harvest as assessed by midvein scoring.

In some embodiments, the lettuce plant of the present application exhibits longer shelf life compared to a wild type variety under the same conditions. Shelf life can be assessed by a number of factors by organoleptic scoring, for example and without limitation, on a qualitative basis across several categories, including: off odor, typical aroma, moisture, texture, leaf color, decay/mold, cut edge discoloration, and taste. A total score combining values from each category provides an overall assessment of a plant. In some embodiments, shelf life is scored after processing the leaf plant by cutting the leaves into pieces. In some embodiments, shelf life is scored after processing the leaf plant by cutting the leaves into pieces and packaging the cut leaves. In some embodiments, the shelf life is scored after storage under optimal conditions of light and temperature. In some embodiments, the shelf life is scored after storage under suboptimal conditions of light and temperature.

In some embodiments, the shelf life of the lettuce plant of the present application exhibits more than 1 day, more than 2 days, more than 3 days, more than 4 days, more than 5 days, more than 6 days, more than 7 days, more than 8 days, more than 9 days, more than 10 days, more than 11 days, more than 12 days, more than 13 days, more than 14 days, more than 15 days, more than 16 days, more than 17 days, more than 18 days, more than 19 days, or more than 21 days of commercially-suitable shelf life compared to a wild type variety under the same conditions.

In some embodiments, the shelf life of the lettuce plant of the present application exhibits reduced failure rate at days after harvest compared to a wild type variety under the same conditions as assessed by organoleptic scoring. As used herein, the "failure rate" means the percentage of replicates at a particular time point of a shelf life study that, assessed by organoleptic scoring, is unsuitable for marketability. In some embodiments, the shelf life of the lettuce plant of the present application exhibits a reduced failure rate of 13 days after harvest as assessed by organoleptic scoring. In some embodiments, the lettuce plant exhibits 0% failure rate 13 days post-harvest as assessed by organoleptic scoring. In some embodiments, the lettuce plant exhibits less than 5% failure rate 13 days post-harvest as assessed by organoleptic scoring. In some embodiments, the lettuce plant exhibits less than 10% failure rate 13 days post-harvest as assessed by organoleptic scoring. In some embodiments, the shelf life of the lettuce plant of the present application exhibits reduced failure rate of 21 days after harvest as assessed by organoleptic scoring. In some embodiments, the lettuce plant exhibits 0% failure rate 21 days post-harvest as assessed by organoleptic scoring. In some embodiments, the lettuce plant exhibits less than 5%, less than 10%, less than 20%, less than 30%, less than 40%, or less than 50% failure rate 21 days post-harvest as assessed by organoleptic scoring.

A recognized problem that is associated with harvested vegetables or harvested vegetable parts is that the levels of plant phytochemicals, such as plant secondary metabolites, start to decrease almost immediately post-harvest. For example, as harvested vegetables are processed for freezing and/or canning or are simply placed in refrigerators, they lose much of their nutritional content in terms of the levels of phytochemicals found therein. Such phytochemicals include vitamins, e.g., vitamins A, C, E, K, and/or folate, carotenoids such as beta-carotene, lycopene, the xanthophyll carotenoids such as lutein and zeaxanthin, phenolics comprising the flavonoids such as the flavonols (e.g., quercetin, rutin, caffeic acids), sugars, and other food products such as anthocyanins, among many others.

The lettuce plants of the present application also exhibit higher levels of polyphenolics in comparison to a wild type variety. In one embodiment, the level of polyphenolics is 5%, 10%, 15%, 20% or more than 20% higher than a wild type variety. The lettuce plants of the present application also retain higher levels of polyphenolics after harvest in comparison to a wild type variety. In one embodiment, the level of polyphenolics is 5%, 10%, 15%, 20%, or greater than 20% higher than a wild type variety at 7, 14, or 21 days after harvest.

The lettuce plants of the present application also exhibit higher levels of vitamin A or beta-carotene in comparison to a wild type variety. In one embodiment, the level of vitamin A is higher than a wild type variety. In some embodiments, the level of vitamin A is at least 5%, 10%, 15%, 20%, 25%, 30%, 35%, 40%, 45%, 50%, 60%, 70%, 80%, 90%, 100%, or more than 100% higher than the level of vitamin A in a wild type variety. The lettuce plants of the present application also retain higher levels of beta carotene at 21 days after harvest in comparison to a wild type variety under the same conditions. In one embodiment, the level of beta carotene is at least 5%, 10%, 15%, 20%, 25%, 30%, 35%, 40%, 45%, 50%, 60%, 70%, 80%, 90%, 100%, or more than 100% higher than the level of beta carotene in a wild type variety at 21 days after harvest in comparison to a wild type variety under the same conditions.

The lettuce plants of the present application also exhibit higher levels of vitamin C in comparison to a wild type variety. In one embodiment, the level of vitamin C is higher than a wild type variety. In some embodiments, the level of vitamin C is at least 5%, 10%, 15%, 20%, 25%, 30%, 35%, 40%, 45%, 50%, 60%, 70%, 80%, 90%, 100%, or more than 100% higher than the level of vitamin C in a wild type variety. The lettuce plants of the present application also retain higher levels of vitamin C at 21 days after harvest in comparison to a wild type variety under the same conditions. In one embodiment, the level of vitamin C is at least 10-fold, 15-fold, 20-fold, 25-fold, 30-fold or 35-fold higher than the level of vitamin C in a wild type variety at 21 days after harvest in comparison to a wild type variety under the same conditions.

The lettuce plants of the present application also exhibit higher levels of vitamin K in comparison to a wild type variety. In one embodiment, the level of vitamin K is higher than a wild type variety. In some embodiments, the level of vitamin K is at least 5%, 10%, 15%, 20%, 25%, 30%, 35%, 40%, 45%, 50%, 60%, 70%, 80%, 90%, 100%, or more than 100% higher than the level of vitamin K in a wild type variety.

In another embodiment, the lettuce plants of the present application also exhibit reduced fermentation levels over time after harvest in comparison to a wild type variety under the same conditions. In some embodiments, the lettuce plants of the present application produce less $CO_2$ over time after harvest in comparison to a wild type variety under the same conditions. In some embodiments, the level of $CO_2$ produced is at least 5%, 10%, 15%, or 20% less than the level of level of $CO_2$ produced by a wild type variety at 6, 10, 14, 17, or 21 days after harvest.

In some embodiments, the lettuce plants of the present application also retain higher carbohydrate levels over time after harvest in comparison to a wild type variety under the same conditions. In some embodiments, the carbohydrate levels are at least 10%, 20%, 30%, 40%, 50%, 60%, 70%, 80%, 90%, 100%, or more than 100% higher than the level of carbohydrates of a wild type variety at 30 days after harvest.

Constructs for Mutating PPO Genes

Vectors may be used to modify PPO genes in lettuce plants of the present application. Such vectors comprise at least one polynucleotide encoding a gRNA that targets a PPO gene of interest operably linked to a promoter that is active in plants. In some embodiments, the vector comprises a plurality of sequences encoding gRNAs targeting one or more PPO genes of interest. In some embodiments, the gRNA encoding sequences are arranged in a polycistronic arrangement.

In some embodiments, the gRNAs target at least one of the PPO-A, PPO-B, PPO-D, PPO-E, PPO-G, PPO-O, PPO-P, PPO-R, PPO-C, PPO-J, PPO-M, PPO-N, PPO-Q, and PPO-S genes in a plant. In some embodiments, the gRNAs target at least two of the PPO-A, PPO-B, PPO-D, PPO-E, PPO-G, PPO-O, PPO-P, PPO-R, PPO-C, PPO-J, PPO-M, PPO-N, PPO-Q, and PPO-S genes in a plant.

To achieve combinations of PPO gene mutations disclosed herein, one of skill in the art may design gRNAs to target the combinations of PPO genes desired. For example, a vector may comprise sequences encoding gRNAs that target PPO-B and PPO-S genes. In other embodiments, the vector comprises sequences encoding gRNAs that target PPO-B, PPO-R, and PPO-S genes. In other embodiments, the vector comprises sequences encoding gRNAs that target PPO-B, PPO-G, PPO-R, and PPO-S genes. In other embodiments, the vector comprises sequences encoding gRNAs that target PPO-B, PPO-D, PPO-E, and PPO-S genes. In still other embodiments, the vector comprises sequences encoding gRNAs that target PPO-B, PPO-G, and PPO-R genes. In other embodiments, the vector comprises sequences encoding gRNAs that target PPO-B, PPO-D, PPO-E, PPO-G, and PPO-S genes. In further embodiments, the vector comprises sequences encoding gRNAs that target PPO-A, PPO-B, PPO-D, PPO-E, and PPO-S genes. In still other embodiments, the vector comprises sequences encoding gRNAs that target PPO-A, PPO-B, PPO-D, PPO-E, PPO-G, and PPO-S genes.

In some embodiments, a gRNA may target multiple PPO genes simultaneously. In some embodiments, a gRNA may target PPO-A, PPO-B and/or PPO-C. In some embodiments, a gRNA may target PPO-D, PPO-E, PPO-N and/or PPO-P.

gRNAs targeting PPO genes for knockout may be predicted using a number of available programs to design gRNA sequences based on the nucleic acid sequences of the PPO genes. Without limiting thereto, the PPO genes targeted in the present application have the nucleic acid sequences of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, and SEQ ID NO:27.

Without limitation, gRNA sequences of the present application include SEQ ID NOs:35-40 and SEQ ID NOs:119-124 (Tables 2 and 6).

Vectors may comprise a polynucleotide encoding a gene editing nuclease operably linked to a promoter that is operable in plants. The nuclease may be any nuclease that acts with gRNAs to make double stranded cuts in target sites in the chromosome. Examples of gene editing nucleases that may be used include, but are not limited to, Cas9, MAD7, Cpf1, and chimeric synthetic nucleases such as SynNuc1 (SEQ ID NO:30). SynNuc1 may be encoded by the polynucleotide sequence of SEQ ID NO:29. Non-limiting examples of gene and protein sequences of synthetic nucleases are provided as follows:

```
SynNuc1 gene sequence (SEQ ID NO: 29):
ATGGGTTTGG ACTCTACTGC GCCTAAGAAA AAGAGAAAAG TCGGGATTCA CGGCGTGCCA

GCGGCCATGA CTCAGTTCGA GGGTTTCACT AACCTGTACC AAGTGTCCAA GACCCTGAGG

TTCGAGCTGA TCCCGCAAGG AAAGACCCTG AAGCACATCC AGGAACAGGG CTTCATCGAA

GAGGATAAGG CCCGCAACGA CCACTACAAG GAACTGAAGC CCATTATTGA TCGGATCTAC

AAGACCTACG CCGACCAGTG CTTGCAGCTG GTGCAGCTGG ACTGGGAAAA TCTGTCCGCC

GCGATTGATT CCTACCGGAA GGAGAAAACC GAAGAGACTC GCAACGCTCT CATTGAGGAA

CAGGCCACCT ACCGGAACGC CATTCACGAC TACTTTATTG CCGCACTGA CAACCTCACC

GATGCAATCA ACAAGCGCCA CGCCGAGATC TACAAGGGCC TGTTCAAGGC GGAACTGTTT

AACGGGAAGG TCCTGAAGCA ACTGGGAACT GTGACCACCA CCGAGCATGA GAACGCCCTG

CTCCGCTCCT TCGACAAGTT CACCACCTAC TTCTCGGGAT TCTACGAGAA TCGCAAAAAC

GTGTTCAGCG CGGAAGATAT CTCAACCGCC ATCCCCCACC GGATTGTGCA GGACAACTTC

CCTAAGTTCA AGGAAAACTG CCATATCTTC ACGCGCCTGA TCACTGCTGT GCCGAGTCTG

AGAGAGCACT TCGAGAACGT GAAGAAGGCT ATCGGCATCT TCGTGTCCAC CTCGATTGAG

GAAGTGTTCT CCTTCCCGTT CTACAATCAG CTCCTGACTC AAACCCAGAT TGACCTGTAC

AACCAGCTTC TGGGGGGGAT TTCCCGGGAA GCGGGAACTG AGAAGATCAA GGGACTCAAC

GAAGTGCTGA ACCTGGCAAT CCAGAAGAAC GACGAAACCG CGCACATCAT CGCAAGCCTC

CCTCACCGCT TCATTCCTCT GTTCAAGCAA ATTCTTTCCG ACCGCAACAC CCTGTCGTTC

ATCCTGGAAG AATTCAAGAG CGACGAAGAA GTCATTCAGA GCTTCTGCAA GTACAAGACT

CTGCTGAGGA ACGAAAACGT GCTGGAAACC GCCGAGGCCC TGTTCAACGA ACTGAACTCA

ATCGACCTGA CGCACATTTT CATTTCCCAT AAGAAGCTGG AAACTATCTC CTCCGCCCTC

TGTGACCACT GGGACACCCT GAGAAATGCG TTGTATGAGC GCCGGATCTC CGAGTTGACT

GGGAAGATTA CTAAGTCCGC GAAGGAAAAA GTGCAGCGCT CCCTGAAACA CGAAGATATC

AACCTTCAGG AGATCATCTC AGCCGCCGGA AAGGAACTGT CAGAGGCCTT CAAGCAAAAG

ACTTCAGAGA TCCTGTCGCA CGCCCACGCC GCTTTGGACC AGCCCCTGCC CACCACCCTG

AAGAAGCAGG AAGAAAAGGA AATCCTGAAG TCTCAGCTCG ACTCACTGCT GGGCTGTAC

CATCTCCTCG ATTGGTTCGC CGTCGACGAG TCCAACGAAG TCGACCCGGA ATTCTCGGCC

CGGCTGACCG GTATCAAGCT TGAGATGGAG CCAAGCCTCT CCTTTTACAA CAAGGCCCGG

AACTACGCCA CCAAAAAGCC TTACTCAGTG GAAAAGTTCA AGCTTAACTT TCAAATGCCG

ACCCTGGCCA GCGGCTGGGA CGTGAACAAG GAGAAGAACA ACGGCGCCAT CCTGTTTGTG

AAGAACGGAC TGTATTACCT TGGAATTATG CCCAAACAGA AGGGTCGCTA CAAGGCACTG

TCCTTCGAGC CGACCGAAAA GACTTCGGAA GGTTTTGACA AGATGTACTA CGATTACTTC
```

-continued

```
CCGGACGCGG CTAAGATGAT CCCCAAGTGC AGCACTCAGC TGAAGGCCGT GACCGCACAC

TTTCAAACCC ATACCACCCC GATTCTTCTG AGCAACAACT TTATCGAGCC ACTGGAGATT

ACCAAGGAAA TCTACGACCT GAACAACCCC GAAAAGGAAC CTAAAAAGTT TCAGACCGCC

TACGCCAAGA AAACTGGCGA CCAGAAGGGA TACAGAAAG CCCTCTGCAA GTGGATTGAC

TTCACCCGGG ATTTCCTGTC CAAGTACACT AAGACCACTT CCATTGACCT CTCGTCGCTG

CGGCCGTCCT CGCAATACAA GGACCTGGGG GAGTACTACG CCGAGCTCAA CCCGCTGCTC

TACCACATAA GCTTCCAGCG GATTGCCGAG AAAGAAATCA TGGACGCCGT CGAAACCGGA

AAGCTGTACC TCTTCCAAAT CTATAACAAG GACTTCGCGA AGGGTCACCA TGGAAAGCCA

AACCTCCACA CCCTCTATTG GACCGGACTC TTCTCGCCGG AAAACCTGGC CAAGACATCC

ATCAAGTTGA ATGGGCAGGC CGAACTCTTC TACCGCCCCA AGTCTCGGAT GAAGCGAATG

GCCCACCGGC TGGGAGAAAA GATGCTCAAC AAGAAGCTAA AGGACCAAAA GACCCCAATC

CCTGACACCC TGTACCAGGA ACTGTACGAT TACGTGAACC ACAGGCTTAG CCACGACTTA

TCCGACGAAG CCCGGGCGCT GCTGCCGAAC GTCATCACCA AGGAAGTGTC GCACGAGATC

ATCAAGGACC GCCGGTTTAC CTCCGACAAA TTCTTCTTCC ACGTGCCCAT TACCCTGAAC

TACCAGGCCG CCAACTCACC CGGATTCATC AACGACCGGA TCCTGCAGTA TATCGCGAAG

GAGAAGGATC TTCACGTGAT CGGAATTGAC CGGGGGGAGA GGAACCTGAT CTACGTGTCC

GTGATTGACA CTTGTGGGAA CATCGTAGAG CAGAAGTCCT TCAACATCGT GAACGGCTAC

GACTACCAGA TCAAGCTCAA GCAACAGGAG GGCGCACGGC AGATCGCAAG AAAGGAATGG

AAGGAAATCG GAAAAATCAA GGAAATCAAA GAGGGATACC TGAGCCTCGT CATCCACGAG

ATCAGCAAGA TGGTCATTAA GTACAATGCG ATCATCGCCA TGGAGGACTT GTCCTACGGA

TTCAAGAAAG GACGGTTCAA AGTGGAGAGA CAAGTGTATC AGAAGTTCGA GACTATGCTC

ATCAACAAGC TGAACTACCT GGTGTTCAAG GATATCAGCA TTACGGAAAA CGGCGGACTC

CTCAAGGGAT ACCAGCTGAC TTACATTCCC GATAAGCTGA AGAATGTCGG TCATCAGTGC

GGCTGTATTT TCTACGTGCC GGCAGCCTAC ACCTCCAAGA TCGACCCTAC TACCGGTTTC

GTGAACATTT TTAAGTTCAA AGATCTCACC GTGGACGCAA AGCGCGAATT CATTAAGAAG

TTCGACTCAA TCCGCTACGA CAGCGAGAAG AACCTGTTCT GCTTCACTTT CGACTACAAC

AACTTCATTA CCCAAAACAC CGTCATGTCC AAGTCCAGCT GGAGCGTGTA CACCTATGGA

GTGCGGATCA AGCGGCGGTT TGTGAACGGC CGGTTCTCGA ATGAGTCCGA CACAATTGAT

ATCACCAAAG ATATGGAAAA GACACTGGAG ATGACTGATA TCAACTGGAG GGATGGCCAC

GATTTGAGAC AGGACATTAT TGACTACGAG ATAGTCCAGC ATATCTTTGA GATTTTCAGA

CTGACCGTGC AGATGCGCAA TTCCCTGTCG GAACTGGAAG ATCGGGACTA CGATAGACTG

ATTAGCCCCG TGCTGAACGA AAACAACATC TTCTACGATT CCGCCAAAGC TGGAGATGCG

CTGCCAAAAG ACGCTGACGC TAACGGCGCC TACTGCATCG CGCTGAAGGG CCTCTACGAA

ATCAAGCAAA TCACCGAGAA CTGGAAGGAG GACGGAAAGT TCTCCCGCGA CAAGCTGAAG

ATCTCAAACA AGGACTGGTT TGACTTCATC CAGAACAAGC GGTACCTGAA GCGCCCTGCT

GCTACCAAAA AGGCCGGCCA GGCCAAGAAG AAAAAGGGCT CGTACCCCTA CGATGTGCCG

GATTAGGCCT ACCCTTACGA TGTCCCCGAC TACGCTTACC CGTACGACGT GCCTGACTAC

GCCTAA

SynNuc1 protein sequence (SEQ ID NO: 30):
MGLDSTAPKK KRKVGIHGVP AAMTQFEGFT NLYQVSKTLR FELIPQGKTL KHIQEQGFIE

EDKARNDHYK ELKPIIDRIY KTYADQCLQL VQLDWENLSA AIDSYRKEKT EETRNALIEE
```

```
QATYRNAIHD YFIGRTDNLT DAINKRHAEI YKGLFKAELF NGKVLKQLGT VTTTEHENAL

LRSFDKFTTY FSGFYENRKN VFSAEDISTA IPHRIVQDNF PKFKENCHIF TRLITAVPSL

REHFENVKKA IGIFVSTSIE EVFSFPFYNQ LLTQTQIDLY NQLLGGISRE AGTEKIKGLN

EVLNLAIQKN DETAHIIASL PHRFIPLFKQ ILSDRNTLSF ILEEFKSDEE VIQSFCKYKT

LLRNENVLET AEALFNELNS IDLTHIFISH KKLETISSAL CDHWDTLRNA LYERRISELT

GKITKSAKEK VQRSLKHEDI NLQEIISAAG KELSEAFKQK TSEILSHAHA ALDQPLPTTL

KKQEEKEILK SQLDSLLGLY HLLDWFAVDE SNEVDPEFSA RLTGIKLEME PSLSFYNKAR

NYATKKPYSV EKFKLNFQMP TLASGWDVNK EKNNGAILFV KNGLYYLGIM PKQKGRYKAL

SFEPTEKTSE GFDKMYYDYF PDAAKMIPKC STQLKAVTAH FQTHTTPILL SNNFIEPLEI

TKEIYDLNNP EKEPKKFQTA YAKKTGDQKG YREALCKWID FTRDFLSKYT KTTSIDLSSL

RPSSQYKDLG EYYAELNPLL YHISFQRIAE KEIMDAVETG KLYLFQIYNK DFAKGHHGKP

NLHTLYWTGL FSPENLAKTS IKLNGQAELF YRPKSRMKRM AHRLGEKMLN KKLKDQKTPI

PDTLYQELYD YVNHRLSHDL SDEARALLPN VITKEVSHEI IKDRRFTSDK FFFHVPITLN

YQAANSPGFI NDRILQYIAK EKDLHVIGID RGERNLIYVS VIDTCGNIVE QKSFNIVNGY

DYQIKLKQQE GARQIARKEW KEIGKIKEIK EGYLSLVIHE ISKMVIKYNA IIAMEDLSYG

FKKGRFKVER QVYQKFETML INKLNYLVFK DISITENGGL LKGYQLTYIP DKLKNVGHQC

GCIFYVPAAY TSKIDPTTGF VNIFKFKDLT VDAKREFIKK FDSIRYDSEK NLFCFTFDYN

NFITQNTVMS KSSWSVYTYG VRIKRRFVNG RFSNESDTID ITKDMEKTLE MTDINWRDGH

DLRQDIIDYE IVQHIFEIFR LTVQMRNSLS ELEDRDYDRL ISPVLNENNI FYDSAKAGDA

LPKDADANGA YCIALKGLYE IKQITENWKE DGKFSRDKLK ISNKDWFDFI QNKRYLKRPA

ATKKAGQAKK KKGSYPYDVP DYAYPYDVPD YAYPYDVPDY A
```

Useful promoters for driving expression of the polynucleotide encoding gRNAs encoding PPO genes of interest are promoters operable in plants including, but not limited, to an *Arabidopsis thaliana* U6 promoter, a 35S promoter, and a CsVMV promoter. The promoter that drives expression of the gRNA(s) may be the same or different than the promoter that drives expression of the gene editing nuclease. Exemplary promoter sequences are given in SEQ ID NOs:31-34.

```
tU6 promoter (SEQ ID NO: 31):
AAAAGCTTCG TTGAACAACG GAAACTCGAC TTGCCTTCCG CACAATACAT CATTTCTTCT

TAGCTTTTTT TCTTCTTCTT CGTTCATACA GTTTTTTTTT GTTTATCAGC TTACATTTTC

TTGAACCGTA GCTTTCGTTT TCTTCTTTTT AACTTTCCAT TCGGAGTTTT TGTATCTTGT

TTCATAGTTT GTCCCAGGAT TAGAATGATT AGGCATCGAA CCTTCAAGAA TTTGATTGAA

TAAAACATCT TCATTCTTAA GATATGAAGA TAATCTTCAA AAGGCCCCTG GGAATCTGAA

AGAAGAGAAG CAGGCCCATT TATATGGGAA AGAACAATAG TATTTCTTAT ATAGGCCCAT

TTAAGTTGAA ACAATCTTC AAAAGTCCCA CATCGCTTAG ATAAGAAAAC GAAGCTGAGT

TTATATACAG CTAGAGTCGA AGTAGTGATT

CaMV 35S promoter (SEQ ID NO:32):
GGTCCGATGT GAGACTTTTC AACAAAGGGT AATATCCGGA AACCTCCTCG GATTCCATTG

CCCAGCTATC TGTCACTTTA TTGTGAAGAT AGTGGAAAAG GAAGGTGGCT CCTACAAATG

CCATCATTGC GATAAAGGAA AGGCCATCGT TGAAGATGCC TCTGCCGACA GTGGTCCCAA

AGATGGACCC CCACCCACGA GGAGCATCGT GGAAAAAGAA GACGTTCCAA CCACGTCTTC

AAAGCAAGTG GATTGATGTG ATGGTCCGAT GTGAGACTTT TCAACAAAGG GTAATATCCG

GAAACCTCCT CGGATTCCAT TGCCCAGCTA TCTGTCACTT TATTGTGAAG ATAGTGGAAA

AGGAAGGTGG CTCCTACAAA TGCCATCATT GCGATAAAGG AAAGGCCATC GTTGAAGATG
```

-continued

```
CCTCTGCCGA CAGTGGTCCC AAAGATGGAC CCCCACCCAC GAGGAGCATC GTGGAAAAAG

AAGACGTTCC AACCACGTCT TCAAAGCAAG TGGATTGATG TGATATCTCC ACTGACGTAA

GGGATGACGC ACAATCCCAC TATCCTTCGC AAGACCCTTC CTCTATATAA GGAAGTTCAT

TTCATTTGGA GAGGACACGC GACAAGCTGA CTCTAGCAGA TCCTCCAGA

CsVMV promoter (SEQ ID NO: 33):
CAGAAGGTAA TTATCCAAGA TGTAGCATCA AGAATCCAAT GTTTACGGGA AAAACTATGG

AAGTATTATG TGAACTCAGC AAGAAGCAGA TCAATATGCG GCACATATTC AACCTATGTT

CAAAAATGAA GAATGTACAG ATACAAGATC CTATACTGCC AGAATACGAA GAAGAATACA

TAGAAATTGA AAAAGAAGAA CCAGGCGAAG AAAAGAATCT TGAAGACGTA AGCACTGACG

ACAACAATGA AAAGAAGAAG ATAAGGTCGG TGATTGTGAA AGAGACATAG AGGACACATG

TAAGGTGGAA AATGTAAGGG CGGAAAGTAA CCTTATCACA AAGGAATCTT ATCCCCCACT

ACTTATCCTT TTATATTTTT CCGTGTCATT TTTGCCCTTG AGTTTTCCTA TATAAGGAAC

CAAGTTCGGC ATTTGTGAAA ACAAGAAAAA ATTTGGTGTA AGCTATTTTC TTTGAAGTAC

TGAGGATACA ACTTCAGAGA AATTTGTAAG TTTG

AtUBQ 10 promoter (SEQ ID NO: 34):
GAACTTATTC AAAGAATGTT TTGTGTATCA TTCTTGTTAC ATTGTTATTA ATGAAAAAAT

ATTATTGGTC ATTGGACTGA ACACGAGTGT TAAATATGGA CCAGGCCCCA AATAAGATCC

ATTGATATAT GAATTAAATA ACAAGAATAA ATCGAGTCAC CAAACCACTT GCCTTTTTTA

ACGAGACTTG TTCACCAACT TGATACAAAA GTCATTATCC TATGCAAATC AATAATCATA

CAAAAATATC CAATAACACT AAAAAATTAA AAGAAATGGA TAATTTCACA ATATGTTATA

CGATAAAGAA GTTACTTTTC CAAGAAATTC ACTGATTTTA TAAGCCCACT TGCATTAGAT

AAATGGCAAA AAAAACAAA AAGGAAAAGA AATAAAGCAC GAAGAATTCT AGAAAATACG

AAATACGCTT CAATGCAGTG GGACCCACGG TTCAATTATT GCCAATTTTC AGCTCCACCG

TATATTTAAA AAATAAAACG ATAATGCTAA AAAAATATAA ATCGTAACGA TCGTTAAATC

TCAACGGCTG GATCTTATGA CGACCGTTAG AAATTGTGGT TGTCGACGAG TCAGTAATAA

ACGGCGTCAA AGTGGTTGCA GCCGGCACAC ACGAGTCGTG TTTATCAACT CAAAGCACAA

ATACTTTTCC TCAACCTAAA AATAAGGCAA TTAGCCAAAA ACAACTTTGC GTGTAAACAA

CGCTCAATAC ACGTGTCATT TTATTATTAG CTATTGCTTC ACCGCCTTAG CTTTCTCGTG

ACCTAGTCGT CCTCGTCTTT TCTTCTTCTT CTTCTATAAA ACAATACCCA AAGAGCTCTT

CTTCTTCACA ATTCAGATTT CAATTTCTCA AAATCTTAAA AACTTTCTCT CAATTCTCTC

TACCGTGATC AAGGTAAATT TCTGTGTTCC TTATTCTCTC AAAATCTTCG ATTTTGTTTT

CGTTCGATCC CAATTTCGTA TATGTTCTTT GGTTTAGATT CTGTTAATCT TAGATCGAAG

ACGATTTTCT GGGTTTGATC GTTAGATATC ATCTTAATTC TCGATTAGGG TTTCATAGAT

ATCATCCGAT TTGTTCAAAT AATTTGAGTT TTGTCGAATA ATTACTCTTC GATTTGTGAT

TTCTATCTAG ATCGGTGTT AGTTTCTAGT TTGTGCGATC GAATTTGTCG ATTAATCTGA

GTTTTTCTGA TTAACAG
```

Methods of Modifying PPO Genes in Plants

Another aspect of the present application is directed to a method of reducing the PPO activity of a lettuce plant. This method involves introducing a mutation into each of at least two different PPO genes of a lettuce plant, where said mutations reduce the amount and/or activity of PPO protein compared to a wild type lettuce plant.

Mutating or otherwise modifying PPO genes in a plant such as lettuce may be done by any method known in the art such that the combinations of PPO gene mutations disclosed herein are achieved. PPO genes of the present application include PPO-A, PPO-B, PPO-C, PPO-D, PPO-E, PPO-G, PPO-J, PPO-M, PPO-N, PPO-O, PPO-P, PPO-Q, PPO-R, and PPO-S. Any method known in the art to make lettuce with any of the following PPO gene mutations is embraced by the present application: mutations in at least two different PPO genes; PPO-B and PPO-S mutations; PPO-B and PPO-R mutations; PPO-B, PPO-R, and PPO-S mutations; PPO-B, PPO-G, PPO-R, and PPO-S mutations; PPO-B, PPO-G, and PPO-R mutations; PPO-B, PPO-D, PPO-E, PPO-G, and PPO-S mutations; PPO-A, PPO-B, PPO-D, PPO-E, and PPO-S mutations; and PPO-A, PPO-B, PPO-D, PPO-E, PPO-G, and PPO-S mutations. Any combination of PPO gene mutation that imparts improved plant traits, including those described herein, may be made according to this aspect of the present application.

Examples of how mutations may be made include, but are not limited to, homologous recombination, insertional mutagenesis to mutate a gene by inserting a sequence into the coding sequence of the gene, the use of gene editing nucleases (e.g., TALENs, zinc finger nucleases, meganucleases, and CRISPR/Cas9 type editing), serine recombinases, chemical mutagenesis, radiation, and recombinagenic oligonucleotides.

Gene editing is a type of genetic engineering in which DNA is inserted, replaced, or removed from a genome using artificially engineered nucleases, or "molecular scissors." The nucleases create specific double-stranded breaks ("DSBs") at desired locations in the genome, and harness the cell's endogenous mechanisms to repair the induced break by natural processes of homologous recombination ("HR") and nonhomologous end-joining ("NHEJ"). There are currently four main families of engineered nucleases being used: Zinc finger nucleases ("ZFNs"), Transcription Activator-Like Effector Nucleases ("TALENs"), the CRISPR/Cas system, and engineered meganuclease with a re-engineered homing endonucleases. Any method of genome engineering may be used in the embodiments of the present application.

ZFNs are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms. ZFNs consist of an engineered zinc finger DNA-binding domain fused to the cleavage domain of the FokI restriction endonuclease. ZFNs can be used to induce double-stranded breaks (DSBs) in specific DNA sequences and thereby promote site-specific homologous recombination with an exogenous template. The exogenous template contains the sequence that is to be introduced into the genome.

TALEN is a sequence-specific endonuclease that includes a transcription activator-like effector ("TALE") and a FokI endonuclease. The transcription activator-like effector is a DNA binding protein that has a highly conserved central region with tandem repeat units of 34 amino acids. The base preference for each repeat unit is determined by two amino acid residues called the repeat-variable di-residue, which recognizes one specific nucleotide in the target DNA. Arrays of DNA-binding repeat units can be customized for targeting specific DNA sequences. As with ZFNs, dimerization of two TALENs on targeted specific sequences in a genome results in FokI-dependent introduction of double stranded breaks, stimulating homology directed repair ("HDR") and Non-homologous end joining (NHEJ) repair mechanisms.

Meganucleases with re-engineered homing nucleases can also be used to effect genome modification in lettuce in the methods described herein. Meganucleases are endodeoxyribonucleases characterized by a large recognition site (double-stranded DNA sequences of 12 to 40 base pairs). This site generally occurs only once in any given genome. For example, the 18-base pair sequence recognized by the I-SceI meganuclease would on average require a genome twenty times the size of the human genome to be found once by chance. Meganucleases are considered to be the most specific naturally occurring restriction enzymes. Among meganucleases, the LAGLIDADG family of homing endonucleases has become a valuable tool for the study of genomes and genome engineering over the past fifteen years. By modifying their recognition sequence through protein engineering, the targeted sequence can be changed.

CRISPR/Cas type RNA-guided endonucleases provide an efficient system for inducing genetic modifications in genomes of many organisms and can be used in the methods described herein to introduce one or more genetic modifications in a lettuce plant genome that result in suppression or altered activity of a native lettuce PPO gene. In some embodiments the endonuclease is SynNuc1, but can also be an endonuclease from one of many related CRISPR systems that have been described. Non-limiting examples of gene editing nucleases include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, Mad7, SynNuc1, homologs thereof, or modified versions, and endonuclease inactive versions thereof. CRISPR/Cas systems can be a type I, a type II, or a type III system.

Use of such systems for gene editing has been widely described. For example, the use of CRISPR guide RNA in conjunction with CRISPR-Cas9 technology to target RNA is described in Wiedenheft et al., "RNA-Guided Genetic Silencing Systems in Bacteria and Archaea," Nature 482: 331-338 (2012); Zhang et al., "Multiplex Genome Engineering Using CRISPR/Cas Systems," Science 339:819-23 (2013); and Gaj et al., "ZFN, TALEN, and CRISPR/Cas-based Methods for Genome Engineering," Cell 31:397-405 (2013), which are hereby incorporated by reference in their entirety. Other nucleases that may be used in gene editing include, but are not limited to, Cpf1, MAD7, and synthetic nucleases such as SynNuc1 (SEQ ID NO:30). In some embodiments, the nuclease is SynNuc1.

There are two distinct components to a CRISPR/Cas system, a guide RNA and an endonuclease, such as Cas9. The guide RNA is a combination of the endogenous bacterial CRISPR RNA ("crRNA") and trans-activating crRNA ("tracrRNA") into a single chimeric guide RNA ("gRNA") transcript. The gRNA combines the targeting specificity of the crRNA with the scaffolding properties of the tracrRNA into a single transcript. When the gRNA and Cas9 are expressed in the cell, the genomic target sequence can be modified or permanently disrupted. The gRNA/Cas9 complex is recruited to the target sequence by the base-pairing between the gRNA sequence which has a region of complementarity to the target sequence in the genomic DNA. For successful binding of Cas9, the genomic target sequence must also contain the correct Protospacer Adjacent Motif ("PAM") sequence immediately following the target sequence. The binding of the gRNA/Cas9 complex localizes the Cas9 to the genomic target sequence so that the wild type Cas9 can cut both strands of DNA causing a DSB. Cas9 generates DSBs through the combined activity of two nuclease domains, RuvC and HNH. Cas9 will cut 3-4 nucleotides upstream of the PAM sequence. A DSB can be repaired through one of two general repair pathways: (1) NHEJ DNA repair pathway or (2) the HDR pathway. The NHEJ repair pathway often results in insertions/deletions (InDels) at the DSB site that can lead to frameshifts and/or premature stop codons, effectively disrupting the open reading frame (ORF) of the targeted gene. The HDR pathway requires the presence of a repair template, which is used to fix the DSB. HDR faithfully copies the sequence of the repair template to the cut target sequence. Specific nucleotide changes can be introduced into a targeted gene by the use of HDR with a repair template. CRISPR specificity can be controlled by level of homology and binding strength of the specific gRNA for a given gene target, or by modification of the Cas endonuclease itself. For example, a D10A mutant of the RuvC domain, retains only the HNH domain and generates a DNA nick rather than a DSB.

When the guide RNA and the gene editing endonuclease are expressed in the cell, the genomic target sequence can be modified or permanently disrupted. The guide RNA/gene editing endonuclease complex is recruited to the target sequence by the base-pairing between the guide RNA sequence and the complementary sequence of the target sequence in the genomic DNA. In some embodiments, CRISPR gene editing is used to generate a lettuce PPO gene mutation by causing nucleotide insertions or deletions (indels) at the DSB site. In some embodiments, a point mutation, insertions, deletions, or any combination thereof, can be generated in a PPO gene in the lettuce genome. In yet other embodiments, multiple PPO gene targets can be modified using CRISPR gene editing in a single experiment using single or multiple guide RNAs having specificity for the different gene targets. In some embodiments, two PPO gene targets are mutated. In other embodiments, more than two PPO genes are mutated. Thus, a wide range of genetic modifications in the lettuce genome using the described methods and CRISPR gene editing can be attained.

Although insertion of recombinant DNA into the plant genome may be used to generate genome modifications using CRISPR gene editing, such genome modifications can be achieved without inserting recombinant DNA into the lettuce genome. In some embodiments, a ribonucleotide particle or ribonucleoprotein ("RNP") is preassembled and delivered to a target lettuce explant. Furthermore, where recombinant DNA is inserted into the lettuce plant genome to effect genome modification, plants having edited genomes, but lacking recombinant DNA, may be obtained by segregation using standard breeding techniques such as crossing and backcrossing. Alternatively, transient expression of gene editing components, including guide RNA and a native or modified endonuclease through recombinant DNA in lettuce cells can also result in genome modification, since gene editing components are no longer required once the desired modification is generated. In such embodiments, mutations are effected in the plant cell genome as a result of transient expression of gene editing constructs, and such mutations are inherited in future generations without the need to segregate away transgenes used to express the gene editing components required for genome modification.

In other embodiments, genetic modification results in reduced gene expression of PPO genes. Reduction of gene expression can be achieved by a variety of techniques including antisense gene suppression, co-suppression, ribozymes, microRNA or genome editing. In some embodiments, recombinant DNA antisense molecules may include sequences that correspond to one or more PPO genes or sequences that effect control over the gene expression or over a splicing event. Thus, the antisense sequence may correspond to a gene coding region, 5'-untranslated region (UTR), the 3'-UTR, intron or any combination of these. In other embodiments, catalytic polynucleotides referred to as ribozymes or deoxyribozymes may be expressed and targeted to a specific mRNA of interest, such one or more PPO genes. The expressed catalytic nucleic acid contains an antisense sequence for specific recognition of a target nucleic acid, and a nucleic acid cleaving enzymatic activity. The ribozyme hybridizes to and cleaves the target nucleic acid molecule resulting in suppression of gene activity. Alternatively, RNA interference (RNAi) may be used specifically inhibiting the production of one or more PPO genes. PPO genes can be silenced by small interfering RNA (siRNA) molecules that cause endonucleatic cleavage of the target mRNA molecules or by microRNA (miRNA) molecules that suppress translation of the mRNA molecule. The design and production of suitable dsRNA molecules for PPO genes may be down-regulated by co-suppression. The mechanism of co-suppression is thought to involve post-transcriptional gene silencing (PTGS) and may be similar to antisense suppression. It involves introducing an extra copy of a gene or a fragment thereof into a plant in the sense orientation with respect to a promoter for its expression.

In one embodiment, the present application relates to a lettuce plant with reduced expression of at least two PPO genes and/or reduced amount/or activity of the PPO proteins, where reduced expression of the at least PPO gene and/or reduced activity of the at least two PPO proteins is achieved by genomic editing. In one embodiment, the present application relates to a lettuce plant with at least two genome edited PPO genes, where the lettuce plant exhibits characteristics selected from the group consisting of reduced tip burn, reduced browning, reduced yellowing of the midvein, increased polyphenolics, increased vitamins, increased vitamin retention, lower levels of $CO_2$ production, and higher levels of carbohydrates as compared to a wild type plant. In one embodiment, the method of introducing a human-induced mutation into the at least two PPO genes is carried out by gene editing.

In other embodiments, a polynucleotide structure for modification of a lettuce plant genome comprises one or more RNPs. In such embodiments, polynucleotide structures are employed outside of a plant cell to produce the guide RNA and endonuclease components, which are then preassembled and delivered to a target plant tissue. In such embodiments, multiple guide RNAs targeting multiple lettuce PPO genes can be designed and assembled with a single type of RNA guided endonuclease, for example SynNuc1. A lettuce plant part having regenerable cells is targeted for delivery of RNP structures.

Chemical and/or radiation mutagenesis can be used to develop the mutations of the present application. These mutagens can create point mutations, deletions, insertions, transversions, and/or transitions, or combinations thereof. Radiation mutagenesis includes, without limitation, ultraviolet light, x-rays, gamma rays, and fast neutrons. Chemical mutagens include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a) anthracene (DMBA), ethylene oxide, hexamethylphosphoramide, bisulfan, diepoxyalkanes (diepoxyoctane (DEO), diepoxybutane (DEB), and the like), 2-methoxy-6-chloro-9

[3-(ethyl-2-chloro-ethyl)aminopropylamino] acridine dihydrochloride (ICR-170), sodium azide, formaldehyde, or combinations thereof.

One of skill in the art will understand that a variety of lettuce plant materials including, but not limited to, seeds, leaves, stems, roots, vegetative buds, floral buds, meristems, embryos, cotyledons, endosperm, sepals, petals, pistils, carpels, stamens, anthers, microspores, pollen, pollen tubes, ovules, ovaries, other plant tissue or plant cells including protoplasts, may be edited and/or mutagenized in order to create the PPO-mutated lettuce plants disclosed herein.

Introduction of polynucleotide constructs or RNPs into plants may be performed by introducing the constructs or RNPs into protoplasts. Protoplasts may be made by any means known in the art such as, but not limited to that found in Engler & Grogan, "Isolation, Culture and Regeneration of Lettuce Leaf Mesophyll Protoplasts," *Plant Sci. Lett.* 28:223-229 (1983); Nishio, "Simple and Efficient Protoplast Culture Procedure of Lettuce, *Lactuca sativa* L.," *Jap. J. Breeding* 38(2):165-171 (1988), which are hereby incorporated by reference in their entirety.

Delivery of DNA constructs for modification of a plant genome can be accomplished by plant transformation, including, for example, infection with a microbe, such as *Rhizobia* or *Agrobacterium* infection. The Ti (or Ri) plasmid of *Agrobacterium* enables the highly successful transfer of a foreign nucleotide molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety). In some embodiments, transformation involves fusion of protoplasts with other entities, either minicells, cells, lysosomes, or other fusible lipid-surfaced bodies (Fraley et al., "Liposome-Mediated Delivery of Tobacco Mosaic Virus RNA into Tobacco Protoplasts: Sensitive Assay for Monitoring Liposome-Protoplast Interactions," *Proc. Natl. Acad. Sci. USA* 79:1859-63 (1982), which is hereby incorporated by reference in its entirety).

Wounding of a target plant tissue prior to or during DNA delivery, for example using *Agrobacterium* or a *Rhizobia* species, such as Ensifer *adhaerens*, may also be employed to cause transformation. Various methods of wounding are employed in plant transformation methods, including for example, microprojectile bombardment; treatment with glass beads; cutting, scratching or slicing; sonication; or silicon carbide fibers or whiskers.

Transformation of protoplasts may be performed using any method known in the art including, but not limited to polyethylene glycol treatment (Lelivelt et al., "Plastid Transformation in Lettuce (*Lactuca sativa* L.) by Polyethylene Glycol Treatment of Protoplasts," *Meth. Mol. Biol.* 1132: 317-330 (2014); Lelivelt et al., "Stable Plastid Transformation in Lettuce (*Lactuca sativa* L.)," *Plant Mol. Biol.* 58:763-774 (2005), which are hereby incorporated by reference in their entirety); using Sheen's protocol (Sheen, J. (2002) at URL genetics.mgh.harvard.edu/sheenweb/); Yoo & Sheen, "*Arabidopsis* Mesophyll Protoplasts: A Versatile Cell System for Transient Gene Expression Analysis," Nat. Protocol. 2(7):1565-1572 (2007), which are hereby incorporated by reference in their entirety); gene gun delivery (biolistics); electroporation, nanoparticle-based gene delivery, such as RNPs, gold nanoparticles, starch nanoparticles, silica nanoparticles and the like, and *Agrobacterium*-mediated delivery (for a review of these methods, see Demirer & Landry, "Delivering Genes to Plants SBE Supplement," (2017) *SBE Supplement: Plant Synth. Biol.* 40-45, which is hereby incorporated by reference in its entirety) and a serine recombinase-mediated delivery.

The gene edited protoplasts may be grown into plants with the mutated PPO genes of choice. Methods of cultivating protoplasts into plants may be done by any means known in the art. See, for example, Enomoto and Ohyama, "Regeneration of Plants from Protoplasts of Lettuce and its Wild Species," In: Bajaj Y. P. S. (eds) *Plant Protoplasts and Genetic Engineering* I. Biotechnology in Agriculture and Forestry, vol 8. Springer, Berlin, Heidelberg (1989), which is hereby incorporated by reference in its entirety.

Any method of transformation that results in efficient transformation of the host cell of choice is appropriate for practicing the present application.

A further aspect of the present application is directed to a method of editing PPO genes of lettuce plant. This method involves introducing into a lettuce plant a polynucleotide construct comprising a first nucleic acid sequence encoding a gene editing nuclease, a promoter that is functional in plants operably linked to said first nucleic acid sequence, a second nucleic acid sequence encoding a plurality of gRNAs in a polycistronic arrangement targeting at least two PPO genes of choice to edit, and a second promoter that is functional in plants, operably linked to said second nucleic acid sequence.

Another aspect of the present application is directed to a polynucleotide construct for editing polyphenol oxidase genes of a plant comprising a nucleic acid sequence encoding a plurality of gRNAs targeting at least two PPO genes operably linked to a promoter.

In some embodiments, the lettuce plant of the present application is free of any plant pest sequences. In some embodiments, the lettuce of the present application is free of any selectable marker. In some embodiments, the lettuce of the present application is free of any heterologous nucleotides. In some embodiments, breeding of lettuce plants of the present application is used to select lines comprising the PPO mutations and where the heterologous nucleotides have been segregated away, such that the lettuce genome contains no heterologous nucleotides. In some embodiments, a serine recombinase-mediated method may be used to ensure the lettuce is free of any heterologous nucleotides.

In the serine recombinase-mediated method, the vector comprises at least one att site for integrating into the plant chromosome. The plant contains a complementary pseudo att site and contacting a pair of recombination attachment sites, attB and attP engineered in the vector and the plant's own pseudo att sites, with a corresponding recombinase mediates recombination between the recombination attachment sites. Thus, one can obtain integration of a plasmid that contains one recombination site into a plant cell chromosome that includes the corresponding recombination site. In some embodiments, the att site on the vector is an attP site. In some embodiments, the att site on the vector is an attB site. In some embodiments, the serine recombinase is provided as a polynucleotide encoding the serine recombinase of choice operably linked to a promoter that is operable in the plant. The polynucleotide may be part of the vector that also expresses the gRNAs and editing nuclease or it may be on a separate vector. In other embodiments, a serine recombinase protein is introduced into the same cell as the polynucleotide construct described herein. Useful serine recombinases include, but are not limited to BXB1, SF370.1, SPβc2, A118, φC31, TP901-1, Tn3, and gamma delta.

In some embodiments, a serine recombinase-mediated insertion of the polynucleotide construct of the present application is used and the gRNA-mediated editing is allowed to occur and then the polynucleotide vector is excised from the chromosome using a cognate Recombination Directionality Factor (RDF) (Smith & Thorpe, "Diversity in the Serine Recombinases," *Mol. Microbiol.* 44:299-307 (2002), which is hereby incorporated by reference in its entirety) of the serine recombinase used to integrate the polynucleotide construct. In some embodiments the serine recombinase used is an Spβc2 serine recombinase, and the excising RDF is the cognate RDF for Spβc2. With the polynucleotide construct excised from the chromosome, the plant is free of plant pest sequences including any selectable markers.

Methods of Breeding PPO Mutant Genes into Multiple Types of Lettuce Cultivars

The PPO mutations of the present application can be transferred to other varieties of lettuce through breeding to develop new, unique lettuce cultivars and hybrids. Backcross breeding has been used to transfer genes for a simply inherited, highly heritable trait into a desirable homozygous cultivar or inbred line which is the recurrent parent. The source of the trait to be transferred is called the donor parent, such as the PPO mutant lettuce lines described in the present application. After the initial cross of a plant of the present application to another plant, individuals possessing the PPO mutations of the donor parent are selected and repeatedly crossed (backcrossed) to the recurrent parent. The resulting plants can be selfed to produce plants with homozygous PPO mutations. The resulting plant is expected to have the attributes of the recurrent parent (e.g., cultivar) and the desirable trait, such as the PPO mutations of the present application, transferred from the donor parent. Backcrossing methods can also be used with the lettuce plants of the present application to improve or introduce one or more characteristic into the lettuce cultivar of the present application.

In some embodiments, a plant for breeding is a lettuce such as, but not limited to, a variety of leaf lettuce, romaine lettuce, Frisée lettuce, butter lettuce, Bibb lettuce, Boston lettuce, iceberg lettuce, kale, spinach, radicchio, or endive. In certain embodiments, the lettuce is a romaine lettuce, such as, but not limited to, Green Forest, Paris Island, Avalanche, Rubicon, Musena, Costal Star, Ideal Cos, Topenga, Ridgeline, Green Towers, Helvius, Jerico, Fresh Heart, Claremont, Show Stopper, Spretnak, Caesar, Salvius, Marilyn, Defender, Concept, King Henry, Pipeline, Rome 59, Valley Heart, Wildcat, Bali, or Mondo.

Molecular Breeding Evaluation Techniques

In some embodiments, the combination of PPO mutations or the breeding of PPO mutations into new lettuce plants, or cultivars are performed using molecular markers to track the mutations. The term "marker" refers to a nucleotide sequence or a fragment of such sequence, e.g., a single nucleotide deletion, used as a point of reference at an identifiable physical location on a chromosome (e.g., restriction enzyme cutting site, gene) whose inheritance can be tracked. Markers can be derived from genomic nucleotide sequences or from expressed nucleotide sequences (e.g., from a spliced RNA, cDNA, etc.). The term can also refer to nucleic acid sequences complementary to or flanking a marker. The term can also refer to nucleic acid sequences used as a molecular markers probe, primer, primer pair, or a molecule that can be used to identify the presence of a marker locus, e.g., a nucleic acid probe that is complementary to a marker locus sequence, and is capable of amplifying sequence fragments using PCR and modified PCR reaction methods.

A marker may be tracked using a marker assay. The term "marker assay" refers generally to a molecular markers assay, such as PCR, KASP, PACE or SSR, for example, used to identify whether a certain DNA sequence or SNP, for example, is present in a sample of DNA. For example, a marker assay can include a molecular markers assay, e.g., KASP assay, which can be used to test whether PPO mutation is present. Markers corresponding to genetic polymorphisms between members of a population can be detected by methods commonly used in the art including, PCR-based sequence specific amplification methods, detection of restriction fragment length polymorphisms (RFLPs), detection of amplified variable sequences of the plant genome, detection of simple sequence repeats (SSRs), detection of single nucleotide polymorphisms (SNPs), or detection of amplified fragment length polymorphisms (AFLPs), and detection of randomly amplified polymorphic DNA (RAPD). In other embodiments, nucleic acids may be detected with other high throughput hybridization technologies including microarrays, gene chips, LNA probes, nanoStrings, and fluorescence polarization detection among others. Other forms of nucleic acid detection can include next generation sequencing methods such as DNA SEQ or RNA SEQ using any known sequencing platform including, but not limited to: Roche 454, Solexa Genome Analyzer, AB SOLiD, Illumina GA/HiSeq, Ion PGM, MiSeq, among others.

Detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full service analysis tools capable of handling nucleic acid/protein marker extractions, detection, storage and analysis.

Although certain embodiments have been depicted and described in detail herein, it will be apparent to those skilled in the relevant art that various modifications, additions, substitutions, and the like can be made without departing from the spirit of the present application and these are therefore considered to be within the scope of the present application The following examples are intended to illustrate but not limit the invention.

EXAMPLES

Example 1—Chimeric Nuclease and PPO Gene Editing in Lettuce Protoplasts Construction of SynNuc1 Vector Targeting Eight Lettuce Polyphenol Oxidase (PPO) Genes Through a Polycistronic gRNA A vector was synthesized containing polycistronic gRNAs containing six independent gRNAs (A, E, G, O, R, and S, SEQ ID NOs:41-46, Table 2). These guide RNAs target eight different lettuce PPO genes (PPO-A, PPO-B, PPO-C, PPO-E, PPO-G, PPO-0, PPO-R, and PPO-S, corresponding to SEQ ID NOs:1, 3, 5, 9, 11, 19, 25, and 27). Vector pID536 also contained a novel chimeric nuclease (SynNuc1, SEQ ID NO:29). A schematic illustration of vector pID536 is shown in FIG. 1. The gRNA for PPO-A (SEQ ID NO:35) targeted three PPO genes (PPO-A, PPO-B, and PPO-C). The gRNAs for PPO-E, PPO-G, PPO-0, PPO-R, and PPO-S (SEQ ID NOs:36-40) targeted respective PPO genes singly.

TABLE 2

Guide RNAs for PPO Gene Editing Using Cas12a-Type Nuclease

| Name | Targets Gene(s) | Sequence (5' to 3') | SEQ ID NO: |
|---|---|---|---|
| gRNA-A | PPO-A, PPO-B, and PPO-C | ATGGGTAGTCCTTATCGTGCAGG | 35 |
| gRNA-E | PPO-E | CGTCCACCATGCGAATGTCGACA | 36 |
| gRNA-G | PPO-G | TTCGGTGGTGAGTATCGTGCCGG | 37 |
| gRNA-O | PPO-O | CGATGAGTCTAGACAAACCAACG | 38 |
| gRNA-R | PPO-R | TTTGGTGGCGAGTTTCGGGCTGG | 39 |
| gRNA-S | PPO-S | ATGCAACAAGCTTCTTCGGTGGC | 40 |

Protoplast cell transfections were performed with a vector ID536 in containing SynNuc1 driven by a CaMV 35S promoter along with a polycistronic gRNAs targeting eight different lettuce PPO genes driven by the *Arabidopsis* U6 promoter. Protoplasts were isolated from six week old wild type Romaine lettuce plants (about 1 g of leaf tissue) and transfected following Sheen's protocol (Sheen, "A Transient Expression Assay Using *Arabidopsis* Mesophyll Protoplasts," available on line at URL genetics.mgh.harvard.edu/sheenweb/(2002); Yoo et al., "*Arabidopsis* Mesophyll Protoplasts: A Versatile Cell System for Transient Gene Expression Analysis," *Nature Protocols* 2:1565-1575 (2007), which are hereby incorporated by reference in their entirety). Transfected protoplasts were incubated at 25° C. in the dark for about 60 hours.

Sixty hours post-transfection, protoplasts from three independent transfection reactions were pooled together and genomic DNA (gDNA) was extracted with 400 μl urea buffer (6.9 M Urea, 350 mM NaCl, 50 mM Tris-Cl pH 8.0, 20 mM EDTA pH 8.0, 1% Sarkosyl) followed by a phenol:chloroform:isoamyl alcohol and a chloroform:isoamyl alcohol steps. DNA precipitation was done at −80° C. for 20 minutes in an equal volume of isopropanol. Finally, DNA was washed once with 70% ethanol and resuspended in 20 μl of distilled (DI) water. gDNA concentration was estimated using a nanodrop 8000 (Thermo Fisher Scientific, Waltham, MA) then diluted at 30 ng/μl for further analysis.

PCR Amplification of Targeted Region for Gene Editing

Lettuce PDS and/or PPO targeted region were PCR amplified using Phusion Hot Start II (Thermo Fisher Scientific, Waltham, MA) and specific set of primers for each target gene (Table 3, SEQ ID NOs:19-36) using 60 ng/2 μl gDNA following the manufacturer instructions. PCR reactions were run using an Eppendorf MasterCycler EP gradient instrument (Eppendorf, Enfield, CT).

TABLE 3

PCR Primers for Amplification of Gene Editing Targeted Genes

| Target Gene | Primer Name | Primer ID | Primer Sequence | SEQ ID NO: | Amplicon size (bp) |
|---|---|---|---|---|---|
| PDS | LsPDS-G2_DS_AT_F | AJ40 | GTTATGTAACTAACTTTTTCACATTATGC | 41 | 200 |
|  | LsPDS-G2_DS_AT_R | AJ41 | ATGTGGGAAGAAATATCAAATATG | 42 |  |
| PPO-A | PPO-A_ZL_G1A | X35 | ATAGGGTCTCTGGCTGCAGA | 43 | 233 |
|  | PPO-A_ZL_G1S1 | X82 | CGATCGAAACAAACCTCCACAAA | 44 |  |
| PPO-B | PPO-B_ZL_G1S | X25 | GGACCATCAACCACCGTCTT | 45 | 217 |
|  | PPO-B_ZL_G1A1 | X88 | AACTGGGTTATGTGGTGTGTTCT | 46 |  |
| PPO-C | PPO-C_ZL_G1S | X26 | GCGAAACATCAACCACCGAC | 47 | 231 |
|  | PPO-C_ZL_G1A1 | X89 | GGTCCAGATATGAACCGGGTTAT | 48 |  |
| PPO-E | PPO-E_ZL_G1S1 | X84 | CTGGGTGGGTAATTCTAGGATGG | 49 | 227 |
|  | PPO-E_ZL_G1A1 | X91 | CTCGGTTGTAGACACGTACAAGA | 50 |  |
| PPO-G | PPO-G_ZL_G1S | X29 | AGGTCACTTGCAAGGAGTCG | 51 | 246 |
|  | PPO-G_ZL_G1A1 | X94 | TTAAGTTCTCTTGGGTCACCGAC | 52 |  |
| PPO-O | PPOO_ZL_G1S1 | X86 | ATACCAACTACACCTGCCACTTT | 53 | 265 |
|  | PPOO_ZL_G1A1 | X95 | TATGTCCGTTCCTGTGCTTATGT | 54 |  |
| PPO-R | PPO-R_ZL_G1S | X33 | TCCGCAACGTCAACCATGTA | 55 | 222 |
|  | PPO-R_ZL_G1A1 | X96 | CCTCTATTGATCCGACAGATGGG | 56 |  |
| PPO-S | PPO-S_ZL_G1S1 | X87 | ACGAAAGTCACCTTCGGTATGAA | 57 | 237 |
|  | PPO-S_ZL_G1A1 | Y01 | ATCTGTGAACAGCCGTATGACAA | 58 |  |

Deep Sequencing of PCR Product to Assess Gene Editing Frequency

Next Generation Sequencing ("NGS") was used to deeply sequence the specific PCR products for each target gene and assess gene editing frequency by comparing the number of pair reads showing a mutation (indels) at the target site to the number of pair reads depicting a wild type pattern. NGS was performed by the Center for Computational and Integrative Biology DNA Core Facility at Massachusetts General Hospital, Boston, USA using standard protocols.

Results: SynNuc1 is Successful in Generating CRISPR-Guided DNA Double-Stranded Breaks in Multiple Genes at Once All PPO targeted regions were PCR amplified from genomic DNA extracted of these transfected protoplasts then submitted to NGS. Table 4 shows the mutation frequencies observed in all eight lettuce PPO genes at their targeted sites. For example, 0.2% of protoplasts had mutations in PPO-A after transfection with pID536.

TABLE 4

Gene Editing Frequencies Observed in Lettuce PPO Genes using SynNuc1Gene

| PPO Gene | Mutation Frequency (%) of SynNuc1 |
|---|---|
| PPO-A | 0.2 |
| PPO-B | 0.1 |
| PPO-C | 0.06 |
| PPO-E | 0 |
| PPO-G | 0.07 |
| PPO-O | 0 |
| PPO-R | 0 |
| PPO-S | 0 |

PPO gene mutations were observed in half of the targeted PPO genes. PPO-A, PPO-B, and PPO-C were targeted by the same gRNA while PPO-G was targeted by a different gRNA as were the other four PPO genes (PPO-E, PPO-O, PPO-R, and PPO-S). Mutations generated after NHEJ repair of the breaks created by SynNuc1 in four PPO genes ranged from one base pair to 5 base pair deletions as well as insertion of one to 37 base pairs. FIGS. 2A-B show examples of mutations generated after repair of the breaks created by SynNuc1 for PPO-B (FIG. 2A) and PPO-G (FIG. 2B). Indels were observed at the targeted cutting site located either 22 base pairs upstream from the protospacer adjacent motif (PAM), TTTN for SynNuc1.

Example 2—Expression of PPO Genes in Lettuce

Figure 4:
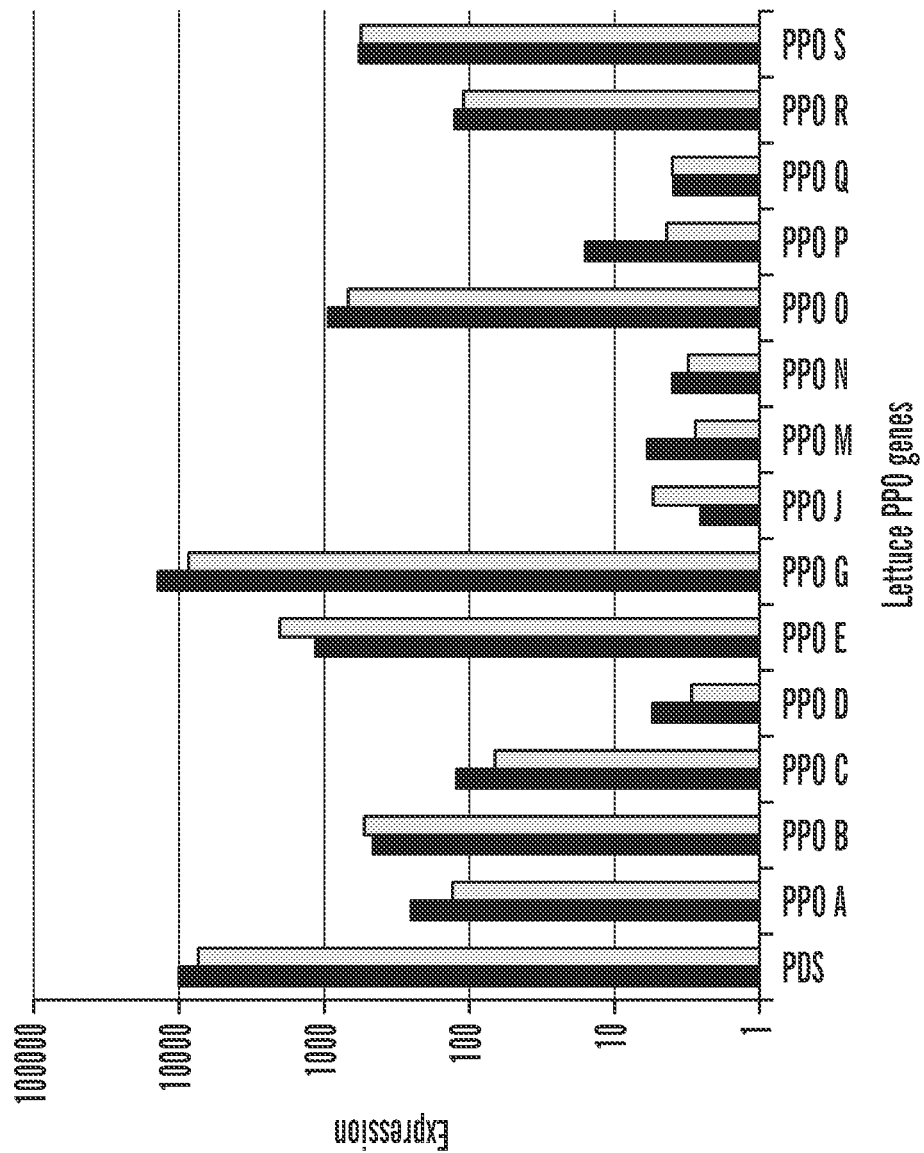
FIG. 4 is a graph showing the expression of PPO types using two sets of primers (shown by black and grey bars) for each PPO gene, and these were used to monitor expression levels in leaves. The PDS gene was used as an expression level control.

The lettuce genome contains at least 19 putative PPO genes. The expression levels of PPO genes in lettuce vary significantly. FIG. 4 shows the relative expression profile of PPO genes in the leaves of grocery store lettuce. Two sets of primers (shown by black and grey bars) for each PPO gene were used to monitor expression levels in leaves (Table 5, SEQ ID NOs:59-114). Expression of the PDS gene was evaluated using primers SEQ ID NOs:115-118 and used as an expression level control. Eleven PPO genes (excluding PPO-J and PPO-M which had the lowest expression) were selected as targets for gene editing. Romaine lettuce bought at the grocery store was chopped in pieces and three samples were collected: 1) fresh, 2) stored at 4° C. for 4 h, and 3) stored at 4° C. for 3 d before being frozen. RNA was extracted using QIAgen RNeasy Plant Mini Kit following manufacturer instruction. RNA from all three samples were pool together before cDNA synthesis. cDNA was synthesized using Quanta qScript cDNA Synthesis Kit then 100 ng of cDNA was used to perform qRT-PCR.

TABLE 5

PPO Gene Expression Analysis Primers

| Target Gene | Primer Name | Primer Sequence | SEQ ID NO: | Amplicon size (bp) |
|---|---|---|---|---|
| PPO-A grey | PPOA 3F<br>PPOA 3R | TCTCAAGTTCCCATAGCACGA<br>TGCATACGCCAATGAGTTTGA | 59<br>60 | 183 |
| PPO-A black | PPOA 41F<br>PPOA 41R | AGCACGAATCACGAACCATC<br>TGAGGTCCGGTGCCATAATC | 61<br>62 | 194 |
| PPO-B grey | PPOB 19F<br>PPOB 19R | TTCATATCTGGGCCGGTGAG<br>ACAAGAACGAAGAATCAAGCCA | 63<br>64 | 189 |
| PPO-B black | PPOB 21F<br>PPOB 21R | CCCTCTGAACAAACGTCCAA<br>TGAACTGGGTTATGTGGTGTG | 65<br>66 | 158 |
| PPO-C grey | PPOC 13F<br>PPOC 13R | GGCCTTGGAGGTCTTTATGGT<br>AGCCGGACCACATTTACTGA | 67<br>68 | 102 |
| PPO-C black | PPOC 29F<br>PPOC 29R | CCATCACAAGCCACCTCTTAC<br>ACGTTTCTCCTATCAAGTTTGCC | 69<br>70 | 194 |
| PPO-D grey | PPOD 1F<br>PPOD 11R | AAATCCCGTGGCTCCATAGTC<br>TTCGCTTCCTGCTTGTTCTTC | 71<br>72 | 184 |
| PPO-D black | PPOD 25F<br>PPOD 25R | TTTACGTCCACCATGCCAAC<br>AGTCGTATCCCATTGCAGTCA | 73<br>74 | 186 |
| PPO-E grey | PPOE 13F<br>PPOE 13R | TGTACGTGTCTACAACCGAGA<br>CGATTCCAGCAGACTTAGCAG | 75<br>76 | 140 |
| PPO-E black | PPOE 15F<br>PPOE 15R | GCAAATGAGCTGTTGTTCGTG<br>TATGTGGCAACTGTGCGAAAC | 77<br>78 | 148 |
| PPO-G grey | PPOG 8F<br>PPOG 8R | CAGTTGCCACACAAACACAAG<br>GATCCAGACCTTGGGACAATC | 79<br>80 | 134 |
| PPO-G black | PPOG 22F<br>PPOG 22R | ATTAGCGGTGGTGGATCAGTC<br>GTTTGCCTCCCTGCATCTTC | 81<br>82 | 187 |
| PPO-J grey | PPOJ 9F<br>PPOJ 9R | TATCACGACGCCAAACTTCTC<br>CTATGTGCCGCTGGTCTAATC | 83<br>84 | 174 |
| PPO-J black | PPOJ 10F<br>PPOJ 10R | ATAAGGCCGTCAGAAGCAGAG<br>AACGAAACTGTGTGGGTGTTC | 85<br>86 | 200 |
| PPO-M grey | PPOM 8F<br>PPOM 8R | GGCCTGAAACTGCTAGAACAA<br>AACCCGCATACTCGCTATCA | 87<br>88 | 168 |
| PPO-M black | PPOM 9F<br>PPOM 9R | GCGAAGATACGACTGACGACT<br>CCAGCGACATACTTACCACCA | 89<br>90 | 115 |
| PPO-N grey | PPON 19F<br>PPON 19R | ACTTCTACTCCGCAGGCTATG<br>GTGCATGGTGTCTCCTGTTC | 91<br>92 | 102 |
| PPO-N black | PPON 21F<br>PPON 21R | TAACGACAATGACCCACACAG<br>GTGGAATGGAAAGAAGAGCCA | 93<br>94 | 148 |
| PPO-O grey | PPOO 2F<br>PPOO 2R | ACATAAGCACAGGAACGGACA<br>CACCACCACATCTTCGTCATC | 95<br>96 | 124 |
| PPO-O black | PPOO 6F<br>PPOO 6R | ATGGCCGGAATACCAACTACA<br>CCGCTGTCTCCTCATCCTC | 97<br>98 | 199 |
| PPO-P grey | PPOP 11F<br>PPOP 11R | TGTATGTGGATGACAAGGACGA<br>CTTCTCGCCTGATTGATGGTG | 99<br>100 | 101 |
| PPO-P black | PPOP 21F<br>PPOP 21R | GGATGCCGAACAATGAAGACA<br>CCTGATACCCAACTCTTTCCAG | 101<br>102 | 119 |
| PPO-Q grey | PPOQ 4F<br>PPOQ 4R | AGGACCAAGGAGGACAAACAG<br>TGCGAAACTACCAGCAAACTC | 103<br>104 | 159 |
| PPO-Q black | PPOQ 15F<br>PPOQ 15R | GACAATGGAACCGAGACCAC<br>CCAAACCTAACTCCGCTCATC | 105<br>106 | 110 |

TABLE 5-continued

PPO Gene Expression Analysis Primers

| Target Gene | Primer Name | Primer Sequence | SEQ ID NO: | Amplicon size (bp) |
|---|---|---|---|---|
| PPO-R grey | PPOR 15F<br>PPOR 15R | ACGTCAACCATGTATCACCAGA<br>CTTAACGGGTCAGTAGCGTTG | 107<br>108 | 142 |
| PPO-R black | PPOR 20F<br>PPOR 20R | GCAACTCCAGATTCACAACTCA<br>GCGTCAAAGACAGGGTTTCTC | 109<br>110 | 195 |
| PPO-S grey | PPOS 11F<br>PPOS 11R | CCTATTGACTGTTGCCCTCTG<br>ATCGAGATACCCGACTGGAAG | 111<br>112 | 120 |
| PPO-S black | PPOS 22F<br>PPOS 22R | GGAATTTGCTCCTGGGTCTC<br>ATACGGCATCTTTGCATGGTC | 113<br>114 | 126 |
| PDS grey | PDS 14F<br>PDS 14R | AAATGCTGACGTGGCCTGA<br>CTTTCTCATCCAGTCCTGAACAC | 115<br>116 | 119 |
| PDS black | PDS 36F<br>PDS 36R | CAGCTGAGGAATGGATTTCAAGA<br>GGGTCGACATGGTTCACAATC | 117<br>118 | 185 |

Figure 5:
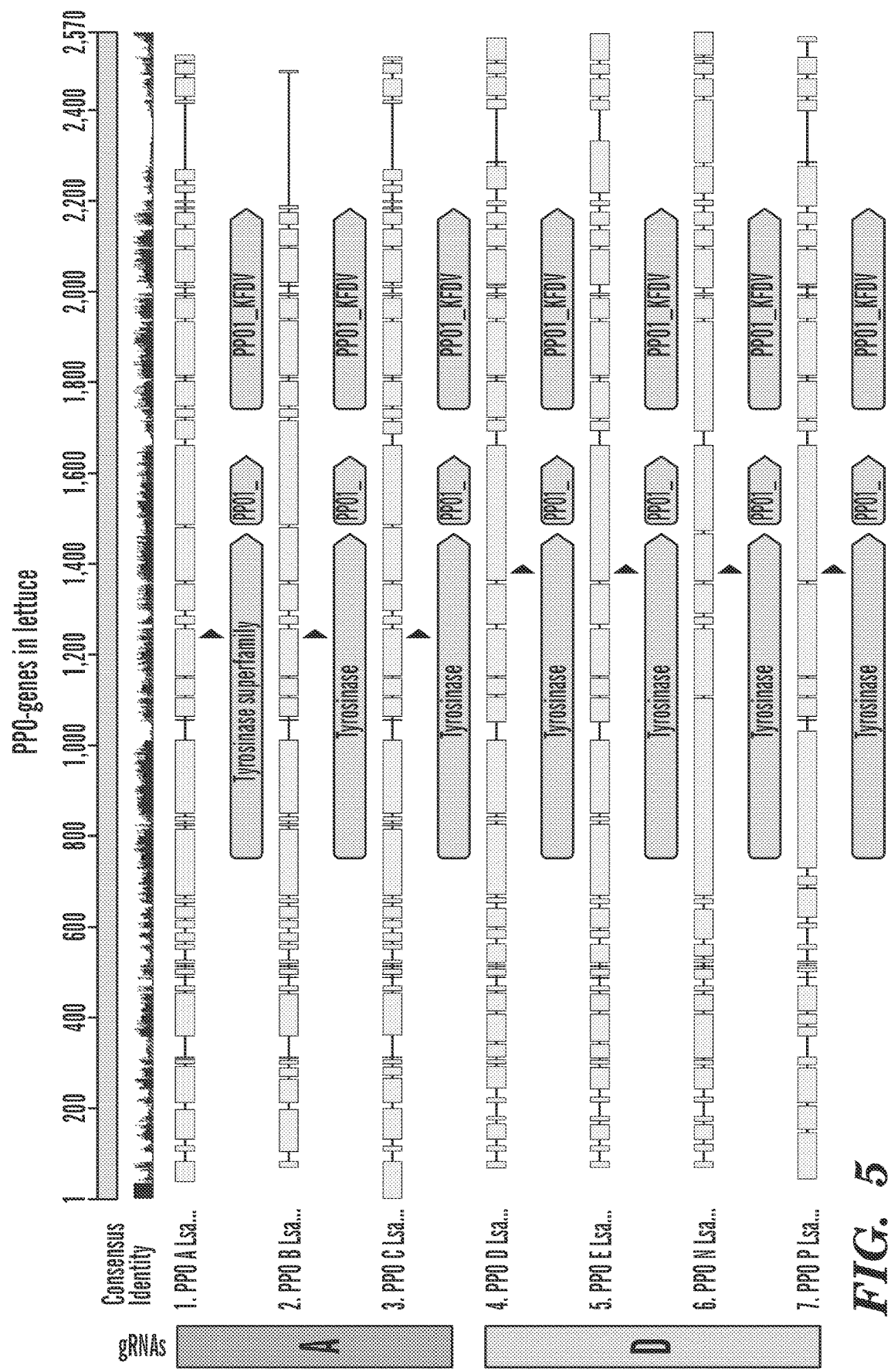
FIG. 5 shows an alignment of 11 Romaine lettuce PPO genes. Except for PPO-O, all PPO-gRNAs were designed to target the metal-binding domain of each respective PPO. Boxes represent exons. The gRNAs (A, D, G, O, R, and S) are shown at left of the respective genes and the positions of gRNAs in the genes are shown with arrowheads. The gRNA-A targeted 3 PPO genes (A, B, and C) and gRNA-D targeted 4 PPO genes (D, E, N, and P).
Figure 5:
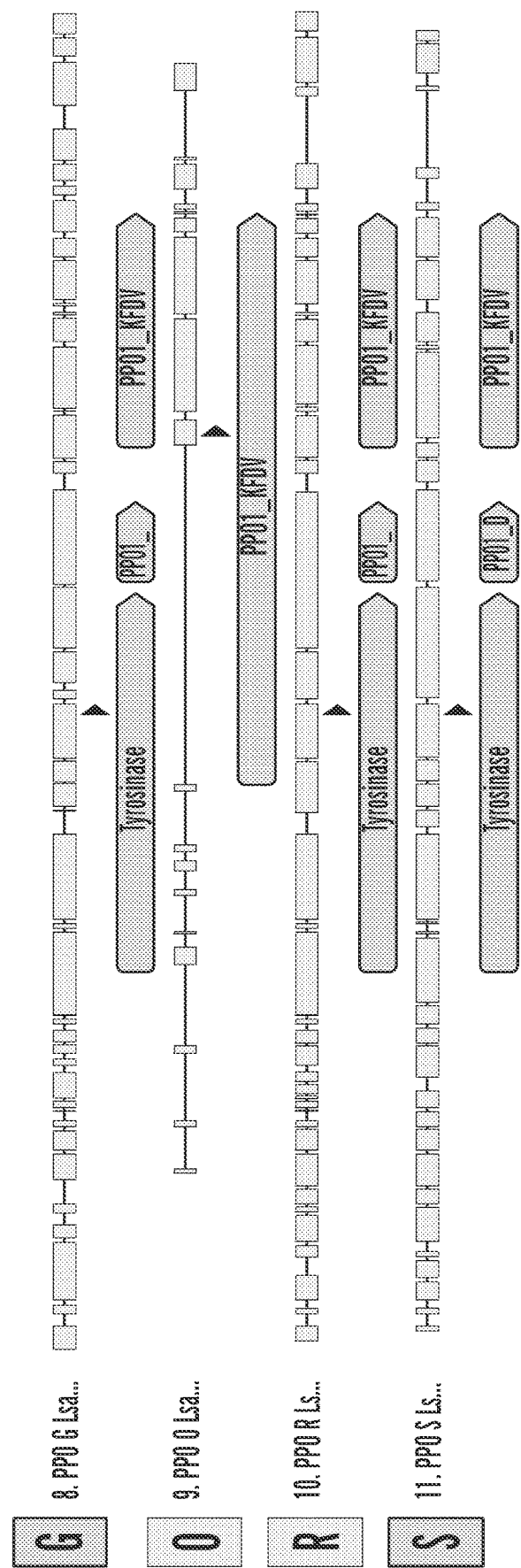

Example 3—Editing of PPO Genes by *Agrobacterium*-Mediated Transformation and Screening Six gRNAs (gRNA-AA, gRNA-DD, gRNA-GG, gRNA-OO, gRNA-RR, and gRNA-SS, corresponding to SEQ ID NOs:119-124, Table 6) were arranged in a polycistronic fashion on a vector for targeting PPO genes in a romaine lettuce variety. gRNA-AA targets PPO-A, PPO-B, and PPO-C, while gRNA-DD targets PPO-D, PPO-E, PPO-N, and PPO-P. In this way, 11 PPO genes were targeted by the polycistronic construct (FIG. 5). The construct also contained a coding sequence for a Cas9-type gene editing nuclease. Two vectors were made with the construct in opposite orientations, ID123 and ID124 (FIGS. 3A-B and FIGS. 9A-B).

TABLE 6

Guide RNAs for PPO Gene Editing using Cas9-Type Nuclease

| Name | Targets Gene(s) | Sequence (5' to 3') | SEQ ID NO: |
|---|---|---|---|
| gRNA-AA | PPO-A, PPO-B and, PPO-C | TGGGTAGTCCTTATCGTGC | 119 |
| gRNA-DD | PPO-D, PPO-E, PPO-N and, PPO-P | TGGGGAACTTCTACTCCGC | 120 |
| gRNA-GG | PPO-G | TCGGTGGTGAGTATCGTGC | 121 |
| gRNA-OO | PPO-O | AAACCAACGACGGTGATGG | 122 |
| gRNA-RR | PPO-R | TTGGTGGCGAGTTTCGGGC | 123 |
| gRNA-SS | PPO-S | TCGGTGGCAAATATGTAGC | 124 |

Plants were regenerated following *Agrobacterium*-mediated transformation with ID123 and ID124 using published methods (Curtis, "Lettuce (*Lactuca sativa* L.)," in *Agrobacterium Protocols, Second Edition, Volume* 1, eds. Kan Wang, pp 449-458 (2006), which is hereby incorporated by reference in its entirety).

Events were selected on kanamycin and kanamycin positive events were analyzed for the presence of guide RNA and gene editing nuclease coding sequences cassette intactness and transgene copy number. A total 145 $T_0$ lines from ID123 and 72 $T_0$ lines from ID124 were obtained. Over 90% of lines from both constructs were low or single copy events. Approximately 50 single or low copy $T_0$ events from both ID and ID constructs were analyzed for mutations in PPO genes using Surveyor™ Mutation Detection kit (Integrated DNA Technologies, Newark, NJ), and mutations in targeted PPO genes were further confirmed by PCR-amplicon sequencing. Listed in FIG. 6 are seven key events that had indels in different targeted PPO genes. $T_0$ lines 8-8-4 and 8-14-13 from ID123 had 7 and 8 PPO genes mutated, respectively. $T_0$ line 13-01-17 from construct ID124 was also advanced for further analysis. The 13-01-17 $T_0$ line had 5 PPO genes mutated. Mutations in PPO genes are listed in Table 1.

Analysis of T1 Segregated Events, Mutations in PPO Genes, and PPO Enzymatic Activity Thirty-two $T_1$ siblings from $T_0$ line 8-8-4 and 20 siblings from line 8-14-13 were screened for presence or absence of the expression cassette and mutations in targeted PPO genes. All transgene free $T_1$ siblings were also analyzed for PPO enzymatic activity. Seven millimeter leaf disks harvested from the outermost healthy leaf free of the mid-rib were flash frozen then grind in a Tissuelyzer for 1 minute @ 25 Hz. Samples were re-frozen in liquid nitrogen and homogenized for an additional minute before adding 250 µl of protein extraction buffer containing 100 mM sodium phosphate pH 6.8, 1% PVPP and, 1% NP-40 and shake by hand for 30 seconds. After microcentrifugation for 30 seconds at maximum speed, 125 µl of the supernatant was transferred to a filter plate. The flow through collected after microcentrifugation for one minute at maximum speed was used as crude protein extract in the PPO assay. PPO assay was performed in a flat bottom 96-well assay plate containing 10 mM pyrocatechol in a solution containing 100 mM sodium phosphate pH 6.8 and 0.015% SDS. Thirty microliter of crude protein extract was quickly added to the pyrocatechol substrate using a multichannel pipet and measurement of PPO activity at 410 nm was rapidly initiated since activity will level off within a few minutes. Table 7 below, shows the transgene-free $T_1$ siblings, their PPO genotypes, and PPO enzymatic activity in leaves.

TABLE 7

Mutations Observed in $T_1$ Plants

| ID Control | Homo-PPO | Het-PPO | PPO-activity High |
|---|---|---|---|
| 8-8-4-5 | ADES | B | Undetectable |
| 8-8-4-23 | BDES | — | Low |
| 8-8-4-24 | BDEGS | — | Undetectable |
| 8-8-4-30 | DES | BA | Low |
| 8-8-4-73 | BES | GA | Low |
| 8-8-4-88 | BDES | GA | Low |
| 8-8-4-96 | BDEGS | A | Undetectable |
| 8-8-4-97 | ABES | G | Low |
| 8-8-4-101 | ABS | GE | Undetectable |
| 8-14-13-4 | OR | GESBPD | Undetectable |
| 8-14-13-5 | BOPRS | — | High |
| 8-14-13-7 | DEOS | BR | Undetectable |
| 8-14-13-10 | GOR | ESPD | Undetectable |
| 8-14-13-11 | O | GESBRPD | High |
| 8-14-13-16 | OPS | GBR | Low |

TABLE 7-continued

Mutations Observed in $T_1$ Plants

| ID Control | Homo-PPO | Het-PPO | PPO-activity |
|---|---|---|---|
| 8-14-13-38 | BDEORS | G | Undetectable |
| 8-14-13-44 | OPS | GBR | High |
| 13-1-17-1 | ARS | GB | High |
| 13-1-17-4 | A | GSR | High |
| 13-1-17-7 | BS | GR | High |
| 13-1-17-9 | B | SR | High |
| 13-1-17-17 | S | GBA | High |

Figure 7:
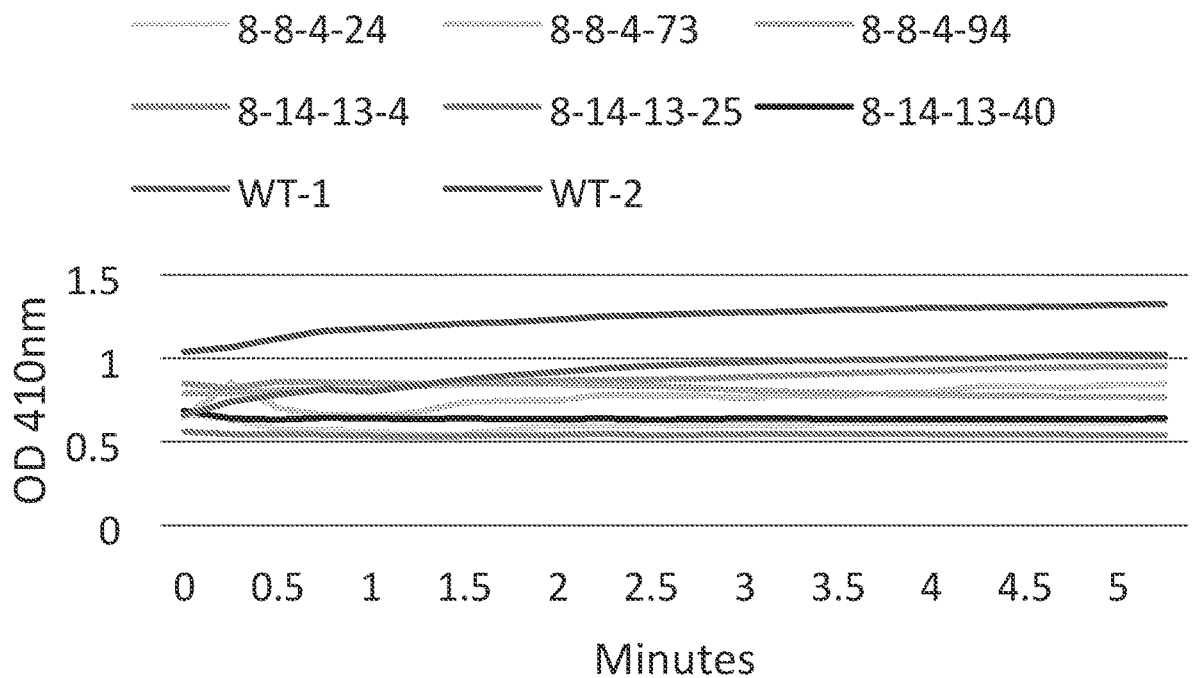
FIG. 7 shows PPO enzymatic activity of T1-siblings 8-8-4-24, 8-8-4-73, 8-8-4-94, 8-14-13-4, 8-14-13-25, 8-14-13-40, and two wild type genotypes. PPO enzymatic activity was analyzed in twelve week old growth-chamber grown lettuce leaves.

As shown in Table 7, PPO genotypes had variable levels of PPO enzyme activity in leaves. There was no clear single PPO gene found as a sole contributor to the PPO level in lettuce leaves. PPO activity of T1-siblings 8-8-4-24, 8-8-4-73, 8-8-4-94, 8-14-13-4, 8-14-13-25, 8-14-13-40 and two wild type genotypes are shown in FIG. 7.

A representative number from each of the $T_1$ events shown in Table 7 were advanced to $T_2$ in an effort to fix the heterozygous PPO edits as homozygous. FIG. 8 shows the advanced $T_2$ siblings with their respective homozygous PPO genes alongside the $T_1$ and $T_0$ parents showing the progression to homozygosity.

PPO activity was also measured in the T3 generation plants that were harvested from indoor aeroponic or outdoor field growth environments using the PPO enzyme activity assay as described above. Under aeroponic conditions, the control variety had a PPO specific activity of about 2900 (units/mg protein), whereas GVR-107 (14-2-24-21) had an average PPO specific activity of about 300 (10% of control) and GVR-108 (14-2-24-5) had a PPO specific activity of about 850 (29% of control). Under field conditions, the control lettuce variety had a specific activity of 2240, whereas GVR-102 (14-2-73-14) had an average PPO specific activity of about 680 (30% of control), GVR-105 (15-1-9-11) had an average PPO specific activity of about 280 (12.5% of control), and GVR-110 (14-2-96-13) had an average PPO specific activity of about 130 (6% of control).

Example 4—Plant Pest Element Screening

Figure 9A:
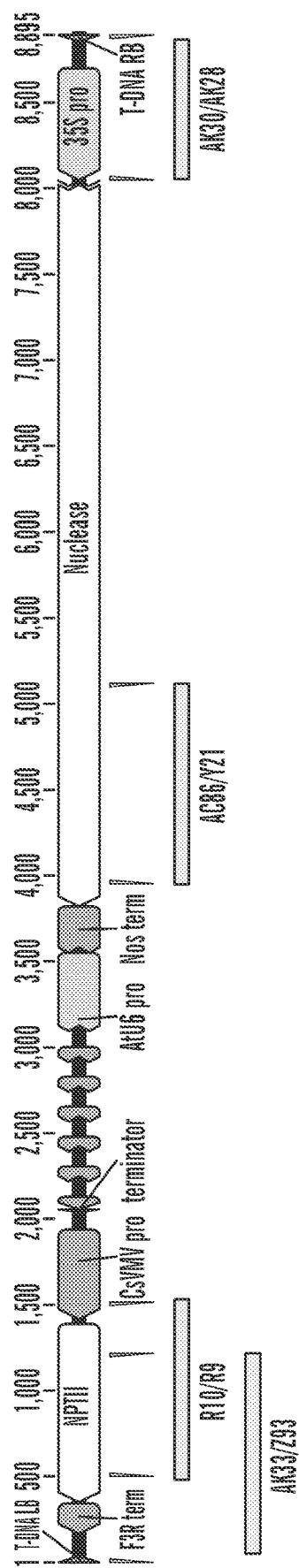
FIGS. 9A-C show schematic illustrations of the ID construct (FIG. 9A) and the ID construct (FIG. 9B). NPTII is the plant selectable marker conferring kanamycin resistance in the transformed plants. The gene editing nuclease expression is driven by the CaMV 35S promoter. Positions of PCR primers used to detect the boundaries of the ID123 and ID124 constructs are indicated in FIGS. 9A-B.
Figure 9B:
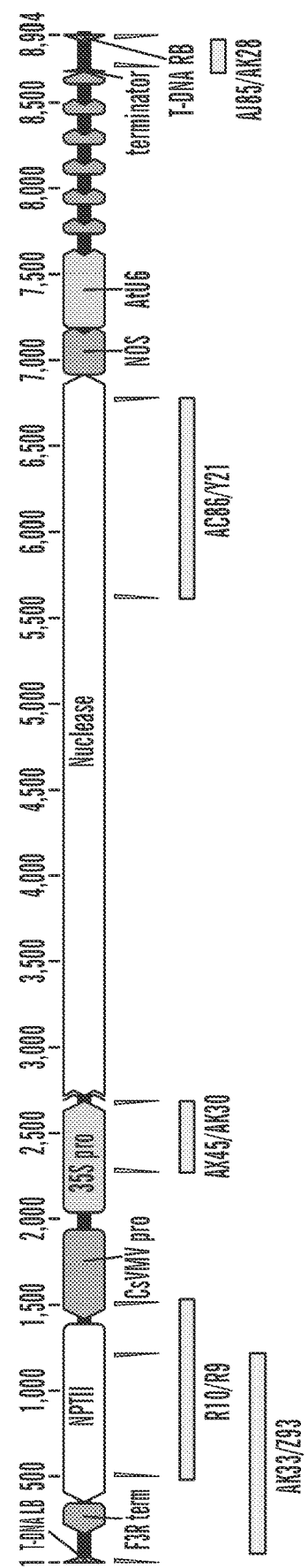

As PPO mutant lines were advanced to the $T_2$ generation, multiple PPO gene edits were fixed, i.e., homozygous at both alleles, and only a small percentage remained heterozygous. At this stage the $T_1$ parents were screened by PCR to ensure that none had plant pest sequences remaining in the genome. Initial scoring was based on failure to amplify a portion of the NptII gene using NptII primers (SEQ ID NOs:125-126). Absence of the plant pest DNA sequences was confirmed by three additional sets of PCR primers designed to amplify different parts of the construct CsVMV: (R9/R10, SEQ ID NOs:125-126), Border: (AK33/Z93, SEQ ID NOs:129-130), and Border/CaMV35S: (AK28/AK30 SEQ ID NOs:131-132). An additional primer set: (A178/A181 SEQ ID NOs:135-136) which amplifies the endogenous PDS gene was included in all PCR reactions as a positive control for DNA quality. Primers used to screen for plant pest elements are shown in Table 8. FIG. 9A and FIG. 9B are diagrammatic representations of the ID123 and ID124 constructs showing the location of the genetic elements and each primer set.

TABLE 8

Primers Used to Screen for Plant Pest Elements

| Target Gene | Plasmid ID | Primer Name | Primer ID | Primer Sequence | SEQ ID NO: | Amplicon size (bp) |
|---|---|---|---|---|---|---|
| CsVMV & NPTII | ID123 & ID124 | CsVMV_AT_F9138 | R9 | TAAGGAACCAAGTTCGGC | 125 | 1018 |
| | | NPTII_AT_R10141 | R10 | ACACCAAGCCTTCCACAG | 126 | |
| CaMV 35S | ID124 | 35S_AT_F | AK30 | GTCTGGAGGATCTGCTAGAGTC | 127 | 417 |
| | | p35S-int_AT_F | AX45 | CGTCTTCAAAGCAAGTGGA | 128 | |
| LB & NPTII | ID123 & ID124 | LBATF | AK33 | TGGCAGGATATATTGTGGTG | 129 | 1219 |
| | | Kan_ZL_F1 | Z93 | GTACTCTTGCCGACTACAACATC | 130 | |
| RB & CaMV 35S | ID123 | 35S_AT_F | AK30 | GTCTGGAGGATCTGCTAGAGTC | 131 | 843 |
| | | RBATR | AK28 | GTTTACCCGCCAATATATCCT | 132 | |
| RB | ID124 | ID173_gRNA_RB_GSP1_GW_AT_F | AJ85 | AGGGCGAATTCGACCCAGCTTTCTTG | 133 | 185 |
| | | RBATR | AK28 | GTTTACCCGCCAATATATCCT | 134 | |
| PDS | N/A | LsPDS_ATG_AT_F | A178 | ATGTCTCTGTTTGGAAATGTTTC | 135 | 1758 |
| | | LsPDS_1.6kb_AT_R | A181 | TCCCATCACTCAATAGAAAGTTC | 136 | |
| Cas9 | ID123 & ID124 | Cas9_ZL_F5 | Y21 | AATGACAAACTCATCAGGGAAGTG | 137 | 1169 |

Plant events were screened with all four primer pairs with the results confirming that no plant pest DNA remained.

Figure 9C:
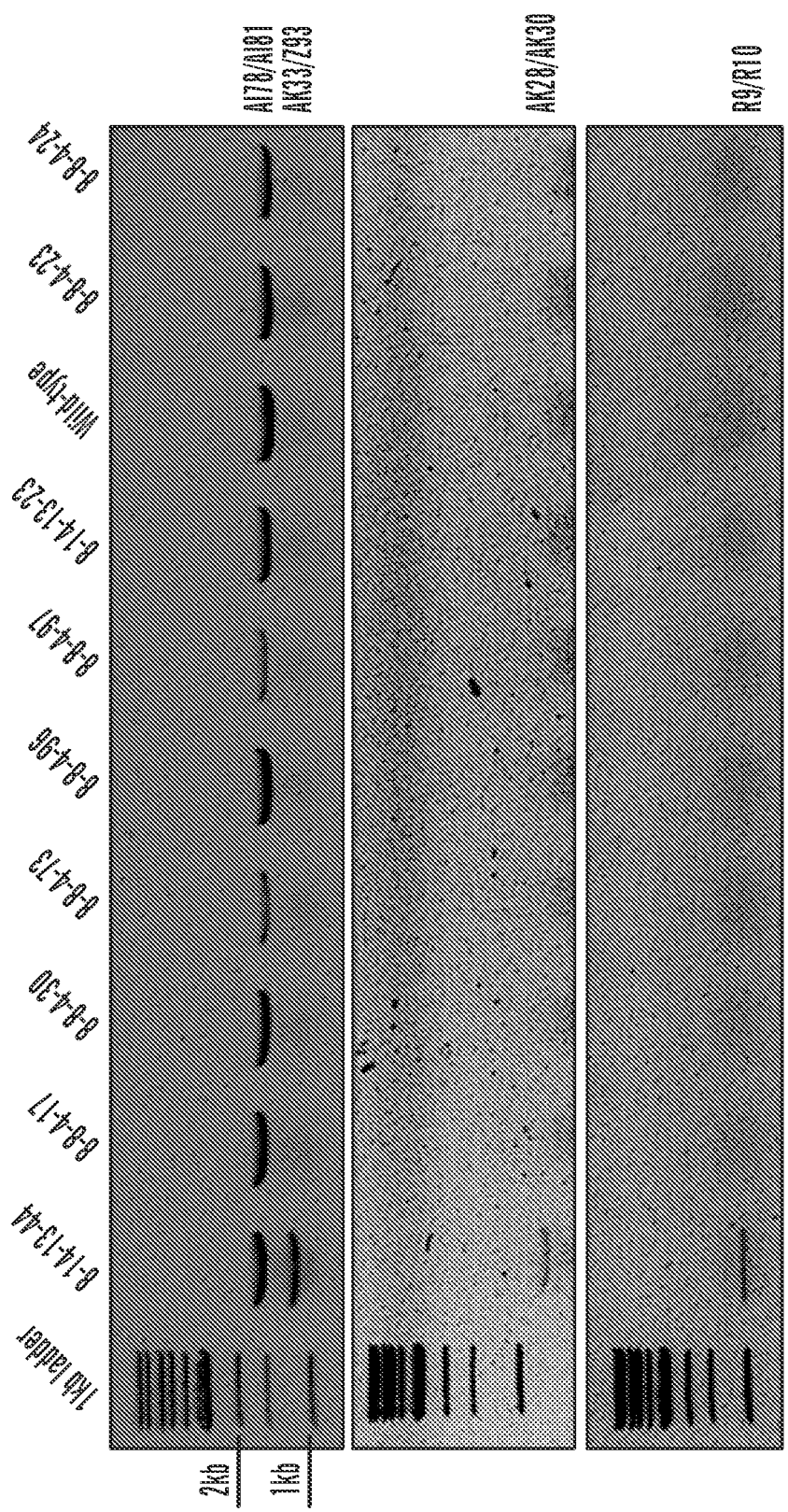

Results of this PCR screen using the primers shown in FIG. 9C. Primers A178/A181 amplify the endogenous PDS gene and are a PCR positive control. RB primers did not amplify any 8-8-4 lines including the control and all other primer combos indicate absence of pest sequences. T1 PPO mutant lines appear indistinguishable from wild type indicating the absence of plant pest sequences.

As shown in FIG. 10, the PPO mutant lines were sequenced to confirm the PPO mutations, to be sure of homozygosity, and to check that seed lot purity had been maintained. $T_2$ plants were sampled and DNA was extracted. PPO genes were amplified by PCR across the region targeted by the respective gRNAs. At the $T_2$ generation, all the mutations confirmed the earlier sequencing and showed the progression to homozygosity except with respect to PPO-B in 14-2-73-14, 14-2-96-13, 14-2-96-9, and 14-2-97-17 in which the mutation in PPO-B was heterozygous (FIG. 10). Sequencing was repeated twice on $T_3$ generation plants.

The PPO mutant lines of FIG. 10 were grown to assess the phenotype of non-browning and any other observable trait.

Example 5—Chromosomal Locations of PPO Genes in the Lettuce Genome

Figure 19:
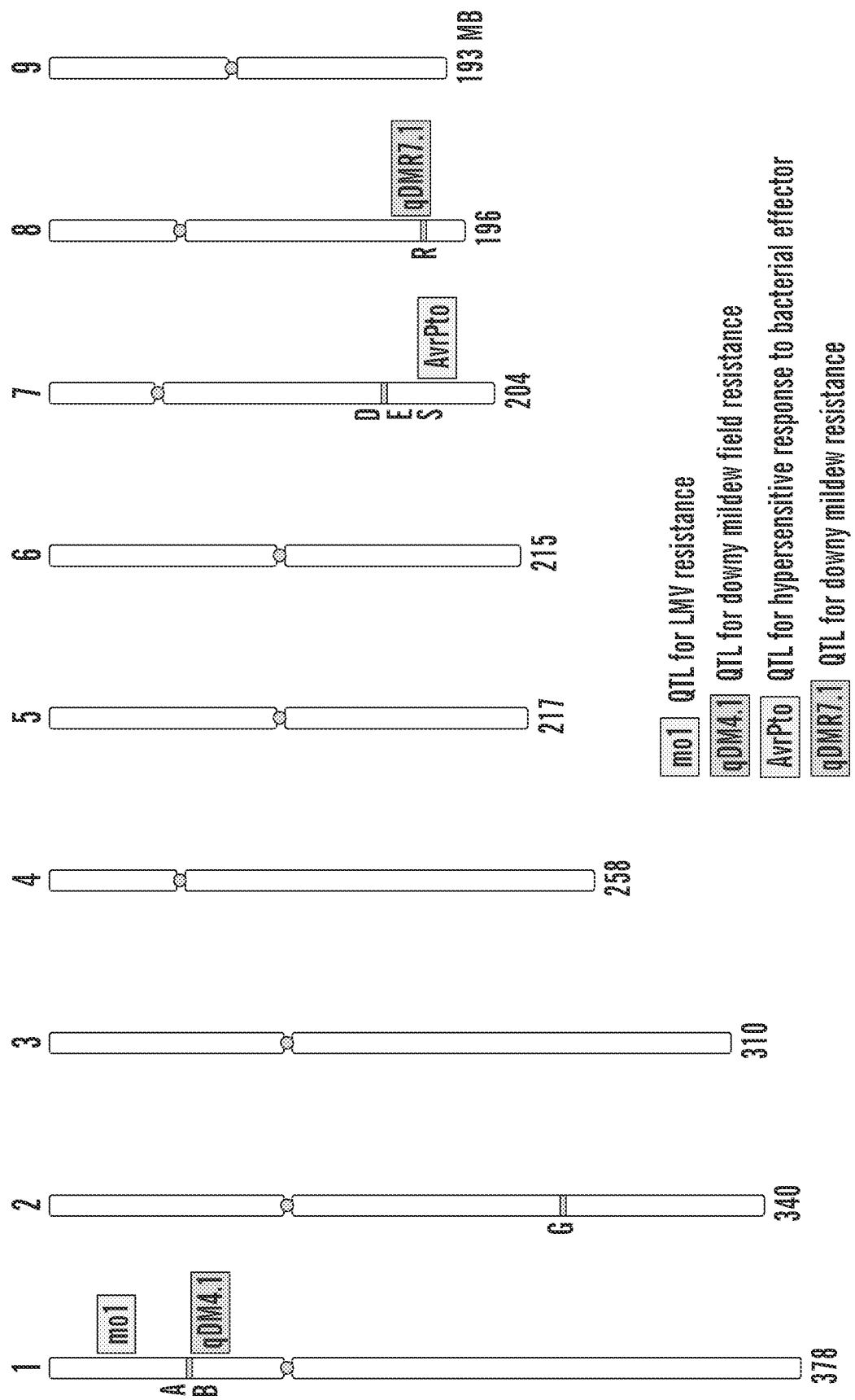
FIG. 19 provides a graphical representation of the locations of PPO genes on the 9 lettuce chromosomes.

An analysis was completed to pinpoint the locations of the PPO genes across the lettuce genome. This is useful in two ways. From this information, it can be determined if any linkage drag would be associated with breeding the PPO mutations into other lettuce varieties. It can also be determined whether a breeding strategy is feasible. Based on the linkage of the 7 KO PPO genes to only 3 physical locations on 3 chromosomes, it is possible to breed the mutations of the best performing modified lettuce varieties to another variety and carry over the PPO edits. FIG. 19 is a representation of the nine lettuce chromosomes showing the location of 7 PPO genes and their relationship to known QTLs for disease resistance.

Example 6—Phenotypic Analysis of PPO Mutant Lines—Leaf Tip Burn

Evaluation of T2 lines were grown in aeroponic conditions by AeroFarms ("AF"). Plants were evaluated against unmodified wild type romaine lettuce of the same variety, Isogenic ("control"). It was noted that some of the PPO mutant lines showed greatly enhanced resistance to tip burn. Tip burn is a major issue for lettuce quality and is influenced by factors including lack of calcium in young, rapidly developing leaves. Therefore, the PPO mutant lines shown in FIG. 10 were evaluated for both non-browning and tip burn phenotypes at harvest (day 0), and at days 3, 7, 9, 10, 14, 16, 19, 22, and 26 post-harvest under conditions of light and cold that are considered optimal for this lettuce or at 70° F. in the dark (poor conditions).

Figure 11:
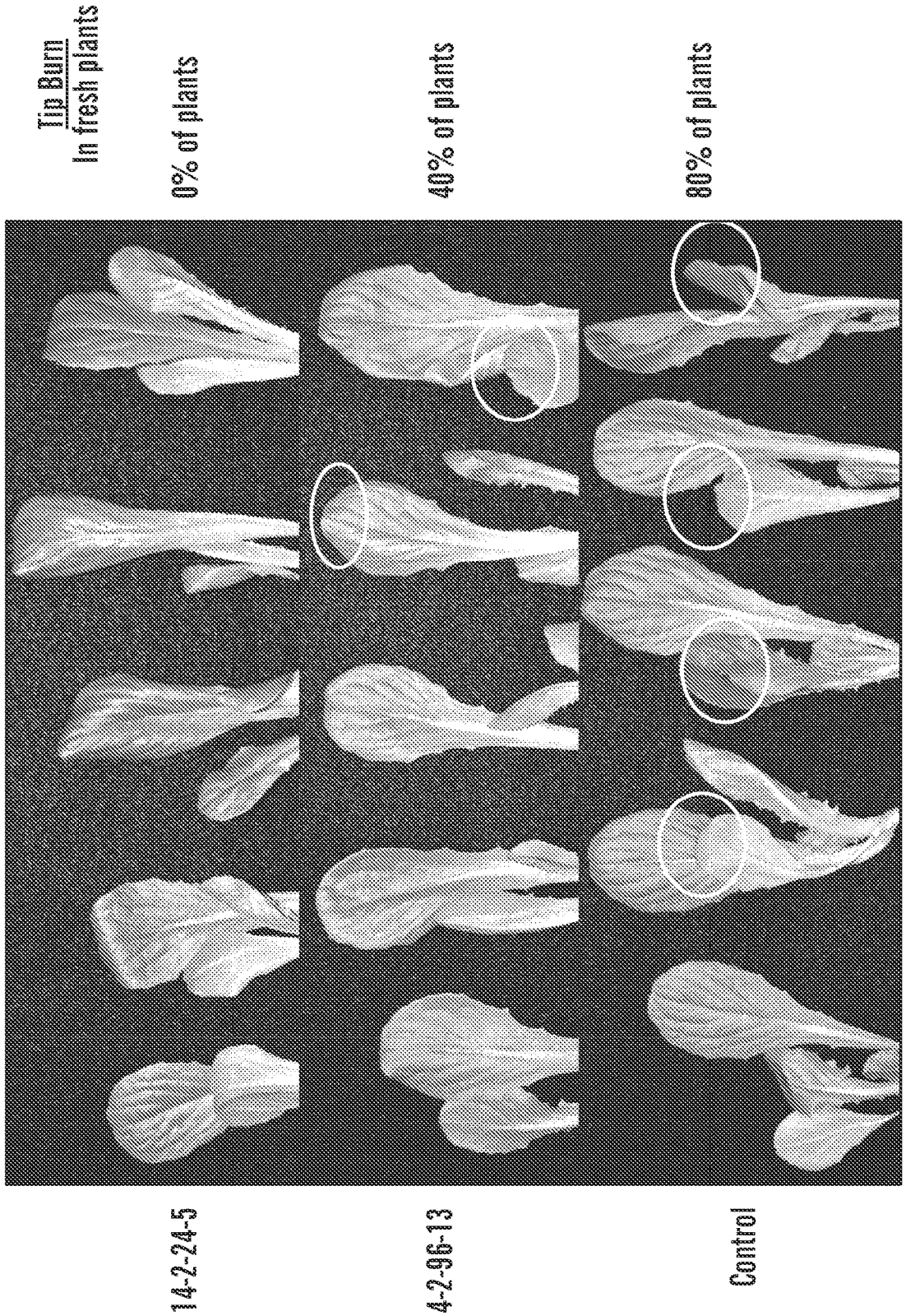
FIG. 11 provides photographic images of freshly harvested T3 plants 14-2-24-5 and 14-2-96-13 compared to unmodified isogenic (wild type) control lettuce. Isogenic controls showed tip burn in 80% of the plants while only 40% of 14-2-96-13 plants showed tip burn. 14-2-24-5 showed no tip burn at all.

The plants were examined at harvest and it was noted that 80% of the control wild type plants (which are known to exhibit resistance to tip burn) nevertheless exhibited tip burn. In sharp contrast, only 40% of the 15-2-96-13 plants showed tip burn and none of the 14-2-24-5 plants showed tip burn at harvest (FIG. 11). This was a remarkable difference in the new PPO mutant variety.

Figure 12:
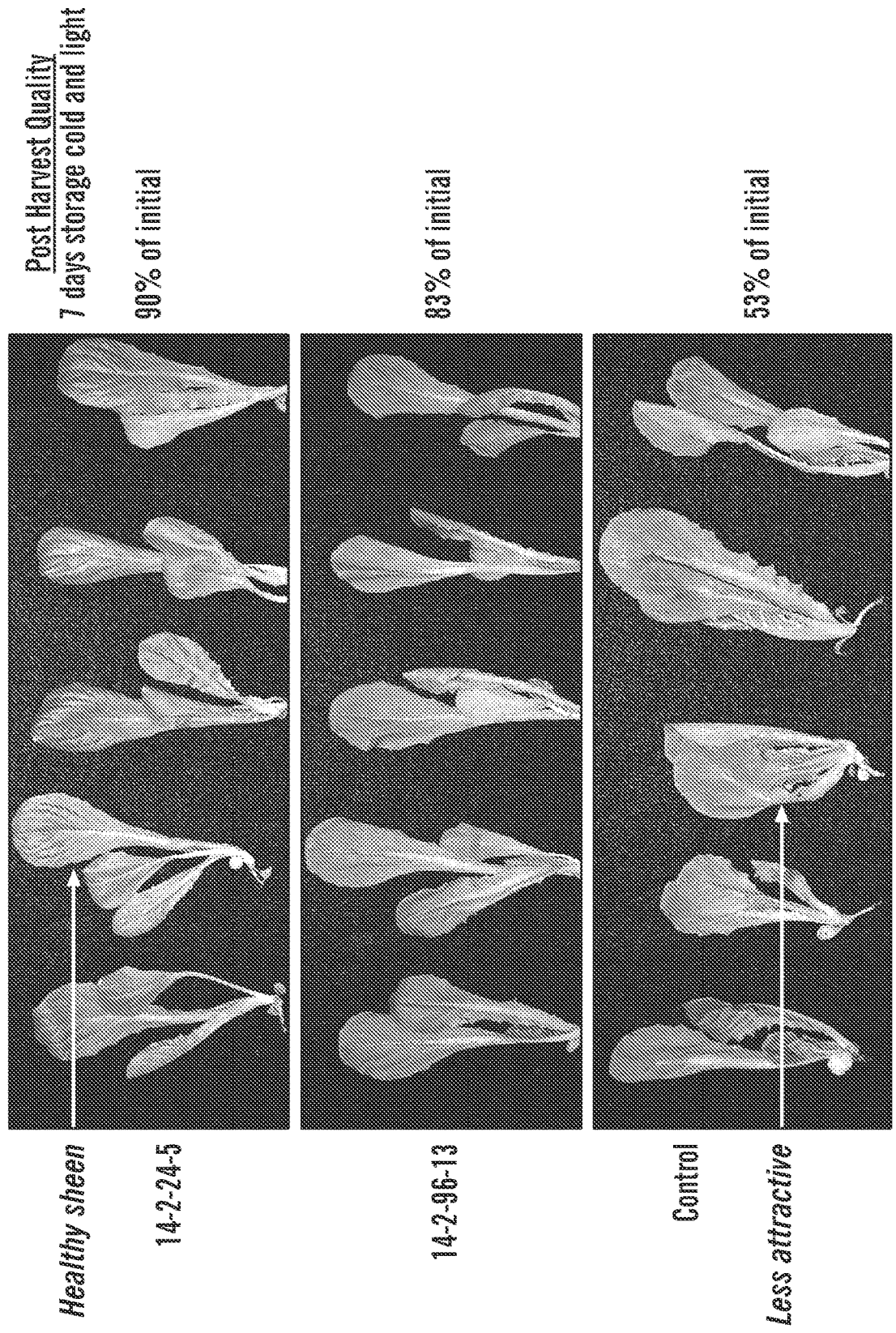
FIG. 12 provides photographic images of T3 plants 14-2-24-5 and 14-2-96-13 compared to unmodified Isogenic control lettuce after 7 days of cold storage and light. A significant percentage of 14-2-24-5 and 14-2-96-13 plants appeared healthy and saleable, while only 53% of the control lettuce appeared attractive.

Plants were assessed 7 days post-harvest after storage under optimal conditions. While only 53% of the control plants maintained a healthy sheen and appearance from day 0, 83% of 14-2-96-13 plants and 90% of 14-2-24-5 plants maintained their healthy sheen and appearance (FIG. 12).

Figure 13:
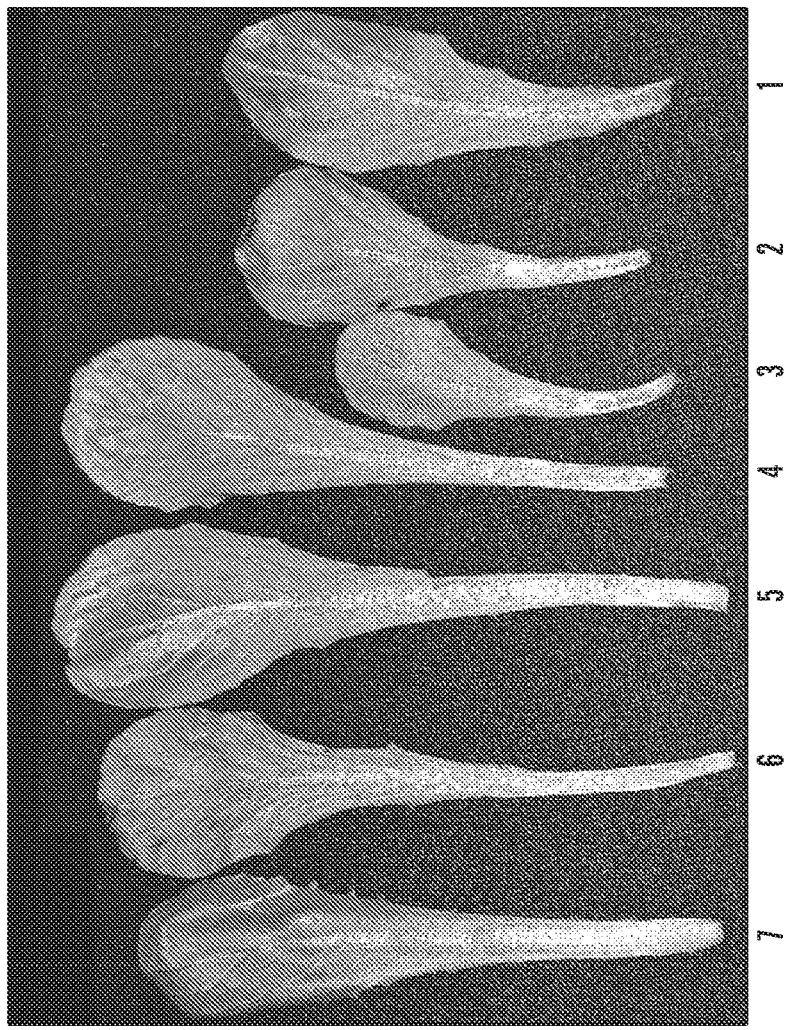
FIG. 13 provides photographic images showing the scale and representative leaves for rating appearance of lettuce leaves.
Figure 14:
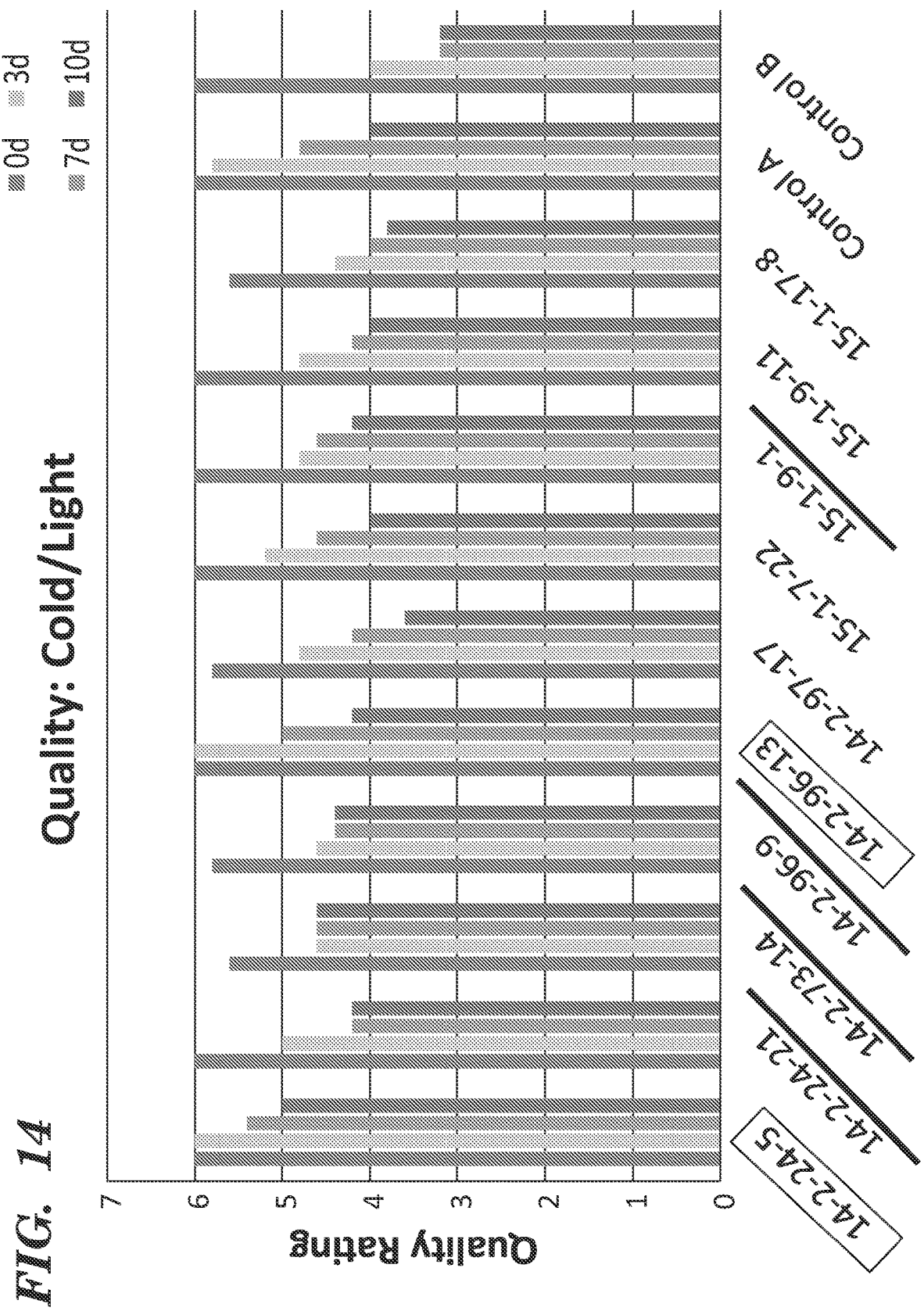
FIG. 14 is a graph assessing browning by overall quality of indicated plant lines at harvest (day 0), and days 3, 7, and 10 post-harvest stored in cold/light conditions. Underlined lines showed better qualities over time than control. Boxed lines showed optimal results.
Figure 15:
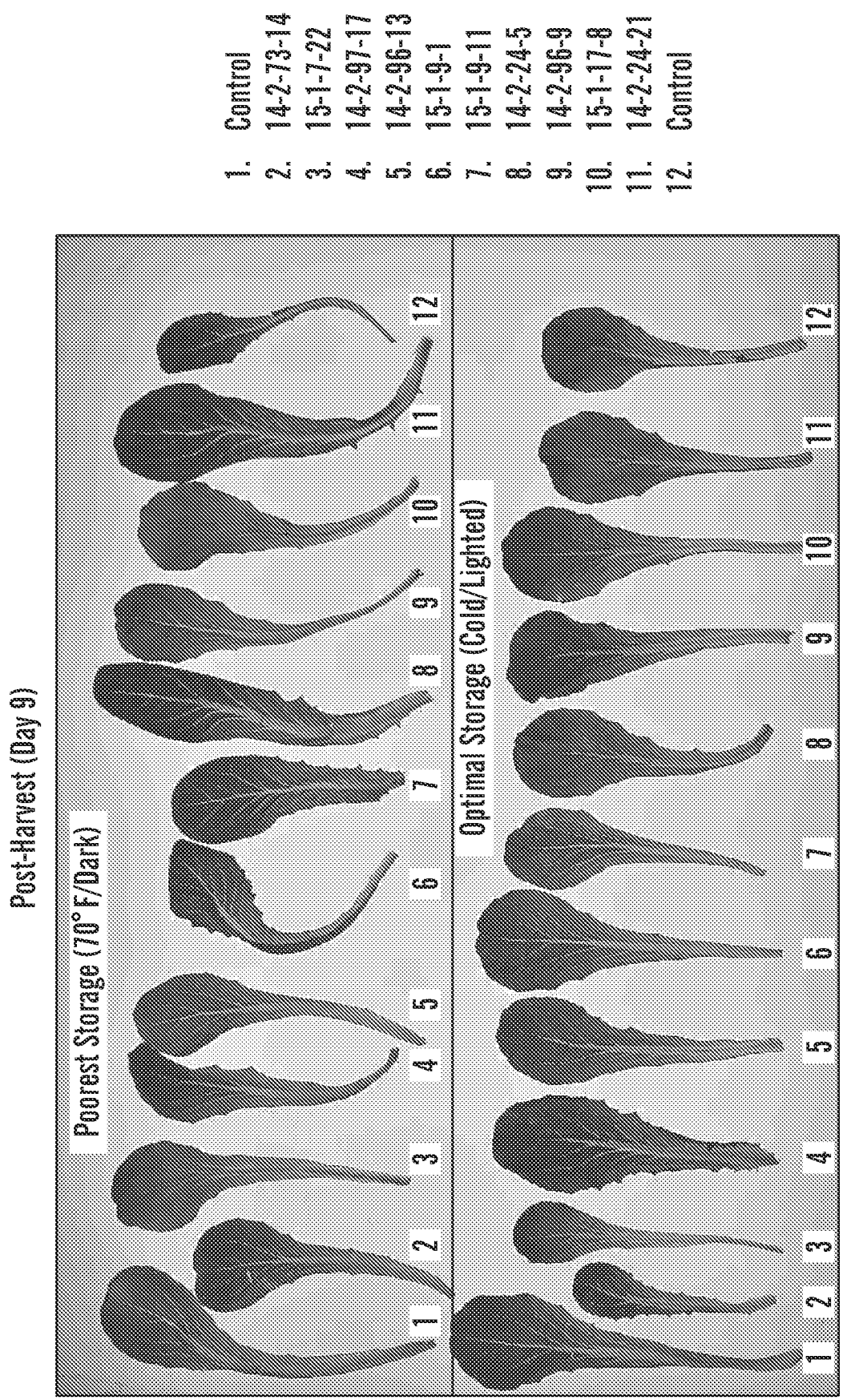
FIG. 15 provides photographic images showing a comparison of the indicated plant lines at 9 days post-harvest in poor conditions (70° F./dark) (top panel) and in optimal storage conditions (cold/light) (bottom panel).
Figure 16:
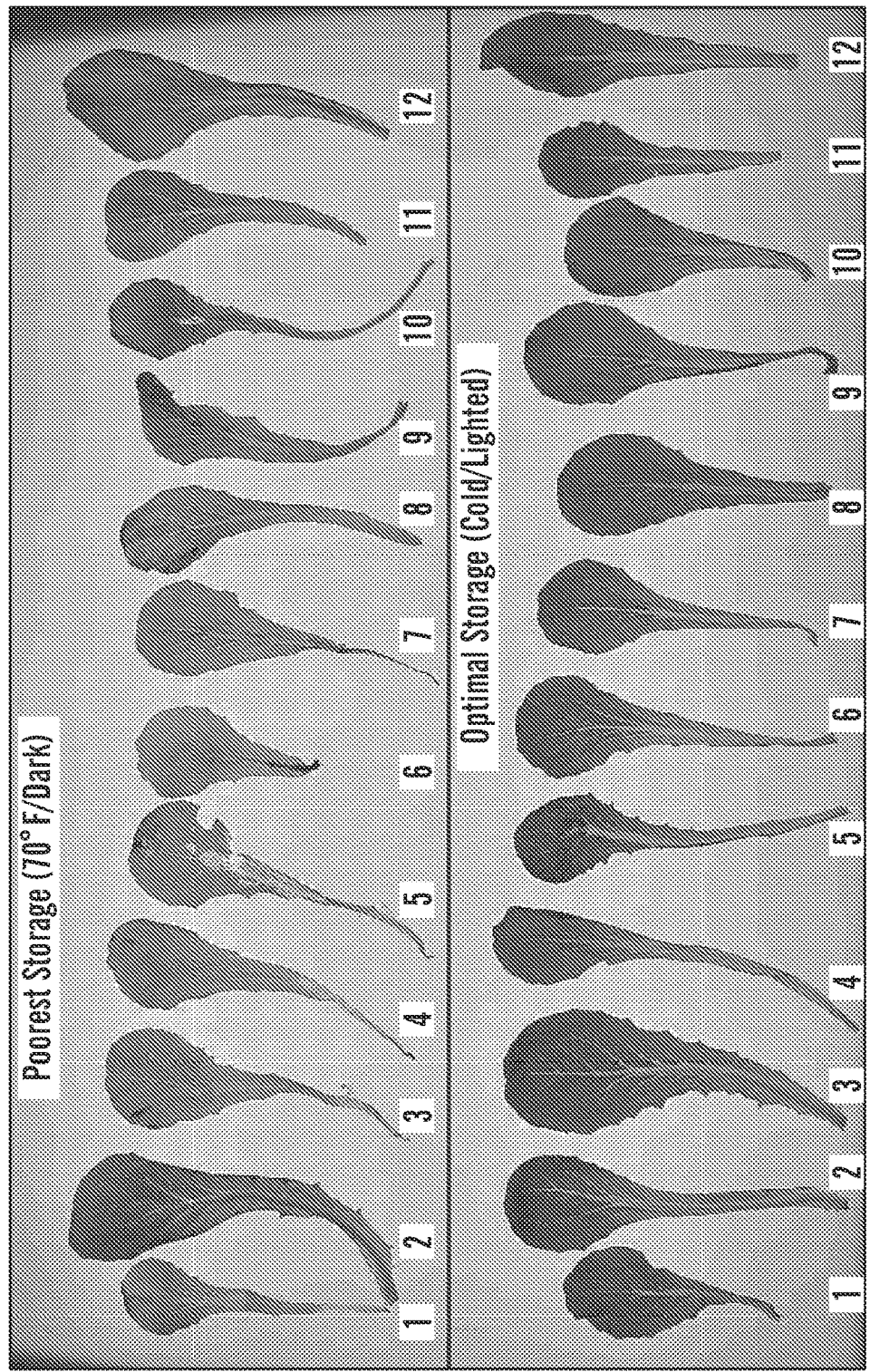
FIG. 16 provides photographic images showing a comparison of the indicated plant lines at 14 days post-harvest in poor conditions (70° F./dark) (top panel) and in optimal storage conditions (cold/light) (bottom panel).
Figure 17:
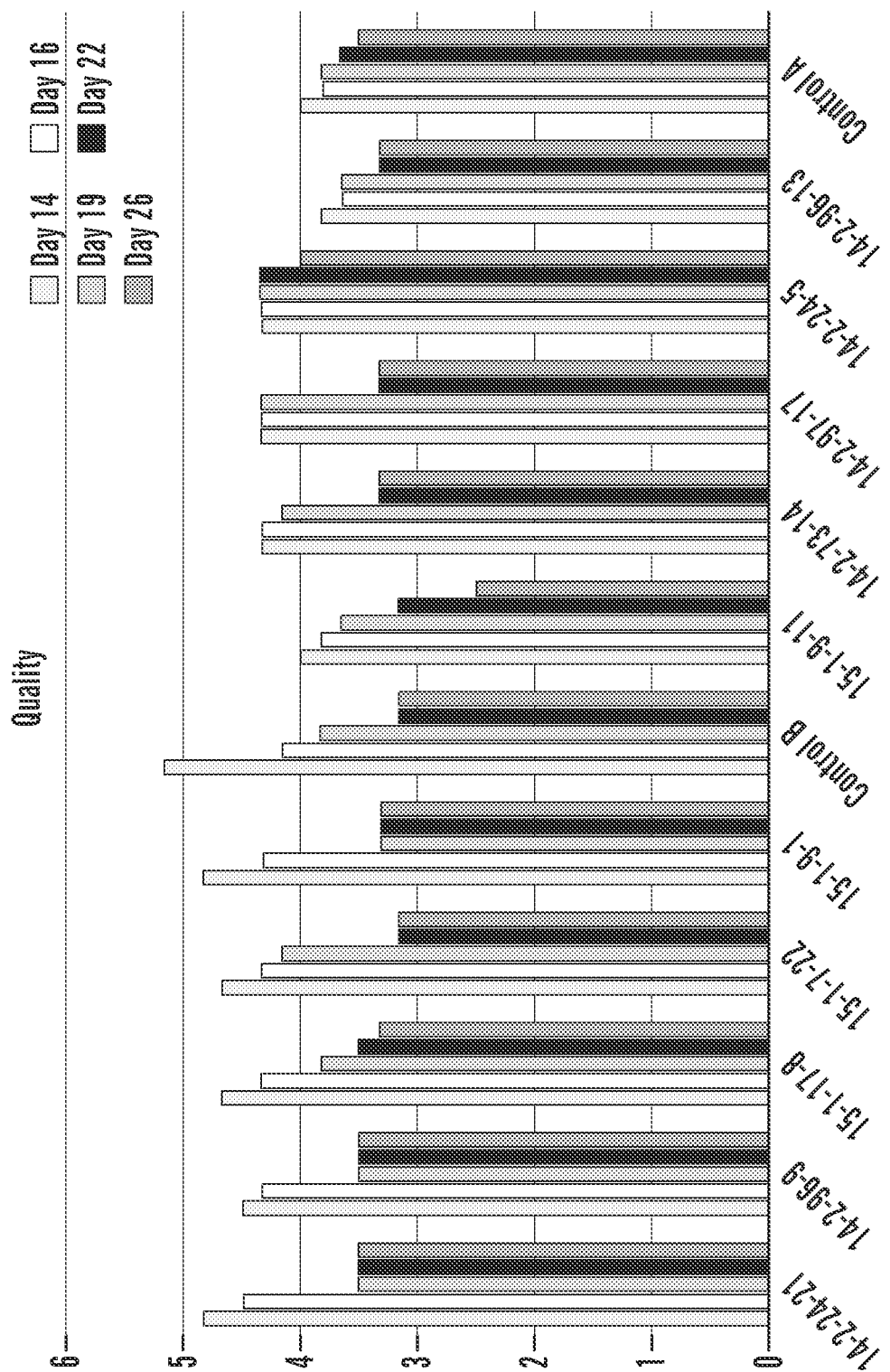
FIG. 17 shows a pair of graphs assessing browning by overall quality (left) and midvein quality (right) for the indicated plant lines at days 14, 16, 19, 22, and 26 post-harvest.
Figure 17:
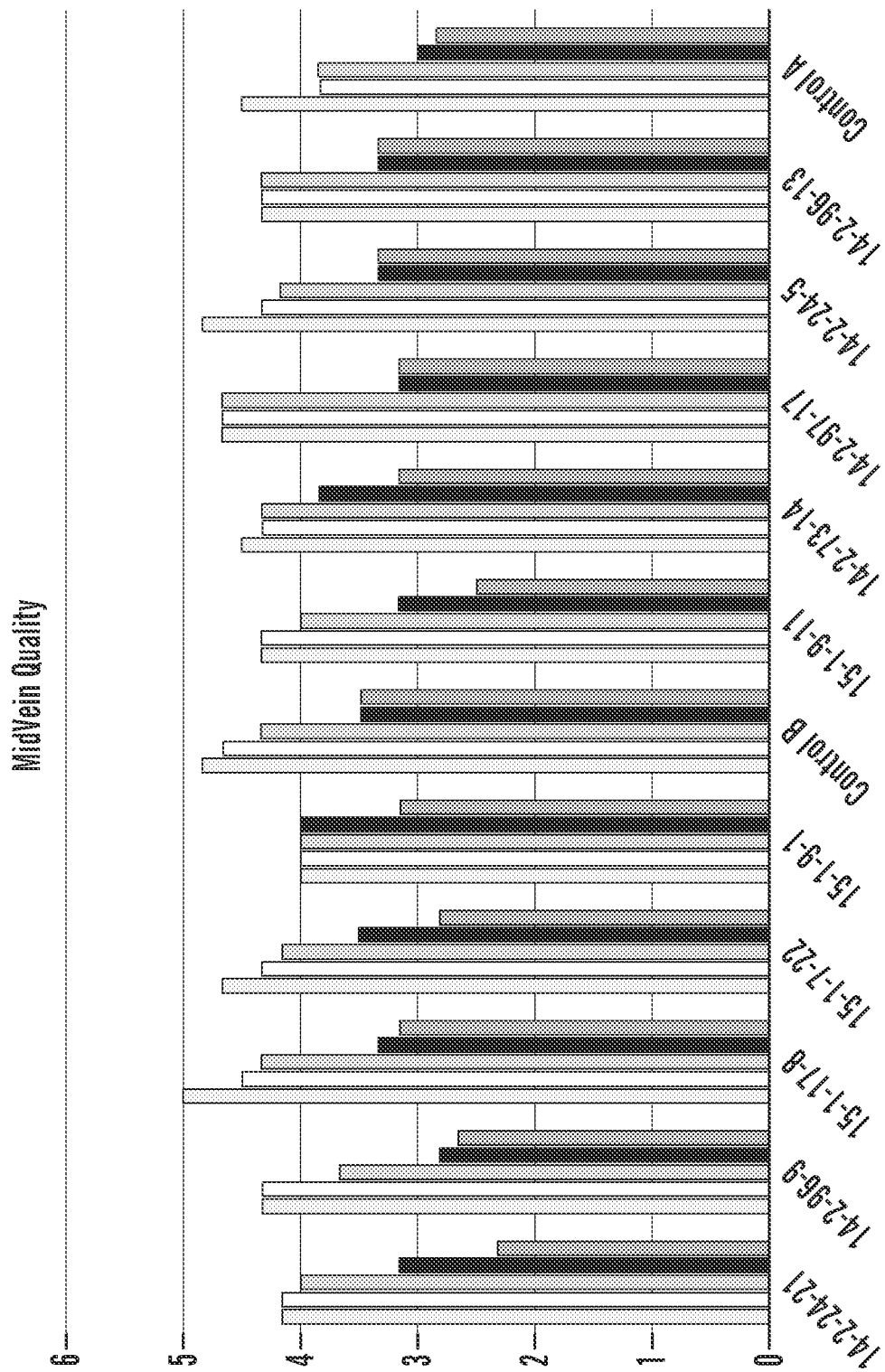
Figure 18B:
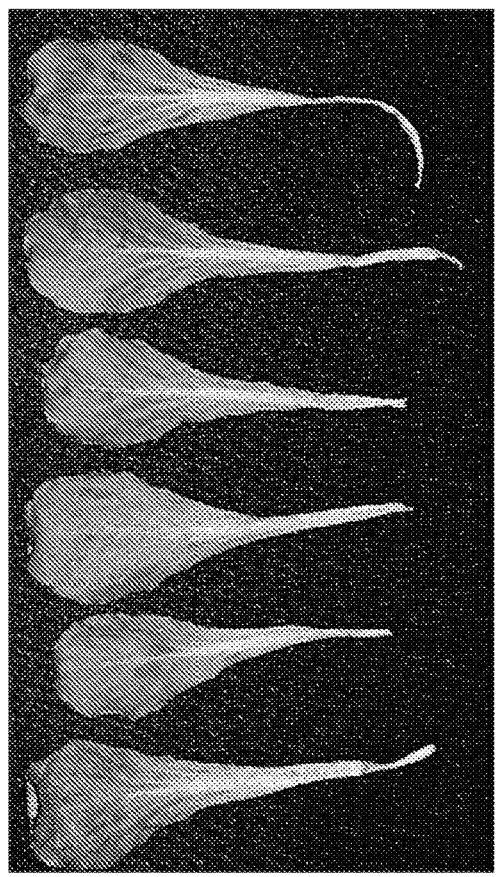
FIGS. 18A-B are photographic images showing 14-2-24-5 leaves (FIG. 18A) and control Isogenic leaves (FIG. 18B) after 26 days in cold and light storage.
Figure 18A:

To assess the appearance of the plants, a rating system shown in FIG. 13 (right) was used in which the plants were rated on a 1-7 scale. Examples of leaves exemplary of each rating are shown in FIG. 13 (left). The quality of each of the modified lines and the control lines were assessed at harvest (day 0) and at days 7 and 10 post-harvest after storage under optimal conditions using the 1-7 rating scale. The results are shown in FIG. 14. The PPO mutant lines that are boxed showed the best overall appearance, and the underlined PPO mutant lines also showed good appearance as compared to the control plants through day 10 post-harvest. A comparison of examples of leaves from the PPO mutant lines and the control is shown in FIG. 15 under poorest conditions (top panel) and optimal conditions (bottom panel) at day 9 post-harvest. FIG. 16 shows examples of leaves of the PPO mutant lines and control plant under poorest conditions (top panel) and optimal conditions (bottom panel) at day 14 post-harvest. FIG. 17 shows the assessment of overall quality (left) and midvein quality (right) of control and PPO mutant plants as days 14, 16, 19, 22, and 26 post-harvest. The best PPO mutant lines were 14-2-24-5 and 14-2-95-13. Examples of the leaves of 14-2-24-5 plants and control plants at day 26 post-harvest under optimal conditions is shown in FIG. 18A and FIG. 18B, respectively.

Example 7—Shelf Life Assessment

Six lines of lettuce that had been edited to knockout PPO genes were selected along with one unmodified parental control to determine the effect of PPO knockout mutations on shelf life of the modified lettuce. The selected varieties were GVR-110 (14-2-96-13) with PPO-A, PPO-B, PPO-D, PPO-E, PPO-G, and PPO-S knockout mutations; GVR-108 (14-2-24-5) with PPO-B, PPO-D, PPO-E, PPO-G, and PPO-S knockout mutations; GVR-105 (15-1-9-11) with PPO-B, PPO-G, and PPO-R knockout mutations; GVR-107 (14-2-24-21) with PPO-B, PPO-D, PPO-E, PPO-G, and PPO-S knockout mutations; GVR-101 (15-1-9-1) with PPO-B, PPO-G, PPO-R, and PPO-S knockout mutations; and GVR-102 (14-2-73-14) with PPO-A, PPO-B, PPO-D, PPO-E, and PPO-S knockout mutations. Clamshell packages containing either a selected line or a control lettuce were stored in a cool room with light. Triplicate clam shells were opened on 3 days (12, 20, and 28 days post-harvest) and scored.

Lettuce with each clamshells were scored on a qualitative basis across several categories, including: off odor, typical aroma, moisture, texture, leaf color, decay/mold, cut edge discoloration, and taste. A total score is an overall rating from the 9 individual scores: 0-5 is product is of excellent quality; 6-8 is product is of very good quality; 9-12 is product is of acceptable quality; 13+ product is of unacceptable quality.

Figure 20:
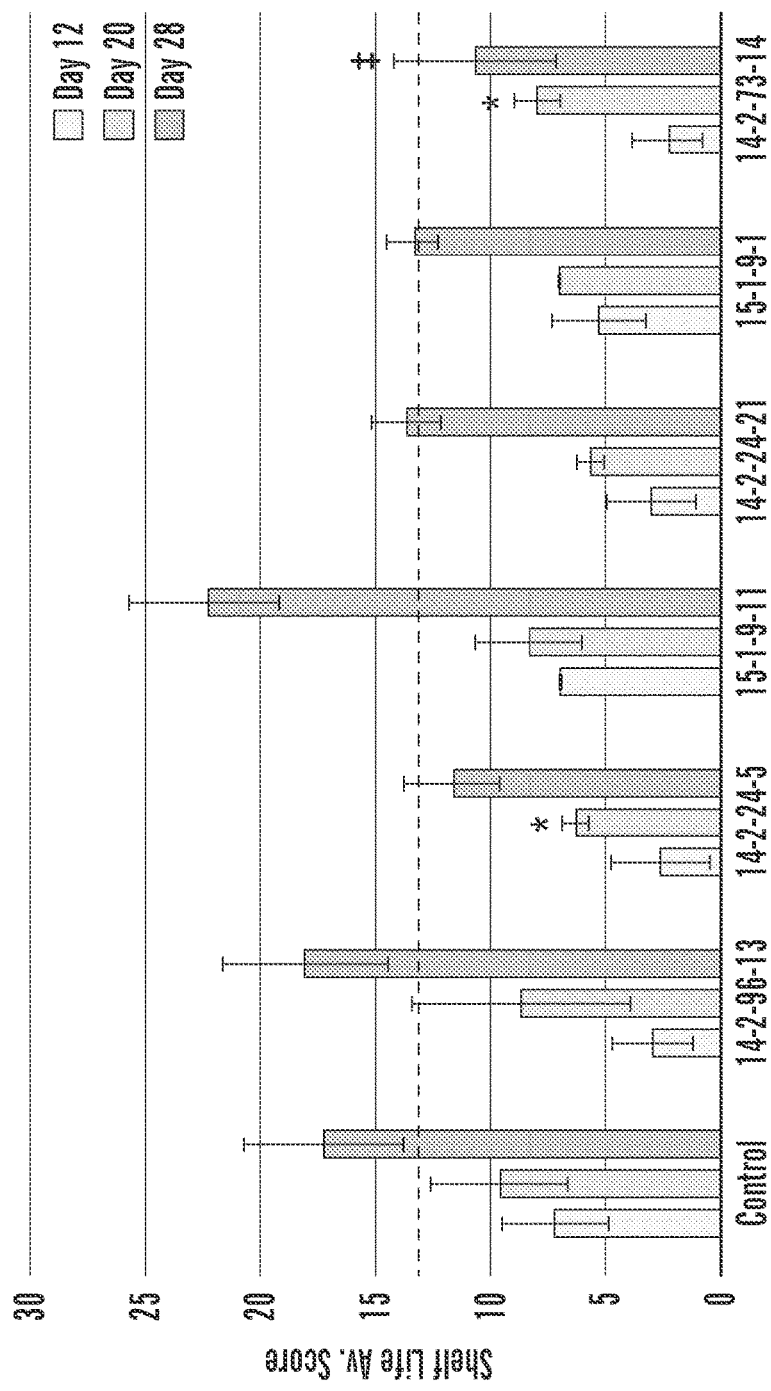
FIGS. 20A-B show the shelf life assessment of lines of lettuce as compared to control over days 12, 20, and 28 post-harvest.

As shown in FIG. 20A, at Day 12 post-harvest, the control and all PPO mutant lines had acceptable shelf life (a shelf life score of less than 13 as shown by the dashed line). At Day 20, the control and all PPO mutant lines had acceptable shelf life scores with lines 14-2-24-5 and 14-2-73-14 having statistically significantly better shelf life scores than the control (*). On Day 28, only PPO mutant line 14-2-73-14 had a statistically significantly better score than the control (‡). FIG. 20B shows the projected number of days that each PPO mutant line would have a shelf life score below 13 (i.e., an "acceptable" score), and the number of days of shelf life improvement over control. PPO mutant lines 14-2-24-5, 14-2-24-21, 15-1-9-1, and 14-2-73-14 each had more than 1 day projected to be added to the shelf life over control, and lines 14-2-24-5 and 14-2-73-14 each had more than 8 days projected to be added to shelf life.

Example 8—Browning Assay

Figure 21:
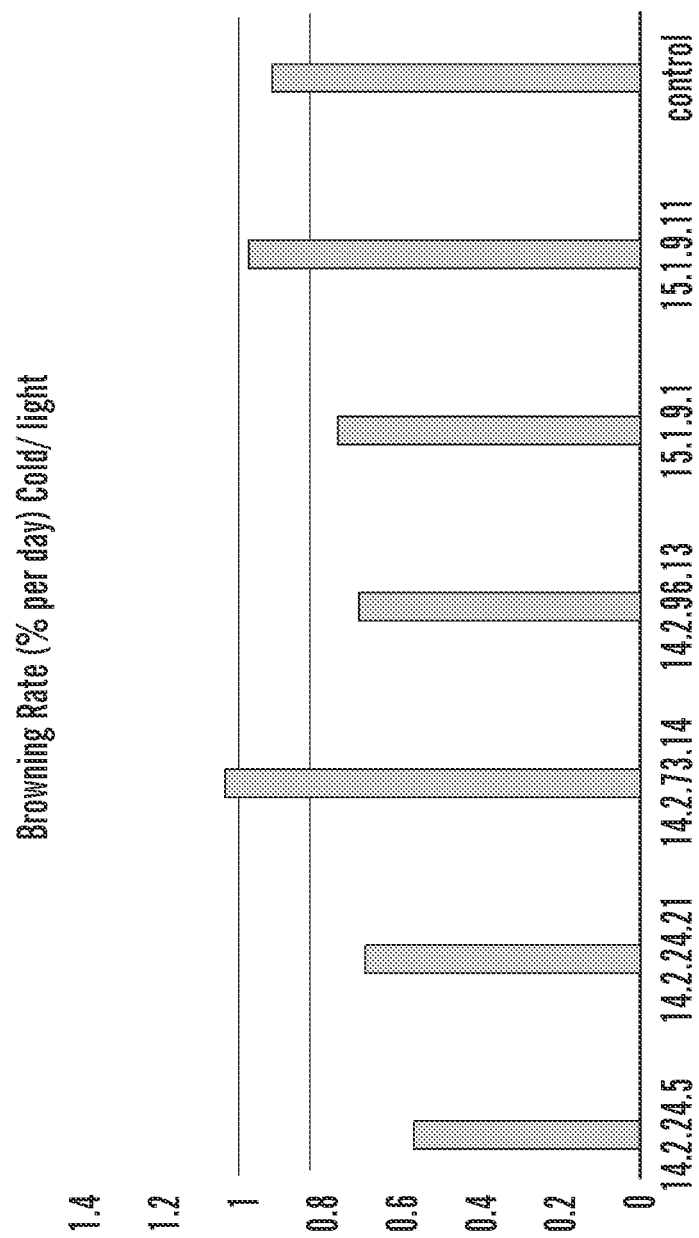
FIG. 21 is a graph showing the browning rate as a percentage per day under cold/light conditions for 6 lines and 1 control lettuce; gray lines represent the standard deviation of 4 replicates of control and 1% is the maximum value.
Figure 22:
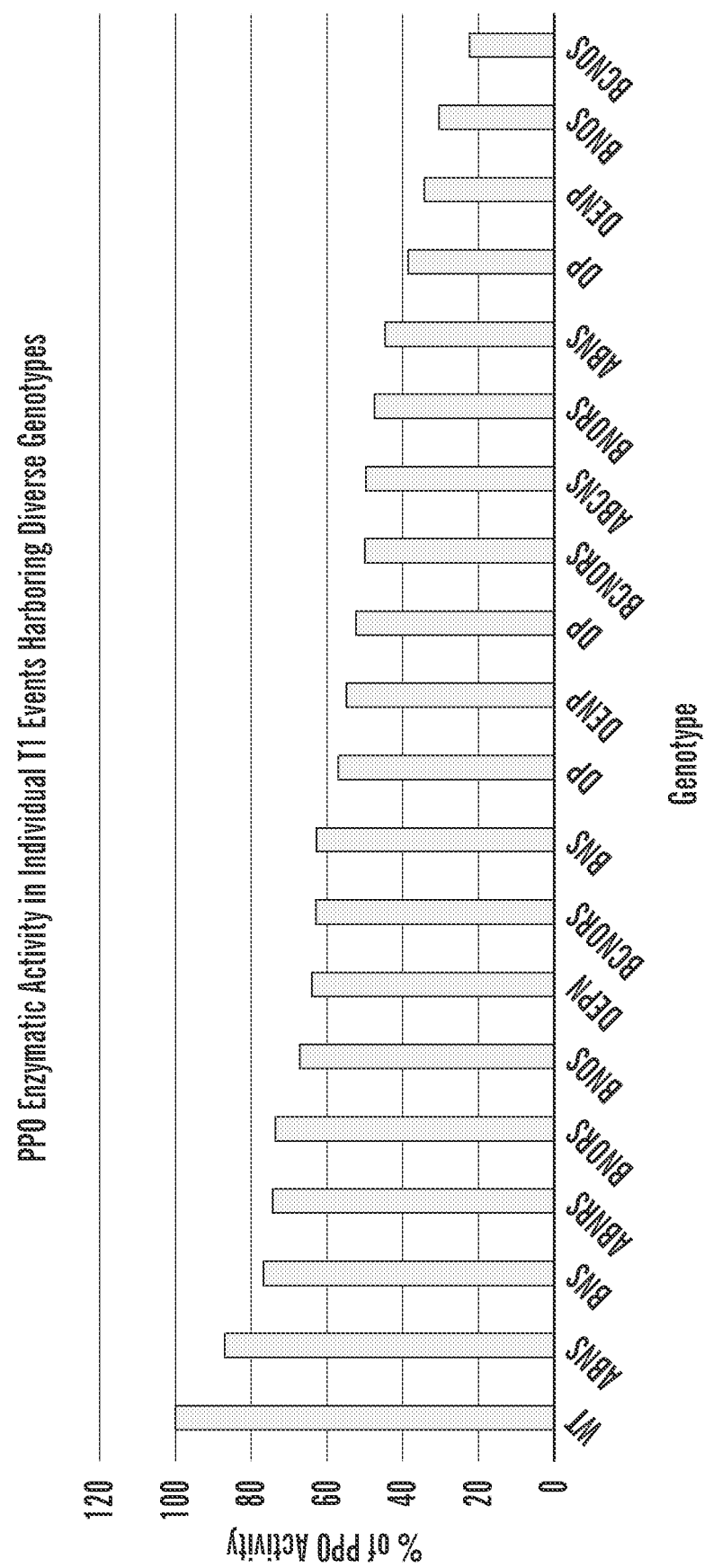
FIG. 22 is a graph showing % PPO activity in lettuce lines with various PPO gene mutation combinations compared to wild type isogenic controls.

An assay was performed on punched out portions of leaves from each of the 6 PPO mutant lines in Example 7 by examining both area and color intensity of browning across the leaf disk under conditions of cold and light. Four replicates were made for each PPO mutant line and control. The plot shown in FIG. 21 shows the browning rate per day of each PPO mutant line as compared to the control. The grey lines on represent the standard deviation of the control. The graph shows that four of the PPO mutant lines (14-2-24-5, 14-2-24-21, 14-2-96-13, and 15-1-9-1) showed less browning than the control. Leaf discs of 5/16 inch in size were harvested, incubated under cold/light, and browning rate measured using the WinDIAS machine vision system.

Example 9—High Vitamin Levels and Vitamin Retention in PPO Mutant Lines

PPO mutant lines retained more vitamins after harvest than conventional varieties. PPO mutant lines were grown under both indoor aeroponic (Trial 5) and outdoor field conditions (Trials 1-4, and 6) and tested for vitamin content (Table 9). Trial 1 was field grown lettuce from spring in Salinas, CA, measured at full maturity harvest. Trial 2 was aeroponic grown lettuce in Davis, CA, measured at 21 days after planting. Trial 3 was aeroponic grown lettuce in Davis, CA, measured at 21 days after planting. Trial 4 was outdoor grown lettuce from winter in Yuma, AZ, measured at full maturity harvest. Trial 5 was aeroponic grown lettuce by a partner, measured at 21 days after planting. Trial 6 is outdoor grown lettuce from spring in Salinas, CA, measured at full maturity harvest. In each trial, PPO mutant lines selected from GVR-102 (14-2-73-14), GVR-105 (15-1-9-11), GVR-107 (14-2-24-21), GVR-108 (14-2-24-5), and/or GVR-110 (14-2-96-13) were grown with control lines having no PPO mutations and, in some trials, additional commercial lines (e.g., Red Romaine and/or Isogenic commercial ("GF com"), Trials 4 and 5). Vitamin A was measured in each trial and vitamins C, E, K and folate were measured in a subset of trials. Measurements were taken at two time-points in Trial 5, at harvest and after 21 days of a shelf life study described in Example 13, infra.

TABLE 9

Methods Used for Proximate Analysis

| Analysis | Method |
|---|---|
| Proximate | |
| Protein | AOAC 981.10 |
| Fat | AOAC 960.39 |
| Moisture | AOAC 925.10 |
| Ash | AOAC 923.03 |
| Carbohydrates | Calculated |
| Calories | Calculated |
| Minerals | EPA 7000B |
| K | |
| Vitamin A | AOAC 2001.13 |
| Vitamin K | AOAC 999.15 (HPLC with PCR/FD method) |
| Folate | internal method N248 (based on USP29) |
| Dietary Fiber | AOAC 991.43 |

Most PPO mutant lines, especially GVR-108 and GVR-110, had higher levels of vitamin A compared to control lines in every trial (Table 10). In many trials, PPO mutant lines had double the amount of vitamin A compared to the control line. In trial 5, all of the PPO mutant lines retained double the amount of vitamin A compared to the control at 21 days post-harvest as shown by the second value. The values labeled with an asterisk (*) are significantly higher than the Isogenic control.

Vitamin C was higher in PPO mutant line GVR-110, especially, compared to the Isogenic controls in multiple trials. Vitamin C was retained in some PPO mutant lines after storage (Trial 4). Vitamin E and vitamin K was higher in most PPO mutant lines than controls as well. Folate was higher in the field grown PPO mutant lines compared to the controls in 2 of 3 trials, and GVR-110 had higher folate in all three trials. PPO mutant lines had higher levels of vitamins than control lines and retained more vitamins after storage.

TABLE 10

Vitamin Levels in PPO Mutant Lines and Controls (WT)

| | Sample | Vitamin A (IU/100 g) | Vitamin C (mg/100 g) | Vitamin E (IU/100 g) | Vitamin K (mg/100 g) | Folate (mg/100 g) |
|---|---|---|---|---|---|---|
| Trial 1 | GVR-102 (73.14) | 1177 | | | .126 | .400 |
| (K) | GVR-105 (9.11) | 1353 | | | .202 | .434 |
| | GVR-110 (96.13) | 2200 | | | .130 | .558 |
| | WT | 695 | | | 0 | .266 |
| Trial 2 | GVR-102 (73.14) | 3873 | 1.1 | 0.475 | | |
| (A1) | GVR-105 (9.11) | 3370 | 1.3 | 0.475 | | |
| | GVR-110 (96.13) | 3878 | 3.1 | 0.225 | | |
| | WT | 3355 | 1 | 0.275 | | |
| Trial 3 | GVR-107 (24.21) | 2808 | | | | |
| (A2) | GVR-108 (24.5) | 2940 | | | | |
| | WT | 2863 | | | | |
| Trial 4 | GF Com | 503 | 0.1 | | 0.3 | 0.025 |
| (N) | GVR-102 (73.14) | 947 | 0.2 | | 0.9 | 0.024 |
| | GVR-105 (9.11) | 567 | 0.0 | | 0.4 | 0.030 |
| | GVR-107 (24.21) | 1410 | 0.1 | | 1.2 | 0.039 |
| | GVR-108 (24.5) | 1293 | 0.2 | | 2.1 | 0.041 |
| | GF | 1037 | 0.1 | | 1.0 | 0.043 |
| | GVR-110 (96.13) | 1183 | 0.4 | | 2.5 | 0.049 |
| Trial 5 | Red Romaine | 3934/390 | 470/>10 | 141/157 | | |
| (AF) | GVR-102 (73.14) | 5556/535* | 342/>10 | 112/112 | | |

TABLE 10-continued

Vitamin Levels in PPO Mutant Lines and Controls (WT)

| Sample | Vitamin A (IU/100 g) | Vitamin C (mg/100 g) | Vitamin E (IU/100 g) | Vitamin K (mg/100 g) | Folate (mg/100 g) |
|---|---|---|---|---|---|
| GVR-107 (24.21) | 5676/405* | 378/381* | 111/102 | | |
| GVR-108 (24.5) | 5345/429* | 431/395* | 115/113 | | |
| GVR-110 (96.13) | 6757/369 | 445/360* | 109/55 | | |
| GF | 5946/156 | 398/>10 | 100/104 | | |
| GVR-102 (73.14) | 980 | | | | 0.0131 |
| GVR-108 (24.5) | 1200 | | | | 0.0219 |
| GVR-110 (96.13) | 1850 | | | | 0.0258 |
| WT | 230 | | | | 0.0111 |

Example 10—Lettuce Processing Evaluation for Visual Quality

Lettuce was grown in an open field in Salinas, CA during spring of 2020, harvested, and tested for shelf life. Two to three heads of lettuce from PPO mutant line (GVR-110) and control variety (Isogenic) were removed from the cold room immediately prior to processing. Lettuce was trimmed (outer leaves or broken leaves and tops and butts removed), halved, interior heart tissue removed, and remaining head quartered. Immediately after the head was halved, a photo was taken for maturity assessment. Lettuce was cut with a sharp knife into salad size pieces (approximately 2×2 cm) and then rinsed in 5° C. water containing 50 ppm sodium hypochlorite pH 7.0 for 20 seconds (~4 volumes water per weight lettuce), manually spun with a salad spinner with 40-50 revolutions, packaged in plastic bags (100-150 g per bag; 6×12×2 inches), and placed at 2.5° C. until all lettuce for that day was cut and packaged. These bags were completely randomized among the evaluation days and placed within 6 hours at 5° C. The above procedure was repeated for Blocks 2 and 3 on two subsequent days. There were three separate bags (replicates) for each evaluation time point.

Three bags per entry were evaluated the day of processing (day 0) and again after 7, 10, 14, 20, and 27 days (depending on quality). Lettuce pieces were evaluated for overall visual quality, discoloration on cut edges, decay, and any other defects or observations, with one score for the entire replicate bag. Photos were taken of the produce in each bag on each evaluation period.

Figure 23:
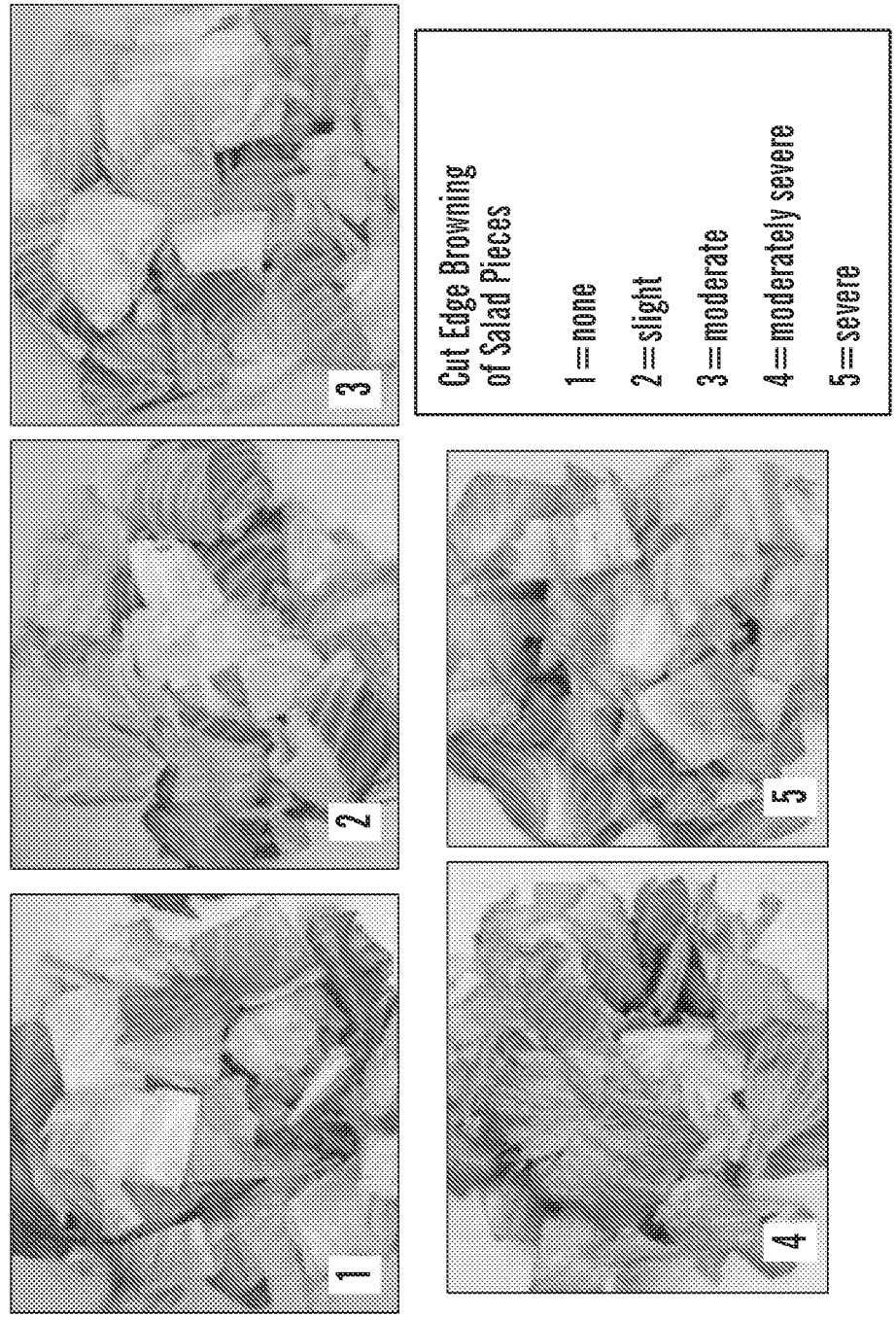
FIG. 23 is a group of photographic images and a rating scale used to score browning in cut lettuce pieces after storage.

Discoloration defects (leaf surface or stem and ethylene-induced) were scored on a 1 to 5 scale, where 1=none, 2=slight, 3=moderate, 4=moderately severe, and 5=maximum or severe (FIG. 23). This scale was referenced to digital color photographs. A single score was given per sample.

Overall visual quality was scored on a 9 to 1 scale, where 9=excellent, fresh appearance, 7=good, 5=fair, 3=fair (useable but not saleable), 1=unusable. Intermediate numbers were assigned where appropriate. One visual quality score was given to an entire sample. A score of 6 is considered the limit of marketability.

Figure 24A:
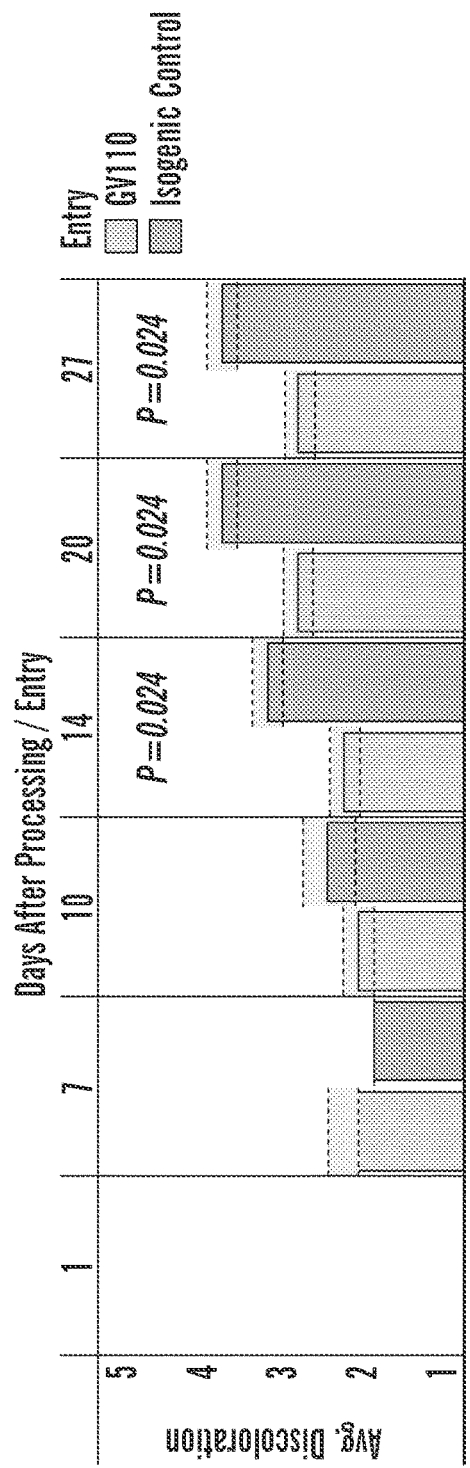
FIGS. 24A-B are graphs showing the results of a shelf-life study of PPO mutant line GVR-110 (14-2-96-13) ("GV110") compared to the control line, Isogenic.
Figure 24B:
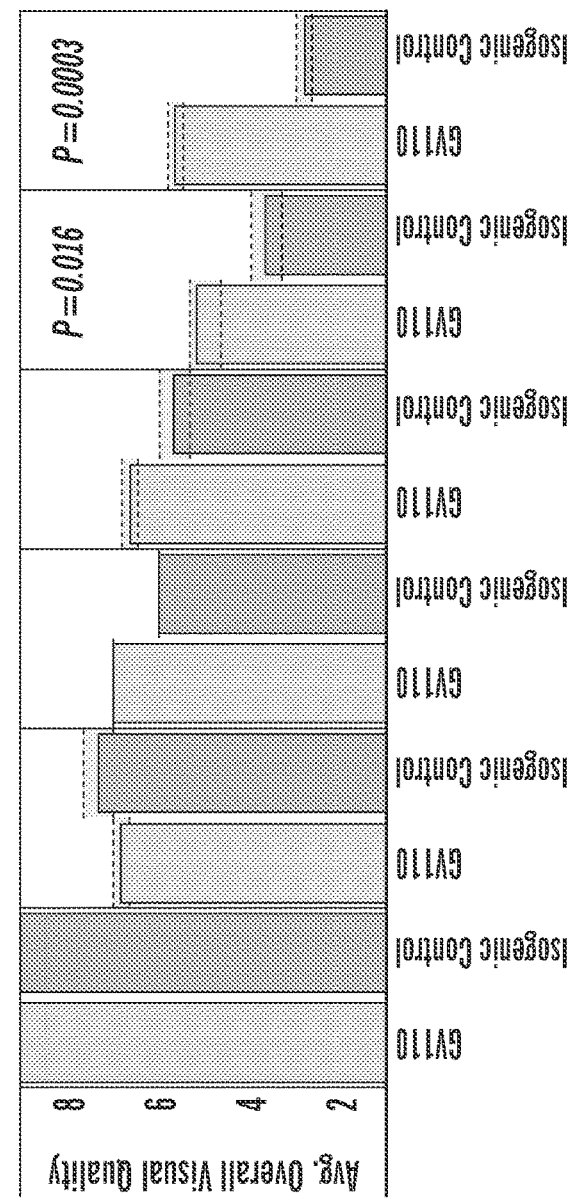

As shown in FIGS. 24A-B, PPO mutant line, GVR-110, outperformed the isogenic control line. The average discoloration of GVR-110 at 14, 20, and 27 days after processing was significantly lower than the control (P<0.024 at each time-point, FIG. 24A). The overall visual quality of PPO mutant line, GVR-110 remained high through 27 days after processing, retaining a score of almost 6 compared to Green Forest score of about 3 at the same stage (FIG. 24B). The improved visual quality of GVR-100 was significantly higher than the isogenic control at 20 days after processing (P<0.016) and 27 days after processing (P<0.0003).

Example 11—Retention of Polyphenolic Levels in PPO Mutant Lines

Figure 25:
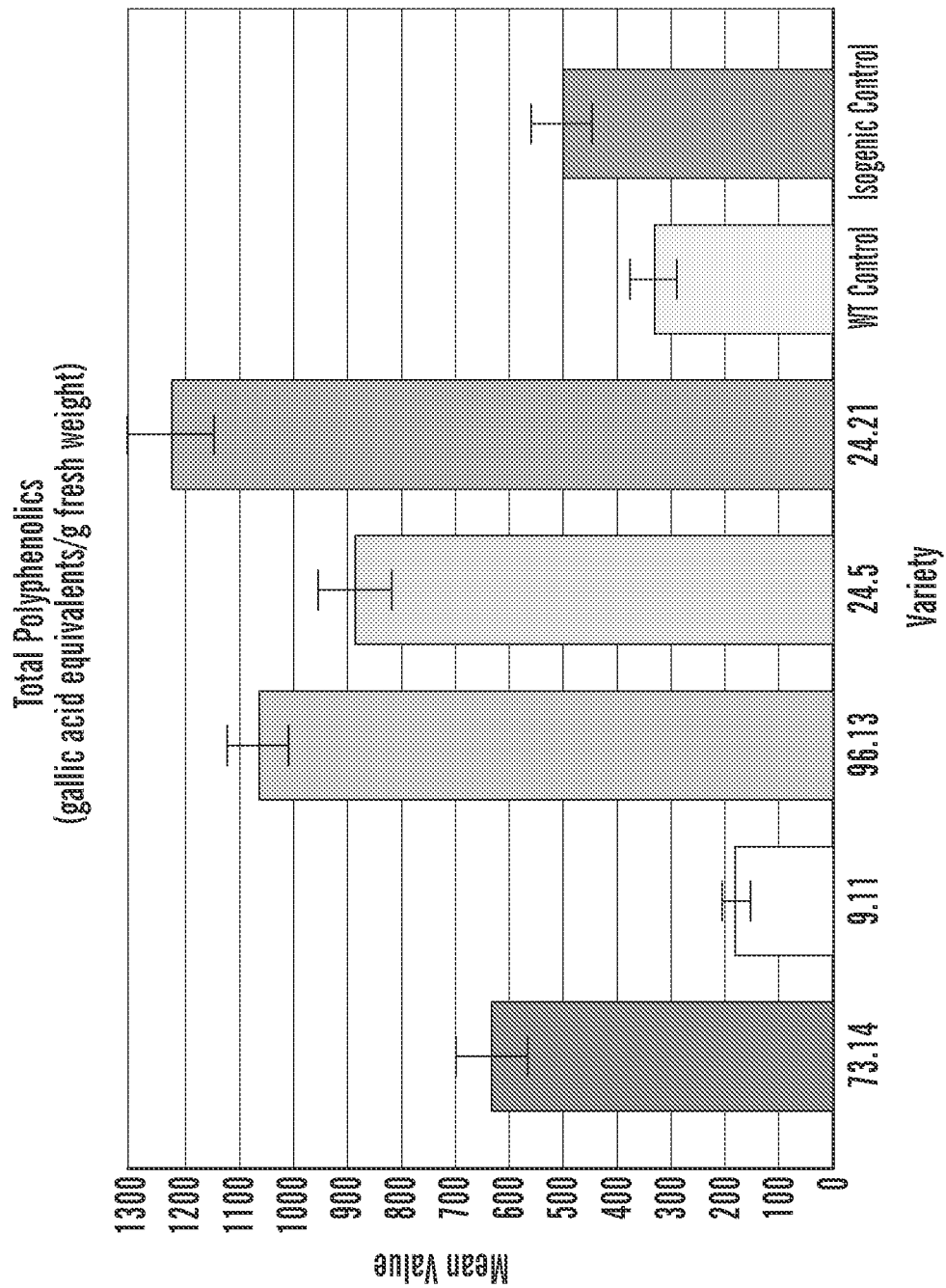
FIG. 25 is a graph showing the total polyphenolics levels in various PPO mutant lines compared to control lettuce lines.

Polyphenolic levels were measured using the Folin-Ciocalteu (F-C) method. In summary, seven millimeter leaf disks harvested in strip-tubes were flash frozen before being homogenized in 2 ml ice-cold 95% methanol in a Tissuelyzer for 5 minutes at 30 Hz. Samples were then incubated at room temperature for 48 hrs in the dark before microcentrifugation for 5 minutes at 13,000 g. One hundred microliter supernatant was collected in fresh microcentrifuge tubes to which 200 µl of 10% F-C reagent was added. After thorough vortexing, 800 µl of 700 mM of sodium carbonate was added and tubes were incubated for 2 hrs at room temperature before measuring the absorbance at 765 nm. Phenolic content was extrapolated using a gallic acid standard curve. Two days after harvest, PPO mutant lines had higher levels of polyphenolics compared to control lettuce lines (FIG. 25). Polyphenolic levels ranged from around 1210 gallic acid equivalents ("GAE")/g fresh weight ("gFW") in GVR-107 (14-2-24-21), to 1060 GAE/gFW in GVR-110 (14-2-96-13) and 890 GAE/gFW in GVR-108 (14-2-24-5) compared to only 310-500 GAE/gFW in controls.

Figure 26:
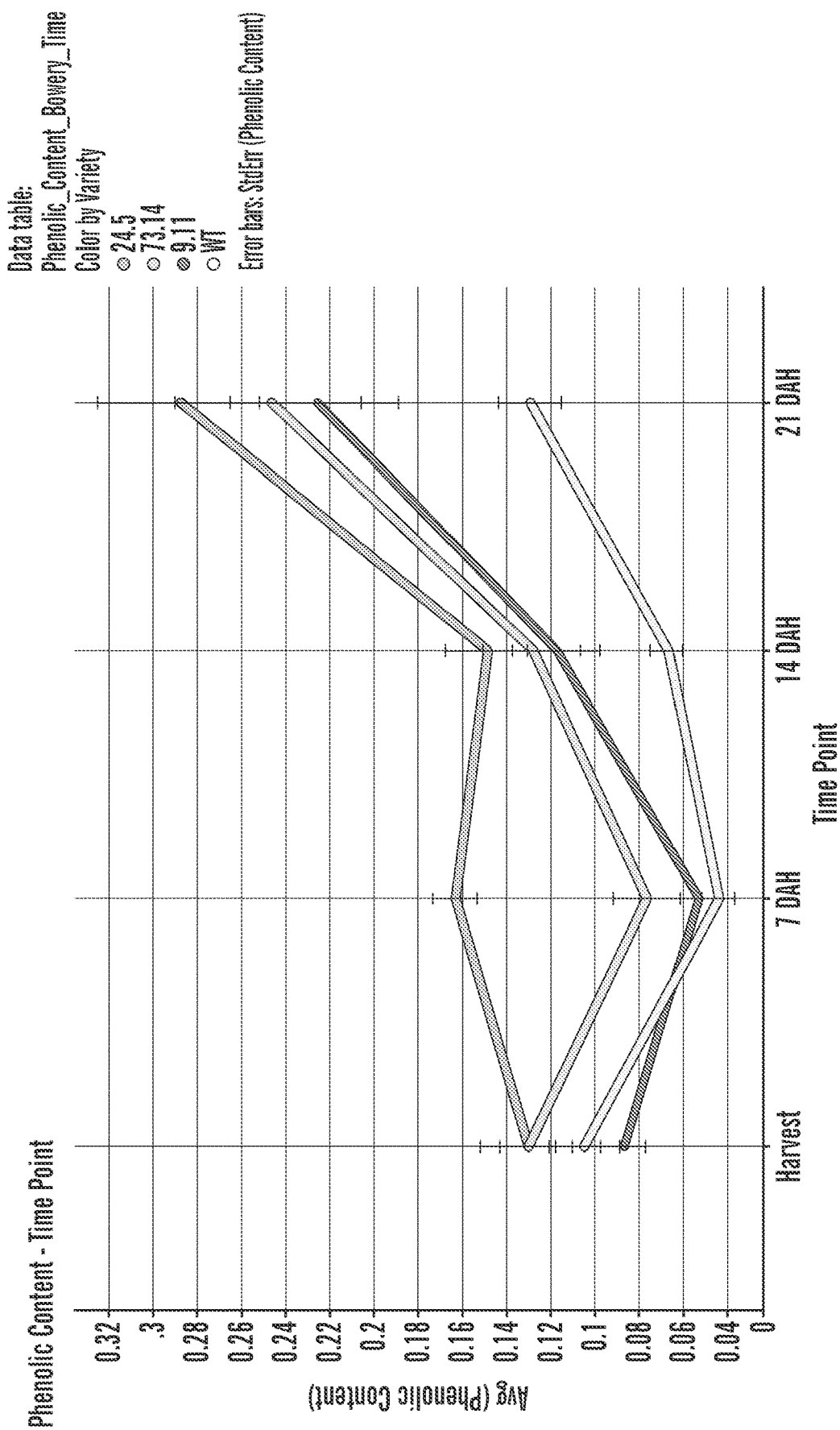
FIG. 26 is a graph showing the average polyphenolic levels over time (at harvest, and 7, 14, and 21 days after harvest ("DAH")) of PPO mutant lines 24-5, 76-14, and 9-11 compared to a wild type line.

An analysis of phenolic levels at harvest, and at 7, 14, and 21 days after harvest showed that PPO mutant lines retained high levels of phenolics over time (FIG. 26). PPO mutant line GVR-108 (14-2-24-5) had an average phenolic content of 0.13 at harvest, which increased to 0.16 at 7 and 14 days after harvest ("DAH"), and increased further to 0.29 at 21 DAH. In contrast, the control variety started at around 0.11 average phenolic content at harvest, decreased to less than 0.05 at 7 DAH, and then increased to 0.07 at 14 DAH and only reached 0.13 at 21 DAH.

Figure 27:
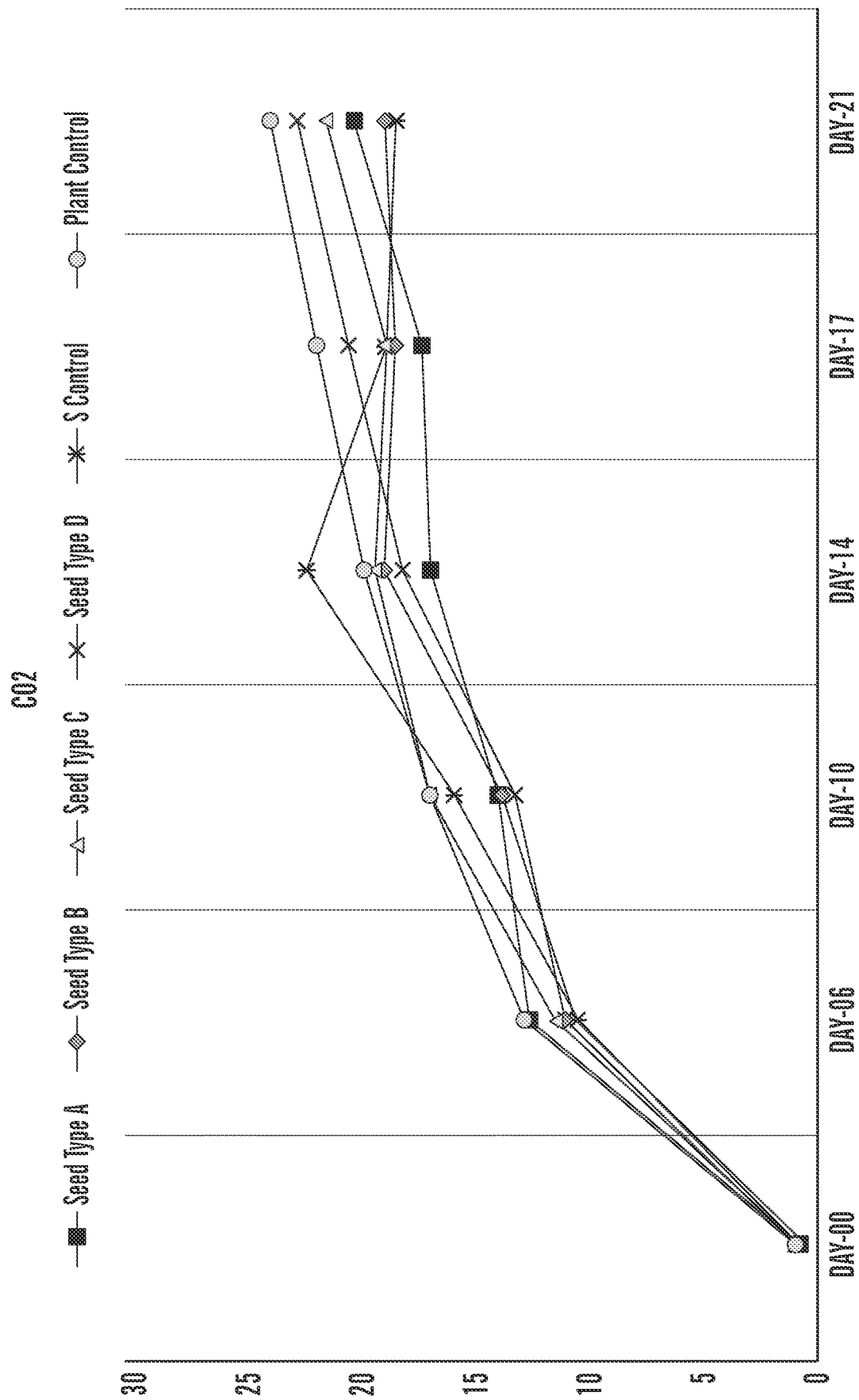
FIG. 27 is a graph showing $CO_2$ production due to fermentation of cut lettuce during a shelf life study at day 0, 6, 10, 14, 17, and 21 after processing. PPO mutant lines GVR-102 ("Seed Type A"), GVR-107 ("Seed Type B"), GVR-108 ("Seed Type C"), and GVR-110 ("Seed Type D") were evaluated for $CO_2$ production along with isogenic control ("Plant Control"), and a control supplied by the seed supplier ("S Control").

Example 12—Fermentation, Organoleptic Evaluation, and Nutritional Analysis of Field Grown PPO Mutant Lines Fermentation in PPO mutant lines compared to controls in chopped lettuce leaves after harvest was assessed by $CO_2$ production (FIG. 27). Lettuce heads from the field were harvested, trimmed, and cooled prior to transport to a commercial facility of a third party partner. The lettuce leaves were washed, dried, and packaged in 10 ounce Caesar romaine film with a gas flush using the partner's proprietary protocol. Samples were stored in a shelf life cage at 34° F. until day 6, and then transferred into a cooler at 40° F. and stored until expiration. Head space was analyzed for $CO_2$ at harvest (day 0) and at day 6, 10, 14, 17, and 21 days after harvest. PPO mutant lines GVR-102 ("Seed Type A"), GVR-107 ("Seed Type B"), GVR-108 ("Seed Type C"), and GVR-110 ("Seed Type D") were evaluated for $CO_2$ production along with isogenic control ("Plant Control"), and a control supplied by the seed supplier ("S Control") (FIG. 27). The control accumulated more $CO_2$ at each time point compared to the majority of the PPO mutant lines. The control had $CO_2$ levels of 24% by day 21 after harvest compared to only 19% for PPO mutant line GVR-107 (FIG. 27). Plant control samples at days 17-21 after processing were considered strongly fermented. There was only minor fermentation observed in PPO mutant lines GVR-102, 107, 108, and 110.

Figure 28:
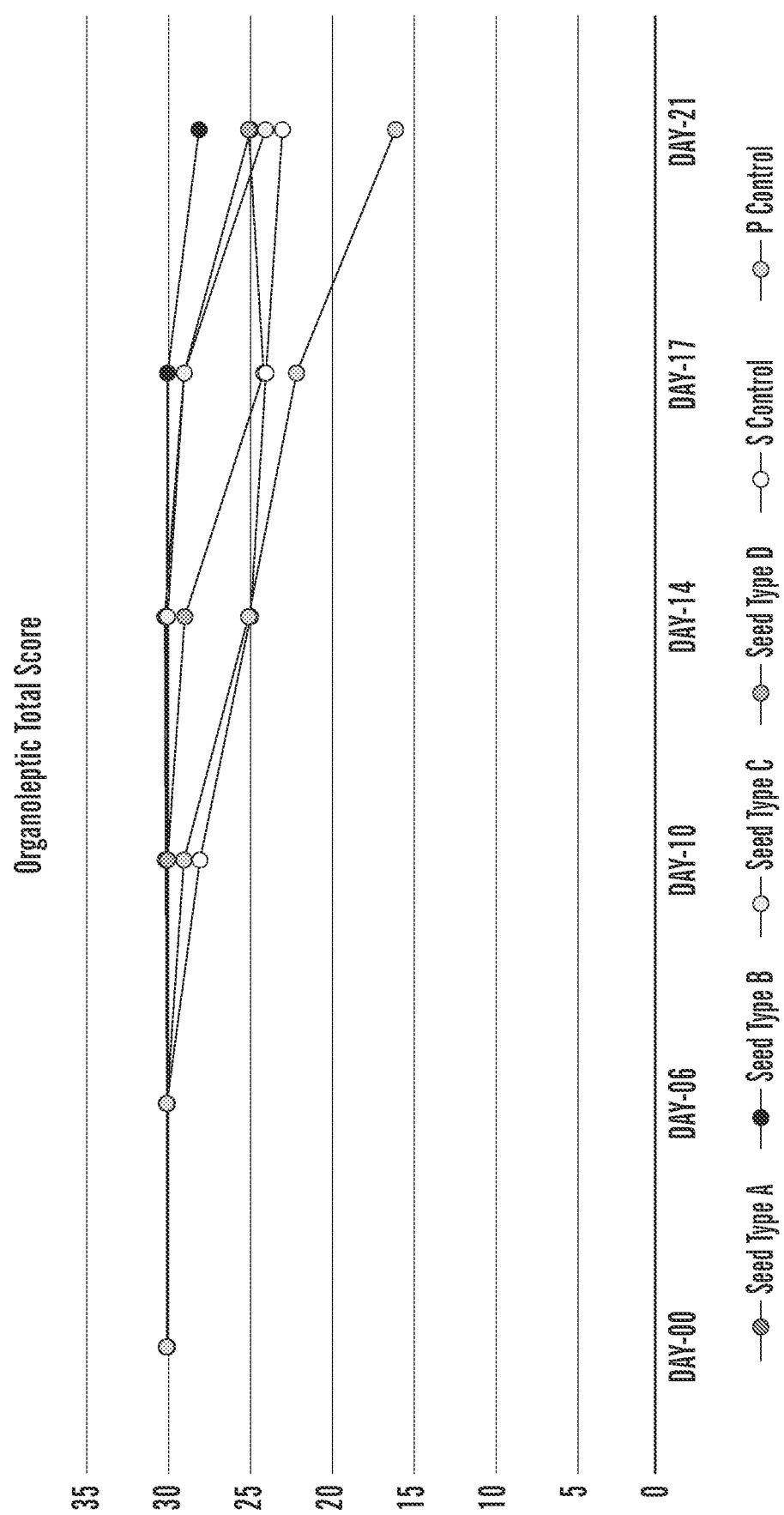
FIG. 28 is a graph showing the organoleptic total score of the same lines shown in FIG. 27 over the course of a shelf life study at day 0, 6, 10, 14, 17, and 21 after processing. PPO mutant lines GVR-102 ("Seed Type A"), GVR-107 ("Seed Type B"), GVR-108 ("Seed Type C"), and GVR-110 ("Seed Type D") were evaluated for organoleptic parameters along with isogenic control ("Plant Control"), and a control supplied by the seed supplier ("S Control").

The appearance, color, aroma, flavor, texture and moisture of the PPO mutant lines was tested and compared to the controls at day 0, 6, 10, 14, 17, and 21 days after processing. Each parameter was given a score of 1-5, with 5 being the best score and 1 the worst score. Six bags of lettuce were tested at each time point. The combined scores for each line tested at each time point over time is shown in FIG. 28. Plant control samples at days 17-21 after processing were strongly fermented, bruised and wet and looked poor overall (FIG. 28). All of the PPO mutant lines were considered edible and acceptable with no significant pinking or oxidation except minor fermentation at 21 days after processing.

A nutritional evaluation of GVR-102, GVR-108, and GVR-110 and a control was performed at day 30 after processing, and is shown in FIG. 29. As described in Example 9, the PPO mutant lines retained more vitamin A at 30 days after processing. PPO mutant lines also retained more carbohydrates in agreement with the reduction in fermentation seen in PPO mutant lines. Overall, carbohydrates were about 1.6 to 2-fold higher in PPO mutant lines compared to the control.

Example 13—Shelf Life Study of Aeroponic Grown PPO Mutant Lines

PPO mutant lines GVR-102 (14-2-73-14), GVR-107 (14-2-24-21), GVR-108 (14-2-24-5), and/or GVR-110 (14-2-96-13) were grown with an isogenic control line having no PPO mutations and also with a Red Romaine lettuce variety in flats aeroponically for 14 days using standard light intensity and spectrum. Each line was measured for shelf-life at 0, 7, 13, 21, and 27 days post-harvest. The lines were tested for organoleptic characteristics at 3, 7, 11, 17, and 21 days post-harvest. Vitamins were tested at harvest and at 21 days post-harvest as described in Example 9, supra (Trial 5 (AF)). Multispectral imaging using a Phenospex indicated no significant difference in green color for PPO mutant lines compared to the isogenic control (each was about 0.5 average greenness), and a significant difference compared to Red Romaine (0.2 average greenness).

Figure 30A:
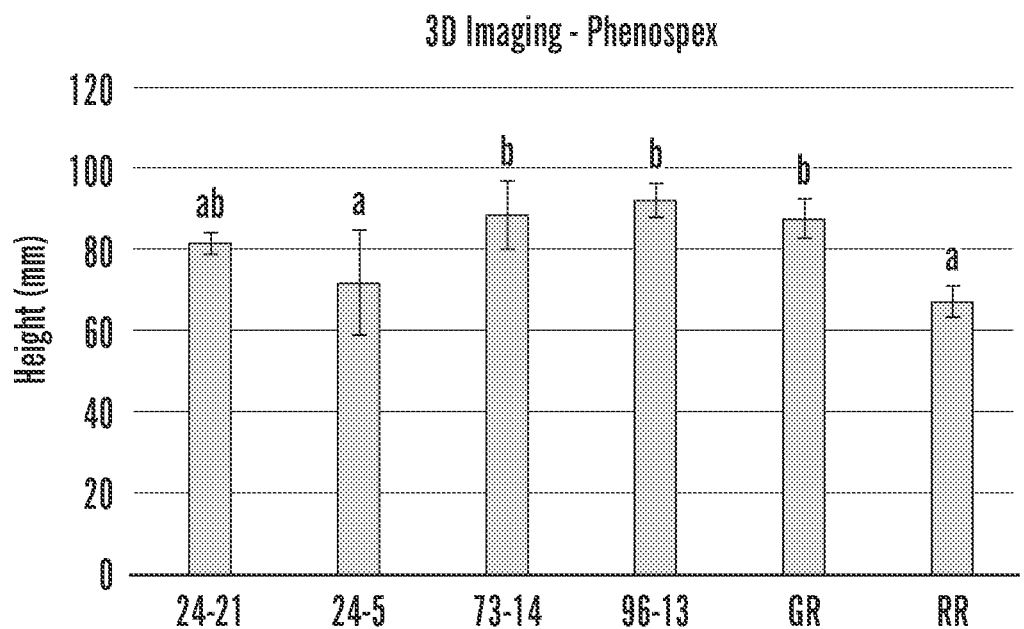
FIGS. 30A-B are graphs showing the height (FIG. 30A) and whole plant area (FIG. 30B) measurements of hydroponically grown PPO mutant lines GVR-102 ("73-14"), GVR-107 ("24-21"), GVR-108 ("24-5"), and GVR-110 ("96-13") compared to controls Green Romaine (isogenic) ("GR") and Red Romaine variety ("RR").
Figure 30B:
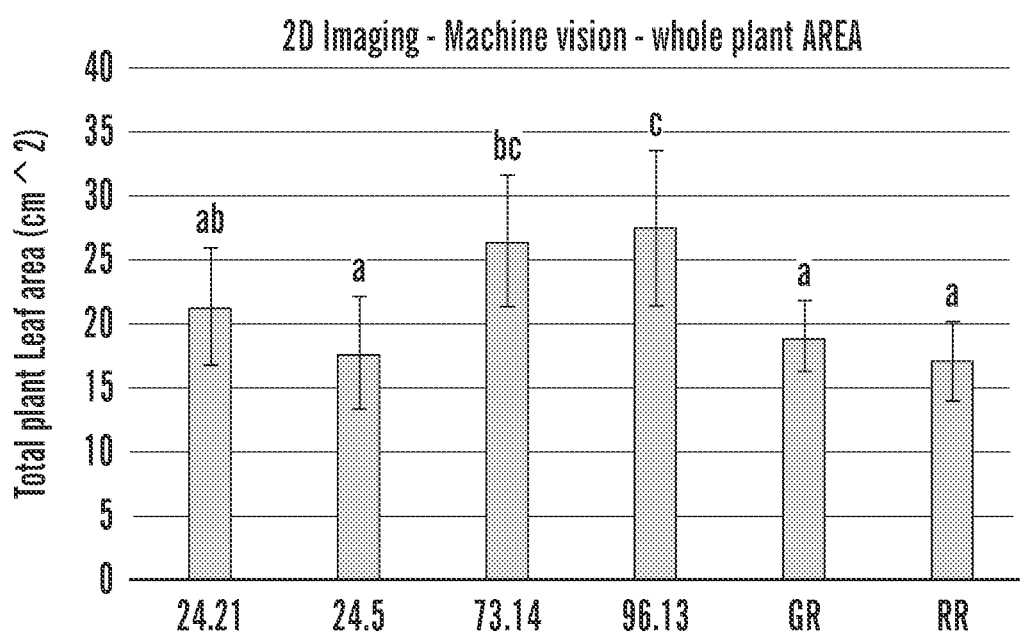

As shown in FIG. 30A, PPO mutant line GVR-108 ("24-5") was shorter than the green romaine control ("GR"), and was more similar to the Red Romaine variety ("RR"). GVR-102 ("73-14"), GVR-107 ("24-21"), and GVR-110 ("96-13") were not significantly different in height compared to the control. Total plant leaf area, as shown in FIG. 30B, was significantly higher for PPO mutant lines, GVR-102 ("73-14"), GVR-107 ("24-21"), and GVR-110 ("96-13") compared to the green romaine control ("GR"). Overall yields, were similar for all PPO mutant lines compared to the isogenic control, except for GVR-108 ("24-5"), which may have been impacted by a pump mutation during the trial.

Figures 31A, 31B:
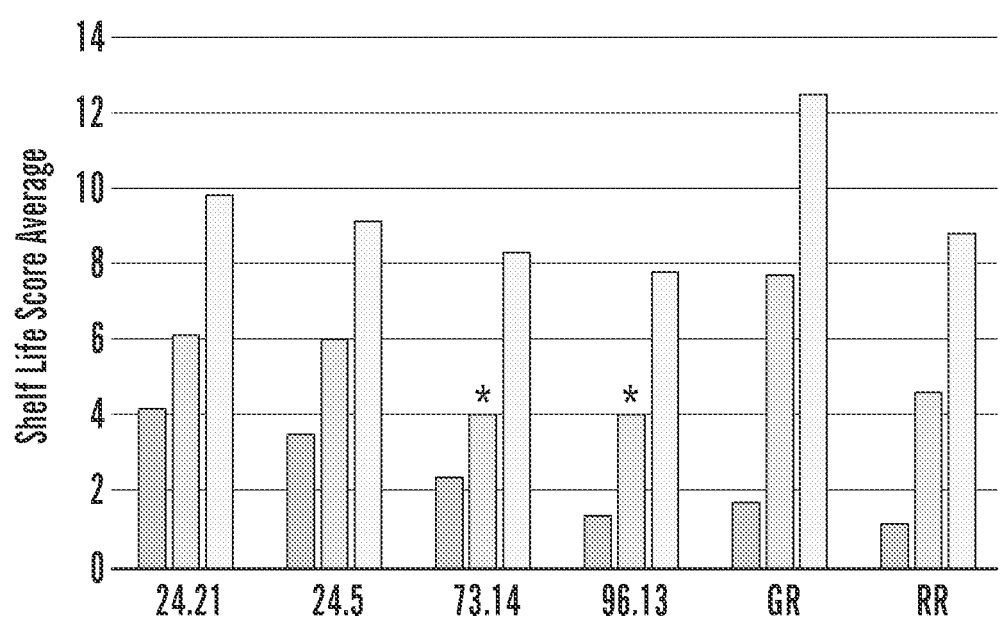
FIGS. 31A-B are a chart and graph showing the results of a shelf life study of the hydroponically grown PPO mutant lines of FIGS. 30A-B.

The shelf life evaluation of the PPO mutant lines showed that the failure rate of the PPO mutant lines was lower compared to the controls (FIG. 31A). At day 21, 67% of replicates failed for the isogenic control, whereas 0% failed for GVR-110 ("96-13"), and only 17% failed for GVR-107 ("24-21") and GVR-108 ("24-5"). Shelf-life scoring averages at 7d, 13d, and 21d after harvest are shown in FIG. 31B. The shelf-life scoring of GVR-102 ("73-14") and GVR-110 ("96-13") were significantly better compared to the isogenic control ("GR") at 13 days post-harvest (FIG. 31B).

Organoleptic evaluation of the lettuce lines in the trial included scoring appearance, taste, texture, aroma and overall sensory on a scale of 1-5 with 1 being poor and 5 meaning the best score. All varieties scored similarly for taste.

Example 14—Sequencing of Multiple Lettuce Varieties for PPO Genes

A 7-mm leaf disk was collected from 7-10 days old seedlings of three new lettuce varieties, Romaine background PI658678 and SM13-R2 in addition to Coastline, a multi-leaf lettuce. Genomic DNA was extracted from each leaf disk using a CTAB protocol. Genomic DNA was amplified using primer combination listed in Table 11 to amplify the tyrosinase domain of each PPO target gene, and then PCR products were clean-up prior Sanger sequencing. Sequencing data were analyzed using Geneious by alignment to the reference isogenic gene sequences.

TABLE 11

Primers Used To Amplify PPO Genes In Multiple Varieties

| PPO Target | Primer Name | Primer Orientation | Primer Sequence | SEQ ID NO: |
|---|---|---|---|---|
| PPO-A | AV67 | F | GGCAGCTCATTTGGCTAATA | 138 |
|  | AV70 | R | CGAAGAATCAAGCGAGTCTT | 139 |
| PPO-B | AR93 | F | GCAGCTCATTTGGCTAATG | 140 |
|  | AM43 | R | CGAAGAATCAAGCCAATCTT | 141 |
| PPO-D | AM95 | F | GATTCAAGCCATGAAGAATCTC | 142 |
|  | X90 | R | TGTGTCCCTTGATTCCCAAATCT | 143 |
| PPO-E | AN06 | F | AGCCACTGCCGATTACAT | 144 |
|  | AT29 | R | CGTATGATGCATTTAGCCAGT | 145 |
| PPO-G | AN13 | F | CTAAGAATGAGGCGTTCAGG | 146 |
|  | PPOG-22R | R | GTTTGCCTCCCTGCATCTTC | 147 |
| PPO-S | PPOS-11F | F | ATTGCGCTTACTGCAATG | 148 |
|  | X45 | R | TCTGTCGGTTCTTTGCCTCC | 149 |

Figure 32A:
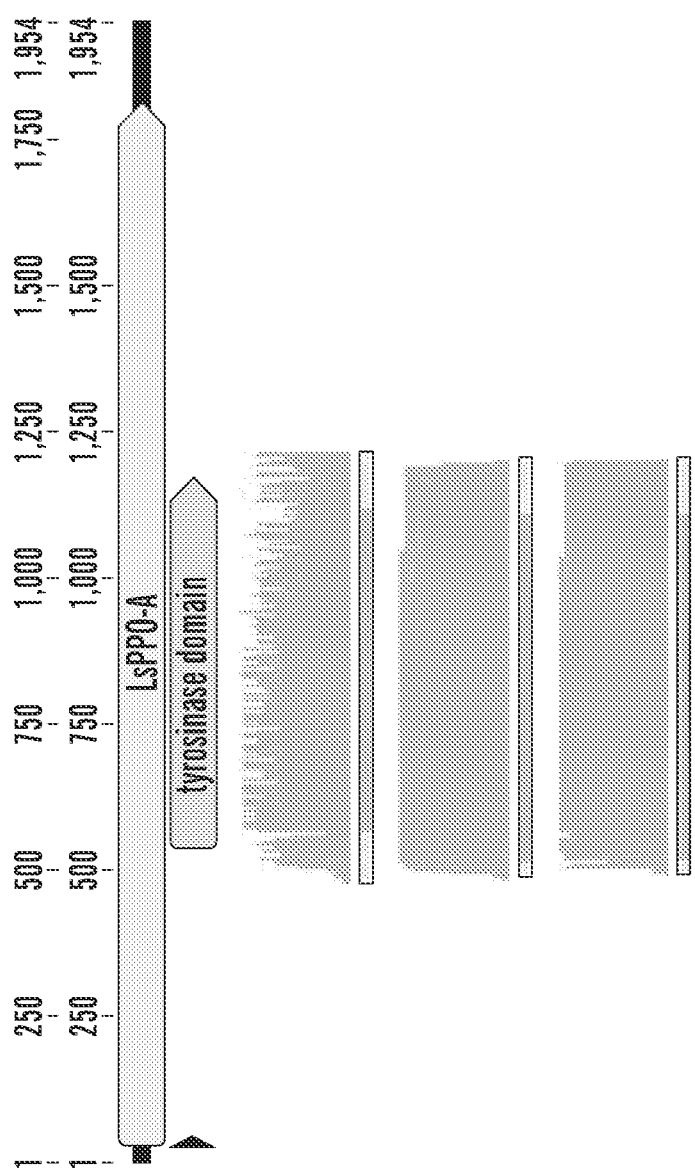
FIGS. 32A-F are illustrations of sequence identities of PPO genes compared to other lettuce varieties in their tyrosinase domains.
Figure 32B:
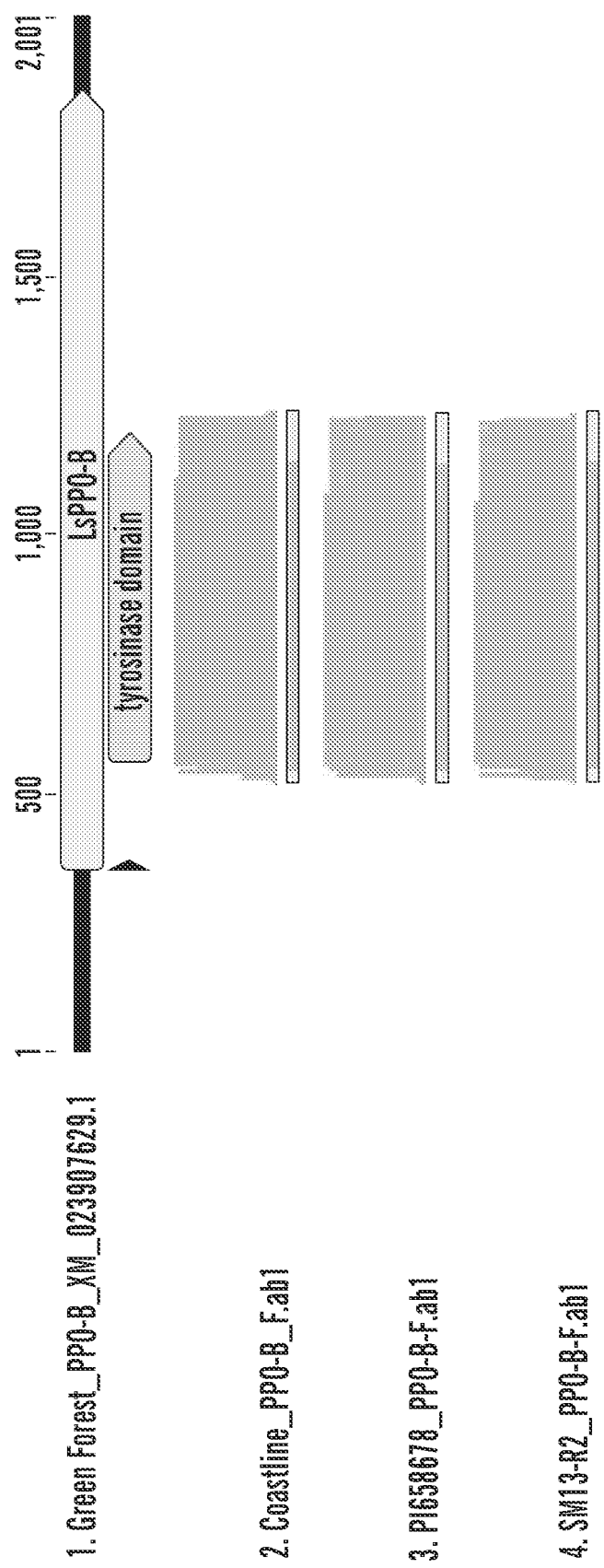
Figure 32C:
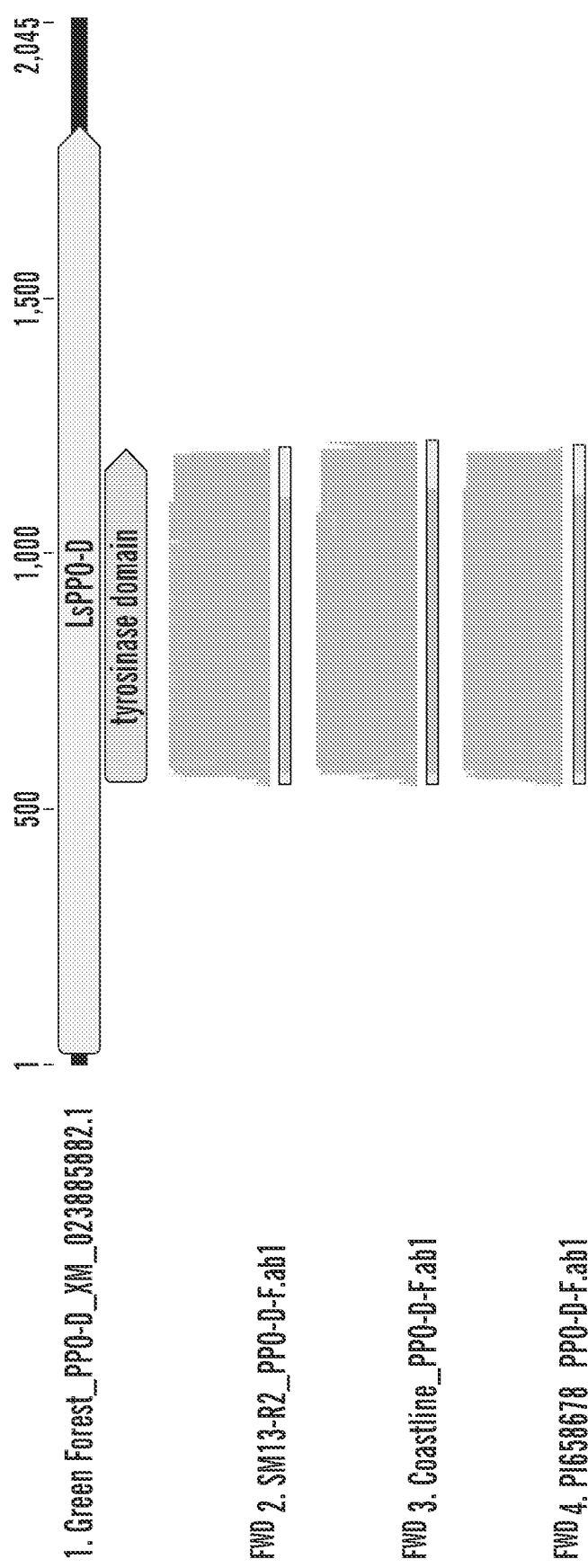
Figure 32D:
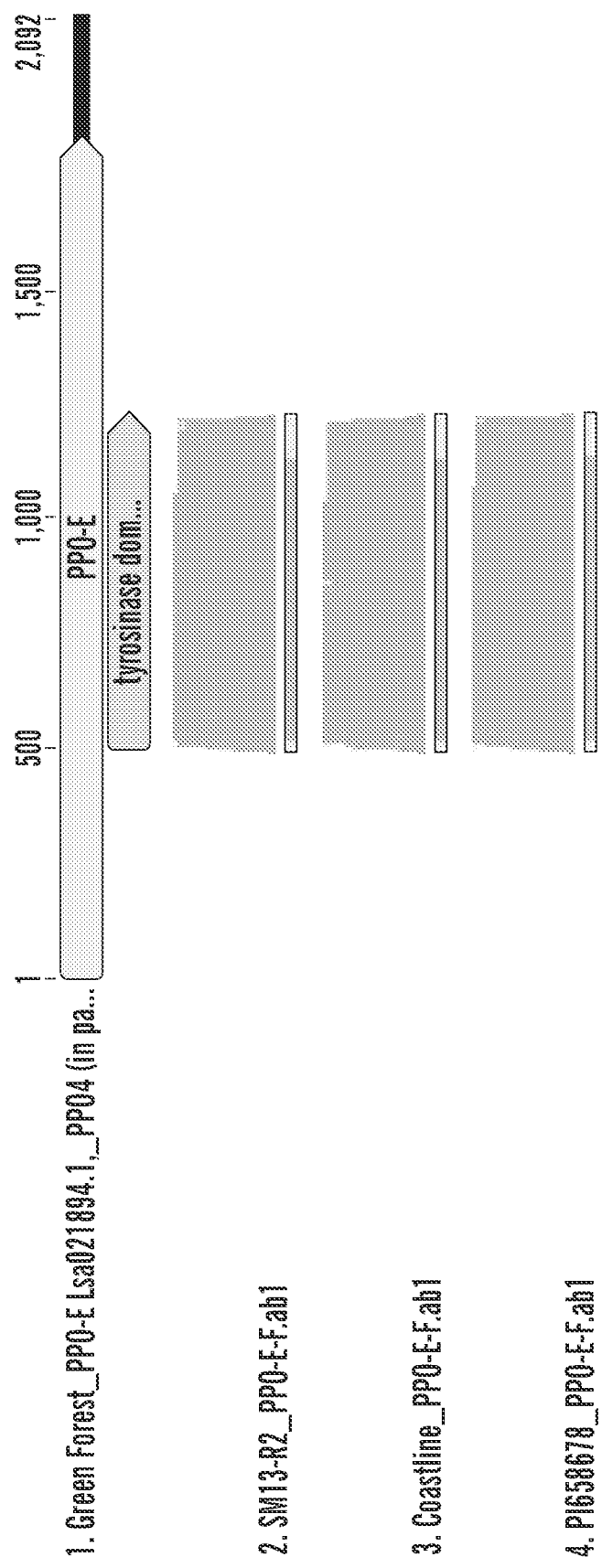
Figure 32E:
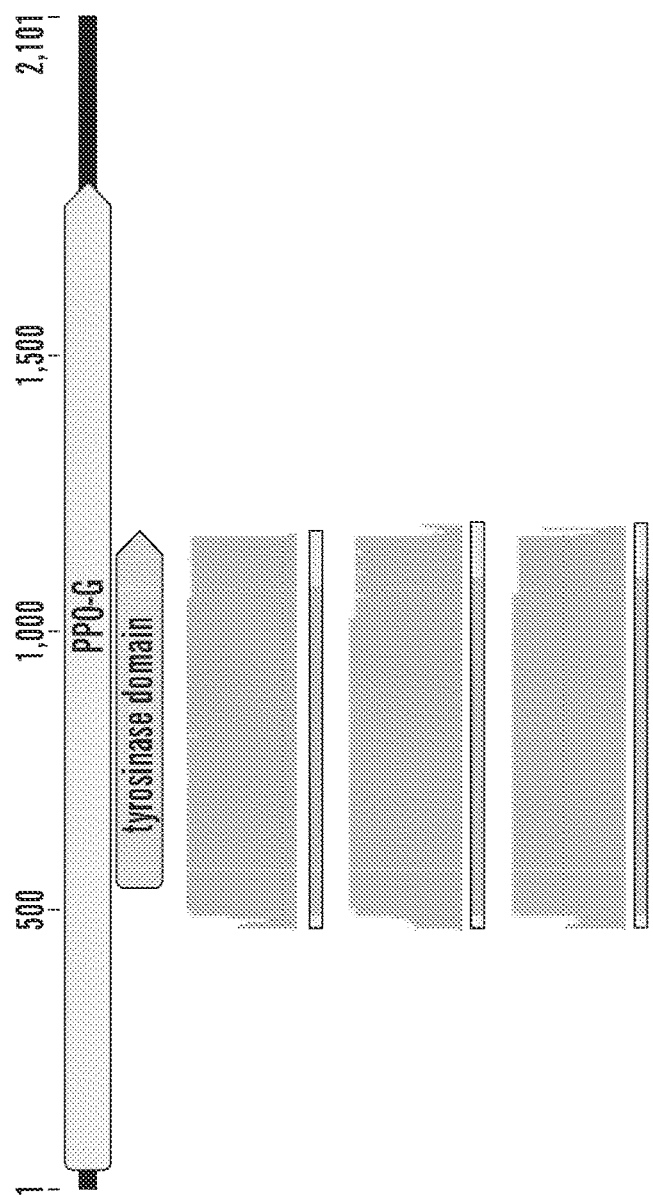
Figure 32F:
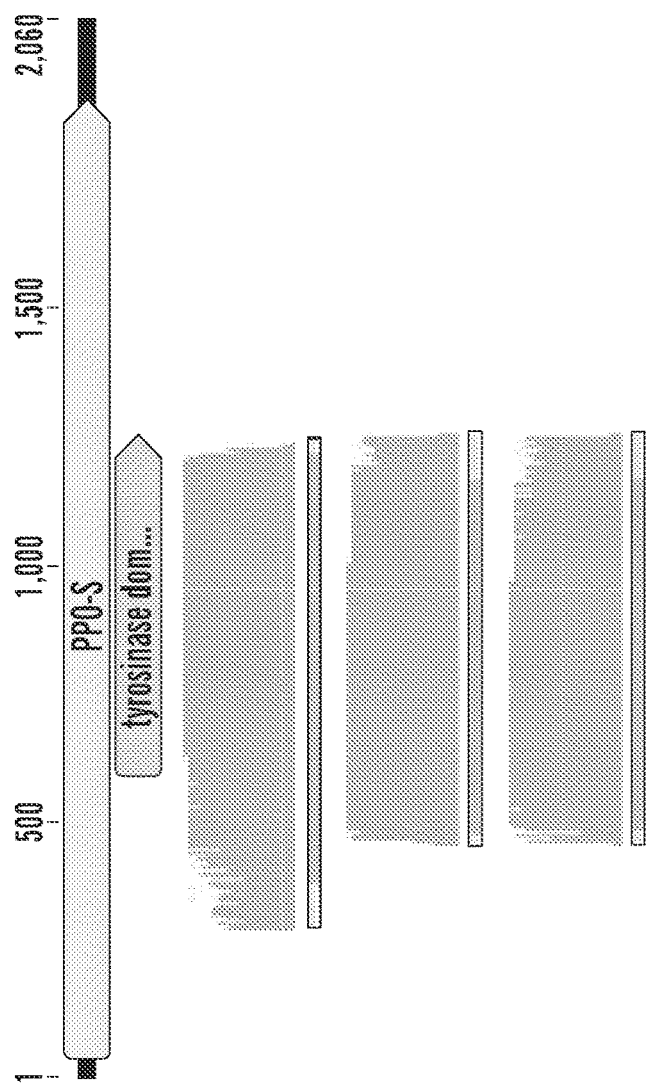

FIGS. 32A-F shown an alignment of the tyrosinase domain of selected PPO target gene from three new lettuce varieties against the isogenic control lettuce reference genes. Alignments in FIGS. 32A-F correspond to PPO-A (FIG. 32A), PPO-B (FIG. 32B), PPO-D (FIG. 32C), D) PPO-E (FIG. 32D), PPO-G (FIG. 32E), and PPO-S (FIG. 32F). The tyrosinase domain of each PPO target gene for the three new lettuce varieties proved to be 100% identical to the isogenic control reference target genes. The consensus tyrosinase domain sequences for each PPO target gene of these multiple lettuce varieties are given in Table 12.

TABLE 12

| Consensus Tyrosinase Domains of Multiple Lettuce Variety PPO Genes | | |
|---|---|---|
| PPO Target | Tyrosinase Domain Nucleotide Sequences (5' to 3') | SEQ ID NO: |
| PPO-A Tyrosinase Domain Consensus | CCTCGTAGTTTCAAGCAACAAGCTGCTGTTCATTGTGCGTATT GCGATGGGGCATACGATCAAGTCGGTTTCCCTGATCTCGAGCT TCAAGTCCATGGCTCATGGTTGTTCTTACCTTTCCACCGCTAT TACTTATACTTCTTCGAGAAAATTTGTGGCAAATTAATCGATG ATCCAAATTTCGCAATCCCTTTTTGGAACTGGGATGCACCTGA TGGCATGAAGATCCCTGATATTTACACGAATAAGAAATCTCCG TTGTACGATGCTCTTCGTGATGCGAAGCATCAACCACCGTCTC TGATTGATCTTGACTACAATGGTGACGATGAAAATCTTAGCCG ATCGAAACAAACCTCCACAAATCTCACAATTATGTACAGACAA ATGGTGTCTAGTTCCAAGACTGCTAGTCTTTTCATGGGTAGTC CTTATCGTGCAGGTGATGAGGCTAGCCCTGGCTCTGGCTCGCT CGAGAGCATACCACATGGCCCGGTTCATATCTGGACCGGAGAT AGGAACCAGCAAAATGGTGAAGACATGGGTAACTTTTATTCTG CAGCCAGAGACCCTATTTTCTATGCACATCATGCGAATATCGA CAGAATGTGGTCAGTTTGGAAAACTCTA | 150 |
| PPO-B Tyrosinase Domain Consensus | CCTCGTAGCTTTAAGCAGCAAGCAAATGTTCATTGTGCCTATT GCGATGGCGCGTATGACCAAGTCGGTTTTCCAGATCTGGAGCT TCAAGTACATAACTCATGGCTGTTCTTCCCTTTCCATCGCTAT TACATGTACTTCTTCGAGAAAATTTGTGGCAAGTTAATTGATG ACCCAAATTTCGCAATTCCATTTTGGAACTGGGATGCACCAGA TGGGATGAAAATCCCTGATATTTACACAAATAAGAAATCTTCG TTGTATGATCCTCTTCGCGATGTGGACCATCAACCACCGTCTT TGATTGATCTTGACTTCAATGGTGTCGACGAAAATCTTAGCCC CTCTGAACAAACGTCCAAAAATCTCACAGTTATGTATAGACAA ATGGTGTCTAGTTCCAAGACTTCTACTCTTTTCATGGGTAGTC CTTATCGTGCAGGCGATGATGCTAGCCCTGGTAGTGGTTCGAT CGAGAACACACCACATAACCCAGTTCATATCTGGGCCGGTGAG TGGAAGCATAATAATGGCAAAAACATGGGCAAACTTTATTCTG CAGCCAGGGACCCTCTTTTCTATGCACATCATGGGAATATTGA TAGAATGTGGTCAGTTTGGAAAACACTA | 151 |
| PPO-D Tyrosinase Domain Consensus | TCCACACAGTTGGAAGCAACAAGCTAAGATCCACTGCGCTTAT TGCAACGGTGGTTACAATCAAGAACAGAGTGGTTTCCCGGACA TACAACTCCAGATTCACAACACATGGCTCTTCTTTCCTTTCCA CCGATGGTACCTCTACTTCTACGAGAGGATTTTGGGGAAGTTG ATTAATGATCCAACTTTCGCTTTACCATACTGGAACTGGGATA ACCCTACCGGAATGGTGCTCCCTGCCATGTTCGAAACCGACGG CAAAAGGAACCCTATCTTTGACCCTTACAGGAATGCCACACAC CTCCCACCAGCTATCTTTGAAGTGGGATATAATGGGACAGACA GTGGCGCCACTTGTATAGACCAGATAAGCGCTAATCTGTCTTT GATGTACAAGCAAATGATCACCAACGCTCCTGATACAACAACG TTCTTCGGTGGAGAATTTGTTGCTGGGGATGACCCTCTTAACA AAGAGTTTAACGTTGCTGGGTCCATAGAGGCTGGGGTTCACAC TGCGGCGCATAGATGGGTGGGTGATCCTAGGATGGCCAACAGC GAGGACATGGGGAACTTCTACTCCGCAGGGTATGATCCTCTCT TTTACGTCCACCATGCCAACGTCGACCGGATGTGGAAAATCTG GAAAGATTTG | 152 |
| PPO-E Tyrosinase Domain Consensus | CCCACATAGCTGGAAGCAACAAGGCAAGATTCACTGTGCTTAT TGCAACGGTGGTTACAATCAAGAACAAAGTGGTTACCCGAATT TACAACTTCAGATTCACAACTCATGGCTCTTCTTTCCTTTCCA CCGGTGGTACCTCTATTTCTACGAGAAGATATTGGGGAAGTTG ATTAATGATCCAACTTTCGCTCTACCTTACTGGAACTGGGATA ACCCTACTGGAATGGTTATTCCTGCCATGTTCGAACAGAACAG CAAAACTAACTCTCTGTTTGACCCTTTAAGGGATGCGAAACAC CTCCCACCTTCTATCTTTGATGTTGAATATGCTGGTGCAGACA CTGGTGCCACTTGTATAGACCAGATAGCCATTAATCTGTCTTC AATGTACAGACAGATGGTCACCAACTCCACTGATACAAAACGA TTCTTCGGTGGCGAATTTGTAGCTGGAAATGACCCTCTTGCGA GCGAGTTCAACGTAGCTGGGACCGTAGAAGCTGGGGTTCACAC TGCGGCTCACCGCTGGGTGGTAATTCTAGGATGGCCAACAGC GAAGACATGGGGAACTTCTACTCCGCAGGATATGATCCTCTCT TTTACGTCCACCATGCGAATGTCGACAGGATGTGGCAAATCTG GAAAGATATT | 153 |
| PPO-G Tyrosinase Domain Consensus | TCCTCGAAACTTTCTGCAACAAGCACACATTCACTGTGCTTAC TGCAATGGCGCTTACACTCAATCTTCAAGTGGATTTCCCGATA TTGAAATCCAGATTCATAACTCATGGCTGTTCTTCCCCTTCCA CCGTTGGTATCTCTACTTTTACGAGAGAATCCTGGGGAGCTTG ATCGATGATCCCACTTTCGCTTTGCCATTCTGGAACTGGGACA CCCCTGCCGGAATGACAATTCCGAATACTTTAACGATCCCAA AAACGCAGTTTTTGATCCCAAAAGAAACCAAGGTCACTTGCAA GGAGTCGTCGATCTGGGTTACAATGGGAAAGATTCAGACACTA CTGATATCGAAAAGGTGAAGAACAATCTCGCGATAATGTATCG | 154 |

TABLE 12-continued

Consensus Tyrosinase Domains of Multiple Lettuce Variety PPO Genes

| PPO Target | Tyrosinase Domain Nucleotide Sequences (5' to 3') | SEQ ID NO: |
|---|---|---|
| | TCAAATGGTGACAAACGCCACCGACCCCACAGCTTTCTTCGGT GGTGAGTATCGTGCCGGAATCGAACCCATTAGCGGTGGTGGAT CAGTCGAACAAAGCCCACACACACCTGTTCACCGGTGGGTCGG TGACCCAAGAGAACTTAACGGTGAAAACCTCGGTAACTTCTAC TCCGCCGGTCGTGACACGCTCTTTTACTGTCACCATTCCAACG TCGATCGAATGTGGTCGTTGTGGAAGATGCAG | |
| PPO-S Tyrosinase Domain Consensus | CCCACGCAGTTTCAATAACCAAGCTAAAGTTCATTGCGCTTAC TGCAATGGCAGTTACACTCAAAACGGTCAAGAACTCCAGATTC ACAACTCCTGGCTCTTCTTTCCCTTCCATCGGTGGTACCTTTA TTTCTACGAGAGGATACTGGGAGATCTCATTGGTGATTCGACA TTCGGGTTACCCTACTGGAACTGGGACAACCCCGAAGGAATGA CAATTCCACACTTCTTCGTAGAGAAACAATGTAACAACTATAA GTTCGAAAACGGAGAAAACCCTCTATATGATAAGTATCGGGAC GAAAGTCACCTTCGGTATGAATTGGTCGATCTTGACTACTCAG GGAGAAACCGCGACCTGTGTTACGATCAGAAAGAAATCAATCT GGCTACTATGAATAGGCAGATGATGCGCAACGCCTTTGATGCA ACAAGCTTCTTCGGTGGCAAATATGTAGCCGGTGATGAACCGA TTCCCCGAGGAGATAATGTAGTTGGATCCGTGGAGGCTGGTTG TCATACGGCTGTTCACAGATGGGTTGGGAACCCTGATCCAAAA GGGAATAAAGAGGACATGGGCAACTTCTACTCTGCGGGATATG ATCCTTTGTTCTACGTCCACCATTCTAATGTGGACCGAATGTG GACTCTTTGGAAGCAAATG | 155 |

Example 15—*Fusarium* Testing of PPO Mutant Lines

Twenty-four 2" pots of each material were sown in the greenhouse. Plants were grown for 21 days (between 23 and 27° C.) in fertilized peat potting medium. Plants were inoculated with 5 ml of a spore suspension of *Fusarium oxysporum* f. sp. *lactucae* race 1 (grown in Czapek-Dox broth, adjusted to a concentration of 1 million spores/ml). Two replicates of up to 8 plants per line/variety were randomly ordered. Roots were evaluated at 21 days post inoculation following a 1-9 scale (1, susceptible and 9, resistant).

Figure 33:
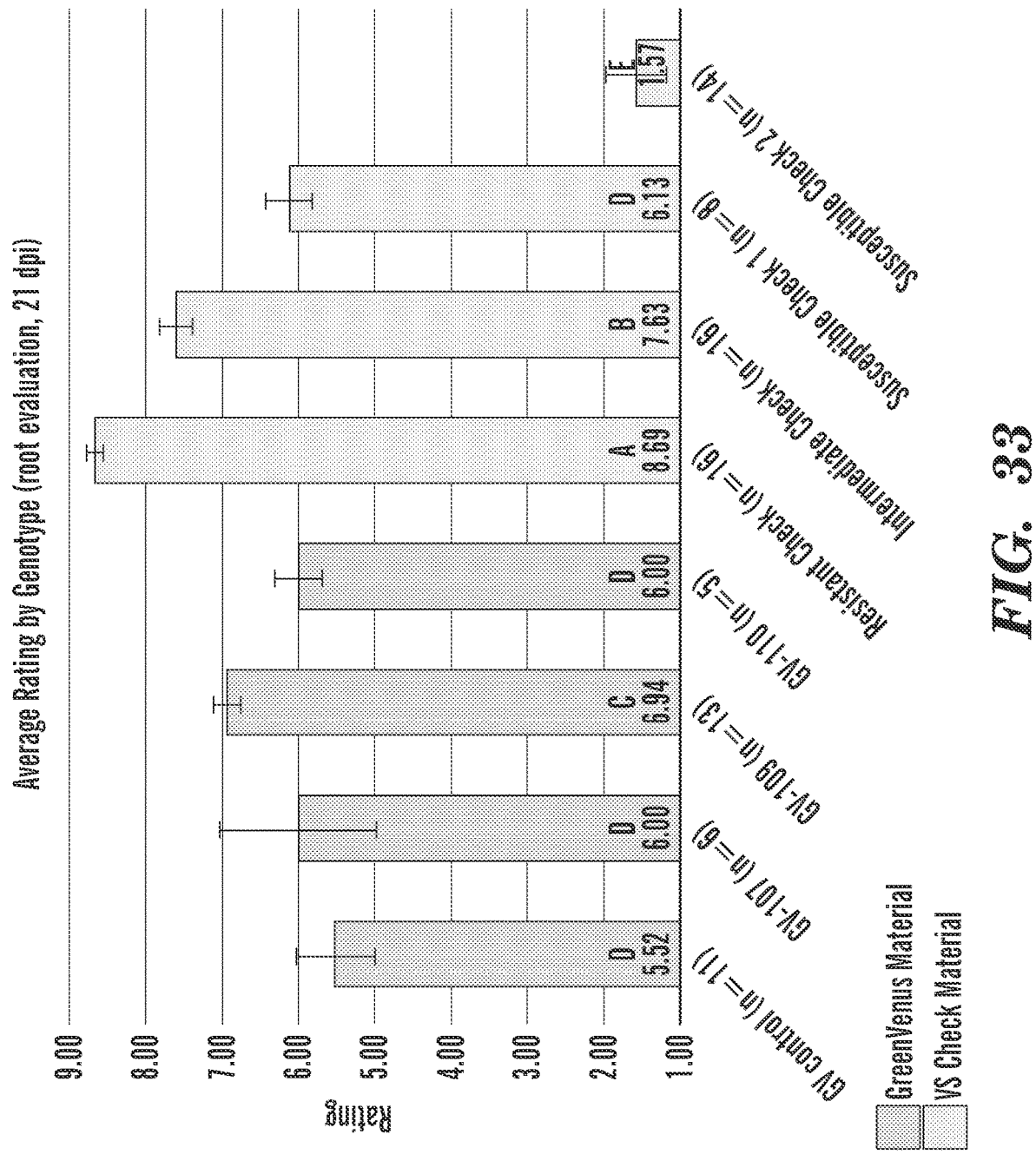
FIG. 33 is a graph showing a lack of any significant differences in disease resistance in PPO edited lettuce lines compared to their isogenic controls.

As shown in FIG. 33, although some reports in the literature show that some PPOs may be important for disease resistance, unexpectedly, no significant differences were observed between PPO edited lines compared to their isogenic controls.

Example 16—Field Yield of PPO Mutant Lines

Lettuce varieties of the present application along with the respective market standard Romaine were planted in full bed trials in Salinas, CA (planted in spring and harvested mid-summer). Romaine heads were quantified for yield and head characteristics as in weight, height, heart length, and core length.

Figure 34:
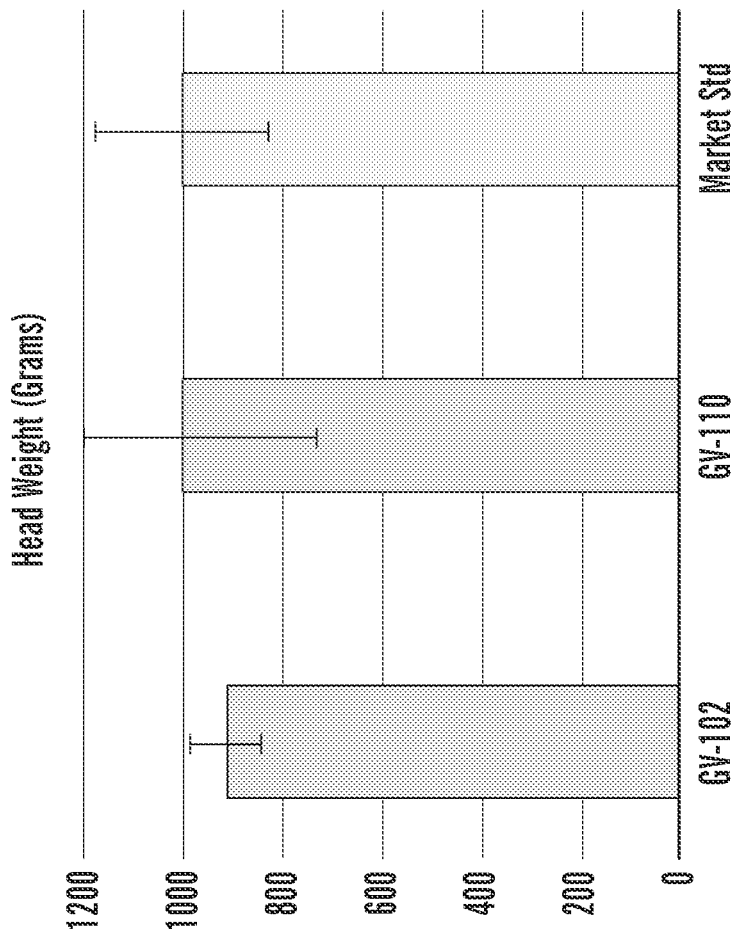
FIG. 34 is a graph showing that lettuce plants of the present application with multiple PPO edits performed equivalent to market standard.

Data as shown in FIG. 34 indicate that the lettuce varieties with multiple PPO edits performed equivalent to market standard.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A genetically modified mutant lettuce plant comprising at least one or more non-naturally occurring mutations in each of at least a PPO-E gene encoding a PPO-E protein having at least 99% amino acid sequence identity to the amino acid sequence as set forth in SEQ ID NO:10 and a PPO-S gene encoding a PPO-S protein having at least 98% amino acid sequence identity to the amino acid sequence as set forth in SEQ ID NO:28, wherein said mutations eliminate or reduce activity of said PPO-E and PPO-S proteins by at least 30% in said genetically modified mutant lettuce plant as compared to a wild type lettuce plant of a same variety, wherein said mutations comprise deletions or insertions of nucleotides in the coding sequences of (i) SEQ ID NO: 9 (PPO-E) which encodes SEQ ID NO: 10 and (ii) SEQ ID NO: 27 (PPO-S) which encodes SEQ ID NO: 28, and wherein the genetically modified mutant lettuce plant at harvest comprises one or more characteristics comprising reduced tip burn; higher levels of polyphenolics; higher levels of vitamin A; higher levels of beta-carotene; higher levels of vitamin C; or higher levels of vitamin K as compared to said wild type lettuce plant of the same variety lacking said mutations.

2. The genetically modified mutant lettuce plant of claim 1, wherein at least one of said mutations occurs in the coding sequence of both alleles of the PPO-E and/or the PPO-S genes.

3. The genetically modified mutant lettuce plant of claim 1, wherein at least one of said mutations occurs in the coding sequence of only one allele of the PPO-E and/or the PPO-S genes.

4. The genetically modified mutant lettuce plant of claim 1, wherein said lettuce is leaf lettuce, romaine lettuce, Frisée lettuce, butter lettuce, Bibb lettuce, Boston lettuce, or iceberg lettuce.

5. The genetically modified mutant lettuce plant of claim 4, wherein said lettuce is romaine lettuce.

6. The genetically modified mutant lettuce plant of claim 1, wherein the activity of said PPO-E and PPO-S proteins is reduced by at least 50% as compared to said wild-type lettuce plant of the same variety lacking said mutations.

7. The genetically modified mutant lettuce plant of claim 1, wherein the genetically modified mutant lettuce plant at post-harvest comprises one or more characteristic comprising reduced browning; increased shelf life; lower levels of $CO_2$ production; higher levels of carbohydrates; or less yellowing as assessed by midvein scoring as compared to said wild type lettuce plant of the same variety lacking said mutations.

8. The genetically modified mutant lettuce plant of claim 7, wherein said post-harvest is 7, 13, 14, 21, 27, or 30 days after harvest.

9. The genetically modified mutant lettuce plant of claim 1, wherein said mutations comprise a knockout mutation eliminating the activity of said PPO-E and PPO-S proteins.

10. The genetically modified mutant lettuce plant of claim 1, wherein said mutation in PPO-E is an insertion between nucleotides 1112 and 1113 of SEQ ID NO: 9.

11. The genetically modified mutant lettuce plant of claim 1, wherein the mutation in PPO-S is an insertion between nucleotides 1044 and 1045 of SEQ ID NO: 27, a deletion of three nucleotides between nucleotides 1045-1047 of SEQ ID NO: 27, or a deletion of seven nucleotides between nucleotides 1045-1051 of SEQ ID NO: 27.

12. The genetically modified mutant lettuce plant of claim 1, wherein the genetically modified mutant lettuce plant is free of any plant pest DNA sequences.

13. The genetically modified mutant lettuce plant of claim 1, wherein the genetically modified mutant lettuce plant is free of any selectable marker.

14. A method of making a genetically modified mutant lettuce plant with reduced PPO activity, said method comprising:

introducing at least one or more a non-naturally occurring mutations into each of at least a PPO-E gene encoding a PPO-E protein having at least 99% amino acid sequence identity to the amino acid sequence as set forth in SEQ ID NO:10 and a PPO-S gene encoding a PPO-S protein having at least 98% amino acid sequence identity to the amino acid sequence as set forth in SEQ ID NO:28 of a lettuce plant, wherein said mutations reduce the activity of said PPO-E and PPO-S proteins by at least 30% in said genetically modified mutant lettuce plant as compared to a wild type lettuce plant of a same variety, wherein said mutations comprise deletions or insertions of nucleotides in the coding sequences of (i) SEQ ID NO: 9 (PPO-E) which encodes SEQ ID NO: 10 and (ii) SEQ ID NO: 27 (PPO-S) which encodes SEQ ID NO: 28, and wherein said genetically modified mutant lettuce plant at harvest comprises one or more characteristics comprising reduced tip burn; higher levels of polyphenolics; higher levels of vitamin A; higher levels of beta-carotene; higher levels of vitamin C; or higher levels of vitamin K as compared to a said wild type lettuce plant of the same variety lacking said mutations.

15. The genetically modified mutant lettuce plant of claim 1, wherein the level of polyphenolics is 5% higher than said wild type lettuce plant of the same variety lacking said mutations.

* * * * *

SEQUENCE LISTING

```
<160> NUMBER OF SEQ ID NOS: 169

<210> SEQ ID NO 1
<211> LENGTH: 1954
<212> TYPE: DNA
<213> ORGANISM: Lactuca sativa

<400> SEQUENCE: 1
acaatatctg cacgctcaaa ataagacaat ggcatctctt gcacaatcac caaccaccac      60
caccaccacc ggtggacggt gcttctcctc ctcctccacg tactcttctt ccttctcttt     120
caaatcatct caagttccca tagcacgaat cacgaaccat cgccatgcag tttcatgcaa     180
aggcgcccta gatgatgatg accatcacca tgaaaactca ggcaaatttg ataggagaaa     240
cgtcttatta ggtctcggag gtctttacgg cgccgccgcc actttggggt caaactcatt     300
ggcgtatgca gctccgatta tggcaccgga cctcacaaaa tgtggtccgg ctgacttacc     360
```

```
ccaagggct gtacctacaa actgttgccc tccatacacc acaaagattc acgatttcaa    420
acttccacca ccgtcaacca ccttccgagt ccgtccggca gctcatttgg ctaataaaga   480
ttacatagcc aagttcaata aagccatcga gctcatgaaa gctctcccag atgacgatcc   540
tcgtagtttc aagcaacaag ctgctgttca ttgtgcgtat gcgatgggg catacgatca    600
agtcggtttc cctgatctcg agcttcaagt ccatggctca tggttgttct tacctttcca   660
ccgctattac ttatacttct tcgagaaaat ttgtggcaaa ttaatcgatg atccaaattt   720
cgcaatccct ttttggaact gggatgcacc tgatggcatg aagatccctg atatttacac   780
gaataagaaa tctccgttgt acgatgctct tcgtgatgcg aagcatcaac accgtctct    840
gattgatctt gactacaatg gtgacgatga aaatcttagc cgatcgaaac aaacctccac   900
aaatctcaca attatgtaca gacaaatggt gtctagttcc aagactgcta gtcttttcat   960
gggtagtcct tatcgtgcag gtgatgaggc tagccctggc tctggctcgc tcgagagcat  1020
accacatggc ccggttcata tctggaccgg agataggaac cagcaaaatg gtgaagacat  1080
gggtaacttt tattctgcag ccagagaccc tattttctat gcacatcatg cgaatatcga  1140
cagaatgtgg tcagtttgga aaactctagg aggaagaagg aatgatttta cagataaaga  1200
ctggcttgat tcttcgttct tgttctacga tgagaacgct gaaatggttc gagtcaaggt  1260
gagggattgt ctcgactcca agaagcttgg gtacgtttat caggatgtag agataccatg  1320
gctaaaaagc aaacccgaac cacgtctgaa agggctttg agcaagatca agaagctcgc   1380
tgtagctcga gccgatgaac acatacccct tgcaaaagat gttttccgg cgagtcttga   1440
taaggtgata aaagtgctgg ttccaaggcc gaagaaatca aggagcaaga acagaaaga   1500
ggatgaagaa gaaatttttgg tgatagaagg aattgaactg aagagagatg agtttgcgaa  1560
gtttgatgtg tttgtgaacg atgaagatga cgggatgagg gccacggctg ataagacgga  1620
gttcgccgga agttttgtta atgtccctca taagcataag catgggaaga atgtgaagac  1680
aagattgagg ttaggaataa gtgagctttt ggaggatttg ggagctgaag atgatgacaa  1740
cgtgttggtg acattggtgc cgaaaaacaa aggtggtgaa gtttccatta agggattaa   1800
aatcgagcat gaggattgat aaaaataact tttcattttc ttgaaaaata aaaaactatg  1860
attttgagtt gtttcggtaa atatgttgtc gcttggttaa tgtatcatca ataaaaataa  1920
atttcgaaat caaagttgga tttgaacccc acaa                              1954
```

<210> SEQ ID NO 2
<211> LENGTH: 596
<212> TYPE: PRT
<213> ORGANISM: Lactuca sativa

<400> SEQUENCE: 2

```
Met Ala Ser Leu Ala Gln Ser Pro Thr Thr Thr Thr Thr Gly Gly
1               5                   10                  15

Arg Cys Phe Ser Ser Ser Ser Thr Tyr Ser Ser Ser Phe Ser Phe Lys
                20                  25                  30

Ser Ser Gln Val Pro Ile Ala Arg Ile Thr Asn His Arg His Ala Val
            35                  40                  45

Ser Cys Lys Gly Ala Leu Asp Asp Asp His His Glu Asn Ser
        50                  55                  60

Gly Lys Phe Asp Arg Arg Asn Val Leu Leu Gly Leu Gly Gly Leu Tyr
65                  70                  75                  80

Gly Ala Ala Ala Thr Phe Gly Ser Asn Ser Leu Ala Tyr Ala Ala Pro
                85                  90                  95
```

```
Ile Met Ala Pro Asp Leu Thr Lys Cys Gly Pro Ala Asp Leu Pro Gln
            100                 105                 110

Gly Ala Val Pro Thr Asn Cys Cys Pro Pro Tyr Thr Thr Lys Ile His
        115                 120                 125

Asp Phe Lys Leu Pro Pro Ser Thr Thr Phe Arg Val Arg Pro Ala
    130                 135                 140

Ala His Leu Ala Asn Lys Asp Tyr Ile Ala Lys Phe Asn Lys Ala Ile
145                 150                 155                 160

Glu Leu Met Lys Ala Leu Pro Asp Asp Pro Arg Ser Phe Lys Gln
                165                 170                 175

Gln Ala Ala Val His Cys Ala Tyr Cys Asp Gly Ala Tyr Asp Gln Val
                180                 185                 190

Gly Phe Pro Asp Leu Glu Leu Gln Val His Gly Ser Trp Leu Phe Leu
        195                 200                 205

Pro Phe His Arg Tyr Tyr Leu Tyr Phe Phe Glu Lys Ile Cys Gly Lys
    210                 215                 220

Leu Ile Asp Asp Pro Asn Phe Ala Ile Pro Phe Trp Asn Trp Asp Ala
225                 230                 235                 240

Pro Asp Gly Met Lys Ile Pro Asp Ile Tyr Thr Asn Lys Lys Ser Pro
                245                 250                 255

Leu Tyr Asp Ala Leu Arg Asp Ala Lys His Gln Pro Pro Ser Leu Ile
                260                 265                 270

Asp Leu Asp Tyr Asn Gly Asp Asp Glu Asn Leu Ser Arg Ser Lys Gln
            275                 280                 285

Thr Ser Thr Asn Leu Thr Ile Met Tyr Arg Gln Met Val Ser Ser Ser
        290                 295                 300

Lys Thr Ala Ser Leu Phe Met Gly Ser Pro Tyr Arg Ala Gly Asp Glu
305                 310                 315                 320

Ala Ser Pro Gly Ser Gly Ser Leu Glu Ser Ile Pro His Gly Pro Val
                325                 330                 335

His Ile Trp Thr Gly Asp Arg Asn Gln Gln Asn Gly Glu Asp Met Gly
            340                 345                 350

Asn Phe Tyr Ser Ala Ala Arg Asp Pro Ile Phe Tyr Ala His His Ala
        355                 360                 365

Asn Ile Asp Arg Met Trp Ser Val Trp Lys Thr Leu Gly Gly Arg Arg
    370                 375                 380

Asn Asp Phe Thr Asp Lys Asp Trp Leu Asp Ser Ser Phe Leu Phe Tyr
385                 390                 395                 400

Asp Glu Asn Ala Glu Met Val Arg Val Lys Val Arg Asp Cys Leu Asp
                405                 410                 415

Ser Lys Lys Leu Gly Tyr Val Tyr Gln Asp Val Glu Ile Pro Trp Leu
            420                 425                 430

Lys Ser Lys Pro Glu Pro Arg Leu Lys Arg Ala Leu Ser Lys Ile Lys
        435                 440                 445

Lys Leu Ala Val Ala Arg Ala Asp Glu His Ile Pro Phe Ala Lys Asp
    450                 455                 460

Val Phe Pro Ala Ser Leu Asp Lys Val Ile Lys Val Leu Val Pro Arg
465                 470                 475                 480

Pro Lys Lys Ser Arg Ser Lys Lys Gln Lys Glu Asp Glu Glu Ile
                485                 490                 495

Leu Val Ile Glu Gly Ile Glu Leu Lys Arg Asp Glu Phe Ala Lys Phe
            500                 505                 510
```

```
Asp Val Phe Val Asn Asp Glu Asp Gly Met Arg Ala Thr Ala Asp
            515                 520                 525

Lys Thr Glu Phe Ala Gly Ser Phe Val Asn Val Pro His Lys His Lys
530                 535                 540

His Gly Lys Asn Val Lys Thr Arg Leu Arg Leu Gly Ile Ser Glu Leu
545                 550                 555                 560

Leu Glu Asp Leu Gly Ala Glu Asp Asp Asn Val Leu Val Thr Leu
                565                 570                 575

Val Pro Lys Asn Lys Gly Gly Glu Val Ser Ile Lys Gly Ile Lys Ile
                580                 585                 590

Glu His Glu Asp
        595

<210> SEQ ID NO 3
<211> LENGTH: 2001
<212> TYPE: DNA
<213> ORGANISM: Lactuca sativa

<400> SEQUENCE: 3
ttatataaat atagatcact tcacataatc tcatgcatcg tgctcaaaat tatgacatcc      60
tttgcatcat caccgaccaa aaccctaaca ggcacggcct ccaggagtga aaggaggatc    120
tcttcctcat ccaactactc ttcttccttc tcttttaagt catctcaagt tcccatagcc    180
agaatctcca aacatcgcca tgcagtttca tgcaaaaccc tagatgacga tcaccaccac    240
catgcaaact ccggcaaact tgataggaga acatcctgt taggcctcgg tggtctttat     300
ggtactgccg ccacttttgg gtctaattca ccagccattg cagctccgat catggcaccc    360
gacctctcaa aatgtggtcc ggccgacttg cccgaaggtg ctgtatccac agactgttgc    420
cctccataca ccacaaagat tctcgatttc aaacttccac caccgtcaaa caccttccga    480
gtccgtccgg cagctcattt ggctaatgaa gattacatag gcaagttcaa taaagccatc    540
gagctcatga agctctccc agatgacgat cctcgtagct ttaagcagca agcaaatgtt    600
cattgtgcct attgcgatgg cgcgtatgac caagtcggtt ttccagatct ggagcttcaa    660
gtacataact catggctgtt cttccctttc catcgctatt acatgtactt cttcgagaaa    720
atttgtggca agttaattga tgacccaaat ttcgcaattc cattttggaa ctgggatgca    780
ccagatggga tgaaaatccc tgatatttac acaaataaga aatcttcgtt gtatgatcct    840
cttcgcgatg tggaccatca accaccgtct ttgattgatc ttgacttcaa tggtgtcgac    900
gaaaatctta gcccctctga acaaacgtcc aaaaatctca cagttatgta tagacaaatg    960
gtgtctagtt ccaagacttc tactcttttc atgggtagtc cttatcgtgc aggcgatgat   1020
gctagccctg gtagtggttc gatcgagaac acaccacata acccagttca tatctgggcc   1080
ggtgagtgga agcataataa tggcaaaaac atgggcaaac tttattctgc agccagggac   1140
cctctttttct atgcacatca tgggaatatt gatagaatgt ggtcagtttg aaaacacta   1200
ggtggaagaa ggaaggactt tactgataaa gattggcttg attcttcgtt cttgtttttac  1260
gatgagaacg ctgagttgaa tcgagtcaag gtgagggatt gtctcgacac caagaatctt   1320
ggctacgttt atcaagatgt agagatacca tggctaaaaa gcaaacctgt tccacgtcgg   1380
acaaagccca agcagaagcc caaaacaaa acaacaagc aagctgtggc tcgagccgac     1440
gaatacatac catttgcaaa agatgttttt ccggcgagtc ttaatgaggt catcaaagtg   1500
ctggttccac ggcccaagat atcaaggagt aagaaacaga agaagaaga agaagagatt   1560
ttggtgatcg aaggaattga agtgaagata gatgagtttg tgaagtttga tgtgtttgtc   1620
```

```
aatgatgaag atgacgggat gagggccacc gcagataaga cggagtttgc cggaagtttt    1680
gtgaatgtcc ctcatactca taagcatggg aagaatttga agacgagatt gaggctaggg    1740
ataagtgagc ttttggagga tttgaatgct gaagatgatg aaaatgtgtt ggtgacattg    1800
gtgcccaaaa ctaggggtag tggaatttcc attgcagaga tcaaaatcga gcatgaagaa    1860
tgatcaaaat acgttcactt tctctaaaat aaaaataaag gaacgtttat gatggaggaa    1920
tatattatgt ttttcgatat gtattaccat ataaaaataa ttttcgcaat caaataaagg    1980
aacgtttatg atggaggaat a                                              2001

<210> SEQ ID NO 4
<211> LENGTH: 603
<212> TYPE: PRT
<213> ORGANISM: Lactuca sativa

<400> SEQUENCE: 4
```

Met Thr Ser Phe Ala Ser Ser Pro Thr Lys Thr Leu Thr Gly Thr Ala
1               5                   10                  15

Ser Arg Ser Glu Arg Arg Ile Ser Ser Ser Asn Tyr Ser Ser Ser
            20                  25                  30

Phe Ser Phe Lys Ser Ser Gln Val Pro Ile Ala Arg Ile Ser Lys His
        35                  40                  45

Arg His Ala Val Ser Cys Lys Thr Leu Asp Asp His His His
    50                  55                  60

Ala Asn Ser Gly Lys Leu Asp Arg Arg Asn Ile Leu Leu Gly Leu Gly
65                  70                  75                  80

Gly Leu Tyr Gly Thr Ala Ala Thr Phe Gly Ser Asn Ser Pro Ala Ile
                85                  90                  95

Ala Ala Pro Ile Met Ala Pro Asp Leu Ser Lys Cys Gly Pro Ala Asp
            100                 105                 110

Leu Pro Glu Gly Ala Val Ser Thr Asp Cys Cys Pro Pro Tyr Thr Thr
        115                 120                 125

Lys Ile Leu Asp Phe Lys Leu Pro Pro Ser Asn Thr Phe Arg Val
    130                 135                 140

Arg Pro Ala Ala His Leu Ala Asn Glu Asp Tyr Ile Gly Lys Phe Asn
145                 150                 155                 160

Lys Ala Ile Glu Leu Met Lys Ala Leu Pro Asp Asp Pro Arg Ser
                165                 170                 175

Phe Lys Gln Gln Ala Asn Val His Cys Ala Tyr Cys Asp Gly Ala Tyr
            180                 185                 190

Asp Gln Val Gly Phe Pro Asp Leu Glu Leu Gln Val His Asn Ser Trp
        195                 200                 205

Leu Phe Phe Pro Phe His Arg Tyr Tyr Met Tyr Phe Glu Lys Ile
    210                 215                 220

Cys Gly Lys Leu Ile Asp Asp Pro Asn Phe Ala Ile Pro Phe Trp Asn
225                 230                 235                 240

Trp Asp Ala Pro Asp Gly Met Lys Ile Pro Asp Ile Tyr Thr Asn Lys
                245                 250                 255

Lys Ser Ser Leu Tyr Asp Pro Leu Arg Asp Val Asp His Gln Pro Pro
            260                 265                 270

Ser Leu Ile Asp Leu Asp Phe Asn Gly Val Asp Glu Asn Leu Ser Pro
        275                 280                 285

Ser Glu Gln Thr Ser Lys Asn Leu Thr Val Met Tyr Arg Gln Met Val
    290                 295                 300

Ser Ser Ser Lys Thr Ser Thr Leu Phe Met Gly Ser Pro Tyr Arg Ala
305                 310                 315                 320

Gly Asp Asp Ala Ser Pro Gly Ser Gly Ser Ile Glu Asn Thr Pro His
            325                 330                 335

Asn Pro Val His Ile Trp Ala Gly Glu Trp Lys His Asn Asn Gly Lys
            340                 345                 350

Asn Met Gly Lys Leu Tyr Ser Ala Ala Arg Asp Pro Leu Phe Tyr Ala
            355                 360                 365

His His Gly Asn Ile Asp Arg Met Trp Ser Val Trp Lys Thr Leu Gly
370                 375                 380

Gly Arg Arg Lys Asp Phe Thr Asp Lys Asp Trp Leu Asp Ser Ser Phe
385                 390                 395                 400

Leu Phe Tyr Asp Glu Asn Ala Glu Leu Asn Arg Val Lys Val Arg Asp
            405                 410                 415

Cys Leu Asp Thr Lys Asn Leu Gly Tyr Val Tyr Gln Asp Val Glu Ile
            420                 425                 430

Pro Trp Leu Lys Ser Lys Pro Val Pro Arg Thr Lys Pro Lys Gln
            435                 440                 445

Lys Pro Lys Asn Lys Asn Asn Lys Gln Ala Val Ala Arg Ala Asp Glu
450                 455                 460

Tyr Ile Pro Phe Ala Lys Asp Val Phe Pro Ala Ser Leu Asn Glu Val
465                 470                 475                 480

Ile Lys Val Leu Val Pro Arg Pro Lys Ile Ser Arg Ser Lys Lys Gln
            485                 490                 495

Lys Glu Glu Glu Glu Ile Leu Val Ile Gly Ile Glu Val Lys
            500                 505                 510

Ile Asp Glu Phe Val Lys Phe Asp Val Phe Val Asn Asp Glu Asp
            515                 520                 525

Gly Met Arg Ala Thr Ala Asp Lys Thr Glu Phe Ala Gly Ser Phe Val
530                 535                 540

Asn Val Pro His Thr His Lys His Gly Lys Asn Leu Lys Thr Arg Leu
545                 550                 555                 560

Arg Leu Gly Ile Ser Glu Leu Leu Glu Asp Leu Asn Ala Glu Asp Asp
            565                 570                 575

Glu Asn Val Leu Val Thr Leu Val Pro Lys Thr Arg Gly Ser Gly Ile
            580                 585                 590

Ser Ile Ala Glu Ile Lys Ile Glu His Glu Glu
        595                 600

<210> SEQ ID NO 5
<211> LENGTH: 1967
<212> TYPE: DNA
<213> ORGANISM: Lactuca sativa

<400> SEQUENCE: 5
ctcttcacat atttcatgca cgctcaaact acaagactat ggcatccttt tcaccatcac      60
aagccacctc ttacacgagt ggaaggaggt tctcttcctc atcgacctac tcttcttcct     120
tctcttttaa gtcatctcaa gttcccatag ccagaatctc caaacatcgc catgcagttt     180
catgcaaaac cctagatgat gatcaccacc accatgcaaa ttccggcaaa cttgatagga     240
gaaacgtcct tttaggcctt ggaggtcttt atggtactgc cgccaacttt gggtctaatt     300
cactggcctt tgcagatccg atcatgggac ccgacctcag taaatgtggt ccggctgagt     360
taccccaagg ggctatacct acaaaattgtt gtcctccatt caccacaaag attatcgatt     420

-continued

```
tcaaacttcc accacagtca aacccctcc gtgttcgacc agctgcacat ttggttgata    480
aagactacat agacaaattc agtaaagcta tcgaactcat gaaagctctc ccagatgacg    540
atcctcgtag tttcaagcaa caagctaatg ttcactgtgc ctattgtgat gccgcatatg    600
tccaactcgg ttatccagat gtggagcttc aagtacataa ctcatggctg ttcttccctt    660
tccatcgttg ttacctatac ttctttgaga aaatttgtgg caaattaatt gatgacccaa    720
cttttgcaat tccattttgg aactgggatg cgccagttgg gatgaaaatc cctgatattt    780
acacagataa gaattcttcg ttatacgata ctcttcgtga tgcgaaacat caaccaccga    840
ctgtggttga tcttgactac aatggtttcg acaacaatct tagcccctct gaacaaacgt    900
ccacaaatct cacgattatg tatagacaaa tggtgtctaa tgccaagact gctagtcttt    960
tcatgggtag tccttatcgt gcaggtgatg accctagccc tggtgctggc tcgctcgaga   1020
gcgtgccaca taacccggtt catatctgga ccggggatag gaaccagcca aatggtgaag   1080
acatgggtaa ctttattct gcaggcaaag accctatttt ctttgcacat catgggaatc   1140
tcgatagatt gtggtcagtt tggaaaacac taggtggaag aaggaaggat tttactgata   1200
atgattggct tgattcttcg ttcttgttgt acgatgagaa cgctgagttg aatcgagtca   1260
aggtgaggga ttgtgtcgac tccaagaata tgaattatgt ttatcaagat gttgagttac   1320
catggctaga aagcaaacct gttccacgac tgcaaaaggc ttccagaaac atcaagaagc   1380
atgcccatga acacataccc tttgcaaaag atgtttttcc ggcgagtctt gataaggtga   1440
tcaaagtgcg ggttccaagg cttaagaaat caaggaccaa gaaacagaaa gaggaggaag   1500
aagagatttt ggttattgaa gggattgaag tgaagagaga tgagtttgtg aagtttgatg   1560
tgttggtgaa cgatgatgat gatgggaccc aggccacagc agctaaaacg gagttcgccg   1620
gaagttttgc gagtgtccct catatgcata agcatggaa gaattggaag acgaaattga   1680
ggatagggat aactgacctt ttggaggatt tgaaggatga agaagatcac aatgtgttgg   1740
tgacattggt gcccaaaact agtggtggtg atatttccat tggagggatc aaaatcgagc   1800
atgaagaatg ttaaacagac gttctcactt tctataaata aaataaaaga aagtctatga   1860
tctattaaga tattatgttt ctctatatgt attaccatat aaaagtaatt atcacaataa   1920
agttatatat gattcgaact tgtgaatgtt aattgcaagt cattgaa                 1967
```

<210> SEQ ID NO 6
<211> LENGTH: 591
<212> TYPE: PRT
<213> ORGANISM: Lactuca sativa

<400> SEQUENCE: 6

```
Met Ala Ser Phe Ser Pro Ser Gln Ala Thr Ser Tyr Thr Ser Gly Arg
1               5                   10                  15

Arg Phe Ser Ser Ser Ser Thr Tyr Ser Ser Ser Phe Ser Phe Lys Ser
                20                  25                  30

Ser Gln Val Pro Ile Ala Arg Ile Ser Lys His Arg His Ala Val Ser
            35                  40                  45

Cys Lys Thr Leu Asp Asp Asp His His His Ala Asn Ser Gly Lys
        50                  55                  60

Leu Asp Arg Arg Asn Val Leu Leu Gly Leu Gly Gly Leu Tyr Gly Thr
65                  70                  75                  80

Ala Ala Asn Phe Gly Ser Asn Ser Leu Ala Phe Ala Asp Pro Ile Met
                85                  90                  95
```

```
Gly Pro Asp Leu Ser Lys Cys Gly Pro Ala Glu Leu Pro Gln Gly Ala
                100                 105                 110

Ile Pro Thr Asn Cys Cys Pro Pro Phe Thr Thr Lys Ile Ile Asp Phe
            115                 120                 125

Lys Leu Pro Pro Gln Ser Asn Pro Leu Arg Val Arg Pro Ala Ala His
        130                 135                 140

Leu Val Asp Lys Asp Tyr Ile Asp Lys Phe Ser Lys Ala Ile Glu Leu
145                 150                 155                 160

Met Lys Ala Leu Pro Asp Asp Pro Arg Ser Phe Lys Gln Gln Ala
                165                 170                 175

Asn Val His Cys Ala Tyr Cys Asp Ala Ala Tyr Val Gln Leu Gly Tyr
            180                 185                 190

Pro Asp Val Glu Leu Gln Val His Asn Ser Trp Leu Phe Phe Pro Phe
        195                 200                 205

His Arg Cys Tyr Leu Tyr Phe Phe Glu Lys Ile Cys Gly Lys Leu Ile
        210                 215                 220

Asp Asp Pro Thr Phe Ala Ile Pro Phe Trp Asn Trp Asp Ala Pro Val
225                 230                 235                 240

Gly Met Lys Ile Pro Asp Ile Tyr Thr Asp Lys Asn Ser Ser Leu Tyr
                245                 250                 255

Asp Thr Leu Arg Asp Ala Lys His Gln Pro Pro Thr Val Val Asp Leu
            260                 265                 270

Asp Tyr Asn Gly Phe Asp Asn Leu Ser Pro Ser Glu Gln Thr Ser
        275                 280                 285

Thr Asn Leu Thr Ile Met Tyr Arg Gln Met Val Ser Asn Ala Lys Thr
290                 295                 300

Ala Ser Leu Phe Met Gly Ser Pro Tyr Arg Ala Gly Asp Asp Pro Ser
305                 310                 315                 320

Pro Gly Ala Gly Ser Leu Glu Ser Val Pro His Asn Pro Val His Ile
                325                 330                 335

Trp Thr Gly Asp Arg Asn Gln Pro Asn Gly Glu Asp Met Gly Asn Phe
            340                 345                 350

Tyr Ser Ala Gly Lys Asp Pro Ile Phe Phe Ala His His Gly Asn Leu
        355                 360                 365

Asp Arg Leu Trp Ser Val Trp Lys Thr Leu Gly Gly Arg Arg Lys Asp
370                 375                 380

Phe Thr Asp Asn Asp Trp Leu Asp Ser Ser Phe Leu Leu Tyr Asp Glu
385                 390                 395                 400

Asn Ala Glu Leu Asn Arg Val Lys Val Arg Asp Cys Val Asp Ser Lys
                405                 410                 415

Asn Met Asn Tyr Val Tyr Gln Asp Val Glu Leu Pro Trp Leu Glu Ser
            420                 425                 430

Lys Pro Val Pro Arg Leu Gln Lys Ala Ser Arg Asn Ile Lys Lys His
        435                 440                 445

Ala His Glu His Ile Pro Phe Ala Lys Asp Val Phe Pro Ala Ser Leu
450                 455                 460

Asp Lys Val Ile Lys Val Arg Val Pro Arg Leu Lys Lys Ser Arg Thr
465                 470                 475                 480

Lys Lys Gln Lys Glu Glu Glu Glu Ile Leu Val Ile Glu Gly Ile
                485                 490                 495

Glu Val Lys Arg Asp Glu Phe Lys Phe Asp Val Leu Val Asn Asp
            500                 505                 510

Asp Asp Asp Gly Thr Gln Ala Thr Ala Ala Lys Thr Glu Phe Ala Gly
```

```
               515                 520                 525
Ser Phe Ala Ser Val Pro His Met His Lys His Gly Lys Asn Trp Lys
            530                 535                 540

Thr Lys Leu Arg Ile Gly Ile Thr Asp Leu Leu Glu Asp Leu Lys Asp
545                 550                 555                 560

Glu Glu Asp His Asn Val Leu Val Thr Leu Val Pro Lys Thr Ser Gly
                565                 570                 575

Gly Asp Ile Ser Ile Gly Gly Ile Lys Ile Glu His Glu Glu Cys
            580                 585                 590

<210> SEQ ID NO 7
<211> LENGTH: 2045
<212> TYPE: DNA
<213> ORGANISM: Lactuca sativa

<400> SEQUENCE: 7
```

| | | | | | |
|---|---|---|---|---|---|
| accacaccac | ctatagatga | tggcttccct | cagcttgtcc | actcttccca | cctccacccc | 60 |
| cacaaaaaag | cctttatttt | ccaaaacctc | ctcccacgtg | aagcaatccc | atcgcttcaa | 120 |
| agtctcatgc | aactccgccg | ctaacaacaa | tgagaaaaca | gtcaaaaact | ctgaaacccc | 180 |
| gaagctcata | ctacccaaaa | caccacttga | aatgcagaat | gttgaccgga | aaacctgct | 240 |
| cctggggctt | ggaggtctct | acggcgctgc | caacttgaca | tccatcccat | cagcctttgg | 300 |
| cactcccatc | gctgctccgg | acaatatttc | agattgtgtt | actgcgtcgt | caaacctcca | 360 |
| gaacgccaat | gacgctgtaa | ggggtttagc | ttgttgccct | ccagtactct | caacagataa | 420 |
| accaaaagat | tacgtcttgc | ctaccaaccc | agtccttcgt | gttcgaccag | ctgcacagag | 480 |
| agctactgac | gagtacatcg | taaagtacaa | agcagcgatt | caagccatga | gaatctccc | 540 |
| cgacgagcat | ccacacagtt | ggaagcaaca | agctaagatc | cactgcgctt | attgcaacgg | 600 |
| tggttacaat | caagaacaga | gtggtttccc | ggacatacaa | ctccagattc | acaacacatg | 660 |
| gctcttcttt | cctttccacc | gatggtacct | ctacttctac | gagaggattt | tggggaagtt | 720 |
| gattaatgat | ccaactttcg | ctttaccata | ctggaactgg | gataacccta | ccggaatggt | 780 |
| gctccctgcc | atgttcgaaa | ccgacggcaa | aaggaaccct | atctttgacc | ttacaggaa | 840 |
| tgccacacac | ctcccaccag | ctatctttga | agtgggatat | aatgggacag | acagtggcgc | 900 |
| cacttgtata | gaccagataa | gcgctaatct | gtctttgatg | tacaagcaaa | tgatcaccaa | 960 |
| cgctcctgat | acaacaacgt | tcttcggtgg | agaatttgtt | gctggggatg | accctcttaa | 1020 |
| caaagagttt | aacgttgctg | gtccatagaa | ggctggggtt | cacactgcgg | cgcatagatg | 1080 |
| ggtgggtgat | cctaggatgg | ccaacagcga | ggacatgggg | aacttctact | ccgcagggta | 1140 |
| tgatcctctc | ttttacgtcc | accatgccaa | cgtcgaccgg | atgtggaaaa | tctgaaaga | 1200 |
| tttgggaatc | aagggacaca | ctgaaccgac | gtccaccgac | tggctagatg | cttcatacgt | 1260 |
| gtttatgat | gagaacgaag | agcttgtacg | tgtctataac | cgagacagtg | taaacatgac | 1320 |
| tgcaatggga | tacgactatg | aaaggtccga | aatcccgtgg | ctccatagtc | gatcggttcc | 1380 |
| acataccaag | ggggccaatg | ttgcagctaa | actggtcgga | atcgtgaaga | aggtggaaga | 1440 |
| cgttacattc | ccgttgaagt | taaatgagac | agtgaaggtt | cttgtgaaaa | ggcctactaa | 1500 |
| gaagaggaac | aagaagaaca | gcaggaagc | gaatgagatg | ttgttcttga | ataaaatcaa | 1560 |
| gttcgatggc | gaggagtttg | tcaagtttga | cgtgtttgtc | aatgacgttg | acgatggagt | 1620 |
| ggagactacc | gcagctgaga | gtgagtttgc | tggtagtttc | tcacaattgc | ccatggcca | 1680 |
| taaacatggc | accaagatgt | caatgacgag | tggggcggcg | tttgggctta | cggagctgtt | 1740 |

```
ggaggacatt gaagctgaag atgatgactc tattttggtg actttggtgc ccaagatagg    1800
gtgtgatgat gtgactgtcg gtgagattaa gattaagttg gttcccattg tctgaagttc    1860
attgatgtaa catcgttttc atttgcgttt gtatgcatgg gtaaaacagt tttctgtgtt    1920
tggtcatacg aggatgtttg tggttctcgt aatctaataa tgaccatttt gtcaagtttg    1980
ttgtcatgct tgattgtaac tcctatgttt ggatatcaat aaacattatc gagtactatt    2040
ttagt                                                                 2045
```

<210> SEQ ID NO 8
<211> LENGTH: 612
<212> TYPE: PRT
<213> ORGANISM: Lactuca sativa

<400> SEQUENCE: 8

```
Met Met Ala Ser Leu Ser Leu Ser Thr Leu Pro Thr Ser Thr Pro Thr
1               5                   10                  15

Lys Lys Pro Leu Phe Ser Lys Thr Ser Ser His Val Lys Gln Ser His
            20                  25                  30

Arg Phe Lys Val Ser Cys Asn Ser Ala Ala Asn Asn Asn Glu Lys Thr
        35                  40                  45

Val Lys Asn Ser Glu Thr Pro Lys Leu Ile Leu Pro Lys Thr Pro Leu
    50                  55                  60

Glu Met Gln Asn Val Asp Arg Arg Asn Leu Leu Leu Gly Leu Gly Gly
65                  70                  75                  80

Leu Tyr Gly Ala Ala Asn Leu Thr Ser Ile Pro Ser Ala Phe Gly Thr
                85                  90                  95

Pro Ile Ala Ala Pro Asp Asn Ile Ser Asp Cys Val Thr Ala Ser Ser
            100                 105                 110

Asn Leu Gln Asn Ala Asn Asp Ala Val Arg Gly Leu Ala Cys Cys Pro
        115                 120                 125

Pro Val Leu Ser Thr Asp Lys Pro Lys Asp Tyr Val Leu Pro Thr Asn
    130                 135                 140

Pro Val Leu Arg Val Arg Pro Ala Ala Gln Arg Ala Thr Asp Glu Tyr
145                 150                 155                 160

Ile Val Lys Tyr Lys Ala Ala Ile Gln Ala Met Lys Asn Leu Pro Asp
                165                 170                 175

Glu His Pro His Ser Trp Lys Gln Gln Ala Lys Ile His Cys Ala Tyr
            180                 185                 190

Cys Asn Gly Gly Tyr Asn Gln Glu Gln Ser Gly Phe Pro Asp Ile Gln
        195                 200                 205

Leu Gln Ile His Asn Thr Trp Leu Phe Phe Pro Phe His Arg Trp Tyr
    210                 215                 220

Leu Tyr Phe Tyr Glu Arg Ile Leu Gly Lys Leu Ile Asn Asp Pro Thr
225                 230                 235                 240

Phe Ala Leu Pro Tyr Trp Asn Trp Asp Asn Pro Thr Gly Met Val Leu
                245                 250                 255

Pro Ala Met Phe Glu Thr Asp Gly Lys Arg Asn Pro Ile Phe Asp Pro
            260                 265                 270

Tyr Arg Asn Ala Thr His Leu Pro Pro Ala Ile Phe Glu Val Gly Tyr
        275                 280                 285

Asn Gly Thr Asp Ser Gly Ala Thr Cys Ile Asp Gln Ile Ser Ala Asn
    290                 295                 300

Leu Ser Leu Met Tyr Lys Gln Met Ile Thr Asn Ala Pro Asp Thr Thr
```

```
             305                 310                 315                 320
        Thr Phe Phe Gly Gly Glu Phe Val Ala Gly Asp Asp Pro Leu Asn Lys
                        325                 330                 335
        Glu Phe Asn Val Ala Gly Ser Ile Glu Ala Gly Val His Thr Ala Ala
                        340                 345                 350
        His Arg Trp Val Gly Asp Pro Arg Met Ala Asn Ser Glu Asp Met Gly
                        355                 360                 365
        Asn Phe Tyr Ser Ala Gly Tyr Asp Pro Leu Phe Tyr Val His His Ala
                        370                 375                 380
        Asn Val Asp Arg Met Trp Lys Ile Trp Lys Asp Leu Gly Ile Lys Gly
        385                 390                 395                 400
        His Thr Glu Pro Thr Ser Thr Asp Trp Leu Asp Ala Ser Tyr Val Phe
                        405                 410                 415
        Tyr Asp Glu Asn Glu Glu Leu Val Arg Val Tyr Asn Arg Asp Ser Val
                        420                 425                 430
        Asn Met Thr Ala Met Gly Tyr Asp Tyr Glu Arg Ser Glu Ile Pro Trp
                        435                 440                 445
        Leu His Ser Arg Ser Val Pro His Thr Lys Gly Ala Asn Val Ala Ala
                        450                 455                 460
        Lys Leu Val Gly Ile Val Lys Lys Val Glu Asp Val Thr Phe Pro Leu
        465                 470                 475                 480
        Lys Leu Asn Glu Thr Val Lys Val Leu Val Lys Arg Pro Thr Lys Lys
                        485                 490                 495
        Arg Asn Lys Lys Asn Lys Gln Glu Ala Asn Glu Met Leu Phe Leu Asn
                        500                 505                 510
        Lys Ile Lys Phe Asp Gly Glu Glu Phe Val Lys Phe Asp Val Phe Val
                        515                 520                 525
        Asn Asp Val Asp Asp Gly Val Glu Thr Thr Ala Ala Glu Ser Glu Phe
                        530                 535                 540
        Ala Gly Ser Phe Ser Gln Leu Pro His Gly His Lys His Gly Thr Lys
        545                 550                 555                 560
        Met Ser Met Thr Ser Gly Ala Ala Phe Gly Leu Thr Glu Leu Leu Glu
                        565                 570                 575
        Asp Ile Glu Ala Glu Asp Asp Ser Ile Leu Val Thr Leu Val Pro
                        580                 585                 590
        Lys Ile Gly Cys Asp Asp Val Thr Val Gly Glu Ile Lys Ile Lys Leu
                        595                 600                 605
        Val Pro Ile Val
            610

<210> SEQ ID NO 9
<211> LENGTH: 2107
<212> TYPE: DNA
<213> ORGANISM: Lactuca sativa

<400> SEQUENCE: 9
cttatagcac cacccataga tgatggcttc tctcgccttg tctagtcttc ccacctccac    60
cacaaccaaa aaacccttat tttccaaaac atcctcgcat gttaagccat tccatcgctt   120
caaagtttca tgcaatgcac ccgctgataa caatgacaaa accgtcaata attctgatac   180
cccaaagctc atactaccca aaacaccact tgaaacgcag aacgtagaca ggagaaactt   240
gcttctggga ctcggaggtc tctacggcgc tgccaacttg acgaccattc cgtcagcctt   300
tggcattccc atcgctgctc cagacaatat ttcagactgt gttgctgcga cttcaaacct   360
```

-continued

```
aaggaacagc aaagacgcta taaggggact agcgtgttgt cctccggtgc tttcaacaaa    420
caaaccaatg gattacgtcc ttccttcaaa ccctgtgatt cgtgttcgac cagctgcaca    480
gaaagccact gccgattaca ttgctaagta tcaacaagca attcaagcca tgaaggatct    540
ccccgaggac cacccacata gctggaagca acaaggcaag attcactgtg cttattgcaa    600
cggtggttac aatcaagaac aaagtggtta cccgaattta caacttcaga ttcacaactc    660
atggctcttc tttcctttcc accggtggta cctctatttc tacgagaaga tattggggaa    720
gttgattaat gatccaactt cgctctacc ttactggaac tgggataacc ctactggaat    780
ggttattcct gccatgttcg aacagaacag caaaactaac tctctgtttg ccctttaag    840
ggatgcgaaa cacctcccac cttctatctt tgatgttgaa tatgctggtg cagacactgg    900
tgccacttgt atagaccaga tagccattaa tctgtcttca atgtacagac agatggtcac    960
caactccact gatacaaaac gattcttcgg tggcgaattt gtagctggaa atgaccctct   1020
tgcgagcgag ttcaacgtag ctgggaccgt agaagctggg gttcacactg cggctcaccg   1080
ctgggtgggt aattctagga tggccaacag cgaagacatg ggaacttct actctcgcag    1140
gatatgatcc tctcttttac gtccaccatg cgaatgtcga caggatgtgg caaatctgga   1200
aagatattga caagaagaca cacaaggatc cgacctctgg cgactggcta aatgcatcat   1260
acgtgtttta cgatgagaat gaaaatcttg tacgtgtcta caaccgagac tgtgtagaca   1320
ttaatcggat gggatatgac tacgaaaggt cagcaatccc atggatccgt agtcggccga   1380
ctgcacatgc gaagggggcg aacgttgctg ctaagtctgc tggaatcgtg cagaaggtgg   1440
aggatatcgt attcccgctg aagttaaaca agatagtgaa ggttctagtg aagaggccag   1500
ctacaaacag gaccaaggag gaaaaggaga agcaaatga gctgttgttc gtgaatggaa    1560
tcacgtttga tgctgagcgg tttctaaaga ttgacgtgtt tgtcaacgac gtcgacgatg   1620
gaattcagac caccgctgct gatagtgagt ttgctggtag tttcgcacag ttgccacata   1680
accatggcga caagatgttt atgaggagtg gggcagcgtt cgggatcacg gagctcttgg   1740
aagacattga agctgaaggt gatgactctg ttgttgtgac attggtgccg agaacagggt   1800
gtgatgaagt aactattggc gagatcaaga ttcagctggt tcccattgtt taaagtctat   1860
tgaagtaatg catttcaat tgtcattagt atgcatgggt acgtaaatct gttcgctgtc   1920
tggttatcga ggattttga tgttctcgta accaaataat aaggattgtc attccatgtt   1980
tggaatcgtg taaccgcagg catgcatatg tttgattgtt attttactt gaagcacttc   2040
tgttttagta atctctgttt tcctgttttta caaaaggtaa agaattcgct gtatgtgctt   2100
tgcataa                                                             2107
```

<210> SEQ ID NO 10
<211> LENGTH: 375
<212> TYPE: PRT
<213> ORGANISM: Lactuca sativa

<400> SEQUENCE: 10

```
Met Met Ala Ser Leu Ala Leu Ser Ser Leu Pro Thr Ser Thr Thr Thr
1               5                   10                  15

Lys Lys Pro Leu Phe Ser Lys Thr Ser Ser His Val Lys Pro Phe His
            20                  25                  30

Arg Phe Lys Val Ser Cys Asn Ala Pro Ala Asp Asn Asn Asp Lys Thr
        35                  40                  45

Val Asn Asn Ser Asp Thr Pro Lys Leu Ile Leu Pro Lys Thr Pro Leu
    50                  55                  60
```

Glu Thr Gln Asn Val Asp Arg Arg Asn Leu Leu Gly Leu Gly Gly
65                  70                  75                  80

Leu Tyr Gly Ala Ala Asn Leu Thr Thr Ile Pro Ser Ala Phe Gly Ile
            85                  90                  95

Pro Ile Ala Ala Pro Asp Asn Ile Ser Asp Cys Val Ala Thr Ser
                100                 105                 110

Asn Leu Arg Asn Ser Lys Asp Ala Ile Arg Gly Leu Ala Cys Cys Pro
            115                 120                 125

Pro Val Leu Ser Thr Asn Lys Pro Met Asp Tyr Val Leu Pro Ser Asn
130                 135                 140

Pro Val Ile Arg Val Arg Pro Ala Ala Gln Lys Ala Thr Ala Asp Tyr
145                 150                 155                 160

Ile Ala Lys Tyr Gln Gln Ala Ile Gln Ala Met Lys Asp Leu Pro Glu
            165                 170                 175

Asp His Pro His Ser Trp Lys Gln Gln Gly Lys Ile His Cys Ala Tyr
                180                 185                 190

Cys Asn Gly Gly Tyr Asn Gln Glu Gln Ser Gly Tyr Pro Asn Leu Gln
            195                 200                 205

Leu Gln Ile His Asn Ser Trp Leu Phe Phe Pro Phe His Arg Trp Tyr
210                 215                 220

Leu Tyr Phe Tyr Glu Lys Ile Leu Gly Lys Leu Ile Asn Asp Pro Thr
225                 230                 235                 240

Phe Ala Leu Pro Tyr Trp Asn Trp Asp Asn Pro Thr Gly Met Val Ile
            245                 250                 255

Pro Ala Met Phe Glu Gln Asn Ser Lys Thr Asn Ser Leu Phe Asp Pro
            260                 265                 270

Leu Arg Asp Ala Lys His Leu Pro Pro Ser Ile Phe Asp Val Glu Tyr
275                 280                 285

Ala Gly Ala Asp Thr Gly Ala Thr Cys Ile Asp Gln Ile Ala Ile Asn
290                 295                 300

Leu Ser Ser Met Tyr Arg Gln Met Val Thr Asn Ser Thr Asp Thr Lys
305                 310                 315                 320

Arg Phe Phe Gly Gly Glu Phe Val Ala Gly Asn Asp Pro Leu Ala Ser
            325                 330                 335

Glu Phe Asn Val Ala Gly Thr Val Glu Ala Gly Val His Thr Ala Ala
            340                 345                 350

His Arg Trp Val Gly Asn Ser Arg Met Ala Asn Ser Glu Asp Met Gly
            355                 360                 365

Asn Phe Tyr Ser Arg Arg Ile
370                 375

<210> SEQ ID NO 11
<211> LENGTH: 2101
<212> TYPE: DNA
<213> ORGANISM: Lactuca sativa

<400> SEQUENCE: 11
cgatcaacgt tagcatgcac accaccaaaa gctcatggct tctcttccca caccaacagt      60
tacagctgcc ggagccacca ctaaaaccta ctcttcttct ttcaccacca cttcccctgt     120
catctcttct tggccgttgt tctcgaagaa atgtgccctt aataagccac taaaacacaa     180
aatctcttgc aatgctggtt cttctgagaa ctccttgaac aaccttgatc gccggaatgt     240
tcttctcggt ctcggtggtc ttgccggagc tgtgaacttg acgtctgttc cgtctgtcgg     300

```
agctgcgcca atatccgccc cggatatttc caaatgtggg actaaccctc tttcagggtt    360
tagacctggg gagagcactc ccaccggcgg cgactgttgc ccgcctgact cccccagat    420
catggacttc aagttcccta agaatgaggc gttcagggtg agacccgcag cccatttgct    480
cagccctaag tacattgcta aattcaacga agcgatcaaa cgcatgaagg aacttcccga    540
aaccgatcct cgaaactttc tgcaacaagc acacattcac tgtgcttact gcaatggcgc    600
ttacactcaa tcttcaagtg gatttcccga tattgaaatc cagattcata actcatggct    660
gttcttcccc ttccaccgtt ggtatctcta cttttacgag agaatcctgg ggagcttgat    720
cgatgatccc actttcgctt tgccattctg gaactgggac accctgccg gaatgacaat    780
tccgaaatac tttaacgatc ccaaaaacgc agttttgat cccaaaagaa accaaggtca    840
cttgcaagga gtcgtcgatc tgggttacaa tgggaaagat tcagacacta ctgatatcga    900
aaaggtgaag aacaatctcg cgataatgta tcgtcaaatg gtgacaaacg ccaccgaccc    960
cacagctttc ttcggtggtg agtatcgtgc cggaatcgaa cccattagcg gtggtggatc   1020
agtcgaacaa agcccacaca cacctgttca ccggtgggtc ggtgacccaa gagaacttaa   1080
cggtgaaaac ctcggtaact tctactccgc cggtcgtgac acgctctttt actgtcacca   1140
ttccaacgtc gatcgaatgt ggtcgttgtg aagatgcag ggaggcaaac acaaggacat   1200
caccgatccc gattggctca cacctctttt cgtgttttac gacgaaaaca agaatcttgt   1260
tcgagtgtat gttaaggatt gtttgtacac aaaccagcta gggtacgact accagagagt   1320
cgacgtacca tggctaaaaa gcaagccagt cccacgtgca cccaggtctg gagttgcgag   1380
gaaatccatc ggaaaagtaa aacaggcgaa ggaagtttcc ttcccggtga aactcgacaa   1440
gaccgtgaag gttttggtgg caagaccgaa gaaatcaaga agcaagaagg agaaggagga   1500
ccaagaggag cttttgattg ttcagggtat cacttatgat agcgagaagt acgtgaagtt   1560
tgatgtgtat gtgaacgacg aggacgacga tgctagtgca ccagatcaga ctgagttcgc   1620
cggaagtttc gcacagttgc cacacaaaca caagggtaag acgatgagca agaccaactt   1680
ccgcgccgga ctgacggagc tgctggagga tctggaggcc gacgacgacg acaatgtttt   1740
ggtgacgatt gtcccaaggt ctggatccga agacatcacc attgataaca tcaagatcat   1800
ctacgcttga tttcaagatt tgacgactct cagttgggat cattagttaa atatgtttga   1860
ttaatgatct tgctattccc ttaattatta ttattattat cagcgtagtt cgacccttga   1920
ttagtggtga gggttgatgg ttgtcaccgg aatgtttggg tttgagtccg agttcatgtg   1980
attatgggtc ggatttaaaa taaaatctga gtcgagtctg tggtcatgtc gtaatttggg   2040
gtttcacttt tgaccaaatc aatgttaatt ataatttaaa taaattatta ttagttctcc   2100
a                                                                   2101
```

<210> SEQ ID NO 12
<211> LENGTH: 591
<212> TYPE: PRT
<213> ORGANISM: Lactuca sativa

<400> SEQUENCE: 12

```
Met Ala Ser Leu Pro Thr Pro Thr Val Thr Ala Ala Gly Ala Thr Thr
1               5                   10                  15

Lys Thr Tyr Ser Ser Ser Phe Thr Thr Thr Ser Pro Val Ile Ser Ser
            20                  25                  30

Trp Pro Leu Phe Ser Lys Lys Cys Ala Leu Asn Lys Pro Leu Lys His
        35                  40                  45
```

-continued

```
Lys Ile Ser Cys Asn Ala Gly Ser Ser Glu Asn Ser Leu Asn Asn Leu
 50                  55                  60

Asp Arg Arg Asn Val Leu Leu Gly Leu Gly Gly Leu Ala Gly Ala Val
 65                  70                  75                  80

Asn Leu Thr Ser Val Pro Ser Val Gly Ala Ala Pro Ile Ser Ala Pro
                     85                  90                  95

Asp Ile Ser Lys Cys Gly Thr Asn Pro Leu Ser Gly Phe Arg Pro Gly
                100                 105                 110

Glu Ser Thr Pro Thr Gly Gly Asp Cys Cys Pro Pro Asp Ser Pro Gln
                115                 120                 125

Ile Met Asp Phe Lys Phe Pro Lys Asn Glu Ala Phe Arg Val Arg Pro
130                 135                 140

Ala Ala His Leu Leu Ser Pro Lys Tyr Ile Ala Lys Phe Asn Glu Ala
145                 150                 155                 160

Ile Lys Arg Met Lys Glu Leu Pro Glu Thr Asp Pro Arg Asn Phe Leu
                165                 170                 175

Gln Gln Ala His Ile His Cys Ala Tyr Cys Asn Gly Ala Tyr Thr Gln
                180                 185                 190

Ser Ser Ser Gly Phe Pro Asp Ile Glu Ile Gln Ile His Asn Ser Trp
        195                 200                 205

Leu Phe Phe Pro Phe His Arg Trp Tyr Leu Tyr Phe Tyr Glu Arg Ile
210                 215                 220

Leu Gly Ser Leu Ile Asp Asp Pro Thr Phe Ala Leu Pro Phe Trp Asn
225                 230                 235                 240

Trp Asp Thr Pro Ala Gly Met Thr Ile Pro Lys Tyr Phe Asn Asp Pro
                245                 250                 255

Lys Asn Ala Val Phe Asp Pro Lys Arg Asn Gln Gly His Leu Gln Gly
                260                 265                 270

Val Val Asp Leu Gly Tyr Asn Gly Lys Asp Ser Asp Thr Thr Asp Ile
            275                 280                 285

Glu Lys Val Lys Asn Asn Leu Ala Ile Met Tyr Arg Gln Met Val Thr
290                 295                 300

Asn Ala Thr Asp Pro Thr Ala Phe Phe Gly Gly Glu Tyr Arg Ala Gly
305                 310                 315                 320

Ile Glu Pro Ile Ser Gly Gly Ser Val Glu Gln Ser Pro His Thr
                325                 330                 335

Pro Val His Arg Trp Val Gly Asp Pro Arg Glu Leu Asn Gly Glu Asn
                340                 345                 350

Leu Gly Asn Phe Tyr Ser Ala Gly Arg Asp Thr Leu Phe Tyr Cys His
            355                 360                 365

His Ser Asn Val Asp Arg Met Trp Ser Leu Trp Lys Met Gln Gly Gly
370                 375                 380

Lys His Lys Asp Ile Thr Asp Pro Asp Trp Leu Asn Thr Ser Phe Val
385                 390                 395                 400

Phe Tyr Asp Glu Asn Lys Asn Leu Val Arg Val Tyr Val Lys Asp Cys
                405                 410                 415

Leu Tyr Thr Asn Gln Leu Gly Tyr Asp Tyr Gln Arg Val Asp Val Pro
                420                 425                 430

Trp Leu Lys Ser Lys Pro Val Pro Arg Ala Pro Arg Ser Gly Val Ala
            435                 440                 445

Arg Lys Ser Ile Gly Lys Val Lys Gln Ala Lys Glu Val Ser Phe Pro
450                 455                 460

Val Lys Leu Asp Lys Thr Val Lys Val Leu Val Ala Arg Pro Lys Lys
```

```
                 465                 470                 475                 480
Ser Arg Ser Lys Lys Glu Lys Glu Asp Gln Glu Leu Leu Ile Val
                     485                 490                 495

Gln Gly Ile Thr Tyr Asp Ser Glu Lys Tyr Val Lys Phe Asp Val Tyr
                 500                 505                 510

Val Asn Asp Glu Asp Asp Ala Ser Ala Pro Asp Gln Thr Glu Phe
             515                 520                 525

Ala Gly Ser Phe Ala Gln Leu Pro His Lys His Lys Gly Lys Thr Met
         530                 535                 540

Ser Lys Thr Asn Phe Arg Ala Gly Leu Thr Glu Leu Leu Glu Asp Leu
545                 550                 555                 560

Glu Ala Asp Asp Asp Asp Asn Val Leu Val Thr Ile Val Pro Arg Ser
                 565                 570                 575

Gly Ser Glu Asp Ile Thr Ile Asp Asn Ile Lys Ile Ile Tyr Ala
             580                 585                 590

<210> SEQ ID NO 13
<211> LENGTH: 1982
<212> TYPE: DNA
<213> ORGANISM: Lactuca sativa

<400> SEQUENCE: 13
```

| | | | | | |
|---|---|---|---|---|---|
| gtttttgtat | gttttctttc | caatcttttg | caaccttcac | ttccatcacc | accagaacac    60 |
| taccaaattc | cacctcggat | cgccgctaca | acagttaccc | caaacaaatc | caccaccttc   120 |
| aaatctcatg | caacgtcgca | ccagatgaca | aagagaagtt | agtcgtagtc | ccagaaaccc   180 |
| aaaaacttat | tctgccaaaa | tcatctctcg | acacacttaa | tgtagatcgg | aggaacatgc   240 |
| tcctcgggct | tggcggcctt | tacaccaccg | tcaacttcac | ctcccctgca | gcatttgctg   300 |
| cacctatcac | gacgccaaac | ttctccacat | gcgtgacctc | aaatttaggt | ttccaggacc   360 |
| caaataaggc | cgtcagaagc | agagcatgtt | gtccaccggc | gccagcgacg | tcaacagccc   420 |
| ccaaagactt | tgtgttccct | aaagaccaag | tgatccggat | tagaccagcg | gcacatagaa   480 |
| ccaccaccga | gtacgttgct | aagtacaaag | cagcaatcca | agcgatgaga | gatctcccag   540 |
| atgaacaccc | acacagtttc | gttgcacaag | caaaaattca | ttgcgcttac | tgcaacggtg   600 |
| gttacactca | aatcgcgagt | ggttttccag | ataaagaact | ccagattcac | aactcatggc   660 |
| tcttctttcc | tttccatcgt | tggtacttgt | atttctacga | gagaatcctc | gggaagttaa   720 |
| tcgatgatcc | aactttcgct | ttaccttact | ggaactggga | ccatcccaac | ggaatgacgt   780 |
| ttcccgcatt | tttggaggac | gattctgcct | tcgacgctta | ccgtaatcga | aagcacttac   840 |
| caccagcact | tgttgaccct | aactacagtg | gctcagatag | acacgctact | tgtattcgac   900 |
| agataactag | caatatgaca | ttaatgtata | agcaaatgat | cagcaacgcc | ggtgacacga   960 |
| caagcttctt | tggtagcgaa | tatcgggctg | caacgacgc  | gtatagaaat | ggtgacccat  1020 |
| ctgtcgggtc | gatagaggct | ggttgtcaca | ctgcggtgca | tagatggatg | ggtgaccag   1080 |
| gaatgccgaa | caacgaggac | atggggaact | tctactctgc | ggggtatgac | cctgcgttct  1140 |
| acatccacca | tgccaatgtc | gaccggatgt | ggaaactatg | gaaggatatg | ggcatcaaag  1200 |
| gacactctga | acctacacat | ctggattggc | gtaacgcatc | gtacgtgttt | tatgatgaaa  1260 |
| acgaacagct | tgttcgtgtc | tacaacaaag | attgcgtcag | tttggaaaag | ctaaaatacg  1320 |
| attatgaata | ctccccaccc | ctctggaaaa | taagccgatc | cagtatacgt | cgtacccttc  1380 |
| ccgaacccat | tccatataac | atgaaatctg | ctgaaacggt | taaacaactg | ccagacgtga  1440 |

-continued

```
agttcccctt gaagctagac aagataacga aggtagtagt gaagaggcca gccaaaagca    1500
gaagtcaaga agacaaggaa aaagcaaatg agctgttgtt gattaaagga atcaagttta    1560
atagcgacaa gttcatcaag tttgatgtgt tgtgaatgg acaagatgat gtcagcgaaa     1620
gttttgaaga agagagtgag tttgcaggta gtttcgcgca gttgccacat aaccatggtg    1680
acgacatgtt aatgaagagt ggcataaggt ttgggttaac ggagcttttg gaggaaatgg    1740
aggcggagga tgatgagttt attttggtga ctttggtgcc aaaggtgtgg tttgaggaag    1800
tgaccattga cgaaatcaag gtggagttgg ttcctattat ctgattcata atctaaaatt    1860
gatgagcatc gggtacgtaa ttaacgtagc gtatacgtac caacgctgta aatacaaaaa    1920
agtattatta ttcaactaaa gtaccaaaga gatactcaat ttagttgtag taacggagaa    1980
gg                                                                  1982
```

<210> SEQ ID NO 14
<211> LENGTH: 611
<212> TYPE: PRT
<213> ORGANISM: Lactuca sativa

<400> SEQUENCE: 14

```
Met Phe Ser Phe Gln Ser Phe Ala Thr Phe Thr Ser Ile Thr Thr Arg
1               5                   10                  15

Thr Leu Pro Asn Ser Thr Ser Asp Arg Arg Tyr Asn Ser Tyr Pro Lys
            20                  25                  30

Gln Ile His His Leu Gln Ile Ser Cys Asn Val Ala Pro Asp Asp Lys
        35                  40                  45

Glu Lys Leu Val Val Val Pro Glu Thr Gln Lys Leu Ile Leu Pro Lys
    50                  55                  60

Ser Ser Leu Asp Thr Leu Asn Val Asp Arg Arg Asn Met Leu Leu Gly
65                  70                  75                  80

Leu Gly Gly Leu Tyr Thr Thr Val Asn Phe Thr Ser Pro Ala Ala Phe
                85                  90                  95

Ala Ala Pro Ile Thr Thr Pro Asn Phe Ser Thr Cys Val Thr Ser Asn
            100                 105                 110

Leu Gly Phe Gln Asp Pro Asn Lys Ala Val Arg Ser Arg Ala Cys Cys
        115                 120                 125

Pro Pro Ala Pro Ala Thr Ser Thr Ala Pro Lys Asp Phe Val Phe Pro
    130                 135                 140

Lys Asp Gln Val Ile Arg Ile Arg Pro Ala Ala His Arg Thr Thr Thr
145                 150                 155                 160

Glu Tyr Val Ala Lys Tyr Lys Ala Ala Ile Gln Ala Met Arg Asp Leu
                165                 170                 175

Pro Asp Glu His Pro His Ser Phe Val Ala Gln Ala Lys Ile His Cys
            180                 185                 190

Ala Tyr Cys Asn Gly Gly Tyr Thr Gln Ile Ala Ser Gly Phe Pro Asp
        195                 200                 205

Lys Glu Leu Gln Ile His Asn Ser Trp Leu Phe Pro Phe His Arg
    210                 215                 220

Trp Tyr Leu Tyr Phe Tyr Glu Arg Ile Leu Gly Lys Leu Ile Asp Asp
225                 230                 235                 240

Pro Thr Phe Ala Leu Pro Tyr Trp Asn Trp Asp His Pro Asn Gly Met
                245                 250                 255

Thr Phe Pro Ala Phe Leu Glu Asp Asp Ser Ala Phe Ala Tyr Arg
            260                 265                 270
```

```
Asn Arg Lys His Leu Pro Pro Ala Leu Val Asp Leu Asn Tyr Ser Gly
            275                 280                 285

Ser Asp Arg His Ala Thr Cys Ile Arg Gln Ile Thr Ser Asn Met Thr
        290                 295                 300

Leu Met Tyr Lys Gln Met Ile Ser Asn Ala Gly Asp Thr Thr Ser Phe
305                 310                 315                 320

Phe Gly Ser Glu Tyr Arg Ala Gly Asn Asp Ala Tyr Arg Asn Gly Asp
                325                 330                 335

Pro Ser Val Gly Ser Ile Glu Ala Gly Cys His Thr Ala Val His Arg
            340                 345                 350

Trp Met Gly Asp Pro Gly Met Pro Asn Asn Glu Asp Met Gly Asn Phe
        355                 360                 365

Tyr Ser Ala Gly Tyr Asp Pro Ala Phe Tyr Ile His His Ala Asn Val
370                 375                 380

Asp Arg Met Trp Lys Leu Trp Lys Asp Met Gly Ile Lys Gly His Ser
385                 390                 395                 400

Glu Pro Thr His Leu Asp Trp Arg Asn Ala Ser Tyr Val Phe Tyr Asp
                405                 410                 415

Glu Asn Glu Gln Leu Val Arg Val Tyr Asn Lys Asp Cys Val Ser Leu
            420                 425                 430

Glu Lys Leu Lys Tyr Asp Tyr Glu Tyr Ser Pro Pro Leu Trp Lys Ile
        435                 440                 445

Ser Arg Ser Ser Ile Arg Arg Thr Leu Pro Glu Pro Ile Pro Tyr Asn
450                 455                 460

Met Lys Ser Ala Glu Thr Val Lys Gln Leu Pro Asp Val Lys Phe Pro
465                 470                 475                 480

Leu Lys Leu Asp Lys Ile Thr Lys Val Val Lys Arg Pro Ala Lys
                485                 490                 495

Ser Arg Ser Gln Glu Asp Lys Glu Lys Ala Asn Glu Leu Leu Leu Ile
            500                 505                 510

Lys Gly Ile Lys Phe Asn Ser Asp Lys Phe Ile Lys Phe Asp Val Phe
        515                 520                 525

Val Asn Gly Gln Asp Asp Val Ser Glu Ser Phe Glu Glu Glu Ser Glu
530                 535                 540

Phe Ala Gly Ser Phe Ala Gln Leu Pro His Asn His Gly Asp Asp Met
545                 550                 555                 560

Leu Met Lys Ser Gly Ile Arg Phe Gly Leu Thr Glu Leu Leu Glu Glu
                565                 570                 575

Met Glu Ala Glu Asp Asp Glu Phe Ile Leu Val Thr Leu Val Pro Lys
            580                 585                 590

Val Trp Phe Glu Glu Val Thr Ile Asp Glu Ile Lys Val Glu Leu Val
        595                 600                 605

Pro Ile Ile
        610

<210> SEQ ID NO 15
<211> LENGTH: 1920
<212> TYPE: DNA
<213> ORGANISM: Lactuca sativa

<400> SEQUENCE: 15
atggcttcac tgagcttcac tttagctatg gccaccaccc cctcttcttc cccattcttt      60
tccaaaccag cgaaccaacg tcagttgata aagcacatg ctaagcaaac ccaccgcttc     120
caaatgtcat gcaatgttcc atcagacgac catgaaaaac caatcatcaa taccctcaa      180
```

```
catcaaaagc tcatactacc aaaaacatca ctcgacatgc agaacgtaga cagaaggaat    240
ttgctcctgg ggcttggtgg gctctacagc gccgtcaact tgacgggtct cccatccgct    300
tttgccgatc ctatcacgac tccttctttt aatccaaatt gcagggacgc cggaacgggc    360
ttcgatgtca aaaaggcct tcttagaact actgcatgtt gccctccgga gtccaagaag     420
ggtcccgaga acaattcga attccctaaa catgacgaaa tacgcatcag atatcccata     480
cactgtgccc cggaaggata catgaataaa tttaaggagg cgatgaggct aatgagggct    540
ctcccagatg acgaccctcg cagtttcaag aaccaagcca aaattcattg cgcctactgc    600
aatggcagct acactcaaat ggctacaggt tcccaacaag aactcctgat tcacttcaac    660
tggctgtttt ttcccttcca tcgatggtac ctttatttct tcgagaggat actcggagaa    720
ctgattggtg atccaacatt cgggttacca tactggagct gggacgagcg tgagggaatg    780
aaaattccac ctacgttccg agaaggggga gagtctaacc ctttatatga tatctaccgg    840
aataacattc gcaactatga agctattgtc gatcttgact caatggtaa agatcgcgaa     900 gatacgactg acgactatca gataaaaatc aatcagcatg ctatgtatcg ccagatgatg    960
agaaatgcct tcgatacaaa aagcttcttt ggtggtaagt atgtcgctgg taatacaccc    1020
attgatgcca aagactcttc agttgcatcc atagaggccg ttgtcatac cgcgattcac     1080 agatgggtgc gtgaccctgg aagtccgaat ggtgaagaca tgggtaattt ctactctgcc    1140
gggtatgatc ctttgttcta tgtccaccat tccaatgtcg acaggatgtg ggcactttgg    1200
aaagaaatgg gggaaagcaa ccgcgacccc atacacccag actggttaaa cgcatcatat    1260 gtgtttttacg acgagaaaca aaatcctgtt cgtgtctaca ataaacaatg cgtggatatg    1320
gaaaagctca aatacaaata ccatggtcca gaaatcccca gctgggtcaa ttctcggccg    1380
aaaccaaagt gcagcgcttc ggaaagatcc caaatcgata tcacgtcagc cacaaaagat    1440
gtgaagaacc gaaccctcac caacgtagat acgtttgtgt tagtgaggcc tgaaactgct    1500
agaacaagga ccgtggatga atcagaaata gaggtcttga cgttgaacaa cattagtttc    1560
aacggtaaca aagccgtcaa gtttgacgtg cttgttaacg cttgtaacat tgacacaaac    1620
aagttcaccc cggctgatag cgagtatgcg ggttcttttg caacagttcc acataaccat    1680
gacatgaaaa ttagtactac gttcaggttt cccttaagag agctgttgaa agatattgga    1740
gctgagggaa atacagcaat tcaagtcacc attgtgacgc aagagaaaga aaccgagaat    1800
atcagcattg gcgagatcaa gatcgaggat tactctttag ccgagatctc gaaggcgtca    1860
cttcccactg ggctacaggg tgccggagct aatgtcggcg tcgacgatct aacagaatag   1920
```

<210> SEQ ID NO 16
<211> LENGTH: 639
<212> TYPE: PRT
<213> ORGANISM: Lactuca sativa

<400> SEQUENCE: 16

```
Met Ala Ser Leu Ser Phe Thr Leu Ala Met Ala Thr Thr Pro Ser Ser
1               5                   10                  15

Ser Pro Phe Phe Ser Lys Pro Ala Asn Gln Arg Gln Leu Ile Lys Thr
            20                  25                  30

His Ala Lys Gln Thr His Arg Phe Gln Met Ser Cys Asn Val Pro Ser
        35                  40                  45

Asp Asp His Glu Lys Pro Ile Ile Asn Thr Pro Gln His Gln Lys Leu
    50                  55                  60
```

```
Ile Leu Pro Lys Thr Ser Leu Asp Met Gln Asn Val Asp Arg Arg Asn
 65                  70                  75                  80

Leu Leu Leu Gly Leu Gly Gly Leu Tyr Ser Ala Val Asn Leu Thr Gly
                 85                  90                  95

Leu Pro Ser Ala Phe Ala Asp Pro Ile Thr Thr Pro Ser Phe Asn Pro
                100                 105                 110

Asn Cys Arg Asp Ala Gly Thr Gly Phe Asp Val Lys Lys Gly Leu Leu
                115                 120                 125

Arg Thr Thr Ala Cys Cys Pro Pro Glu Ser Lys Lys Gly Pro Glu Lys
                130                 135                 140

Gln Phe Glu Phe Pro Lys His Asp Glu Ile Arg Ile Arg Tyr Pro Ile
145                 150                 155                 160

His Cys Ala Pro Glu Gly Tyr Met Asn Lys Phe Lys Glu Ala Met Arg
                165                 170                 175

Leu Met Arg Ala Leu Pro Asp Asp Pro Arg Ser Phe Lys Asn Gln
                180                 185                 190

Ala Lys Ile His Cys Ala Tyr Cys Asn Gly Ser Tyr Thr Gln Met Ala
            195                 200                 205

Thr Gly Ser Gln Gln Glu Leu Leu Ile His Phe Asn Trp Leu Phe Phe
210                 215                 220

Pro Phe His Arg Trp Tyr Leu Tyr Phe Phe Glu Arg Ile Leu Gly Glu
225                 230                 235                 240

Leu Ile Gly Asp Pro Thr Phe Gly Leu Pro Tyr Trp Ser Trp Asp Glu
                245                 250                 255

Arg Glu Gly Met Lys Ile Pro Pro Thr Phe Arg Glu Gly Gly Glu Ser
                260                 265                 270

Asn Pro Leu Tyr Asp Ile Tyr Arg Asn Asn Ile Arg Asn Tyr Glu Ala
                275                 280                 285

Ile Val Asp Leu Asp Phe Asn Gly Lys Asp Arg Glu Asp Thr Thr Asp
                290                 295                 300

Asp Tyr Gln Ile Lys Ile Asn Gln His Ala Met Tyr Arg Gln Met Met
305                 310                 315                 320

Arg Asn Ala Phe Asp Thr Lys Ser Phe Phe Gly Gly Lys Tyr Val Ala
                325                 330                 335

Gly Asn Thr Pro Ile Asp Ala Lys Asp Ser Ser Val Ala Ser Ile Glu
                340                 345                 350

Ala Gly Cys His Thr Ala Ile His Arg Trp Val Arg Asp Pro Gly Ser
            355                 360                 365

Pro Asn Gly Glu Asp Met Gly Asn Phe Tyr Ser Ala Gly Tyr Asp Pro
            370                 375                 380

Leu Phe Tyr Val His His Ser Asn Val Asp Arg Met Trp Ala Leu Trp
385                 390                 395                 400

Lys Glu Met Gly Glu Ser Asn Arg Asp Pro Ile His Pro Asp Trp Leu
                405                 410                 415

Asn Ala Ser Tyr Val Phe Tyr Asp Glu Lys Gln Asn Pro Val Arg Val
                420                 425                 430

Tyr Asn Lys Gln Cys Val Asp Met Glu Lys Leu Lys Tyr Lys Tyr His
            435                 440                 445

Gly Pro Glu Ile Pro Ser Trp Val Asn Ser Arg Pro Lys Pro Lys Cys
            450                 455                 460

Ser Ala Ser Glu Arg Ser Gln Ile Asp Ile Thr Ser Ala Thr Lys Asp
465                 470                 475                 480

Val Lys Asn Arg Thr Leu Thr Asn Val Asp Thr Phe Val Leu Val Arg
```

```
                485                 490                 495
Pro Glu Thr Ala Arg Thr Arg Thr Val Asp Glu Ser Glu Ile Glu Val
                500                 505                 510

Leu Thr Leu Asn Asn Ile Ser Phe Asn Gly Asn Lys Ala Val Lys Phe
                515                 520                 525

Asp Val Leu Val Asn Ala Cys Asn Ile Asp Thr Asn Lys Phe Thr Pro
            530                 535                 540

Ala Asp Ser Glu Tyr Ala Gly Ser Phe Ala Thr Val Pro His Asn His
545                 550                 555                 560

Asp Met Lys Ile Ser Thr Thr Phe Arg Phe Pro Leu Arg Glu Leu Leu
                565                 570                 575

Lys Asp Ile Gly Ala Glu Gly Asn Thr Ala Ile Gln Val Thr Ile Val
            580                 585                 590

Thr Gln Glu Lys Glu Thr Glu Asn Ile Ser Ile Gly Glu Ile Lys Ile
                595                 600                 605

Glu Asp Tyr Ser Leu Ala Glu Ile Ser Lys Ala Ser Leu Pro Thr Gly
            610                 615                 620

Leu Gln Gly Ala Gly Ala Asn Val Gly Val Asp Asp Leu Thr Glu
625                 630                 635
```

<210> SEQ ID NO 17
<211> LENGTH: 2222
<212> TYPE: DNA
<213> ORGANISM: Lactuca sativa

<400> SEQUENCE: 17

```
atggcttctt ttagctttta cactcttcct acttccacct ccaccatcaa gaatccctta      60
tttttctaaaa gctcctccca tgtgaagcac tcacatcgct tcaggtcttc atgcaaagcc    120
gctgctgata gcaatgacaa atatgtcgaa atcctgata ccccaaaact catactacca     180
aaatcaccct cgcttgatac gcagaacgtt gacaggagaa acttgctcct gggactcgga    240
ggtctctaca gcgctgccaa cttccaccagc attccgtcag cctttggcgt tcccatcgaa    300
gcaccagaca ttaatatttc aaagtgtgtt actgccaccg taaggggagt ctcagcagag    360
gctataaggg gattaacttg ttgccctccg gtgtttgact catcggccaa accagcgccg    420
tacgaatttc cggataacca ggtaattcgt atgcgaccag cggcacagag agtcagtgca    480
gactacaaaa aagactttcg aaaggcagtt gagataatga aggatataa cgacaatgac    540
ccacacagtt ggacgcaaca agctaaagtt cattgtgcgt actgcaacgg cgcttacact    600
caagtaaaaa gtggtttgga gttcgagaag tatataatcc aagttcacaa ctcatggctc    660
ttctttccat tccaccgttg gtacctctat ttcctcgaga agataatggg aaaggcgctc    720
ggggatgaca ctttcgctct accatactgg aactgggacc accctaccgg aatgacgatt    780
cctgccatgt acgaagacaa attaaaaaat ccggatggca cgttgatac ccctgaaaac     840
actagattca actctctctt tgatccttta aggaatacat cacacatcgc accagctcta    900
attgattttc agtattatcc tcagaaacaa gaagtttata attgtgcaga ccagatagag    960
attaatctgt ctataatgta caatcagatg atcgccaacg cccttgatac aaaatcgttc   1020
tttggtggcg aacttgtggc tggtgaaaac cccaatgaaa acaaaaaggc tgggtccata   1080
gaggatgggg ttcacacgat tgcccaccaa tgggtgggta acaatagatt gaagaacgga   1140
gaagacatgg gaaacttcta ctccgcaggc tatgaccctc tgttttacgg ccaccatgcg   1200
aacgttgacc ggatgtggaa atctggaaa ggtatgaaca ggagacacca tgcaccatcc   1260
```

-continued

```
tcgaccgact ggctagatgc atcctacgta ttttatgatg agaatagaaa acttgtacgt   1320
gtctacaacc gtgactgtgt agacactaga acgatggggt atgattatga gaggtccgag   1380
atcccatgga tccgaaatcg acctaatcca catcccaagg gaggcaaaga taaaggaaat   1440
gctcgcaaac ccgacaaagc gacggtgaag gatctcagtt tcccagtgag gttaaaccag   1500
acattggagg ttcgagtgat gagacctgcg aaaaggacta cggaggacaa ggagcgcacc   1560
gagatcgcga ttgagaagtt ggtccttcaa ggcgtacgat atgattgtga gcgctttgtc   1620
aagttcgatg tgataatgaa cgaccctgat aatggagtcg atgtcacccc agttgacact   1680
gagtttcttg gttatttctc acggttgccc catggcatgg tcgctgaaaa cagaatgaaa   1740
gagattagtg ggatatcatt tgccatcaaa gaccgcttga aaatcctaaa agttgaaaat   1800
gatgattcta ttgttgtgaa aattgtgccc agagcagggt gcgaggatgt aactattcag   1860
aacatcgagg ttgtgatgga tcccgtagac aatattgtac ctttagcgga gagcctggtt   1920
gtgcaagatc ggaacagcga tgaacttact ttggagggcc cgactgcgct ggattcgaat   1980
tcggacgact ctggctcgga gtgataaatt aaatcgtgtc gttgtgtatc ttgtatatgt   2040
gtgatcactt tataagttta agtttgtatt cgaatcgcca atgtggtgat atttgcattt   2100
tgccattatt aataataatc caatgctctt gtagaagaaa ttgctctgag tgtctagagt   2160
tttgtctgaa tgggtacgta cggttacttt tttgtacgtc aataatgcac ttatttgact   2220
ta                                                                   2222
```

<210> SEQ ID NO 18
<211> LENGTH: 667
<212> TYPE: PRT
<213> ORGANISM: Lactuca sativa

<400> SEQUENCE: 18

```
Met Ala Ser Phe Ser Phe Tyr Thr Leu Pro Thr Ser Thr Ser Thr Ile
1               5                   10                  15

Lys Asn Pro Leu Phe Ser Lys Ser Ser His Val Lys His Ser His
            20                  25                  30

Arg Phe Arg Ser Ser Cys Lys Ala Ala Ala Asp Ser Asn Asp Lys Tyr
        35                  40                  45

Val Glu Asn Pro Asp Thr Pro Lys Leu Ile Leu Pro Lys Ser Pro Ser
    50                  55                  60

Leu Asp Thr Gln Asn Val Asp Arg Arg Asn Leu Leu Gly Leu Gly
65                  70                  75                  80

Gly Leu Tyr Ser Ala Ala Asn Phe Thr Ser Ile Pro Ser Ala Phe Gly
                85                  90                  95

Val Pro Ile Glu Ala Pro Asp Ile Asn Ile Ser Lys Cys Val Thr Ala
            100                 105                 110

Thr Val Arg Gly Val Ser Ala Glu Ala Ile Arg Gly Leu Thr Cys Cys
        115                 120                 125

Pro Pro Val Phe Asp Ser Ala Lys Pro Ala Pro Tyr Glu Phe Pro
    130                 135                 140

Asp Asn Gln Val Ile Arg Met Arg Pro Ala Ala Gln Arg Val Ser Ala
145                 150                 155                 160

Asp Tyr Lys Lys Asp Phe Arg Lys Ala Val Glu Ile Met Lys Gly Tyr
                165                 170                 175

Asn Asp Asn Asp Pro His Ser Trp Thr Gln Gln Ala Lys Val His Cys
            180                 185                 190

Ala Tyr Cys Asn Gly Ala Tyr Thr Gln Val Lys Ser Gly Leu Glu Phe
```

```
                195                 200                 205
Glu Lys Tyr Ile Ile Gln Val His Asn Ser Trp Leu Phe Phe Pro Phe
210                 215                 220

His Arg Trp Tyr Leu Tyr Phe Leu Glu Lys Ile Met Gly Lys Ala Leu
225                 230                 235                 240

Gly Asp Asp Thr Phe Ala Leu Pro Tyr Trp Asn Trp Asp His Pro Thr
                245                 250                 255

Gly Met Thr Ile Pro Ala Met Tyr Glu Asp Lys Leu Lys Asn Pro Asp
                260                 265                 270

Gly Asn Val Asp Thr Pro Glu Asn Thr Arg Phe Asn Ser Leu Phe Asp
            275                 280                 285

Pro Leu Arg Asn Thr Ser His Ile Ala Pro Ala Leu Ile Asp Phe Gln
290                 295                 300

Tyr Tyr Pro Gln Lys Gln Glu Val Tyr Asn Cys Ala Asp Gln Ile Glu
305                 310                 315                 320

Ile Asn Leu Ser Ile Met Tyr Asn Gln Met Ile Ala Asn Ala Leu Asp
                325                 330                 335

Thr Lys Ser Phe Phe Gly Gly Glu Leu Val Ala Gly Glu Asn Pro Asn
                340                 345                 350

Glu Asn Lys Lys Ala Gly Ser Ile Glu Asp Gly Val His Thr Ile Ala
            355                 360                 365

His Gln Trp Val Gly Asn Asn Arg Leu Lys Asn Gly Glu Asp Met Gly
370                 375                 380

Asn Phe Tyr Ser Ala Gly Tyr Asp Pro Leu Phe Tyr Gly His His Ala
385                 390                 395                 400

Asn Val Asp Arg Met Trp Lys Ile Trp Lys Gly Met Asn Arg His
                405                 410                 415

His Ala Pro Ser Ser Thr Asp Trp Leu Asp Ala Ser Tyr Val Phe Tyr
                420                 425                 430

Asp Glu Asn Arg Lys Leu Val Arg Val Tyr Asn Arg Asp Cys Val Asp
            435                 440                 445

Thr Arg Thr Met Gly Tyr Asp Tyr Glu Arg Ser Glu Ile Pro Trp Ile
450                 455                 460

Arg Asn Arg Pro Asn Pro His Pro Lys Gly Lys Asp Lys Gly Asn
465                 470                 475                 480

Ala Arg Lys Pro Asp Lys Ala Thr Val Lys Asp Leu Ser Phe Pro Val
                485                 490                 495

Arg Leu Asn Gln Thr Leu Glu Val Arg Val Met Arg Pro Ala Lys Arg
                500                 505                 510

Thr Thr Glu Asp Lys Glu Arg Thr Glu Ile Ala Ile Glu Lys Leu Val
            515                 520                 525

Leu Gln Gly Val Arg Tyr Asp Cys Glu Arg Phe Val Lys Phe Asp Val
530                 535                 540

Ile Met Asn Asp Pro Asp Asn Gly Val Asp Val Thr Pro Val Asp Thr
545                 550                 555                 560

Glu Phe Leu Gly Tyr Phe Ser Arg Leu Pro His Gly Met Val Ala Glu
                565                 570                 575

Asn Arg Met Lys Glu Ile Ser Gly Ile Ser Phe Ala Ile Lys Asp Arg
                580                 585                 590

Leu Lys Ile Leu Lys Val Glu Asn Asp Asp Ser Ile Val Val Lys Ile
            595                 600                 605

Val Pro Arg Ala Gly Cys Glu Asp Val Thr Ile Gln Asn Ile Glu Val
610                 615                 620
```

```
Val Met Asp Pro Val Asp Asn Ile Val Pro Leu Ala Glu Ser Leu Val
625                 630                 635                 640

Val Gln Asp Arg Asn Ser Asp Glu Leu Thr Leu Glu Gly Pro Thr Ala
                645                 650                 655

Leu Asp Ser Asn Ser Asp Asp Ser Gly Ser Glu
            660                 665
```

<210> SEQ ID NO 19
<211> LENGTH: 632
<212> TYPE: DNA
<213> ORGANISM: Lactuca sativa

<400> SEQUENCE: 19

```
ttgaattgtt tattataaag atttagcaga aatgaaaagc tctttgcatt gatcacaagg      60
ttctttaact tcttttttagc aaacccaaca tggccggaat accaactaca cctgccactt   120
ttccgatgag tctagacaaa ccaacgacgg tgatggtggc gaggccagca agaaggaaa     180
gagagaagga ggaagaagaa gtattggtga taagggat agaaatcaat agaaatgagt     240
ttgtgaagtt tgatgtgttc attaacgatg aggatgagga cagcggct ggtggtgggg     300
ctgagaaagc tgagtgtgcc ggtagctttg tgaacgtgcc acataagcac aggaacggac   360
atagtggtga tggtgggaag gtgaaaaaga cacagttgag aattggaata agtgagttat   420
tggaggattt gggtgtcgaa gaagatgacg aagatgtggt ggtgaaattg gtgccaaggt   480
gtgaaaatgt tcatgtcaca attggtggta ttaagattga aatgagtga ttaattaatt   540
aattaatgag ttcttatctt agttattttc ttttgttatc gagtggttta tgatcccta    600
taataaatgt tatacttaat gttgtcaaga tc                                 632
```

<210> SEQ ID NO 20
<211> LENGTH: 146
<212> TYPE: PRT
<213> ORGANISM: Lactuca sativa

<400> SEQUENCE: 20

```
Met Ala Gly Ile Pro Thr Thr Pro Ala Thr Phe Pro Met Ser Leu Asp
1               5                   10                  15

Lys Pro Thr Thr Val Met Val Ala Arg Pro Ala Lys Lys Glu Arg Glu
            20                  25                  30

Lys Glu Glu Glu Val Leu Val Ile Glu Gly Ile Glu Ile Asn Arg
        35                  40                  45

Asn Glu Phe Val Lys Phe Asp Val Phe Ile Asn Asp Glu Asp Glu Glu
    50                  55                  60

Thr Ala Ala Gly Gly Ala Glu Lys Ala Glu Cys Ala Gly Ser Phe
65                  70                  75                  80

Val Asn Val Pro His Lys His Arg Asn Gly His Ser Gly Asp Gly Gly
                85                  90                  95

Lys Val Lys Lys Thr Gln Leu Arg Ile Gly Ile Ser Glu Leu Leu Glu
            100                 105                 110

Asp Leu Gly Val Glu Glu Asp Asp Glu Asp Val Val Lys Leu Val
        115                 120                 125

Pro Arg Cys Glu Asn Val His Val Thr Ile Gly Gly Ile Lys Ile Glu
    130                 135                 140

Asn Glu
145
```

<210> SEQ ID NO 21
<211> LENGTH: 2118
<212> TYPE: DNA
<213> ORGANISM: Lactuca sativa

<400> SEQUENCE: 21

| | | | | | |
|---|---|---|---|---|---|
| tttcccacaa | tccgcgtcta | tataatggag | ctcagcagaa | cggatttaac | acctacgaca | 60 |
| atgatggctt | catatatctt | ttccaccgtt | ccctcagcca | ccgaagtcac | caccaacaac | 120 |
| ttctcccatt | cctcgatatt | ttccaaaact | tccactcacc | gattcaaata | tactcatgaa | 180 |
| aaccaaaccc | atcgtttcaa | agtctcatgc | aacaaaacct | cagacgacaa | atatgataca | 240 |
| ctggaaacat | cacttgacaa | gaagaatgta | gaccgaagaa | acttgcttct | ggggctcggt | 300 |
| ggaactctct | acggtgccgc | caacttgacc | ttcctcccgt | ccgccttctc | ggtgcccatt | 360 |
| gctgctccca | tgtttcaga | ctgtgctatt | gccagtaaag | gtatacacaa | catcaaagat | 420 |
| gctgtaaggg | gggtagcttg | ttgcccacca | gtactgacac | taaattcccc | aaaaaattac | 480 |
| gtcttcccga | aggagaccgc | agttcgtatc | cgtccggcag | cacaaagagc | ctctgacgat | 540 |
| tacattgaca | agtataaagc | agcaattaag | gccatgaggg | atctcccaga | tgaccaccca | 600 |
| cacagtttca | gcaacaagc | caagatccat | tgcgcttatt | gcaatggctc | ttacactcaa | 660 |
| aaagagagtg | gcaaggaata | tgaacacctc | acactccaga | ttcataactc | gtggctcttc | 720 |
| tttcctttcc | accggtggta | cctctatttc | tacgaaagga | tattgggaaa | gttgattgac | 780 |
| gacccaactt | tcgcgatacc | atactggaat | tgggacaacc | ccaccggaat | gataatccct | 840 |
| gacttgtttg | aaaaacccat | ccaagtaagg | gaacgcaaag | aaaacccgt | ctttgacgct | 900 |
| tacagggatg | ccagacacct | cccaccagct | cttgttgata | tcgattataa | cggtgaagac | 960 |
| cgtggcgttt | catgtataga | ccaaataact | attaatttgt | ctgcaatgta | taagcagatg | 1020 |
| atcagtaatg | ctagtgaccc | aacaagcttc | ttcggtggca | gatacgtcgc | tgggatggac | 1080 |
| cacgatgaca | aaaatagtca | tggaaatcca | tcggttgggt | ccatagaagc | tggttgtcac | 1140 |
| acagcggtgc | accgatgggt | ggctgatcct | cggatgccga | caatgaaga | catgggaaac | 1200 |
| ttctactccg | cagggtatga | ccctatcttt | tatgcccacc | acgccaatgt | tgaccggatg | 1260 |
| tggaaaatct | ggaaagagtt | gggtatcagg | ggacaccgtg | aaccaaccga | caaggactgg | 1320 |
| ctagatgcat | catacgtgtt | ttacgatgag | aatgaagaac | ttgtacgtgt | ctataaccga | 1380 |
| gactgtgtgg | acttgaataa | gcttaactac | gactatgaaa | catcccgtat | cccgtgggcc | 1440 |
| aggaatcggc | cgatcccacg | tgctaagaat | cctcaaatgg | cagcgaggtc | agcccgaatg | 1500 |
| gggaggagtt | ttcatgacgt | gcaatttccg | gtgaagttag | acgggatagt | aaaggtgcta | 1560 |
| gtgaagagac | cttatgtaaa | caggactaag | gaggagaagg | agaaagcaaa | tgagatattg | 1620 |
| atgttgaatg | ggatttgttt | tgatagcgag | aagtttgtaa | agtttgatgt | gtatgtggat | 1680 |
| gacaaggacg | atgaaccaga | aaccactgcg | gctgatagcg | agtttgcagg | tagctttgcg | 1740 |
| cagttgcctc | accatcaatc | aggcgagaag | atgttcatga | caagtgccgc | gagattcggg | 1800 |
| ttaacagagt | tgttggagga | cattgaagct | gaagatgatg | aatctattat | ggtgactttg | 1860 |
| gttcctagga | cagggtccga | tgatatcaca | atttcagaga | tcaagattga | gctggtcccc | 1920 |
| atcgtttgaa | cttcaataat | gtaatcgcat | tttcatgtcc | atgtaatatg | ttcgttttct | 1980 |
| gtgttgtgtt | taattaggag | aatttgctga | gttctcttaa | cctcaaaaaa | gggcaataag | 2040 |
| ttggtagcgt | taatgtgtta | tcactcgtgc | atgtgtattt | caattaaagt | tgatcaacta | 2100 |
| ataaaaaatt | ttttgttg | | | | | 2118 |

<210> SEQ ID NO 22
<211> LENGTH: 634
<212> TYPE: PRT
<213> ORGANISM: Lactuca sativa

<400> SEQUENCE: 22

```
Met Glu Leu Ser Arg Thr Asp Leu Thr Pro Thr Thr Met Met Ala Ser
1               5                   10                  15

Tyr Ile Phe Ser Thr Val Pro Ser Ala Thr Glu Val Thr Thr Asn Asn
                20                  25                  30

Phe Ser His Ser Ser Ile Phe Ser Lys Thr Ser Thr His Arg Phe Lys
            35                  40                  45

Tyr Thr His Glu Asn Gln Thr His Arg Phe Lys Val Ser Cys Asn Lys
        50                  55                  60

Thr Ser Asp Asp Lys Tyr Asp Thr Leu Glu Thr Ser Leu Asp Lys Lys
65                  70                  75                  80

Asn Val Asp Arg Arg Asn Leu Leu Gly Leu Gly Gly Thr Leu Tyr
                85                  90                  95

Gly Ala Ala Asn Leu Thr Phe Leu Pro Ser Ala Phe Ser Val Pro Ile
                100                 105                 110

Ala Ala Pro Asn Val Ser Asp Cys Ala Ile Ala Ser Lys Gly Ile His
            115                 120                 125

Asn Ile Lys Asp Ala Val Arg Gly Val Ala Cys Cys Pro Pro Val Leu
        130                 135                 140

Thr Leu Asn Ser Pro Lys Asn Tyr Val Phe Pro Lys Glu Thr Ala Val
145                 150                 155                 160

Arg Ile Arg Pro Ala Ala Gln Arg Ala Ser Asp Asp Tyr Ile Asp Lys
                165                 170                 175

Tyr Lys Ala Ala Ile Lys Ala Met Arg Asp Leu Pro Asp Asp His Pro
            180                 185                 190

His Ser Phe Lys Gln Gln Ala Lys Ile His Cys Ala Tyr Cys Asn Gly
        195                 200                 205

Ser Tyr Thr Gln Lys Glu Ser Gly Lys Glu Tyr Glu His Leu Thr Leu
210                 215                 220

Gln Ile His Asn Ser Trp Leu Phe Phe Pro Phe His Arg Trp Tyr Leu
225                 230                 235                 240

Tyr Phe Tyr Glu Arg Ile Leu Gly Lys Leu Ile Asp Asp Pro Thr Phe
                245                 250                 255

Ala Ile Pro Tyr Trp Asn Trp Asp Asn Pro Thr Gly Met Ile Ile Pro
            260                 265                 270

Asp Leu Phe Glu Lys Pro Ile Gln Val Arg Glu Arg Lys Glu Asn Pro
        275                 280                 285

Val Phe Asp Ala Tyr Arg Asp Ala Arg His Leu Pro Pro Ala Leu Val
290                 295                 300

Asp Ile Asp Tyr Asn Gly Glu Asp Arg Gly Val Ser Cys Ile Asp Gln
305                 310                 315                 320

Ile Thr Ile Asn Leu Ser Ala Met Tyr Lys Gln Met Ile Ser Asn Ala
                325                 330                 335

Ser Asp Pro Thr Ser Phe Phe Gly Gly Arg Tyr Val Ala Gly Met Asp
            340                 345                 350

His Asp Asp Lys Asn Ser His Gly Asn Pro Ser Val Gly Ser Ile Glu
        355                 360                 365

Ala Gly Cys His Thr Ala Val His Arg Trp Val Ala Asp Pro Arg Met
370                 375                 380
```

Pro Asn Asn Glu Asp Met Gly Asn Phe Tyr Ser Ala Gly Tyr Asp Pro
385                 390                 395                 400

Ile Phe Tyr Ala His His Ala Asn Val Asp Arg Met Trp Lys Ile Trp
                405                 410                 415

Lys Glu Leu Gly Ile Arg Gly His Arg Glu Pro Thr Asp Lys Asp Trp
            420                 425                 430

Leu Asp Ala Ser Tyr Val Phe Tyr Asp Glu Asn Glu Glu Leu Val Arg
        435                 440                 445

Val Tyr Asn Arg Asp Cys Val Asp Leu Asn Lys Leu Asn Tyr Asp Tyr
    450                 455                 460

Glu Thr Ser Arg Ile Pro Trp Ala Arg Asn Arg Pro Ile Pro Arg Ala
465                 470                 475                 480

Lys Asn Pro Gln Met Ala Ala Arg Ser Ala Arg Met Gly Arg Ser Phe
                485                 490                 495

His Asp Val Gln Phe Pro Val Lys Leu Asp Gly Ile Val Lys Val Leu
            500                 505                 510

Val Lys Arg Pro Tyr Val Asn Arg Thr Lys Glu Glu Lys Glu Lys Ala
        515                 520                 525

Asn Glu Ile Leu Met Leu Asn Gly Ile Cys Phe Asp Ser Glu Lys Phe
    530                 535                 540

Val Lys Phe Asp Val Tyr Val Asp Asp Lys Asp Glu Pro Glu Thr
545                 550                 555                 560

Thr Ala Ala Asp Ser Glu Phe Ala Gly Ser Phe Ala Gln Leu Pro His
                565                 570                 575

His Gln Ser Gly Glu Lys Met Phe Met Thr Ser Ala Ala Arg Phe Gly
            580                 585                 590

Leu Thr Glu Leu Leu Glu Asp Ile Glu Ala Glu Asp Asp Glu Ser Ile
        595                 600                 605

Met Val Thr Leu Val Pro Arg Thr Gly Ser Asp Asp Ile Thr Ile Ser
    610                 615                 620

Glu Ile Lys Ile Glu Leu Val Pro Ile Val
625                 630

<210> SEQ ID NO 23
<211> LENGTH: 1036
<212> TYPE: DNA
<213> ORGANISM: Lactuca sativa

<400> SEQUENCE: 23 tttttttggca atataaatag tgaacgctag ttctcgtaat tcgggtaggt gtatgatggc      60
ttcttttaac ttgtacaccg ttcccgccgc cactacggcc accaccaaca taatcaaaac     120
taactactac caacttaaga ctcaagcaaa gcaaacccat cgcttgaaag cgtcatgcaa     180
cgcaatcccg gataaaaaca atgataaagc acttgaaact tcacttcaaa tgataaacat     240
tgaccggaga acataatac tccgcctcgg tggtctcttt gtggccagca acatgacctc     300
ggttcctttg gcctacgcta atgcaattgc agctcggtct aatcactcgg tttgtgctgc     360
ttcgccttta ggcatacaga atcttggaac ccccgtaaag gaacccatgg agaatagga     420 agatgtagac acgaataagc tcggatacga atacaaatgg tccgaaatcc catggggaag     480
gagtcaaccg actgaatatg gcaaggattc aaaatttgta gataagtcta taggaataga     540
gaagaaggtg ggggaggtgg aatttccagt gaagttaaac aagacagtta aggtactcgt     600
gaagaggccg gctgttaata ggaccaagga ggacaaacag aaagcgaatg agattttgtt     660

-continued

```
ggtaaatgga gtgagattcg atggtgagaa gtacgtcaag ttcgatgtct ttgtcaacga    720
catagacaat ggaaccgaga ccaccccggc tgacagtgag tttgctggta gtttcgcaca    780
gcttccgcat ggcaaaaccg acaggatgat gatgatgagc ggagttaggt ttgggttaac    840
ggagcttttg gaggacataa aagctgaaga tgatgaatat gttttggtga aattggtgcc    900
taggactggg tgtgatgacg ttacagtttc cgagatcaag attgaactgg agggaataat    960
gtcaatggac aagaagtcaa agtttgttga atctgaatat gagaatgtga ttgattactt   1020
gtacatatgt ttatag                                                   1036
```

<210> SEQ ID NO 24
<211> LENGTH: 327
<212> TYPE: PRT
<213> ORGANISM: Lactuca sativa

<400> SEQUENCE: 24

```
Met Met Ala Ser Phe Asn Leu Tyr Thr Val Pro Ala Ala Thr Thr Ala
1               5                   10                  15

Thr Thr Asn Ile Ile Lys Thr Asn Tyr Tyr Gln Leu Lys Thr Gln Ala
            20                  25                  30

Lys Gln Thr His Arg Leu Lys Ala Ser Cys Asn Ala Ile Pro Asp Lys
        35                  40                  45

Asn Asn Asp Lys Ala Leu Glu Thr Ser Leu Gln Met Ile Asn Ile Asp
    50                  55                  60

Arg Arg Asn Ile Ile Leu Arg Leu Gly Gly Leu Phe Val Ala Ser Asn
65                  70                  75                  80

Met Thr Ser Val Pro Leu Ala Tyr Ala Asn Ala Ile Ala Ala Arg Ser
                85                  90                  95

Asn His Ser Val Cys Ala Ala Ser Pro Leu Gly Ile Gln Asn Leu Gly
            100                 105                 110

Thr Pro Val Lys Glu Pro Met Glu Asn Arg Glu Asp Val Asp Thr Asn
        115                 120                 125

Lys Leu Gly Tyr Glu Tyr Lys Trp Ser Glu Ile Pro Trp Gly Arg Ser
    130                 135                 140

Gln Pro Thr Glu Tyr Gly Lys Asp Ser Lys Phe Val Asp Lys Ser Ile
145                 150                 155                 160

Gly Ile Glu Lys Lys Val Gly Glu Val Glu Phe Pro Val Lys Leu Asn
                165                 170                 175

Lys Thr Val Lys Val Leu Val Lys Arg Pro Ala Val Asn Arg Thr Lys
            180                 185                 190

Glu Asp Lys Gln Lys Ala Asn Glu Ile Leu Leu Val Asn Gly Val Arg
        195                 200                 205

Phe Asp Gly Glu Lys Tyr Val Lys Phe Asp Val Phe Val Asn Asp Ile
    210                 215                 220

Asp Asn Gly Thr Glu Thr Thr Pro Ala Asp Ser Glu Phe Ala Gly Ser
225                 230                 235                 240

Phe Ala Gln Leu Pro His Gly Lys Thr Asp Arg Met Met Met Met Ser
                245                 250                 255

Gly Val Arg Phe Gly Leu Thr Glu Leu Leu Glu Asp Ile Lys Ala Glu
            260                 265                 270

Asp Asp Glu Tyr Val Leu Val Lys Leu Val Pro Arg Thr Gly Cys Asp
        275                 280                 285

Asp Val Thr Val Ser Glu Ile Lys Ile Glu Leu Glu Gly Ile Met Ser
    290                 295                 300
```

```
Met Asp Lys Lys Ser Lys Phe Val Glu Ser Glu Tyr Glu Asn Val Ile
305                 310                 315                 320

Asp Tyr Leu Tyr Ile Cys Leu
            325

<210> SEQ ID NO 25
<211> LENGTH: 2032
<212> TYPE: DNA
<213> ORGANISM: Lactuca sativa

<400> SEQUENCE: 25
gttcgaagaa gtgagtggag taacccaaaa caaaataaca atggcttctt tccaacttgt      60
taacccctta gccagcacca caagaaaact gccagattcc acctccagcc gtcgtctcaa     120
gactcaccct caaaaaaacc accgcttcaa agtctcatgc aacgtcgcac aagatggcaa     180
tgagaagcta ctcttagtcc cagatagcaa aaaccttata ctacctaaac catcactcga     240
cacgcttaat gtagatcgga ggaacttgct actgggactc ggtggccttt acagcaccgt     300
caacttcacc tctcttccgg cggccattgc cgccccatc accacgcctg acatctccac      360
atgcatcccg tcagagcaag gcttcaacgt gcaggactcc gtaagaagca accaatgttg     420
tccgccgatg atgaccacaa ccccgaaaga ctttgtgttc ccaaaagaca aaacaattcg     480
ggttagacca gcggcacata gagccacccc cgagtacata gcaaagtaca aagcagcaat     540
ccaagcgatg aaagatctcc cagatgacca cccacatagt ttcgttcaac aagctaaaat     600
tcattgcgct tactgcaacg gtggttatac tcaagtcgca agtggttatg ctgataagca     660
actccagatt cacaactcat ggctcttctt tcctttccat cgctggtact tgtatttcta     720
cgagagaatc ctcgggaagt taattgatga tcccactttc gctttacctt actggaactg     780
ggacaatccc gccggaatgt catttccagc ttttttttgaa accgacggca agagaaaccc     840
tgtctttgac gcgttccgca acgtcaacca tgtatcacca gaaacagttg tcgatctcga     900
ctacaatggc tcagatagtg gcgctccttg tcttcaacag ataagcacca atcttgctgc     960
aatgtataag cagatgatca gcaacgctac tgacccgtta agtttctttg gtggcgagtt    1020
tcgggctgga gatgacccct ttggaaatag tgacccatct gtcggatcaa tagaggctgg    1080
ttgtcacact gcgatgcaca gatggacggg aaatccgaga atgccaaaca acgaggacat    1140
ggggaatttc tactctgcgg ggtacgaccc tgcgttctac gtccaccatg cgaatgttga    1200
ccgtatgtgg aaagtatgga aggatttagg tatcaaagga cacactgaac ctacggaccc    1260
tgattggctt aatgcatcat atgtgtttta tgatgaaaac gaagagcttg tacgtgttta    1320
caacaaagat tgtgtccaaa ctgaaaactt aaaatatgat ttcgaattat ccccactccc    1380
ttggctcaag aaccgaccgg ttgcacatac caaaccagag accaccacga aacctgttga    1440
aaaggttaaa gtgccggacg tgaagttccc cattaagcta gacaagatac agaaggtcct    1500
tgtgaagcgg ccagcgaaaa accgaagcca atcagaaaaa gaaaagcga ctgagcagtt     1560 gttgatcaaa ggaatcaagt ttaatgtctc caagttcgtc aagtttgatg tgtttgttaa    1620
tgaccaagat gatgttccca caagctctgc atccgagagc gagtttgcag gtagtttcgc    1680
acagttgcct catcaccatg gtggccacaa aaagttaatg acaagtgcag caaggttcgg    1740
tttaacagag ctttttggagg catcggagc cgaggatgat gagtatattt tggtgacatt    1800
ggtgccaaag gtaggggccg aagatctcac cgttgatgaa atcaaagtgg agttggttcc    1860
tattgtttaa acaaccatgt aatccttatct acacaataag gtatatattt aaataattcg    1920
taggccttgc attccattgc atggttgcga cttttatgta cgaatattaa taacttcatt    1980
```

```
gtgtcctttt tctacgagta aatggagtga actcaacatc ttttgcttgt tc           2032
```

<210> SEQ ID NO 26
<211> LENGTH: 609
<212> TYPE: PRT
<213> ORGANISM: Lactuca sativa

<400> SEQUENCE: 26

| Met<br>1 | Ala | Ser | Phe | Gln<br>5 | Leu | Val | Asn | Pro | Phe<br>10 | Ala | Ser | Thr | Thr | Arg<br>15 | Lys |

Leu Pro Asp Ser Thr Ser Arg Arg Leu Lys Thr His Pro Gln Lys
            20                  25                  30

Asn His Arg Phe Lys Val Ser Cys Asn Val Ala Gln Asp Gly Asn Glu
            35                  40                  45

Lys Leu Leu Leu Val Pro Asp Ser Lys Asn Leu Ile Leu Pro Lys Pro
 50                  55                      60

Ser Leu Asp Thr Leu Asn Val Asp Arg Arg Asn Leu Leu Leu Gly Leu
 65                  70                  75                  80

Gly Gly Leu Tyr Ser Thr Val Asn Phe Thr Ser Leu Pro Ala Ala Ile
                85                  90                  95

Ala Ala Pro Ile Thr Thr Pro Asp Ile Ser Thr Cys Ile Pro Ser Glu
                100                 105                 110

Gln Gly Phe Asn Val Gln Asp Ser Val Arg Ser Asn Gln Cys Cys Pro
                115                 120                 125

Pro Met Met Thr Thr Thr Pro Lys Asp Phe Val Phe Pro Lys Asp Lys
    130                 135                 140

Thr Ile Arg Val Arg Pro Ala Ala His Arg Ala Thr Pro Glu Tyr Ile
145                 150                 155                 160

Ala Lys Tyr Lys Ala Ala Ile Gln Ala Met Lys Asp Leu Pro Asp Asp
                165                 170                 175

His Pro His Ser Phe Val Gln Gln Ala Lys Ile His Cys Ala Tyr Cys
                180                 185                 190

Asn Gly Gly Tyr Thr Gln Val Ala Ser Gly Tyr Ala Asp Lys Gln Leu
                195                 200                 205

Gln Ile His Asn Ser Trp Leu Phe Pro Phe His Arg Trp Tyr Leu
    210                 215                 220

Tyr Phe Tyr Glu Arg Ile Leu Gly Lys Leu Ile Asp Asp Pro Thr Phe
225                 230                 235                 240

Ala Leu Pro Tyr Trp Asn Trp Asp Asn Pro Ala Gly Met Ser Phe Pro
                245                 250                 255

Ala Phe Phe Glu Thr Asp Gly Lys Arg Asn Pro Val Phe Asp Ala Phe
                260                 265                 270

Arg Asn Val Asn His Val Ser Pro Glu Thr Val Val Asp Leu Asp Tyr
                275                 280                 285

Asn Gly Ser Asp Ser Gly Ala Pro Cys Leu Gln Gln Ile Ser Thr Asn
    290                 295                 300

Leu Ala Ala Met Tyr Lys Gln Met Ile Ser Asn Ala Thr Asp Pro Leu
305                 310                 315                 320

Ser Phe Phe Gly Gly Glu Phe Arg Ala Gly Asp Asp Pro Phe Gly Asn
                325                 330                 335

Ser Asp Pro Ser Val Gly Ser Ile Glu Ala Gly Cys His Thr Ala Met
                340                 345                 350

His Arg Trp Thr Gly Asn Pro Arg Met Pro Asn Asn Glu Asp Met Gly
                355                 360                 365

```
Asn Phe Tyr Ser Ala Gly Tyr Asp Pro Ala Phe Tyr Val His His Ala
    370                 375                 380

Asn Val Asp Arg Met Trp Lys Val Trp Lys Asp Leu Gly Ile Lys Gly
385                 390                 395                 400

His Thr Glu Pro Thr Asp Pro Asp Trp Leu Asn Ala Ser Tyr Val Phe
                405                 410                 415

Tyr Asp Glu Asn Glu Glu Leu Val Arg Val Tyr Asn Lys Asp Cys Val
            420                 425                 430

Gln Thr Glu Asn Leu Lys Tyr Asp Phe Glu Leu Ser Pro Leu Pro Trp
        435                 440                 445

Leu Lys Asn Arg Pro Val Ala His Thr Lys Pro Glu Thr Thr Thr Lys
    450                 455                 460

Pro Val Glu Lys Val Lys Val Pro Asp Val Lys Phe Pro Ile Lys Leu
465                 470                 475                 480

Asp Lys Ile Gln Lys Val Leu Val Lys Arg Pro Ala Lys Asn Arg Ser
                485                 490                 495

Gln Ser Glu Lys Glu Lys Ala Thr Glu Gln Leu Leu Ile Lys Gly Ile
            500                 505                 510

Lys Phe Asn Val Ser Lys Phe Val Lys Phe Asp Val Phe Val Asn Asp
        515                 520                 525

Gln Asp Asp Val Pro Thr Ser Ser Ala Ser Glu Ser Glu Phe Ala Gly
    530                 535                 540

Ser Phe Ala Gln Leu Pro His His His Gly Gly His Lys Lys Leu Met
545                 550                 555                 560

Thr Ser Ala Ala Arg Phe Gly Leu Thr Glu Leu Leu Glu Asp Ile Gly
                565                 570                 575

Ala Glu Asp Asp Glu Tyr Ile Leu Val Thr Leu Val Pro Lys Val Gly
            580                 585                 590

Ala Glu Asp Leu Thr Val Asp Glu Ile Lys Val Glu Leu Val Pro Ile
        595                 600                 605

Val

<210> SEQ ID NO 27
<211> LENGTH: 2060
<212> TYPE: DNA
<213> ORGANISM: Lactuca sativa

<400> SEQUENCE: 27
aaaggagtat gaagcacacc aaaccaacat ggcttctttg agctttactt tagccactcc      60
caccacctct tcctcgccgt tcttttcaca acaaccacc aaacaacgac ggttgatgaa     120
gacacatggg aagcaaaccc atcgcttcca agtctcatgc aacgtctcat caaataacca     180
tgaaaaacca ctccccaaaa accctcaacc acaaaaactt atactaccac aaacatcact     240
cgacttgcag aacgtcgaca gaaggaattt gctcctgggt ctcggcggag tctacagcac     300
cgccaccttg tccggtctgc caccggcctt tgcagaagct atcaaggctc cgttcaatca     360
gcctgatcga ccatgcaaag atgccgtatc cggcttcgac attaataaaa agctacttag     420
acctattgac tgttgccctc tgtccaaaaa tggcccggag agtcatttca agttccctga     480
taaatcaagc aaaactcgca tcagatatcc actacacaaa cttccagtcg ggtatctcga     540
taaatatatg gatgcgattc agaaaatgaa ggatctccca gatagcgacc cacgcagttt     600
caataaccaa gctaaagttc attgcgctta ctgcaatggc agttacactc aaaacggtca     660
agaactccag attcacaact cctggctctt ctttcccttc catcggtggt acctttattt     720
```

```
ctacgagagg atactgggag atctcattgg tgattcgaca ttcgggttac cctactggaa    780
ctgggacaac cccgaaggaa tgacaattcc acacttcttc gtagagaaac aatgtaacaa    840
ctataagttc gaaaacggag aaaaccctct atatgataag tatcgggacg aaagtcacct    900
tcggtatgaa ttggtcgatc ttgactactc agggagaaac cgcgacctgt gttacgatca    960
gaaagaaatc aatctggcta ctatgaatag gcagatgatg cgcaacgcct ttgatgcaac   1020
aagcttcttc ggtggcaaat atgtagccgg tgatgaaccg attccccgag agataatgt    1080
agttggatcc gtggaggctg gttgtcatac ggctgttcac agatggttg ggaaccctga    1140
tccaaaaggg aataagagg acatgggcaa cttctactct gcgggatatg atcctttgtt    1200
ctacgtccac cattctaatg tggaccgaat gtggactctt tggaagcaaa tgggaggcaa    1260
agaaccgaca gatactgact gggaaaacgc gtcatacgtg ttttacgatg agaaacaaaa    1320
tcccgtacgt gtctacaaca acaatcggt ggatttgagc aaccttaaat acgaatacca    1380
cagctcagcc actccatgga cggatagacc accaagatca cgctgcaaca gacccggtta    1440
cccgaagagg aacaacacaa aggacttccc aaatcagaag gacccgccag aagctttgac    1500
attaaccgat agtactgtga ggcttcgagt aaagaggcct cctgcttcta aaaacaggaa    1560
cgctgagcaa aagaaaagtg aaaaagagat cttgtgcttg attggaatca gtttcgattg    1620
taccgaagct gcaaaatttg acgtgtttgt gaatgattgt gacgaagaac agatcacccc    1680
gtgtgatagt gagaatgtgg gttctttcgc ggctgttcca catgctaaag gcatggcaat    1740
gggttgcaag tctgggatga ggttttcgtt aacagagttg ttggaggaaa caaaagctga    1800
gggggatgag tctattcggg tgacaattgt gccgaggacg acacccggca agaaagtcaa    1860
agtcaccatt gatgctatcg agatccggtt gattccggtt cttgaaaaat aatcaaactg    1920
atcaaatgcg ttgatgatgg attccacaat cacgaaatga ataagttgga gtctgtgtag    1980
ttcgataaac gtacgttgtg atttctaatg catgttttat ttgaatagaa atttgttta    2040
aacaaaagtc tcttcatttc                                               2060

<210> SEQ ID NO 28
<211> LENGTH: 627
<212> TYPE: PRT
<213> ORGANISM: Lactuca sativa

<400> SEQUENCE: 28

Met Ala Ser Leu Ser Phe Thr Leu Ala Thr Pro Thr Ser Ser Ser
1               5                   10                  15

Pro Phe Phe Ser Gln Thr Thr Thr Lys Gln Arg Arg Leu Met Lys Thr
                20                  25                  30

His Gly Lys Gln Thr His Arg Phe Gln Val Ser Cys Asn Val Ser Ser
            35                  40                  45

Asn Asn His Glu Lys Pro Leu Pro Lys Asn Pro Gln Pro Gln Lys Leu
        50                  55                  60

Ile Leu Pro Gln Thr Ser Leu Asp Leu Gln Asn Val Asp Arg Arg Asn
65                  70                  75                  80

Leu Leu Leu Gly Leu Gly Gly Val Tyr Ser Thr Ala Thr Leu Ser Gly
                85                  90                  95

Leu Pro Pro Ala Phe Ala Glu Ala Ile Lys Ala Pro Phe Asn Gln Pro
                100                 105                 110

Asp Arg Pro Cys Lys Asp Ala Val Ser Gly Phe Asp Ile Asn Lys Lys
            115                 120                 125
```

```
Leu Leu Arg Pro Ile Asp Cys Cys Pro Leu Ser Lys Asn Gly Pro Glu
130                 135                 140

Ser His Phe Lys Phe Pro Asp Lys Ser Lys Thr Arg Ile Arg Tyr
145                 150                 155                 160

Pro Leu His Lys Leu Pro Val Gly Tyr Leu Asp Lys Tyr Met Asp Ala
            165                 170                 175

Ile Gln Lys Met Lys Asp Leu Pro Asp Ser Asp Pro Arg Ser Phe Asn
                180                 185                 190

Asn Gln Ala Lys Val His Cys Ala Tyr Cys Asn Gly Ser Tyr Thr Gln
            195                 200                 205

Asn Gly Gln Glu Leu Gln Ile His Asn Ser Trp Leu Phe Phe Pro Phe
210                 215                 220

His Arg Trp Tyr Leu Tyr Phe Tyr Glu Arg Ile Leu Gly Asp Leu Ile
225                 230                 235                 240

Gly Asp Ser Thr Phe Gly Leu Pro Tyr Trp Asn Trp Asp Asn Pro Glu
            245                 250                 255

Gly Met Thr Ile Pro His Phe Phe Val Glu Lys Gln Cys Asn Asn Tyr
                260                 265                 270

Lys Phe Glu Asn Gly Glu Asn Pro Leu Tyr Asp Lys Tyr Arg Asp Glu
            275                 280                 285

Ser His Leu Arg Tyr Glu Leu Val Asp Leu Asp Tyr Ser Gly Arg Asn
            290                 295                 300

Arg Asp Leu Cys Tyr Asp Gln Lys Glu Ile Asn Leu Ala Thr Met Asn
305                 310                 315                 320

Arg Gln Met Met Arg Asn Ala Phe Asp Ala Thr Ser Phe Phe Gly Gly
                325                 330                 335

Lys Tyr Val Ala Gly Asp Glu Pro Ile Pro Arg Gly Asp Asn Val Val
            340                 345                 350

Gly Ser Val Glu Ala Gly Cys His Thr Ala Val His Arg Trp Val Gly
            355                 360                 365

Asn Pro Asp Pro Lys Gly Asn Lys Glu Asp Met Gly Asn Phe Tyr Ser
370                 375                 380

Ala Gly Tyr Asp Pro Leu Phe Tyr Val His His Ser Asn Val Asp Arg
385                 390                 395                 400

Met Trp Thr Leu Trp Lys Gln Met Gly Gly Lys Glu Pro Thr Asp Thr
                405                 410                 415

Asp Trp Glu Asn Ala Ser Tyr Val Phe Tyr Asp Glu Lys Gln Asn Pro
            420                 425                 430

Val Arg Val Tyr Asn Lys Gln Ser Val Asp Leu Ser Asn Leu Lys Tyr
            435                 440                 445

Glu Tyr His Ser Ser Ala Thr Pro Trp Thr Asp Arg Pro Pro Arg Ser
450                 455                 460

Arg Cys Asn Arg Pro Gly Tyr Pro Lys Arg Asn Asn Thr Lys Asp Phe
465                 470                 475                 480

Pro Asn Gln Lys Asp Pro Pro Glu Ala Leu Thr Leu Thr Asp Ser Thr
                485                 490                 495

Val Arg Leu Arg Val Lys Arg Pro Pro Ala Ser Lys Asn Arg Asn Ala
            500                 505                 510

Glu Gln Lys Lys Ser Glu Lys Glu Ile Leu Cys Leu Ile Gly Ile Ser
            515                 520                 525

Phe Asp Cys Thr Glu Ala Ala Lys Phe Asp Val Phe Val Asn Asp Cys
530                 535                 540

Asp Glu Glu Gln Ile Thr Pro Cys Asp Ser Glu Asn Val Gly Ser Phe
```

|     |     |     |     |     |     |     |     |     |     |     |     |
| --- | --- | --- | --- | --- | --- | --- | --- | --- | --- | --- | --- |
| 545 |     |     |     | 550 |     |     |     | 555 |     |     | 560 |
| Ala | Ala | Val | Pro | His | Ala | Lys | Gly | Met | Ala | Met | Gly |
|     |     |     |     |     | 565 |     |     |     | 570 |     |     |
| Cys | Lys | Ser | Gly |     |     |     |     |     |     |     |     |
|     |     | 575 |     |     |     |     |     |     |     |     |     |
| Met | Arg | Phe | Ser | Leu | Thr | Glu | Leu | Leu | Glu | Glu | Thr |
|     |     |     |     |     | 580 |     |     |     | 585 |     |     |
| Lys | Ala | Glu | Gly |     |     |     |     |     |     |     |     |
|     |     | 590 |     |     |     |     |     |     |     |     |     |
| Asp | Glu | Ser | Ile | Arg | Val | Thr | Ile | Val | Pro | Arg | Thr |
|     |     |     |     |     | 595 |     |     |     | 600 |     |     |
| Thr | Pro | Gly | Lys |     |     |     |     |     |     |     |     |
|     |     | 605 |     |     |     |     |     |     |     |     |     |
| Lys | Val | Lys | Val | Thr | Ile | Asp | Ala | Ile | Glu | Ile | Arg |
|     |     |     |     |     | 610 |     |     |     | 615 |     |     |
| Leu | Ile | Pro | Val |     |     |     |     |     |     |     |     |
|     |     | 620 |     |     |     |     |     |     |     |     |     |
| Leu | Glu | Lys |     |     |     |     |     |     |     |     |     |
| 625 |     |     |     |     |     |     |     |     |     |     |     |

<210> SEQ ID NO 29
<211> LENGTH: 4086
<212> TYPE: DNA
<213> ORGANISM: Artificial
<220> FEATURE:
<223> OTHER INFORMATION: synthetic construct

<400> SEQUENCE: 29

| | | | | |
|---|---|---|---|---|
| atgggtttgg | actctactgc | gcctaagaaa | aagagaaaag | tcgggattca | cggcgtgcca | 60 |
| gcggccatga | ctcagttcga | gggtttcact | aacctgtacc | aagtgtccaa | gaccctgagg | 120 |
| ttcgagctga | tcccgcaagg | aaagaccctg | aagcacatcc | aggaacaggg | cttcatcgaa | 180 |
| gaggataagg | cccgcaacga | ccactacaag | gaactgaagc | ccattattga | tcggatctac | 240 |
| aagacctacg | ccgaccagtg | cttgcagctg | gtgcagctgg | actgggaaaa | tctgtccgcc | 300 |
| gcgattgatt | cctaccggaa | ggagaaaacc | gaagagactc | gcaacgctct | cattgaggaa | 360 |
| caggccacct | accggaacgc | cattcacgac | tactttattg | gccgcactga | caacctcacc | 420 |
| gatgcaatca | acaagcgcca | cgccgagatc | tacaaggggc | tgttcaaggc | ggaactgttt | 480 |
| aacgggaagg | tcctgaagca | actgggaact | gtgaccacca | ccgagcatga | aacgccctg | 540 |
| ctccgctcct | tcgacaagtt | caccacctac | ttctcgggat | tctacgagaa | tcgcaaaaac | 600 |
| gtgttcagcg | cggaagatat | ctcaaccgcc | atcccccacc | ggattgtgca | ggacaacttc | 660 |
| cctaagttca | ggaaaactg | ccatatcttc | acgcgcctga | tcactgctgt | gccgagtctg | 720 |
| agagagcact | tcgagaacgt | gaagaaggct | atcggcatct | tcgtgtccac | ctcgattgag | 780 |
| gaagtgttct | ccttcccgtt | ctacaatcag | ctcctgactc | aaacccagat | tgacctgtac | 840 |
| aaccagcttc | tggggggat | tcccgggaa | gcgggaactg | agaagatcaa | gggactcaac | 900 |
| gaagtgctga | acctggcaat | ccagaagaac | gacgaaaccg | cgcacatcat | cgcaagcctc | 960 |
| cctcaccgct | tcattcctct | gttcaagcaa | attctttccg | accgcaacac | cctgtcgttc | 1020 |
| atcctggaag | aattcaagag | cgacgaagaa | gtcattcaga | gcttctgcaa | gtacaagact | 1080 |
| ctgctgagga | cgaaaacgt | gctggaaacc | gccgaggccc | tgttcaacga | actgaactca | 1140 |
| atcgacctga | cgcacatttt | catttcccat | aagaagctgg | aaactatctc | ctccgccctc | 1200 |
| tgtgaccact | gggacaccct | gagaaatgcg | ttgtatgagc | gccggatctc | cgagttgact | 1260 |
| gggaagatta | ctaagtccgc | gaaggaaaaa | gtgcagcgct | ccctgaaaca | cgaagatatc | 1320 |
| aaccttcagg | agatcatctc | agccgccgga | aggaactgt | cagaggcctt | caagcaaaag | 1380 |
| acttcagaga | tcctgtcgca | cgcccacgcc | gctttggacc | agcccctgcc | caccaccctg | 1440 |
| aagaagcagg | aagaaaagga | aatcctgaag | tctcagctcg | actcactgct | tgggctgtac | 1500 |
| catctcctcg | attggttcgc | cgtcgacgag | tccaacgaag | tcgaccccga | attctcggcc | 1560 |

```
cggctgaccg gtatcaagct tgagatggag ccaagcctct ccttttacaa caaggcccgg    1620
aactacgcca ccaaaaagcc ttactcagtg gaaaagttca agcttaactt tcaaatgccg    1680
accctggcca gcggctggga cgtgaacaag gagaagaaca acggcgccat cctgtttgtg    1740
aagaacggac tgtattacct tggaattatg cccaaacaga agggtcgcta caaggcactg    1800
tccttcgagc cgaccgaaaa gacttcggaa ggttttgaca agatgtacta cgattacttc    1860
ccggacgcgg ctaagatgat ccccaagtgc agcactcagc tgaaggccgt gaccgcacac    1920
tttcaaaccc ataccacccc gattcttctg agcaacaact ttatcgagcc actggagatt    1980
accaaggaaa tctacgacct gaacaacccc gaaaaggaac taaaaagtt tcagaccgcc     2040 tacgccaaga aaactggcga ccagaaggga tacagagaag ccctctgcaa gtggattgac    2100
ttcacccggg atttcctgtc caagtacact aagaccactt ccattgacct ctcgtcgctg    2160
cggccgtcct cgcaatacaa ggacctgggg gagtactacg ccgagctcaa cccgctgctc    2220
taccacataa gcttcagcg gattgccgag aaagaaatca tggacgccgt cgaaaccgga    2280
aagctgtacc tcttccaaat ctataacaag gacttcgcga agggtcacca tggaaagcca    2340
aacctccaca ccctctattg gaccggactc ttctcgccgg aaaacctggc caagacatcc    2400
atcaagttga atgggcaggc cgaactcttc taccgcccca gtctcggat gaagcgaatg     2460 gcccaccggc tgggagaaaa gatgctcaac aagaagctaa aggaccaaaa gaccccaatc    2520
cctgacaccc tgtaccagga actgtacgat tacgtgaacc acaggcttag ccacgactta    2580
tccgacgaag cccgggcgct gctgccgaac gtcatcacca aggaagtgtc gcacgagatc    2640
atcaaggacc gccggtttac ctccgacaaa ttcttcttcc acgtgcccat taccctgaac    2700
taccaggccg ccaactcacc cggattcatc aacgaccgga tcctgcagta tatcgcgaag    2760
gagaaggatc ttcacgtgat cggaattgac cggggggaga ggaacctgat ctacgtgtcc    2820
gtgattgaca cttgtgggaa catcgtagag cagaagtcct tcaacatcgt gaacggctac    2880
gactaccaga tcaagctcaa gcaacaggag ggcgcacggc agatcgcaag aaaggaatgg    2940
aaggaaatcg gaaaaatcaa ggaaatcaaa gagggatacc tgagcctcgt catccacgag    3000
atcagcaaga tggtcattaa gtacaatgcg atcatcgcca tggaggactt gtcctacgga    3060
ttcaagaaag gacggttcaa agtggagaga caagtgtatc agaagttcga gactatgctc    3120
atcaacaagc tgaactacct ggtgttcaag gatatcagca ttacggaaaa cggcggactc    3180
ctcaagggat accagctgac ttacattccc gataagctga gaatgtcgg tcatcagtgc     3240 ggctgtattt tctacgtgcc ggcagcctac acctccaaga tcgaccctac taccggtttc    3300
gtgaacattt ttaagttcaa agatctcacc gtggacgcaa agcgcgaatt cattaagaag    3360
ttcgactcaa tccgctacga cagcgagaag aacctgttct gcttcacttt cgactacaac    3420
aacttcatta cccaaaacac cgtcatgtcc aagtccagct ggagcgtgta cacctatgga    3480
gtgcggatca gcggcggtt tgtgaacggc cggttctcga atgagtccga cacaattgat     3540
atcaccaaag atatggaaaa gacactggag atgactgata tcaactggag ggatggccac    3600
gatttgagac aggacattat tgactacgag atagtccagc atatctttga gatttcaga    3660 ctgaccgtgc agatgcgcaa ttccctgtcg gaactggaag atcgggacta cgatagactg    3720
attagccccg tgctgaacga aaacaacatc ttctacgatt ccgccaaagc tggagatgcg    3780
ctgccaaaag acgctgacgc taacggcgcc tactgcatcg cgctgaaggg cctctacgaa    3840
atcaagcaaa tcaccgagaa ctggaaggag gacggaaagt tctcccgcga caagctgaag    3900
atctcaaaca aggactggtt tgacttcatc cagaacaagc ggtacctgaa gcgccctgct    3960
```

-continued

```
gctaccaaaa aggccggcca ggccaagaag aaaaagggct cgtacccta cgatgtgccg    4020 gattacgcct accttacga tgtccccgac tacgcttacc cgtacgacgt gcctgactac    4080
gcctaa                                                              4086
```

<210> SEQ ID NO 30
<211> LENGTH: 1361
<212> TYPE: PRT
<213> ORGANISM: Artificial
<220> FEATURE:
<223> OTHER INFORMATION: synthetic protein

<400> SEQUENCE: 30

```
Met Gly Leu Asp Ser Thr Ala Pro Lys Lys Arg Lys Val Gly Ile
1               5                   10                  15

His Gly Val Pro Ala Ala Met Thr Gln Phe Glu Gly Phe Thr Asn Leu
                20                  25                  30

Tyr Gln Val Ser Lys Thr Leu Arg Phe Glu Leu Ile Pro Gln Gly Lys
            35                  40                  45

Thr Leu Lys His Ile Gln Glu Gln Gly Phe Ile Glu Glu Asp Lys Ala
        50                  55                  60

Arg Asn Asp His Tyr Lys Glu Leu Lys Pro Ile Ile Asp Arg Ile Tyr
65                  70                  75                  80

Lys Thr Tyr Ala Asp Gln Cys Leu Gln Leu Val Gln Leu Asp Trp Glu
                85                  90                  95

Asn Leu Ser Ala Ala Ile Asp Ser Tyr Arg Lys Glu Lys Thr Glu Glu
            100                 105                 110

Thr Arg Asn Ala Leu Ile Glu Glu Gln Ala Thr Tyr Arg Asn Ala Ile
        115                 120                 125

His Asp Tyr Phe Ile Gly Arg Thr Asp Asn Leu Thr Asp Ala Ile Asn
    130                 135                 140

Lys Arg His Ala Glu Ile Tyr Lys Gly Leu Phe Lys Ala Glu Leu Phe
145                 150                 155                 160

Asn Gly Lys Val Leu Lys Gln Leu Gly Thr Val Thr Thr Thr Glu His
                165                 170                 175

Glu Asn Ala Leu Leu Arg Ser Phe Asp Lys Phe Thr Thr Tyr Phe Ser
            180                 185                 190

Gly Phe Tyr Glu Asn Arg Lys Asn Val Phe Ser Ala Glu Asp Ile Ser
        195                 200                 205

Thr Ala Ile Pro His Arg Ile Val Gln Asp Asn Phe Pro Lys Phe Lys
    210                 215                 220

Glu Asn Cys His Ile Phe Thr Arg Leu Ile Thr Ala Val Pro Ser Leu
225                 230                 235                 240

Arg Glu His Phe Glu Asn Val Lys Lys Ala Ile Gly Ile Phe Val Ser
                245                 250                 255

Thr Ser Ile Glu Glu Val Phe Ser Phe Pro Phe Tyr Asn Gln Leu Leu
            260                 265                 270

Thr Gln Thr Gln Ile Asp Leu Tyr Asn Gln Leu Leu Gly Gly Ile Ser
        275                 280                 285

Arg Glu Ala Gly Thr Glu Lys Ile Lys Gly Leu Asn Glu Val Leu Asn
    290                 295                 300

Leu Ala Ile Gln Lys Asn Asp Glu Thr Ala His Ile Ile Ala Ser Leu
305                 310                 315                 320

Pro His Arg Phe Ile Pro Leu Phe Lys Gln Ile Leu Ser Asp Arg Asn
                325                 330                 335
```

```
Thr Leu Ser Phe Ile Leu Glu Glu Phe Lys Ser Asp Glu Glu Val Ile
                340                 345                 350

Gln Ser Phe Cys Lys Tyr Lys Thr Leu Leu Arg Asn Glu Asn Val Leu
            355                 360                 365

Glu Thr Ala Glu Ala Leu Phe Asn Glu Leu Asn Ser Ile Asp Leu Thr
        370                 375                 380

His Ile Phe Ile Ser His Lys Lys Leu Glu Thr Ile Ser Ser Ala Leu
385                 390                 395                 400

Cys Asp His Trp Asp Thr Leu Arg Asn Ala Leu Tyr Glu Arg Arg Ile
                405                 410                 415

Ser Glu Leu Thr Gly Lys Ile Thr Lys Ser Ala Lys Glu Lys Val Gln
            420                 425                 430

Arg Ser Leu Lys His Glu Asp Ile Asn Leu Gln Glu Ile Ile Ser Ala
        435                 440                 445

Ala Gly Lys Glu Leu Ser Glu Ala Phe Lys Gln Lys Thr Ser Glu Ile
    450                 455                 460

Leu Ser His Ala His Ala Ala Leu Asp Gln Pro Leu Pro Thr Thr Leu
465                 470                 475                 480

Lys Lys Gln Glu Glu Lys Glu Ile Leu Lys Ser Gln Leu Asp Ser Leu
                485                 490                 495

Leu Gly Leu Tyr His Leu Leu Asp Trp Phe Ala Val Asp Glu Ser Asn
            500                 505                 510

Glu Val Asp Pro Glu Phe Ser Ala Arg Leu Thr Gly Ile Lys Leu Glu
        515                 520                 525

Met Glu Pro Ser Leu Ser Phe Tyr Asn Lys Ala Arg Asn Tyr Ala Thr
    530                 535                 540

Lys Lys Pro Tyr Ser Val Glu Lys Phe Lys Leu Asn Phe Gln Met Pro
545                 550                 555                 560

Thr Leu Ala Ser Gly Trp Asp Val Asn Lys Glu Lys Asn Asn Gly Ala
                565                 570                 575

Ile Leu Phe Val Lys Asn Gly Leu Tyr Tyr Leu Gly Ile Met Pro Lys
            580                 585                 590

Gln Lys Gly Arg Tyr Lys Ala Leu Ser Phe Glu Pro Thr Glu Lys Thr
        595                 600                 605

Ser Glu Gly Phe Asp Lys Met Tyr Tyr Asp Tyr Phe Pro Asp Ala Ala
    610                 615                 620

Lys Met Ile Pro Lys Cys Ser Thr Gln Leu Lys Ala Val Thr Ala His
625                 630                 635                 640

Phe Gln Thr His Thr Thr Pro Ile Leu Leu Ser Asn Asn Phe Ile Glu
                645                 650                 655

Pro Leu Glu Ile Thr Lys Glu Ile Tyr Asp Leu Asn Asn Pro Glu Lys
            660                 665                 670

Glu Pro Lys Lys Phe Gln Thr Ala Tyr Ala Lys Lys Thr Gly Asp Gln
        675                 680                 685

Lys Gly Tyr Arg Glu Ala Leu Cys Lys Trp Ile Asp Phe Thr Arg Asp
    690                 695                 700

Phe Leu Ser Lys Tyr Thr Lys Thr Thr Ser Ile Asp Leu Ser Ser Leu
705                 710                 715                 720

Arg Pro Ser Ser Gln Tyr Lys Asp Leu Gly Glu Tyr Tyr Ala Glu Leu
                725                 730                 735

Asn Pro Leu Leu Tyr His Ile Ser Phe Gln Arg Ile Ala Glu Lys Glu
            740                 745                 750
```

-continued

Ile Met Asp Ala Val Glu Thr Gly Lys Leu Tyr Leu Phe Gln Ile Tyr
    755                 760                 765

Asn Lys Asp Phe Ala Lys Gly His His Gly Lys Pro Asn Leu His Thr
770                 775                 780

Leu Tyr Trp Thr Gly Leu Phe Ser Pro Glu Asn Leu Ala Lys Thr Ser
785                 790                 795                 800

Ile Lys Leu Asn Gly Gln Ala Glu Leu Phe Tyr Arg Pro Lys Ser Arg
                805                 810                 815

Met Lys Arg Met Ala His Arg Leu Glu Lys Met Leu Asn Lys Lys
                820                 825                 830

Leu Lys Asp Gln Lys Thr Pro Ile Pro Asp Thr Leu Tyr Gln Glu Leu
            835                 840                 845

Tyr Asp Tyr Val Asn His Arg Leu Ser His Asp Leu Ser Asp Glu Ala
850                 855                 860

Arg Ala Leu Leu Pro Asn Val Ile Thr Lys Glu Val Ser His Glu Ile
865                 870                 875                 880

Ile Lys Asp Arg Arg Phe Thr Ser Asp Lys Phe Phe Phe His Val Pro
                885                 890                 895

Ile Thr Leu Asn Tyr Gln Ala Ala Asn Ser Pro Gly Phe Ile Asn Asp
                900                 905                 910

Arg Ile Leu Gln Tyr Ile Ala Lys Glu Lys Asp Leu His Val Ile Gly
            915                 920                 925

Ile Asp Arg Gly Glu Arg Asn Leu Ile Tyr Val Ser Val Ile Asp Thr
930                 935                 940

Cys Gly Asn Ile Val Glu Gln Lys Ser Phe Asn Ile Val Asn Gly Tyr
945                 950                 955                 960

Asp Tyr Gln Ile Lys Leu Lys Gln Gln Glu Gly Ala Arg Gln Ile Ala
                965                 970                 975

Arg Lys Glu Trp Lys Glu Ile Gly Lys Ile Lys Glu Ile Lys Glu Gly
                980                 985                 990

Tyr Leu Ser Leu Val Ile His Glu Ile Ser Lys Met Val Ile Lys Tyr
            995                 1000                1005

Asn Ala Ile Ile Ala Met Glu Asp Leu Ser Tyr Gly Phe Lys Lys
    1010                1015                1020

Gly Arg Phe Lys Val Glu Arg Gln Val Tyr Gln Lys Phe Glu Thr
    1025                1030                1035

Met Leu Ile Asn Lys Leu Asn Tyr Leu Val Phe Lys Asp Ile Ser
    1040                1045                1050

Ile Thr Glu Asn Gly Gly Leu Leu Lys Gly Tyr Gln Leu Thr Tyr
    1055                1060                1065

Ile Pro Asp Lys Leu Lys Asn Val Gly His Gln Cys Gly Cys Ile
    1070                1075                1080

Phe Tyr Val Pro Ala Ala Tyr Thr Ser Lys Ile Asp Pro Thr Thr
    1085                1090                1095

Gly Phe Val Asn Ile Phe Lys Phe Lys Asp Leu Thr Val Asp Ala
    1100                1105                1110

Lys Arg Glu Phe Ile Lys Lys Phe Asp Ser Ile Arg Tyr Asp Ser
    1115                1120                1125

Glu Lys Asn Leu Phe Cys Phe Thr Phe Asp Tyr Asn Asn Phe Ile
    1130                1135                1140

Thr Gln Asn Thr Val Met Ser Lys Ser Ser Trp Ser Val Tyr Thr
    1145                1150                1155

Tyr Gly Val Arg Ile Lys Arg Arg Phe Val Asn Gly Arg Phe Ser

```
              1160              1165              1170

Asn Glu Ser Asp Thr Ile Asp Ile Thr Lys Asp Met Glu Lys Thr
        1175            1180                1185

Leu Glu Met Thr Asp Ile Asn Trp Arg Asp Gly His Asp Leu Arg
        1190            1195                1200

Gln Asp Ile Ile Asp Tyr Glu Ile Val Gln His Ile Phe Glu Ile
        1205            1210                1215

Phe Arg Leu Thr Val Gln Met Arg Asn Ser Leu Ser Glu Leu Glu
        1220            1225                1230

Asp Arg Asp Tyr Asp Arg Leu Ile Ser Pro Val Leu Asn Glu Asn
        1235            1240                1245

Asn Ile Phe Tyr Asp Ser Ala Lys Ala Gly Asp Ala Leu Pro Lys
        1250            1255                1260

Asp Ala Asp Ala Asn Gly Ala Tyr Cys Ile Ala Leu Lys Gly Leu
        1265            1270                1275

Tyr Glu Ile Lys Gln Ile Thr Glu Asn Trp Lys Glu Asp Gly Lys
        1280            1285                1290

Phe Ser Arg Asp Lys Leu Lys Ile Ser Asn Lys Asp Trp Phe Asp
        1295            1300                1305

Phe Ile Gln Asn Lys Arg Tyr Leu Lys Arg Pro Ala Ala Thr Lys
        1310            1315                1320

Lys Ala Gly Gln Ala Lys Lys Lys Lys Gly Ser Tyr Pro Tyr Asp
        1325            1330                1335

Val Pro Asp Tyr Ala Tyr Pro Tyr Asp Val Pro Asp Tyr Ala Tyr
        1340            1345                1350

Pro Tyr Asp Val Pro Asp Tyr Ala
        1355            1360

<210> SEQ ID NO 31
<211> LENGTH: 450
<212> TYPE: DNA
<213> ORGANISM: Arabidopsis thaliana

<400> SEQUENCE: 31
aaaagcttcg ttgaacaacg gaaactcgac ttgccttccg cacaatacat catttcttct      60
tagctttttt tcttcttctt cgttcataca gttttttttt gtttatcagc ttacattttc    120
ttgaaccgta gctttcgttt tcttcttttt aactttccat tcggagtttt tgtatcttgt    180
ttcatagttt gtcccaggat tagaatgatt aggcatcgaa ccttcaagaa tttgattgaa    240
taaaacatct tcattcttaa gatatgaaga taatcttcaa aaggcccctg ggaatctgaa    300
agaagagaag caggcccatt tatatgggaa agaacaatag tatttcttat ataggcccat    360
ttaagttgaa acaatcttc aaaagtccca catcgcttag ataagaaaac gaagctgagt     420
ttatatacag ctagagtcga agtagtgatt                                     450

<210> SEQ ID NO 32
<211> LENGTH: 649
<212> TYPE: DNA
<213> ORGANISM: Cauliflower mosaic virus

<400> SEQUENCE: 32
ggtccgatgt gagactttc aacaaagggt aatatccgga aacctcctcg gattccattg      60
cccagctatc tgtcacttta ttgtgaagat agtggaaaag gaaggtggct cctacaaatg    120
ccatcattgc gataaaggaa aggccatcgt tgaagatgcc tctgccgaca gtggtcccaa    180
```

-continued

| | | |
|---|---|---|
| agatggaccc ccacccacga ggagcatcgt ggaaaaagaa gacgttccaa ccacgtcttc | 240 | |
| aaagcaagtg gattgatgtg atggtccgat gtgagacttt tcaacaaagg gtaatatccg | 300 | |
| gaaacctcct cggattccat tgcccagcta tctgtcactt tattgtgaag atagtggaaa | 360 | |
| aggaaggtgg ctcctacaaa tgccatcatt gcgataaagg aaaggccatc gttgaagatg | 420 | |
| cctctgccga cagtggtccc aaagatggac ccccacccac gaggagcatc gtggaaaaag | 480 | |
| aagacgttcc aaccacgtct tcaaagcaag tggattgatg tgatatctcc actgacgtaa | 540 | |
| gggatgacgc acaatcccac tatccttcgc aagacccttc ctctatataa ggaagttcat | 600 | |
| ttcatttgga gaggacacgc gacaagctga ctctagcaga tcctccaga | 649 | |

<210> SEQ ID NO 33
<211> LENGTH: 514
<212> TYPE: DNA
<213> ORGANISM: Cassava vein mosaic virus

<400> SEQUENCE: 33

| | | |
|---|---|---|
| cagaaggtaa ttatccaaga tgtagcatca agaatccaat gtttacggga aaaactatgg | 60 | |
| aagtattatg tgaactcagc aagaagcaga tcaatatgcg gcacatattc aacctatgtt | 120 | |
| caaaaatgaa gaatgtacag atacaagatc ctatactgcc agaatacgaa gaagaataca | 180 | |
| tagaaattga aaagaagaa ccaggcgaag aaaagaatct tgaagacgta agcactgacg | 240 | |
| acaacaatga aagaagaag ataaggtcgg tgattgtgaa agagacatag aggacacatg | 300 | |
| taaggtggaa aatgtaaggg cggaaagtaa ccttatcaca aaggaatctt atcccccact | 360 | |
| acttatcctt ttatattttt ccgtgtcatt tttgcccttg agtttcccta tataaggaac | 420 | |
| caagttcggc atttgtgaaa acaagaaaaa atttggtgta agctattttc tttgaagtac | 480 | |
| tgaggataca acttcagaga aatttgtaag tttg | 514 | |

<210> SEQ ID NO 34
<211> LENGTH: 1217
<212> TYPE: DNA
<213> ORGANISM: Arabidopsis thaliana

<400> SEQUENCE: 34

| | | |
|---|---|---|
| gaacttattc aaagaatgtt ttgtgtatca ttcttgttac attgttatta atgaaaaaat | 60 | |
| attattggtc attggactga acacgagtgt taaatatgga ccaggcccca aataagatcc | 120 | |
| attgatatat gaattaaata acaagaataa atcgagtcac caaaccactt gccttttta | 180 | |
| acgagacttg ttcaccaact tgatacaaaa gtcattatcc tatgcaaatc aataatcata | 240 | |
| caaaaatatc caataacact aaaaaattaa agaaatggaa taatttcaca atatgttata | 300 | |
| cgataaagaa gttacttttc caagaaattc actgattta taagcccact tgcattagat | 360 | |
| aaatggcaaa aaaaacaaa aaggaaaaga ataaagcac gaagaattct agaaaatacg | 420 | |
| aaatacgctt caatgcagtg ggacccacgg ttcaattatt gccaattttc agctccaccg | 480 | |
| tatatttaaa aaataaaacg ataatgctaa aaaaatataa atcgtaacga tcgttaaatc | 540 | |
| tcaacggctg gatcttatga cgaccgttag aaattgtggt tgtcgacgag tcagtaataa | 600 | |
| acggcgtcaa agtggttgca gccggcacac acgagtcgtg tttatcaact caaagcacaa | 660 | |
| atactttcc tcaacctaaa aataaggcaa ttagccaaaa acaactttgc gtgtaaacaa | 720 | |
| cgctcaatac acgtgtcatt ttattattag ctattgcttc accgccttag ctttctcgtg | 780 | |
| acctagtcgt cctcgtcttt tcttcttctt cttctataaa acaatacccca aagagctctt | 840 | |
| cttcttcaca attcagattt caatttctca aaatcttaaa aactttctct caattctctc | 900 | |

```
taccgtgatc aaggtaaatt tctgtgttcc ttattctctc aaaatcttcg attttgtttt        960
cgttcgatcc caatttcgta tatgttcttt ggtttagatt ctgttaatct tagatcgaag       1020
acgattttct gggtttgatc gttagatatc atcttaattc tcgattaggg tttcatagat       1080
atcatccgat ttgttcaaat aatttgagtt ttgtcgaata attactcttc gatttgtgat       1140
ttctatctag atctggtgtt agtttctagt ttgtgcgatc gaatttgtcg attaatctga       1200
gtttttctga ttaacag                                                     1217
```

<210> SEQ ID NO 35
<211> LENGTH: 23
<212> TYPE: DNA
<213> ORGANISM: Artificial
<220> FEATURE:
<223> OTHER INFORMATION: guideRNA

<400> SEQUENCE: 35
atgggtagtc cttatcgtgc agg                                               23

<210> SEQ ID NO 36
<211> LENGTH: 23
<212> TYPE: DNA
<213> ORGANISM: Artificial
<220> FEATURE:
<223> OTHER INFORMATION: guideRNA

<400> SEQUENCE: 36
cgtccaccat gcgaatgtcg aca                                               23

<210> SEQ ID NO 37
<211> LENGTH: 23
<212> TYPE: DNA
<213> ORGANISM: Artificial
<220> FEATURE:
<223> OTHER INFORMATION: guideRNA

<400> SEQUENCE: 37
ttcggtggtg agtatcgtgc cgg                                               23

<210> SEQ ID NO 38
<211> LENGTH: 23
<212> TYPE: DNA
<213> ORGANISM: Artificial
<220> FEATURE:
<223> OTHER INFORMATION: guideRNA

<400> SEQUENCE: 38
cgatgagtct agacaaacca acg                                               23

<210> SEQ ID NO 39
<211> LENGTH: 23
<212> TYPE: DNA
<213> ORGANISM: Artificial
<220> FEATURE:
<223> OTHER INFORMATION: guideRNA

<400> SEQUENCE: 39
tttggtggcg agtttcgggc tgg                                               23

<210> SEQ ID NO 40
<211> LENGTH: 23
<212> TYPE: DNA
<213> ORGANISM: Artificial
<220> FEATURE:

<223> OTHER INFORMATION: guideRNA

<400> SEQUENCE: 40
atgcaacaag cttcttcggt ggc                                    23

<210> SEQ ID NO 41
<211> LENGTH: 29
<212> TYPE: DNA
<213> ORGANISM: Artificial
<220> FEATURE:
<223> OTHER INFORMATION: oligonucleotide

<400> SEQUENCE: 41
gttatgtaac taacttttc acattatgc                               29

<210> SEQ ID NO 42
<211> LENGTH: 24
<212> TYPE: DNA
<213> ORGANISM: Artificial
<220> FEATURE:
<223> OTHER INFORMATION: oligonucleotide

<400> SEQUENCE: 42
atgtgggaag aaatatcaaa tatg                                   24

<210> SEQ ID NO 43
<211> LENGTH: 20
<212> TYPE: DNA
<213> ORGANISM: Artificial
<220> FEATURE:
<223> OTHER INFORMATION: oligonucleotide

<400> SEQUENCE: 43
atagggtctc tggctgcaga                                        20

<210> SEQ ID NO 44
<211> LENGTH: 23
<212> TYPE: DNA
<213> ORGANISM: Artificial
<220> FEATURE:
<223> OTHER INFORMATION: oligonucleotide

<400> SEQUENCE: 44
cgatcgaaac aaacctccac aaa                                    23

<210> SEQ ID NO 45
<211> LENGTH: 20
<212> TYPE: DNA
<213> ORGANISM: Artificial
<220> FEATURE:
<223> OTHER INFORMATION: oligonucleotide

<400> SEQUENCE: 45
ggaccatcaa ccaccgtctt                                        20

<210> SEQ ID NO 46
<211> LENGTH: 23
<212> TYPE: DNA
<213> ORGANISM: Artificial
<220> FEATURE:
<223> OTHER INFORMATION: oligonucleotide

<400> SEQUENCE: 46
aactgggtta tgtggtgtgt tct                                    23

```
<210> SEQ ID NO 47
<211> LENGTH: 20
<212> TYPE: DNA
<213> ORGANISM: Artificial
<220> FEATURE:
<223> OTHER INFORMATION: oligonucleotide

<400> SEQUENCE: 47
gcgaaacatc aaccaccgac                                                   20

<210> SEQ ID NO 48
<211> LENGTH: 23
<212> TYPE: DNA
<213> ORGANISM: Artificial
<220> FEATURE:
<223> OTHER INFORMATION: oligonucleotide

<400> SEQUENCE: 48
ggtccagata tgaaccgggt tat                                               23

<210> SEQ ID NO 49
<211> LENGTH: 23
<212> TYPE: DNA
<213> ORGANISM: Artificial
<220> FEATURE:
<223> OTHER INFORMATION: oligonucleotide

<400> SEQUENCE: 49
ctgggtgggt aattctagga tgg                                               23

<210> SEQ ID NO 50
<211> LENGTH: 23
<212> TYPE: DNA
<213> ORGANISM: Artificial
<220> FEATURE:
<223> OTHER INFORMATION: oligonucleotide

<400> SEQUENCE: 50
ctcggttgta gacacgtaca aga                                               23

<210> SEQ ID NO 51
<211> LENGTH: 20
<212> TYPE: DNA
<213> ORGANISM: Artificial
<220> FEATURE:
<223> OTHER INFORMATION: oligonucleotide

<400> SEQUENCE: 51
aggtcacttg caaggagtcg                                                   20

<210> SEQ ID NO 52
<211> LENGTH: 23
<212> TYPE: DNA
<213> ORGANISM: Artificial
<220> FEATURE:
<223> OTHER INFORMATION: oligonucleotide

<400> SEQUENCE: 52
ttaagttctc ttgggtcacc gac                                               23

<210> SEQ ID NO 53
<211> LENGTH: 23
<212> TYPE: DNA
<213> ORGANISM: Artificial
<220> FEATURE:
<223> OTHER INFORMATION: oligonucleotide
```

<400> SEQUENCE: 53
ataccaacta cacctgccac ttt                                    23

<210> SEQ ID NO 54
<211> LENGTH: 23
<212> TYPE: DNA
<213> ORGANISM: Artificial
<220> FEATURE:
<223> OTHER INFORMATION: oligonucleotide

<400> SEQUENCE: 54
tatgtccgtt cctgtgctta tgt                                    23

<210> SEQ ID NO 55
<211> LENGTH: 20
<212> TYPE: DNA
<213> ORGANISM: Artificial
<220> FEATURE:
<223> OTHER INFORMATION: oligonucleotide

<400> SEQUENCE: 55
tccgcaacgt caaccatgta                                        20

<210> SEQ ID NO 56
<211> LENGTH: 23
<212> TYPE: DNA
<213> ORGANISM: Artificial
<220> FEATURE:
<223> OTHER INFORMATION: oligonucleotide

<400> SEQUENCE: 56
cctctattga tccgacagat ggg                                    23

<210> SEQ ID NO 57
<211> LENGTH: 23
<212> TYPE: DNA
<213> ORGANISM: Artificial
<220> FEATURE:
<223> OTHER INFORMATION: oligonucleotide

<400> SEQUENCE: 57
acgaaagtca ccttcggtat gaa                                    23

<210> SEQ ID NO 58
<211> LENGTH: 23
<212> TYPE: DNA
<213> ORGANISM: Artificial
<220> FEATURE:
<223> OTHER INFORMATION: oligonucleotide

<400> SEQUENCE: 58
atctgtgaac agccgtatga caa                                    23

<210> SEQ ID NO 59
<211> LENGTH: 21
<212> TYPE: DNA
<213> ORGANISM: Artificial
<220> FEATURE:
<223> OTHER INFORMATION: oligonucleotide

<400> SEQUENCE: 59
tctcaagttc ccatagcacg a                                      21

<210> SEQ ID NO 60
<211> LENGTH: 21

```
<212> TYPE: DNA
<213> ORGANISM: Artificial
<220> FEATURE:
<223> OTHER INFORMATION: oligonucleotide

<400> SEQUENCE: 60
tgcatacgcc aatgagtttg a                                              21

<210> SEQ ID NO 61
<211> LENGTH: 20
<212> TYPE: DNA
<213> ORGANISM: Artificial
<220> FEATURE:
<223> OTHER INFORMATION: oligonucleotide

<400> SEQUENCE: 61
agcacgaatc acgaaccatc                                                20

<210> SEQ ID NO 62
<211> LENGTH: 20
<212> TYPE: DNA
<213> ORGANISM: Artificial
<220> FEATURE:
<223> OTHER INFORMATION: oligonucleotide

<400> SEQUENCE: 62
tgaggtccgg tgccataatc                                                20

<210> SEQ ID NO 63
<211> LENGTH: 20
<212> TYPE: DNA
<213> ORGANISM: Artificial
<220> FEATURE:
<223> OTHER INFORMATION: oligonucleotide

<400> SEQUENCE: 63
ttcatatctg ggccggtgag                                                20

<210> SEQ ID NO 64
<211> LENGTH: 22
<212> TYPE: DNA
<213> ORGANISM: Artificial
<220> FEATURE:
<223> OTHER INFORMATION: oligonucleotide

<400> SEQUENCE: 64
acaagaacga agaatcaagc ca                                             22

<210> SEQ ID NO 65
<211> LENGTH: 20
<212> TYPE: DNA
<213> ORGANISM: Artificial
<220> FEATURE:
<223> OTHER INFORMATION: oligonucleotide

<400> SEQUENCE: 65
ccctctgaac aaacgtccaa                                                20

<210> SEQ ID NO 66
<211> LENGTH: 21
<212> TYPE: DNA
<213> ORGANISM: Artificial
<220> FEATURE:
<223> OTHER INFORMATION: oligonucleotide

<400> SEQUENCE: 66
```
tgaactgggt tatgtggtgt g                                          21

<210> SEQ ID NO 67
<211> LENGTH: 21
<212> TYPE: DNA
<213> ORGANISM: Artificial
<220> FEATURE:
<223> OTHER INFORMATION: oligonucleotide

<400> SEQUENCE: 67
ggccttggag gtctttatgg t                                          21

<210> SEQ ID NO 68
<211> LENGTH: 20
<212> TYPE: DNA
<213> ORGANISM: Artificial
<220> FEATURE:
<223> OTHER INFORMATION: oligonucleotide

<400> SEQUENCE: 68
agccggacca catttactga                                            20

<210> SEQ ID NO 69
<211> LENGTH: 21
<212> TYPE: DNA
<213> ORGANISM: Artificial
<220> FEATURE:
<223> OTHER INFORMATION: oligonucleotide

<400> SEQUENCE: 69
ccatcacaag ccacctctta c                                          21

<210> SEQ ID NO 70
<211> LENGTH: 23
<212> TYPE: DNA
<213> ORGANISM: Artificial
<220> FEATURE:
<223> OTHER INFORMATION: oligonucleotide

<400> SEQUENCE: 70
acgtttctcc tatcaagttt gcc                                        23

<210> SEQ ID NO 71
<211> LENGTH: 21
<212> TYPE: DNA
<213> ORGANISM: Artificial
<220> FEATURE:
<223> OTHER INFORMATION: oligonucleotide

<400> SEQUENCE: 71
aaatcccgtg gctccatagt c                                          21

<210> SEQ ID NO 72
<211> LENGTH: 21
<212> TYPE: DNA
<213> ORGANISM: Artificial
<220> FEATURE:
<223> OTHER INFORMATION: oligonucleotide

<400> SEQUENCE: 72
ttcgcttcct gcttgttctt c                                          21

<210> SEQ ID NO 73
<211> LENGTH: 20
<212> TYPE: DNA
<213> ORGANISM: Artificial

<220> FEATURE:
<223> OTHER INFORMATION: oligonucleotide

<400> SEQUENCE: 73
tttacgtcca ccatgccaac                                                    20

<210> SEQ ID NO 74
<211> LENGTH: 21
<212> TYPE: DNA
<213> ORGANISM: Artificial
<220> FEATURE:
<223> OTHER INFORMATION: oligonucleotide

<400> SEQUENCE: 74
agtcgtatcc cattgcagtc a                                                  21

<210> SEQ ID NO 75
<211> LENGTH: 21
<212> TYPE: DNA
<213> ORGANISM: Artificial
<220> FEATURE:
<223> OTHER INFORMATION: oligonucleotide

<400> SEQUENCE: 75
tgtacgtgtc tacaaccgag a                                                  21

<210> SEQ ID NO 76
<211> LENGTH: 21
<212> TYPE: DNA
<213> ORGANISM: Artificial
<220> FEATURE:
<223> OTHER INFORMATION: oligonucleotide

<400> SEQUENCE: 76
cgattccagc agacttagca g                                                  21

<210> SEQ ID NO 77
<211> LENGTH: 21
<212> TYPE: DNA
<213> ORGANISM: Artificial
<220> FEATURE:
<223> OTHER INFORMATION: oligonucleotide

<400> SEQUENCE: 77
gcaaatgagc tgttgttcgt g                                                  21

<210> SEQ ID NO 78
<211> LENGTH: 21
<212> TYPE: DNA
<213> ORGANISM: Artificial
<220> FEATURE:
<223> OTHER INFORMATION: oligonucleotide

<400> SEQUENCE: 78
tatgtggcaa ctgtgcgaaa c                                                  21

<210> SEQ ID NO 79
<211> LENGTH: 21
<212> TYPE: DNA
<213> ORGANISM: Artificial
<220> FEATURE:
<223> OTHER INFORMATION: oligonucleotide

<400> SEQUENCE: 79
cagttgccac acaaacacaa g                                                  21

```
<210> SEQ ID NO 80
<211> LENGTH: 21
<212> TYPE: DNA
<213> ORGANISM: Artificial
<220> FEATURE:
<223> OTHER INFORMATION: oligonucleotide

<400> SEQUENCE: 80
gatccagacc ttgggacaat c                                         21

<210> SEQ ID NO 81
<211> LENGTH: 21
<212> TYPE: DNA
<213> ORGANISM: Artificial
<220> FEATURE:
<223> OTHER INFORMATION: oligonucleotide

<400> SEQUENCE: 81
attagcggtg gtggatcagt c                                         21

<210> SEQ ID NO 82
<211> LENGTH: 20
<212> TYPE: DNA
<213> ORGANISM: Artificial
<220> FEATURE:
<223> OTHER INFORMATION: oligonucleotide

<400> SEQUENCE: 82
gtttgcctcc ctgcatcttc                                           20

<210> SEQ ID NO 83
<211> LENGTH: 21
<212> TYPE: DNA
<213> ORGANISM: Artificial
<220> FEATURE:
<223> OTHER INFORMATION: oligonucleotide

<400> SEQUENCE: 83
tatcacgacg ccaaacttct c                                         21

<210> SEQ ID NO 84
<211> LENGTH: 21
<212> TYPE: DNA
<213> ORGANISM: Artificial
<220> FEATURE:
<223> OTHER INFORMATION: oligonucleotide

<400> SEQUENCE: 84
ctatgtgccg ctggtctaat c                                         21

<210> SEQ ID NO 85
<211> LENGTH: 21
<212> TYPE: DNA
<213> ORGANISM: Artificial
<220> FEATURE:
<223> OTHER INFORMATION: oligonucleotide

<400> SEQUENCE: 85
ataaggccgt cagaagcaga g                                         21

<210> SEQ ID NO 86
<211> LENGTH: 21
<212> TYPE: DNA
<213> ORGANISM: Artificial
<220> FEATURE:
<223> OTHER INFORMATION: oligonucleotide
```

```
<400> SEQUENCE: 86
aacgaaactg tgtgggtgtt c                                            21

<210> SEQ ID NO 87
<211> LENGTH: 21
<212> TYPE: DNA
<213> ORGANISM: Artificial
<220> FEATURE:
<223> OTHER INFORMATION: oligonucleotide

<400> SEQUENCE: 87
ggcctgaaac tgctagaaca a                                            21

<210> SEQ ID NO 88
<211> LENGTH: 20
<212> TYPE: DNA
<213> ORGANISM: Artificial
<220> FEATURE:
<223> OTHER INFORMATION: oligonucleotide

<400> SEQUENCE: 88
aacccgcata ctcgctatca                                              20

<210> SEQ ID NO 89
<211> LENGTH: 21
<212> TYPE: DNA
<213> ORGANISM: Artificial
<220> FEATURE:
<223> OTHER INFORMATION: oligonucleotide

<400> SEQUENCE: 89
gcgaagatac gactgacgac t                                            21

<210> SEQ ID NO 90
<211> LENGTH: 21
<212> TYPE: DNA
<213> ORGANISM: Artificial
<220> FEATURE:
<223> OTHER INFORMATION: oligonucleotide

<400> SEQUENCE: 90
ccagcgacat acttaccacc a                                            21

<210> SEQ ID NO 91
<211> LENGTH: 21
<212> TYPE: DNA
<213> ORGANISM: Artificial
<220> FEATURE:
<223> OTHER INFORMATION: oligonucleotide

<400> SEQUENCE: 91
acttctactc cgcaggctat g                                            21

<210> SEQ ID NO 92
<211> LENGTH: 20
<212> TYPE: DNA
<213> ORGANISM: Artificial
<220> FEATURE:
<223> OTHER INFORMATION: oligonucleotide

<400> SEQUENCE: 92
gtgcatggtg tctcctgttc                                              20

<210> SEQ ID NO 93
```

```
<211> LENGTH: 21
<212> TYPE: DNA
<213> ORGANISM: Artificial
<220> FEATURE:
<223> OTHER INFORMATION: oligonucleotide

<400> SEQUENCE: 93
taacgacaat gacccacaca g                                              21

<210> SEQ ID NO 94
<211> LENGTH: 21
<212> TYPE: DNA
<213> ORGANISM: Artificial
<220> FEATURE:
<223> OTHER INFORMATION: oligonucleotide

<400> SEQUENCE: 94
gtggaatgga aagaagagcc a                                              21

<210> SEQ ID NO 95
<211> LENGTH: 21
<212> TYPE: DNA
<213> ORGANISM: Artificial
<220> FEATURE:
<223> OTHER INFORMATION: oligonucleotide

<400> SEQUENCE: 95
acataagcac aggaacggac a                                              21

<210> SEQ ID NO 96
<211> LENGTH: 21
<212> TYPE: DNA
<213> ORGANISM: Artificial
<220> FEATURE:
<223> OTHER INFORMATION: oligonucleotide

<400> SEQUENCE: 96
caccaccaca tcttcgtcat c                                              21

<210> SEQ ID NO 97
<211> LENGTH: 21
<212> TYPE: DNA
<213> ORGANISM: Artificial
<220> FEATURE:
<223> OTHER INFORMATION: oligonucleotide

<400> SEQUENCE: 97
atggccggaa taccaactac a                                              21

<210> SEQ ID NO 98
<211> LENGTH: 19
<212> TYPE: DNA
<213> ORGANISM: Artificial
<220> FEATURE:
<223> OTHER INFORMATION: oligonucleotide

<400> SEQUENCE: 98
ccgctgtctc ctcatcctc                                                 19

<210> SEQ ID NO 99
<211> LENGTH: 22
<212> TYPE: DNA
<213> ORGANISM: Artificial
<220> FEATURE:
<223> OTHER INFORMATION: oligonucleotide

<400> SEQUENCE: 99
```
tgtatgtgga tgacaaggac ga        22

<210> SEQ ID NO 100
<211> LENGTH: 21
<212> TYPE: DNA
<213> ORGANISM: Artificial
<220> FEATURE:
<223> OTHER INFORMATION: oligonucleotide

<400> SEQUENCE: 100
cttctcgcct gattgatggt g        21

<210> SEQ ID NO 101
<211> LENGTH: 21
<212> TYPE: DNA
<213> ORGANISM: Artificial
<220> FEATURE:
<223> OTHER INFORMATION: oligonucleotide

<400> SEQUENCE: 101
ggatgccgaa caatgaagac a        21

<210> SEQ ID NO 102
<211> LENGTH: 22
<212> TYPE: DNA
<213> ORGANISM: Artificial
<220> FEATURE:
<223> OTHER INFORMATION: oligonucleotide

<400> SEQUENCE: 102
cctgataccc aactctttcc ag        22

<210> SEQ ID NO 103
<211> LENGTH: 21
<212> TYPE: DNA
<213> ORGANISM: Artificial
<220> FEATURE:
<223> OTHER INFORMATION: oligonucleotide

<400> SEQUENCE: 103
aggaccaagg aggacaaaca g        21

<210> SEQ ID NO 104
<211> LENGTH: 21
<212> TYPE: DNA
<213> ORGANISM: Artificial
<220> FEATURE:
<223> OTHER INFORMATION: oligonucleotide

<400> SEQUENCE: 104
tgcgaaacta ccagcaaact c        21

<210> SEQ ID NO 105
<211> LENGTH: 20
<212> TYPE: DNA
<213> ORGANISM: Artificial
<220> FEATURE:
<223> OTHER INFORMATION: oligonucleotide

<400> SEQUENCE: 105
gacaatggaa ccgagaccac        20

<210> SEQ ID NO 106
<211> LENGTH: 21
<212> TYPE: DNA

```
<213> ORGANISM: Artificial
<220> FEATURE:
<223> OTHER INFORMATION: oligonucleotide

<400> SEQUENCE: 106
ccaaacctaa ctccgctcat c                                             21

<210> SEQ ID NO 107
<211> LENGTH: 22
<212> TYPE: DNA
<213> ORGANISM: Artificial
<220> FEATURE:
<223> OTHER INFORMATION: oligonucleotide

<400> SEQUENCE: 107
acgtcaacca tgtatcacca ga                                            22

<210> SEQ ID NO 108
<211> LENGTH: 21
<212> TYPE: DNA
<213> ORGANISM: Artificial
<220> FEATURE:
<223> OTHER INFORMATION: oligonucleotide

<400> SEQUENCE: 108
cttaacgggt cagtagcgtt g                                             21

<210> SEQ ID NO 109
<211> LENGTH: 22
<212> TYPE: DNA
<213> ORGANISM: Artificial
<220> FEATURE:
<223> OTHER INFORMATION: oligonucleotide

<400> SEQUENCE: 109
gcaactccag attcacaact ca                                            22

<210> SEQ ID NO 110
<211> LENGTH: 21
<212> TYPE: DNA
<213> ORGANISM: Artificial
<220> FEATURE:
<223> OTHER INFORMATION: oligonucleotide

<400> SEQUENCE: 110
gcgtcaaaga cagggtttct c                                             21

<210> SEQ ID NO 111
<211> LENGTH: 21
<212> TYPE: DNA
<213> ORGANISM: Artificial
<220> FEATURE:
<223> OTHER INFORMATION: oligonucleotide

<400> SEQUENCE: 111
cctattgact gttgccctct g                                             21

<210> SEQ ID NO 112
<211> LENGTH: 21
<212> TYPE: DNA
<213> ORGANISM: Artificial
<220> FEATURE:
<223> OTHER INFORMATION: oligonucleotide

<400> SEQUENCE: 112
atcgagatac ccgactggaa g                                             21
```

<210> SEQ ID NO 113
<211> LENGTH: 20
<212> TYPE: DNA
<213> ORGANISM: Artificial
<220> FEATURE:
<223> OTHER INFORMATION: oligonucleotide

<400> SEQUENCE: 113
ggaatttgct cctgggtctc                                          20

<210> SEQ ID NO 114
<211> LENGTH: 21
<212> TYPE: DNA
<213> ORGANISM: Artificial
<220> FEATURE:
<223> OTHER INFORMATION: oligonucleotide

<400> SEQUENCE: 114
atacggcatc tttgcatggt c                                        21

<210> SEQ ID NO 115
<211> LENGTH: 19
<212> TYPE: DNA
<213> ORGANISM: Artificial
<220> FEATURE:
<223> OTHER INFORMATION: oligonucleotide

<400> SEQUENCE: 115
aaatgctgac gtggcctga                                           19

<210> SEQ ID NO 116
<211> LENGTH: 23
<212> TYPE: DNA
<213> ORGANISM: Artificial
<220> FEATURE:
<223> OTHER INFORMATION: oligonucleotide

<400> SEQUENCE: 116
ctttctcatc cagtcctgaa cac                                      23

<210> SEQ ID NO 117
<211> LENGTH: 23
<212> TYPE: DNA
<213> ORGANISM: Artificial
<220> FEATURE:
<223> OTHER INFORMATION: oligonucleotide

<400> SEQUENCE: 117
cagctgagga atggatttca aga                                      23

<210> SEQ ID NO 118
<211> LENGTH: 21
<212> TYPE: DNA
<213> ORGANISM: Artificial
<220> FEATURE:
<223> OTHER INFORMATION: oligonucleotide

<400> SEQUENCE: 118
gggtcgacat ggttcacaat c                                        21

<210> SEQ ID NO 119
<211> LENGTH: 19
<212> TYPE: DNA
<213> ORGANISM: Artificial
<220> FEATURE:

```
<223> OTHER INFORMATION: guideRNA

<400> SEQUENCE: 119
tgggtagtcc ttatcgtgc                                            19

<210> SEQ ID NO 120
<211> LENGTH: 19
<212> TYPE: DNA
<213> ORGANISM: Artificial
<220> FEATURE:
<223> OTHER INFORMATION: guideRNA

<400> SEQUENCE: 120
tggggaactt ctactccgc                                            19

<210> SEQ ID NO 121
<211> LENGTH: 19
<212> TYPE: DNA
<213> ORGANISM: Artificial
<220> FEATURE:
<223> OTHER INFORMATION: guideRNA

<400> SEQUENCE: 121
tcggtggtga gtatcgtgc                                            19

<210> SEQ ID NO 122
<211> LENGTH: 19
<212> TYPE: DNA
<213> ORGANISM: Artificial
<220> FEATURE:
<223> OTHER INFORMATION: guideRNA

<400> SEQUENCE: 122
aaaccaacga cggtgatgg                                            19

<210> SEQ ID NO 123
<211> LENGTH: 19
<212> TYPE: DNA
<213> ORGANISM: Artificial
<220> FEATURE:
<223> OTHER INFORMATION: guideRNA

<400> SEQUENCE: 123
ttggtggcga gtttcgggc                                            19

<210> SEQ ID NO 124
<211> LENGTH: 19
<212> TYPE: DNA
<213> ORGANISM: Artificial
<220> FEATURE:
<223> OTHER INFORMATION: guideRNA

<400> SEQUENCE: 124
tcggtggcaa atatgtagc                                            19

<210> SEQ ID NO 125
<211> LENGTH: 18
<212> TYPE: DNA
<213> ORGANISM: Artificial
<220> FEATURE:
<223> OTHER INFORMATION: oligonucleotide

<400> SEQUENCE: 125
taaggaacca agttcggc                                             18
```

```
<210> SEQ ID NO 126
<211> LENGTH: 18
<212> TYPE: DNA
<213> ORGANISM: Artificial
<220> FEATURE:
<223> OTHER INFORMATION: oligonucleotide

<400> SEQUENCE: 126
acaccaagcc ttccacag                                                 18

<210> SEQ ID NO 127
<211> LENGTH: 22
<212> TYPE: DNA
<213> ORGANISM: Artificial
<220> FEATURE:
<223> OTHER INFORMATION: oligonucleotide

<400> SEQUENCE: 127
gtctggagga tctgctagag tc                                            22

<210> SEQ ID NO 128
<211> LENGTH: 19
<212> TYPE: DNA
<213> ORGANISM: Artificial
<220> FEATURE:
<223> OTHER INFORMATION: oligonucleotide

<400> SEQUENCE: 128
cgtcttcaaa gcaagtgga                                                19

<210> SEQ ID NO 129
<211> LENGTH: 20
<212> TYPE: DNA
<213> ORGANISM: Artificial
<220> FEATURE:
<223> OTHER INFORMATION: oligonucleotide

<400> SEQUENCE: 129
tggcaggata tattgtggtg                                               20

<210> SEQ ID NO 130
<211> LENGTH: 23
<212> TYPE: DNA
<213> ORGANISM: Artificial
<220> FEATURE:
<223> OTHER INFORMATION: oligonucleotide

<400> SEQUENCE: 130
gtactcttgc cgactacaac atc                                           23

<210> SEQ ID NO 131
<211> LENGTH: 22
<212> TYPE: DNA
<213> ORGANISM: Artificial
<220> FEATURE:
<223> OTHER INFORMATION: oligonucleotide

<400> SEQUENCE: 131
gtctggagga tctgctagag tc                                            22

<210> SEQ ID NO 132
<211> LENGTH: 21
<212> TYPE: DNA
<213> ORGANISM: Artificial
<220> FEATURE:
<223> OTHER INFORMATION: oligonucleotide
```

```
<400> SEQUENCE: 132
gtttacccgc caatatatcc t                                           21

<210> SEQ ID NO 133
<211> LENGTH: 26
<212> TYPE: DNA
<213> ORGANISM: Artificial
<220> FEATURE:
<223> OTHER INFORMATION: oligonucleotide

<400> SEQUENCE: 133
agggcgaatt cgacccagct ttcttg                                      26

<210> SEQ ID NO 134
<211> LENGTH: 21
<212> TYPE: DNA
<213> ORGANISM: Artificial
<220> FEATURE:
<223> OTHER INFORMATION: oligonucleotide

<400> SEQUENCE: 134
gtttacccgc caatatatcc t                                           21

<210> SEQ ID NO 135
<211> LENGTH: 23
<212> TYPE: DNA
<213> ORGANISM: Artificial
<220> FEATURE:
<223> OTHER INFORMATION: oligonucleotide

<400> SEQUENCE: 135
atgtctctgt ttggaaatgt ttc                                         23

<210> SEQ ID NO 136
<211> LENGTH: 23
<212> TYPE: DNA
<213> ORGANISM: Artificial
<220> FEATURE:
<223> OTHER INFORMATION: oligonucleotide

<400> SEQUENCE: 136
tcccatcact caatagaaag ttc                                         23

<210> SEQ ID NO 137
<211> LENGTH: 24
<212> TYPE: DNA
<213> ORGANISM: Artificial
<220> FEATURE:
<223> OTHER INFORMATION: oligonucleotide

<400> SEQUENCE: 137
aatgacaaac tcatcaggga agtg                                        24

<210> SEQ ID NO 138
<211> LENGTH: 20
<212> TYPE: DNA
<213> ORGANISM: Artificial
<220> FEATURE:
<223> OTHER INFORMATION: oligonucleotide

<400> SEQUENCE: 138
ggcagctcat ttggctaata                                             20

<210> SEQ ID NO 139
<211> LENGTH: 20
```

```
<212> TYPE: DNA
<213> ORGANISM: Artificial
<220> FEATURE:
<223> OTHER INFORMATION: oligonucleotide

<400> SEQUENCE: 139
cgaagaatca agccagtctt                                              20

<210> SEQ ID NO 140
<211> LENGTH: 19
<212> TYPE: DNA
<213> ORGANISM: Artificial
<220> FEATURE:
<223> OTHER INFORMATION: oligonucleotide

<400> SEQUENCE: 140
gcagctcatt tggctaatg                                               19

<210> SEQ ID NO 141
<211> LENGTH: 20
<212> TYPE: DNA
<213> ORGANISM: Artificial
<220> FEATURE:
<223> OTHER INFORMATION: oligonucleotide

<400> SEQUENCE: 141
cgaagaatca agccaatctt                                              20

<210> SEQ ID NO 142
<211> LENGTH: 22
<212> TYPE: DNA
<213> ORGANISM: Artificial
<220> FEATURE:
<223> OTHER INFORMATION: oligonucleotide

<400> SEQUENCE: 142
gattcaagcc atgaagaatc tc                                           22

<210> SEQ ID NO 143
<211> LENGTH: 23
<212> TYPE: DNA
<213> ORGANISM: Artificial
<220> FEATURE:
<223> OTHER INFORMATION: oligonucleotide

<400> SEQUENCE: 143
tgtgtccctt gattcccaaa tct                                          23

<210> SEQ ID NO 144
<211> LENGTH: 18
<212> TYPE: DNA
<213> ORGANISM: Artificial
<220> FEATURE:
<223> OTHER INFORMATION: oligonucleotide

<400> SEQUENCE: 144
agccactgcc gattacat                                                18

<210> SEQ ID NO 145
<211> LENGTH: 21
<212> TYPE: DNA
<213> ORGANISM: Artificial
<220> FEATURE:
<223> OTHER INFORMATION: oligonucleotide

<400> SEQUENCE: 145
```

-continued

```
cgtatgatgc atttagccag t                                              21

<210> SEQ ID NO 146
<211> LENGTH: 20
<212> TYPE: DNA
<213> ORGANISM: Artificial
<220> FEATURE:
<223> OTHER INFORMATION: oligonucleotide

<400> SEQUENCE: 146
ctaagaatga ggcgttcagg                                                20

<210> SEQ ID NO 147
<211> LENGTH: 20
<212> TYPE: DNA
<213> ORGANISM: Artificial
<220> FEATURE:
<223> OTHER INFORMATION: oligonucleotide

<400> SEQUENCE: 147
gtttgcctcc ctgcatcttc                                                20

<210> SEQ ID NO 148
<211> LENGTH: 18
<212> TYPE: DNA
<213> ORGANISM: Artificial
<220> FEATURE:
<223> OTHER INFORMATION: oligonucleotide

<400> SEQUENCE: 148
attgcgctta ctgcaatg                                                  18

<210> SEQ ID NO 149
<211> LENGTH: 20
<212> TYPE: DNA
<213> ORGANISM: Artificial
<220> FEATURE:
<223> OTHER INFORMATION: oligonucleotide

<400> SEQUENCE: 149
tctgtcggtt ctttgcctcc                                                20

<210> SEQ ID NO 150
<211> LENGTH: 630
<212> TYPE: DNA
<213> ORGANISM: Artificial
<220> FEATURE:
<223> OTHER INFORMATION: consensus sequence

<400> SEQUENCE: 150
cctcgtagtt tcaagcaaca agctgctgtt cattgtgcgt attgcgatgg ggcatacgat     60
caagtcggtt tccctgatct cgagcttcaa gtccatggct catggttgtt cttacctttc    120
caccgctatt acttatactt cttcgagaaa atttgtggca aattaatcga tgatccaaat    180
ttcgcaatcc cttttttggaa ctgggatgca cctgatggca tgaagatccc tgatatttac    240
acgaataaga aatctccgtt gtacgatgct cttcgtgatg cgaagcatca accaccgtct    300
ctgattgatc ttgactacaa tggtgacgat gaaaatctta gccgatcgaa acaaacctcc    360
acaaatctca caattatgta cagacaaatg gtgtctagtt ccaagactgc tagtcttttc    420
atgggtagtc cttatcgtgc aggtgatgag gctagccctg gctctggctc gctcgagagc    480
ataccacatg gcccggttca tatctggacc ggagatagga accagcaaaa tggtgaagac    540
atgggtaact tttattctgc agccagagac cctatttttct atgcacatca tgcgaatatc    600
```

```
gacagaatgt ggtcagtttg gaaaactcta                              630
```

<210> SEQ ID NO 151
<211> LENGTH: 630
<212> TYPE: DNA
<213> ORGANISM: Artificial
<220> FEATURE:
<223> OTHER INFORMATION: consensus sequence

<400> SEQUENCE: 151

```
cctcgtagct ttaagcagca agcaaatgtt cattgtgcct attgcgatgg cgcgtatgac    60
caagtcggtt ttccagatct ggagcttcaa gtacataact catggctgtt cttcccttc   120
catcgctatt acatgtactt cttcgagaaa atttgtggca agttaattga tgacccaaat  180
ttcgcaattc cattttggaa ctgggatgca ccagatggga tgaaaatccc tgatatttac   240
acaaataaga aatcttcgtt gtatgatcct cttcgcgatg tggaccatca accaccgtct   300
ttgattgatc ttgacttcaa tggtgtcgac gaaaatctta gccctctga acaaacgtcc    360
aaaaatctca cagttatgta tagacaaatg gtgtctagtt ccaagacttc tactctttc   420
atgggtagtc cttatcgtgc aggcgatgat gctagccctg gtagtggttc gatcgagaac  480
acaccacata acccagttca tatctgggcc ggtgagtgga agcataataa tggcaaaaac  540
atgggcaaac tttattctgc agccagggac cctcttttct atgcacatca tgggaatatt  600
gatagaatgt ggtcagtttg gaaaacacta                                   630
```

<210> SEQ ID NO 152
<211> LENGTH: 655
<212> TYPE: DNA
<213> ORGANISM: Artificial
<220> FEATURE:
<223> OTHER INFORMATION: consensus sequence

<400> SEQUENCE: 152

```
tccacacagt tggaagcaac aagctaagat ccactgcgct tattgcaacg gtggttacaa    60
tcaagaacag agtggtttcc cggacataca actccagatt cacaacacat ggctcttctt   120
tcctttccac cgatggtacc tctacttcta cgagaggatt ttggggaagt tgattaatga   180
tccaactttc gctttaccat actggaactg ggataaccct accggaatgg tgctccctgc   240
catgttcgaa accgacggca aaggaaccc tatctttgac ccttacagga atgccacaca    300
cctcccacca gctatctttg aagtgggata taatgggaca gacagtggcg ccacttgtat   360
agaccagata agcgctaatc tgtctttgat gtacaagcaa atgatcacca acgctcctga   420
tacaacaacg ttcttcggtg gagaatttgt tgctggggat gaccctctta acaaagagtt   480
taacgttgct gggtccatag aggctggggt tcacactgcg gcgcatagat gggtgggtga   540
tcctaggatg gccaacagcg aggacatggg gaacttctac tccgcagggt atgatcctct   600
cttttacgtc caccatgcca acgtcgaccg gatgtggaaa atctggaaag atttg        655
```

<210> SEQ ID NO 153
<211> LENGTH: 655
<212> TYPE: DNA
<213> ORGANISM: Artificial
<220> FEATURE:
<223> OTHER INFORMATION: consensus sequence

<400> SEQUENCE: 153

```
cccacatagc tggaagcaac aaggcaagat tcactgtgct tattgcaacg gtggttacaa    60
```

```
tcaagaacaa agtggttacc cgaatttaca acttcagatt cacaactcat ggctcttctt    120
tcctttccac cggtggtacc tctatttcta cgagaagata ttggggaagt tgattaatga    180
tccaactttc gctctacctt actggaactg ggataaccct actggaatgg ttattcctgc    240
catgttcgaa cagaacagca aaactaactc tctgtttgac cctttaaggg atgcgaaaca    300
cctcccacct tctatctttg atgttgaata tgctggtgca gacactggtg ccacttgtat    360
agaccagata gccattaatc tgtcttcaat gtacagacag atggtcacca actccactga    420
tacaaaacga ttcttcggtg gcgaatttgt agctggaaat gaccctcttg cgagcgagtt    480
caacgtagct gggaccgtag aagctggggt tcacactgcg gctcaccgct gggtgggtaa    540
ttctaggatg gccaacagcg aagacatggg gaacttctac tccgcaggat atgatcctct    600
cttttacgtc caccatgcga atgtcgacag gatgtggcaa atctggaaag atatt    655
```

```
<210> SEQ ID NO 154
<211> LENGTH: 634
<212> TYPE: DNA
<213> ORGANISM: Artificial
<220> FEATURE:
<223> OTHER INFORMATION: consensus sequence

<400> SEQUENCE: 154
tcctcgaaac tttctgcaac aagcacacat tcactgtgct tactgcaatg gcgcttacac     60
tcaatcttca gtggatttc cgatattga atccagatt cataactcat ggctgttctt    120 cccttccac cgttggtatc tctactttta cgagagaatc ctggggagct tgatcgatga    180
tcccactttc gctttgccat tctggaactg ggacacccct gccggaatga caattccgaa    240
atactttaac gatcccaaaa acgcagtttt tgatcccaaa agaaaccaag gtcacttgca    300
aggagtcgtc gatctgggtt acaatgggaa agattcagac actactgata tcgaaaaggt    360
gaagaacaat ctcgcgataa tgtatcgtca aatggtgaca aacgccaccg accccacagc    420
tttcttcggt ggtgagtatc gtgccggaat cgaacccatt agcggtggtg atcagtcga    480 acaaagccca cacacacctg ttcaccggtg ggtcggtgac ccaagagaac ttaacggtga    540
aaacctcggt aacttctact ccgccggtcg tgacacgctc ttttactgtc accattccaa    600
cgtcgatcga atgtggtcgt tgtggaagat gcag    634
```

```
<210> SEQ ID NO 155
<211> LENGTH: 664
<212> TYPE: DNA
<213> ORGANISM: Artificial
<220> FEATURE:
<223> OTHER INFORMATION: consensus sequence

<400> SEQUENCE: 155
cccacgcagt ttcaataacc aagctaaagt tcattgcgct tactgcaatg gcagttacac     60
tcaaaacggt caagaactcc agattcacaa ctcctggctc ttctttccct tccatcggtg    120
gtacctttat ttctacgaga ggatactggg agatctcatt ggtgattcga cattcgggtt    180
accctactgg aactgggaca accccgaagg aatgacaatt ccacacttct tcgtagagaa    240
acaatgtaac aactataagt tcgaaaacgg agaaaaccct ctatatgata agtatcggga    300
cgaaagtcac cttcggtatg aattggtcga tcttgactac tcagggagaa accgcgacct    360
gtgttacgat cagaaagaaa tcaatctggc tactatgaat aggcagatga tgcgcaacgc    420
ctttgatgca acaagcttct tcggtggcaa atatgtagcc ggtgatgaac cgattccccg    480
aggagataat gtagttggat ccgtggaggc tggttgtcat acggctgttc acagatgggt    540
```

```
tgggaaccct gatccaaaag ggaataaaga ggacatgggc aacttctact ctgcgggata    600
tgatcctttg ttctacgtcc accattctaa tgtggaccga atgtggactc tttggaagca    660
aatg                                                                 664

<210> SEQ ID NO 156
<211> LENGTH: 56
<212> TYPE: DNA
<213> ORGANISM: Lactuca sativa

<400> SEQUENCE: 156
agttccaaga cttctactct tttcatgggt agtccttatc gtgcaggcga tgatgc        56

<210> SEQ ID NO 157
<211> LENGTH: 58
<212> TYPE: DNA
<213> ORGANISM: Lactuca sativa

<400> SEQUENCE: 157
agttccaaga cttctactct tttcatgggt agtccttatc gtgcaggcga tgatgcta      58

<210> SEQ ID NO 158
<211> LENGTH: 57
<212> TYPE: DNA
<213> ORGANISM: Lactuca sativa

<400> SEQUENCE: 158
agttccaaga cttctactct tttcatgggt agtccttatc ggcaggcgat gatgcta       57

<210> SEQ ID NO 159
<211> LENGTH: 58
<212> TYPE: DNA
<213> ORGANISM: Lactuca sativa

<400> SEQUENCE: 159
agttccaaga cttctactct tttcatgggt agtccttatc gtgcaggcga tgatgcta      58

<210> SEQ ID NO 160
<211> LENGTH: 54
<212> TYPE: DNA
<213> ORGANISM: Lactuca sativa

<400> SEQUENCE: 160
agttccaaga cttctactct tttcatgggt agtccttagc aggcgatgat gcta          54

<210> SEQ ID NO 161
<211> LENGTH: 74
<212> TYPE: DNA
<213> ORGANISM: Lactuca sativa

<400> SEQUENCE: 161
gtgacaaacg ccaccgaccc cacagctttc ttcggtggtg agtatcgtgc cggaatcgaa    60
cccattagcg gtgg                                                      74

<210> SEQ ID NO 162
<211> LENGTH: 74
<212> TYPE: DNA
<213> ORGANISM: Lactuca sativa

<400> SEQUENCE: 162
gtgtctaatg ccaagactgc tagtcttttc atgggtagtc cttatcgtgc aggtgatgac    60
```

```
                                              -continued cctagccctg gtgc                                                    74

<210> SEQ ID NO 163
<211> LENGTH: 74
<212> TYPE: DNA
<213> ORGANISM: Lactuca sativa

<400> SEQUENCE: 163
gtgacaaacg ccaccgaccc cacagctttc ttcggtggtg agtatcgtgc cggaatcgaa    60
cccattagcg gtgg                                                    74

<210> SEQ ID NO 164
<211> LENGTH: 74
<212> TYPE: DNA
<213> ORGANISM: Lactuca sativa

<400> SEQUENCE: 164
gtgacaaacg ccaccgaccc cacagctttc ttcggtggtg agtatcgtgc cggaatcgaa    60
cccattagcg gtgg                                                    74

<210> SEQ ID NO 165
<211> LENGTH: 111
<212> TYPE: DNA
<213> ORGANISM: Lactuca sativa

<400> SEQUENCE: 165
gtgacaaacg ccaccgaccc cacagctttc ttcggtggtg acaaacgcca ccgaccccac    60
agctttcttc ggtggtaagt atcgtgccgg aatcgaaccc attagcggtg g           111

<210> SEQ ID NO 166
<211> LENGTH: 111
<212> TYPE: DNA
<213> ORGANISM: Lactuca sativa

<400> SEQUENCE: 166
gtgacaaacg ccaccgaccc cacagctttc ttcggtggtg acaaacgcca ccgaccccac    60
agctttcttc ggttgtgagt atcgtgccgg aatcgaaccc attagcggtg g           111

<210> SEQ ID NO 167
<211> LENGTH: 111
<212> TYPE: DNA
<213> ORGANISM: Lactuca sativa

<400> SEQUENCE: 167
gtgacaaacg ccaccgaccc cacagctttc ttcggtggtg acaaacgcca ccgaccccac    60
agctttcttc ggtggttagt atcgtgccgg aatcgaaccc attagcggtg g           111

<210> SEQ ID NO 168
<211> LENGTH: 74
<212> TYPE: DNA
<213> ORGANISM: Lactuca sativa

<400> SEQUENCE: 168
gtgacaaacg ccaccgaccc cacagctttc ttcggtggtg agtatcgtgc cggaatcgaa    60
cccattagcg gtgg                                                    74

<210> SEQ ID NO 169
<211> LENGTH: 74
<212> TYPE: DNA
<213> ORGANISM: Lactuca sativa
```

```
<400> SEQUENCE: 169
gtgacaaacg ccaccgaccc cacagctttc ttcggtggtg agtatcgtgc cggaatcgaa        60
cccattagcg gtgg                                                         74
```